US009828618B2

(12) United States Patent
Hidesaki et al.

(10) Patent No.: US 9,828,618 B2
(45) Date of Patent: *Nov. 28, 2017

(54) MICROORGANISM HAVING CARBON DIOXIDE FIXATION CYCLE INTRODUCED THEREINTO

(71) Applicant: Mitsui Chemicals, Inc., Tokyo (JP)

(72) Inventors: Tomonori Hidesaki, Singapore (SG); Ryota Fujii, Chiba (JP); Yoshiko Matsumoto, Mobara (JP); Anjali Madhavan, Singapore (SG); Su Sun Chong, Singapore (SG)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/428,928

(22) PCT Filed: Jan. 23, 2014

(86) PCT No.: PCT/JP2014/051402
§ 371 (c)(1),
(2) Date: Mar. 17, 2015

(87) PCT Pub. No.: WO2014/115815
PCT Pub. Date: Jul. 31, 2014

(65) Prior Publication Data
US 2015/0232903 A1 Aug. 20, 2015

(30) Foreign Application Priority Data

Jan. 24, 2013 (JP) ................................ 2013-011536
Jan. 24, 2013 (JP) ................................ 2013-011538

(51) Int. Cl.
| | | |
|---|---|---|
| C12P 19/32 | (2006.01) | |
| C12P 7/04 | (2006.01) | |
| C12P 7/28 | (2006.01) | |
| C12P 13/14 | (2006.01) | |
| C12P 7/48 | (2006.01) | |
| C12P 7/46 | (2006.01) | |
| C12P 7/62 | (2006.01) | |

(52) U.S. Cl.
CPC ............... *C12P 19/32* (2013.01); *C12P 7/04* (2013.01); *C12P 7/28* (2013.01); *C12P 7/46* (2013.01); *C12P 7/48* (2013.01); *C12P 7/625* (2013.01); *C12P 13/14* (2013.01)

(58) Field of Classification Search
None
See application file for complete search history.

(56) References Cited

FOREIGN PATENT DOCUMENTS

| | | | |
|---|---|---|---|
| DE | 10 2007 047 206 A1 | 4/2009 | |
| DE | 1020070 59 248 A1 | 6/2009 | |
| EP | 2 738 247 A1 | 6/2014 | |
| TW | 201311889 | 3/2013 | |
| WO | WO-2009/046929 A2 | 4/2009 | |
| WO | WO-2009/094485 A1 | 7/2009 | |
| WO | WO-2010/071697 A1 | 6/2010 | |
| WO | WO-2011/099006 A2 | 8/2011 | |
| WO | WO 2013/018734 A1 | 2/2013 | |

OTHER PUBLICATIONS

Wendisch et al., Current Opinion in Microbiology 2006, vol. 9, p. 268-274.*
Chistoserdova et al., Journal of Bacteriology, 1994, vol. 176, No. 23, p. 7398-7404.*
Schneider et al., The Journal of Biological Chemistry, 2012, vol. 287, No. 1, p. 757-766 Only.*
Office Action issued in Chinese Patent Application No. 201480002416.5 dated Jun. 23, 2016.
Erb et al., "The Apparent Malate Synthase Activity of Rhodobacter sphaeroides is Due to Two Paralogous Enzymes, (3S)-Malyl-Coenzyme A(CoA)/β-Methylmalyl-CoA Lyase and (3S)-Malyl-CoA Thioesterase", J. Bacteriol, Sep. 2009, pp. 1249-1258, vol. 192, No. 5.
Yim et al., "Metabolic engineering of *Escherichia coli* for direct production of 1, 4-butanediol," Nature Chemical Biology, vol. 7, Jul. 2011, pp. 445-452.
Atomi, Haruyuki, "Review Microbial Enzymes Involved in Carbon Dioxide Fixation," Journal of Bioscience and Bioengineering, vol. 94, No. 6, 2002, pp. 497-505.
Berg, Ivan A., "Minireview Ecological Aspects of the Distribution of Different Autotrophic $CO_2$ Fixation Pathways," Applied and Environmental Microbiology, vol. 77, No. 6, Mar. 2011, pp. 1925-1936.
Atsumi et al., Non-fermentative pathways for synthesis of branched-chain higher alcohols as biofuels, Nature vol. 451(3) Jan. 2008, pp. 86-89.
International Search Report dated Apr. 8, 2014 issued in Application No. PCT/JP2014/051402.

(Continued)

*Primary Examiner* — Kade Ariani
(74) *Attorney, Agent, or Firm* — Foley & Lardner LLP

(57) ABSTRACT

An acetyl-CoA producing microorganism obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e): (a) a carbon dioxide fixation cycle including an enzymatic reaction from malonyl-CoA to malonate semialdehyde or 3-hydroxypropionate; (b) a carbon dioxide fixation cycle including an enzymatic reaction from acetyl-CoA and $CO_2$ to pyruvate; (c) a carbon dioxide fixation cycle including an enzymatic reaction from crotonyl-CoA and $CO_2$ to ethylmalonyl-CoA or glutaconyl-CoA; (d) a carbon dioxide fixation cycle including an enzymatic reaction from $CO_2$ to formate; or (e) at least one selected from the group consisting of malate thiokinase and malyl-CoA lyase.

10 Claims, 2 Drawing Sheets

(56) References Cited

OTHER PUBLICATIONS

Notice of Submission of Opinion issued in Korean Patent Application No. 10-2015-7006510 dated Mar. 28, 2016.
Chatsurachai et al., "An in silico platform for the design of heterologous pathways in nonnative metabolite production," BMC Bioinformatics 13:93 (2012).
Melzer et al., "Flux Design: In silico design of cell factories based on correlation of pathway fluxes to desired properties," BMC Systems Biology 3:120 (2009).
Extended European Search Report issued in European Patent Application No. 14743436.9 dated Sep. 7, 2016.
Office Action dated Mar. 15, 2017 in corresponding Chinese Patent Application No. 201480002416.5.
Office Action issued in Taiwan patent application No. 103102745 dated Aug. 28, 2017.

* cited by examiner

MICROORGANISM HAVING CARBON DIOXIDE FIXATION CYCLE INTRODUCED THEREINTO

CROSS REFERENCE TO RELATED APPLICATIONS

This application is the National Phase of PCT/JP2014/051402, filed Jan. 23, 2014, which claims priority to Japanese Application No. 2013-011536, filed Jan. 24, 2013 and Japanese Application No. 2013-011538, filed Jan. 24, 2013.

TECHNICAL FIELD

The present invention relates to a microorganism having a carbon dioxide fixation cycle introduced thereinto and a method of producing a substance using the microorganism.

BACKGROUND ART

Acetyl-CoA is one of significantly important intermediates in metabolic pathways of microorganisms. Various metabolites are produced via acetyl-CoA. Well-known examples of such substances produced via acetyl-CoA include amino acids such as L-glutamic acid, L-glutamine, L-proline, L-arginine, L-leucine, and L-isoleucine; organic acids such as acetic acid, propionic acid, butyric acid, caproic acid, citric acid, 3-hydroxybutyric acid, 3-hydroxyisobutyric acid, 3-aminoisobutyric acid, 2-hydroxyisobutyric acid, methacrylic acid, and poly-3-hydroxybutyric acid; alcohols such as isopropyl alcohol, ethanol, and butanol; acetone; and polyglutamic acid.

In most microorganisms, acetyl-CoA is produced using a sugar such as glucose as a carbon source. The sugar is first converted into pyruvate via a metabolic pathway called the glycolytic pathway, such as the Embden-Meyerhof pathway, the Entner-Doudoroff pathway, or the pentose phosphate pathway. Subsequently, pyruvate is converted into acetyl-CoA by the action of the enzymes pyruvate decarboxylase, pyruvate formate-lyase, and the like. In this process, since carbon dioxide ($CO_2$) and formate are generated as byproducts, not all of the carbons derived from the sugar are fixed as acetyl-CoA. Therefore, several studies have been carried out with the aim of achieving re-fixation of $CO_2$ in order to increase the yield of acetyl-CoA.

In microorganisms, there are several known pathways for fixing carbon dioxide as a carbon source (Applied and Environmental Microbiology, 2011; 77(6), 1925-1936). Specific examples of the pathways include the Calvin-Benson cycle, the reductive TCA cycle, the Wood-Ljungdahl pathway, the 3-hydroxypropionate cycle, and the 4-hydroxybutyrate cycle. The Calvin-Benson cycle is a $CO_2$ fixation pathway existing in plants and photosynthetic bacteria, and comprising about 12 enzymes. In the Calvin-Benson cycle, $CO_2$ is fixed by ribulose-1,5-bisphosphate carboxylase (RubisCO) and, ultimately, glyceraldehyde 3-phosphate is produced. The reductive TCA cycle is found in microaerophilic bacteria and anaerobic bacteria including green sulfur bacteria, and comprises 11 enzymes. The reductive TCA cycle comprises the $CO_2$ fixation enzymes acetyl-CoA carboxylase and 2-oxoglutarate synthase which requires ferredoxin as a coenzyme. In the reductive TCA cycle, pyruvate is produced from $CO_2$ by the reverse reaction of the usual TCA cycle. The Wood-Ljungdahl pathway is found in anaerobic microorganisms such as acetic acid-producing bacteria, and comprises 9 enzymes. In the Wood-Ljungdahl pathway, $CO_2$ and formate bound to a coenzyme are reduced by formate dehydrogenase, CO dehydrogenase, etc., and, ultimately, converted into acetyl-CoA. The 3-hydroxypropionate cycle is found in *Chloroflexus* bacteria and the like, and comprises 13 enzymes. In the 3-hydroxypropionate cycle, $CO_2$ is fixed by the action of acetyl-CoA (propionyl-CoA) carboxylase, and acetyl-CoA is produced via malonyl-CoA and the like. The 4-hydroxybutyrate cycle exists in archaebacteria and the like. In the 4-hydroxybutyrate cycle, $CO_2$ is fixed by the actions of pyruvate synthase, acetyl-CoA (propionyl-CoA) carboxylase, and phosphoenolpyruvate carboxylase, whereby acetyl-CoA is produced via 4-hydroxybutyryl CoA and the like.

Several approaches of producing a useful substance by introducing a carbon dioxide fixation pathway to a microorganism that produces a useful compound have been proposed. For example, International Publication Nos. WO 2009/094485 and WO 2010/071697 disclose approaches for producing acetyl-CoA from $CO_2$ by using a microorganism to which a pathway similar to the Wood-Ljungdahl pathway of acetic acid bacteria has been introduced. WO 2009/046929 discloses an approach for producing lactic acid from $CO_2$ by using a microorganism to which hydrogenase and tetrahydrofolate lyase have been introduced. WO 2011/099006 proposes a cycle in which $CO_2$ is fixed via a carbon dioxide fixation reaction into acetyl-CoA or a malonyl-CoA reduction reaction. German Patent Application Laid-open No. 102007059248 proposes production of acetyl-CoA via a pathway similar to the 4-hydroxybutyrate cycle.

SUMMARY OF INVENTION

Technical Problem

However, known carbon dioxide fixation cycles are not necessarily efficient from the viewpoints of $CO_2$ fixation and production of useful compounds derived from acetyl-CoA. For example, in the Calvin-Benson cycle, which is a well-known carbon dioxide fixation cycle found in nature, RubisCO working for carbon dioxide fixation is not a very efficient enzyme, since RubisCO has a low reaction rate and causes side reactions such as oxidative degradation (Journal of Bioscience and Bioengineering 2002; 94(6): 497-505). In the Wood-Ljungdahl pathway and the pathways described in WO 2009/094485, WO 2010/071697, WO 2009/046929, a pathway for reducing $CO_2$ into CO or formate is included. However, it is often the case that an enzyme catalyzing this kind of strong reduction reaction only works under a reductive environment, and consequently, such a reduction reaction hardly occurs under normal conditions. Moreover, it is difficult to introduce this enzyme into microorganisms other than strictly anaerobic microorganisms. In the reductive TCA cycle, the reduction reaction by pyruvate synthase and the reduction reaction by 2-oxoglutarate synthase require a strong reduction power using ferredoxin as an electron acceptor, and the reactions do not proceed easily. The 4-hydroxybutyrate cycle, 3-hydroxypropionate cycle, and the pathways described in WO 2009/046929 and WO 2011/099006 utilize reduction reactions of carboxylic acid or a (thio)ester thereof, such as reduction of succinyl-CoA or reduction of malonyl-CoA. However, it is generally difficult to carry out this kind of reaction as an enzymatic reaction, and it is desirable to avoid including this kind of reaction in fermentation pathways where possible (Nature, 2008; 451: 86-89; Nature Chemical Biology, 2011; 7: 445-452). The 4-hydroxybutyrate cycle proceeds via a dehydration reaction such as dehydration of 4-hydroxybutyryl CoA or dehydration of 3-hydroxypropionate, and has the disadvantage that, in water, this kind of dehydration reaction often competes with the reverse reaction (hydration). In the 4-hydroxybutyrate cycle, the 3-hydroxypropionate cycle, and the reductive TCA cycle, the acetyl-CoA produced is converted into other substances within the cycles by the action of malonyl-CoA synthase or pyruvate synthase. Therefore, these cycles are not necessarily efficient in terms of acetyl-CoA production.

When attempting to produce a certain substance by introducing the cycles described above to a microorganism, it is necessary to consider the number of enzymes constituting the cycle and the number of enzymatic activities to be newly imparted. When the number of enzymes constituting the cycle or the number of enzymatic activities to be newly imparted increases, construction and regulation of the cycle become more difficult as well as the burden on the microorganism increases. For example, in order to introduce the Wood-Ljungdahl pathway to *Escherichia coli*, at least 9 genes are required to be introduced. It would practically be a very difficult task to construct a substance-producing pathway by introducing so many genes in a controllable manner. It would clearly be advantageous to construct a cycle that includes a small number of enzymes by introducing a small number of genes, in terms of constructing the cycle as well as in terms of combining it with an intrinsic substance production pathway of the microorganism.

Accordingly, in order to fix $CO_2$ and convert it into acetyl-CoA, it would be preferable that (1) each enzyme constituting the pathway has a sufficiently high activity; (2) the cycle does not include an enzyme that consumes acetyl-CoA; and (3) the cycle has a simple configuration with a small number of newly imparted enzymes. However, none of the cycles for producing acetyl-CoA from $CO_2$ reported so far satisfies all of the conditions (1) to (3), and feasibility was low. In fact, there have been almost no actual examples of constructing a carbon dioxide fixation cycle by imparting an enzymatic activity as proposed in the above references, to an industrially-usable microorganism, converting $CO_2$ into acetyl-CoA, and further converting the acetyl-CoA to a useful compound.

The invention has been made under the above circumstances.

An object of a first invention is to provide a microorganism useful for efficient production of acetyl-CoA using carbon dioxide. In addition, another object of a first invention is to provide a method of producing acetyl-CoA and a useful metabolite derived from acetyl-CoA using the microorganism in high yield.

An object of a second invention is to provide a microorganism belonging to the genus *Aspergillus* or a microorganism belonging to genus *Cupriavidus* that can efficiently convert carbon dioxide into a useful metabolite via acetyl-CoA. In addition, another object of a second invention is to provide a method of producing a useful metabolite using the microorganism.

Solution to Problem

The first invention, capable of solving the above problem, includes the following aspects.

[A1] An acetyl-CoA producing microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e):

(a) a carbon dioxide fixation cycle including an enzymatic reaction from malonyl-CoA to malonate semialdehyde or 3-hydroxypropionate;

(b) a carbon dioxide fixation cycle including an enzymatic reaction from acetyl-CoA and $CO_2$ to pyruvate;

(c) a carbon dioxide fixation cycle including an enzymatic reaction from crotonyl-CoA and $CO_2$ to ethylmalonyl-CoA or glutaconyl-CoA;

(d) a carbon dioxide fixation cycle including an enzymatic reaction from $CO_2$ to formate; or (e) at least one selected from the group consisting of malate thiokinase and malyl-CoA lyase, the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto, wherein, in the microorganism: at least one enzymatic activity selected from the group consisting of pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase, is enhanced; at least one enzymatic activity selected from the group consisting of a malic enzyme and fumarate reductase is inactivated or reduced; or any combination thereof.

[A2] An acetyl-CoA producing microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e):

(a) a carbon dioxide fixation cycle including an enzymatic reaction from malonyl-CoA to malonate semialdehyde or 3-hydroxypropionate;

(b) a carbon dioxide fixation cycle including an enzymatic reaction from acetyl-CoA and $CO_2$ to pyruvate;

(c) a carbon dioxide fixation cycle including an enzymatic reaction from crotonyl-CoA and $CO_2$ to ethylmalonyl-CoA or glutaconyl-CoA;

(d) a carbon dioxide fixation cycle including an enzymatic reaction from $CO_2$ to formate; or (e) at least one selected from the group consisting of malate thiokinase and malyl-CoA lyase, the acetyl-CoA producing microorganism being obtained without imparting any of (a), (b), (c), or (d) to the microorganism, or such that the microorganism exhibits none of the functions of (a), (b), (c), and (d) even if one or more of (a), (b), (c), or (d) is imparted thereto, wherein, in the microorganism, at least one enzymatic activity selected from the group consisting of pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase is enhanced.

[A3] The acetyl-CoA producing microorganism according to [A1] or [A2], wherein enzymatic activities of malate thiokinase and malyl-CoA lyase are imparted.

[A4] The acetyl-CoA producing microorganism according to any one of [A1] to [A3], wherein enzymatic activities of 2-hydroxy-3-oxopropionate reductase and glycerate 3-kinase are enhanced.

[A5] The acetyl-CoA producing microorganism according any one of [A1] to [A4], wherein the acetyl-CoA producing microorganism includes an acetyl-CoA production cycle wherein:
phosphoenolpyruvate or pyruvate is converted to oxaloacetate;
oxaloacetate is converted to 2-hydroxy-3-oxopropionate by malate thiokinase, malyl-CoA lyase, and glyoxylate carboligase;
2-hydroxy-3-oxopropionate is converted to 2-phosphoglycerate; and
2-phosphoglycerate is converted to phosphoenolpyruvate.

[A6] The acetyl-CoA producing microorganism according to any one of [A1] to [A5], wherein the acetyl-CoA producing microorganism includes an acetyl-CoA production cycle including the following (f), (g), (h), (i), (j), (k), (l) and (m):
(f) at least one selected from the group consisting of: pyruvate kinase and pyruvate carboxylase; phosphoenolpyruvate carboxylase; and phosphoenolpyruvate carboxykinase;
(g) malate dehydrogenase;
(h) malate thiokinase;
(i) malyl-CoA lyase;
(j) glyoxylate carboligase;
(k) at least one selected from the group consisting of: 2-hydroxy-3-oxopropionate reductase; and hydroxypyruvate isomerase and hydroxypyruvate reductase;
(l) at least one selected from the group consisting of: glycerate 2-kinase; and glycerate 3-kinase and phosphoglycerate mutase; and
(m) enolase.

[A7] The acetyl-CoA producing microorganism according to any one of [A1] to [A6], wherein the microorganism that does not have any of (a), (b), (c), (d), or (e), is a microorganism belonging to Enterobacteriaceae or a microorganism belonging to coryneform bacteria.

[A8] The acetyl-CoA producing microorganism according to any one of [A1] to [A7], wherein the microorganism that does not have any of (a), (b), (c), (d), or (e), is an *Escherichia* bacterium or a *Pantoea* bacterium belonging to Enterobacteriaceae, or is a *Corynebacterium* bacterium belonging to coryneform bacteria.

[A9] A method of producing acetyl-CoA, the method including: a culture step of culturing the acetyl-CoA producing microorganism according to any one of [A1] to [A8] while contacting the acetyl-CoA producing microorganism with a carbon source material, and a collection step of collecting an intended product obtained by the contacting.

[A10] The method of producing acetyl-CoA according to [A9], further including a supply step of supplying at least one selected from the group consisting of a carbonate ion, a bicarbonate ion, carbon dioxide gas, and a reductant, to a culture medium used for the culturing.

[A11] The method of producing acetyl-CoA according to [A9] or [A10], further including a gas supply step of collecting a gas that contains carbon dioxide generated by the culturing and supplying the gas to a culture medium used for the culturing.

[A12] A method of producing a metabolite producible from acetyl-CoA as an intermediate, including: a culture step of culturing the acetyl-CoA producing microorganism according to any one of [A1] to [A8] while contacting the acetyl-CoA producing microorganism with a carbon source material, and a collection step of collecting the metabolite producible from acetyl-CoA as an intermediate obtained by the contact.

[A13] The method of producing a metabolite producible from acetyl-CoA as an intermediate according to [A12], further including a supply step of supplying at least one selected from the group consisting of a carbonate ion, a bicarbonate ion, carbon dioxide gas, and a reductant, to a culture medium used for the culturing.

[A14] The method of producing a metabolite producible from acetyl-CoA as an intermediate according to [A12] or [A13], further including a gas supply step of collecting a gas that contains carbon dioxide generated by the culturing and supplying the gas to a culture medium used for the culturing.

[A15] The method of producing a metabolite producible from acetyl-CoA as an intermediate according to any one of [A12] to [A14], in which the metabolite producible from acetyl-CoA as an intermediate is isopropyl alcohol, acetone, or glutamic acid.

[A16] A method of producing acetyl-CoA, including:
a culture step of culturing an acetyl-CoA producing microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e):
(a) a carbon dioxide fixation cycle including an enzymatic reaction from malonyl-CoA to malonate semialdehyde or 3-hydroxypropionate;
(b) a carbon dioxide fixation cycle including an enzymatic reaction from acetyl-CoA and $CO_2$ to pyruvate;
(c) a carbon dioxide fixation cycle including an enzymatic reaction from crotonyl-CoA and $CO_2$ to ethylmalonyl-CoA or glutaconyl-CoA;
(d) a carbon dioxide fixation cycle including an enzymatic reaction from $CO_2$ to formate; or
(e) at least one selected from the group consisting of malate thiokinase and malyl-CoA lyase,
the acetyl-CoA producing microoranism being obtained without imparting any of (a), (b), (c), or (d) to the microorganism, or such that the microorganism exhibits none of the functions of (a), (b), (c), or (d) even if one or more of (a), (b), (c), or (d) is imparted thereto; and
a supply step of supplying at least one selected from the group consisting of a carbonate ion or a bicarbonate ion with a total supply amount of 150 mmol/L or more, carbon dioxide gas with an average bubble diameter of 100 μm or more, and sodium sulfite with a total supply amount of from 0.01 g/l to 50 g/L, to a culture medium used for the culturing.

[A17] The method of producing acetyl-CoA according to [A16], further including a gas supply step of collecting a gas that contains carbon dioxide generated by the culturing and supplying the gas to the culture medium used for the culturing.

[A18] The method of producing acetyl-CoA according to [A16] or [A17], wherein the acetyl-CoA producing microorganism includes an acetyl-CoA production cycle in which phosphoenolpyruvate or pyruvate is converted to oxaloacetate, oxaloacetate is converted to 2-hydroxy-3-oxopropionate by malate thiokinase, malyl-CoA lyase, and glyoxylate carboligase, 2-hydroxy-3-oxopropionate is converted to 2-phosphoglycerate, and 2-phosphoglycerate is converted to phosphoenolpyruvate.

[A19] The method of producing acetyl-CoA according to any one of [A16] to [A18], wherein the acetyl-CoA producing microorganism includes an acetyl-CoA production cycle including the following (f), (g), (h), (i), (j), (k), (l), and (m):

(f) at least one selected from the group consisting of: pyruvate kinase and pyruvate carboxylase; phosphoenolpyruvate carboxylase; and phosphoenolpyruvate carboxykinase;

(g) malate dehydrogenase;

(h) malate thiokinase;

(i) malyl-CoA lyase;

(j) glyoxylate carboligase;

(k) at least one selected from the group consisting of: 2-hydroxy-3-oxopropionate reductase; and hydroxypyruvate isomerase and hydroxypyruvate reductase;

(l) at least one selected from the group consisting of: glycerate 2-kinase; and glycerate 3-kinase and phosphoglycerate mutase; and (m) enolase.

[A20] The method of producing acetyl-CoA according to any one of [A16] to [A19], wherein the microorganism that does not have any of (a), (b), (c), (d), or (e), is a microorganism belonging to Enterobacteriaceae or a microorganism belonging to coryneform bacteria.

[A21] The method of producing acetyl-CoA according to any one of [A16] to [A20], wherein the microorganism that does not have any of (a), (b), (c), (d), or (e), is an *Escherichia* bacterium or a *Pantoea* bacterium belonging to Enterobacteriaceae, or is a *Corynebacterium* bacterium belonging to coryneform bacteria.

[A22] A method of producing isopropyl alcohol, including allowing the acetyl-CoA producing microorganism to produce isopropyl alcohol, using, as an intermediate, acetyl-CoA produced by the method of producing acetyl-CoA according to any one of [A16] to [A21].

[A23] A method of producing acetone, including allowing the acetyl-CoA producing microorganism to produce acetone, using, as an intermediate, acetyl-CoA produced by the method of producing acetyl-CoA according to any one of [A16] to [A21].

[A24] A method of producing glutamic acid, including allowing the acetyl-CoA producing microorganism to produce glutamic acid, using, as an intermediate, acetyl-CoA produced by the method of producing acetyl-CoA according to any one of [A16] to [A21].

[A25] A method of producing isopropyl alcohol including: a culture step of culturing the acetyl-CoA producing microorganism according to any one of [A1] to [A8] while contacting the acetyl-CoA producing microorganism with a carbon source material, and a collection step of collecting the isopropyl alcohol obtained by the contacting.

[A26] A method of producing acetone including: a culture step of culturing the acetyl-CoA producing microorganism according to any one of [A1] to [A8] while contacting the acetyl-CoA producing microorganism with a carbon source material, and a collection step of collecting the acetone obtained by the contacting.

[A27] A method of producing glutamic acid including: a culture step of culturing the acetyl-CoA producing microorganism according to any one of [A1] to [A8] while contacting the acetyl-CoA producing microorganism with a carbon source material, and a collection step of collecting the glutamic acid obtained by the contacting.

The second invention to solve the above problem is as follows.

[B1] A microorganism belonging to the genus *Aspergillus* or the genus *Cupriavidus* obtained by imparting at least one enzymatic activity selected from the group consisting of malate thiokinase and malyl-CoA lyase, to a microorganism that does not have any of the following (a2), (b2), (c2), (d2) or (e2):

(a2) a carbon dioxide fixation cycle including an enzymatic reaction from malonyl-CoA to malonate semialdehyde or 3-hydroxypropionate;

(b2) a carbon dioxide fixation cycle including an enzymatic reaction from acetyl-CoA and $CO_2$ to pyruvate;

(c2) a carbon dioxide fixation cycle including an enzymatic reaction from crotonyl-CoA and $CO_2$ to ethylmalonyl-CoA or glutaconyl-CoA;

(d2) a carbon dioxide fixation cycle including an enzymatic reaction from $CO_2$ to formate; or (e2) at least one selected from the group consisting of malate thiokinase and malyl-CoA lyase, the microorganism belonging to the genus *Aspergillus* or the genus *Cupriavidus* being obtained without imparting any of (a2), (b2), (c2), or (d2) to the microorganism, or such that the microorganism exhibits none of the functions of (a2), (b2), (c2), or (d2) even if one or more of (a2), (b2), (c2), or (d2) is imparted thereto.

[B2] The microorganism according to [B1], including an ability to produce acetyl-CoA.

[B3] The microorganism according to [B1] or [B2], the microorganism belonging to the genus *Aspergillus* or the genus *Cupriavidus* being obtained by further imparting at least one enzymatic activity selected from the group consisting of glyoxylate carboligase, 2-hydroxy-3-oxopropionate reductase, and hydroxypyruvate reductase.

[B4] The microorganism according to any one of [B1] to [B3], including an acetyl-CoA production cycle wherein:

phosphoenolpyruvate or pyruvate is converted to oxaloacetate;

oxaloacetate is converted to 2-hydroxy-3-oxopropionate by malate thiokinase, malyl-CoA lyase, and glyoxylate carboligase;

2-hydroxy-3-oxopropionate is converted to 2-phosphoglycerate; and 2-phosphoglycerate is converted to phosphoenolpyruvate.

[B5] The microorganism according to any one of [B1] to [B4], including an acetyl-CoA production cycle including the following (f2), (g2), (h2), (i2), (j2), (k2), (l2), and (m2):

(f2) at least one selected from the group consisting of: pyruvate kinase and pyruvate carboxylase; phosphoenolpyruvate carboxylase; and phosphoenolpyruvate carboxykinase;

(g2) malate dehydrogenase;

(h2) malate thiokinase;

(i2) malyl-CoA lyase;

(j2) glyoxylate carboligase;

(k2) at least one selected from the group consisting of: 2-hydroxy-3-oxopropionate reductase; and hydroxypyruvate isomerase and hydroxypyruvate reductase;

(l2) at least one selected from the group consisting of: glycerate 2-kinase; and glycerate 3-kinase and phosphoglycerate mutase; and (m2) enolase.

[B6] The microorganism according to any one of [B1] to [B5], including a cycle including:

at least one enzymatic reaction selected from the group consisting of the following (a3) and (b3);

the following enzymatic reactions (c3), (d3), (e3), (f3), and (g3); and at least one selected from the group consisting of the following enzymatic reaction (h3), the following enzymatic reactions (i3), (j3), (k3) and (n3), and the following enzymatic reactions (i3), (j3), (l3), (m3) and (n3):
  (a3) an enzymatic reaction from phosphoenolpyruvate to oxaloacetate;
  (b3) an enzymatic reaction from pyruvate to oxaloacetate;
  (c3) an enzymatic reaction from oxaloacetate to malate;
  (d3) an enzymatic reaction from malate to malyl-CoA;
  (e3) an enzymatic reaction from malyl-CoA to glyoxylate and acetyl-CoA;
  (f3) an enzymatic reaction from glyoxylate to glycine;
  (g3) an enzymatic reaction from glycine to serine;
  (h3) an enzymatic reaction from serine to pyruvate;
  (i3) an enzymatic reaction from serine to 3-hydroxypyruvate;
  (j3) an enzymatic reaction from 3-hydroxypyruvate to glycerate;
  (k3) an enzymatic reaction from glycerate to 2-phosphoglycerate;
  (l3) an enzymatic reaction from glycerate to 3-phosphoglycerate;
  (m3) an enzymatic reaction from 3-phosphoglycerate to 2-phosphoglycerate; and
  (n3) an enzymatic reaction from 2-phosphoglycerate to phosphoenolpyruvate.

[B7] The microorganism according to any one of [B1] to [B6], including:
  at least one enzyme selected from the group consisting of the following (a4) and (b4);
  the following enzymes (c4), (d4), (e4), (f4), and (g4); and
  at least one selected from the group consisting of the following enzyme (h4), the following enzymes (i4), (j4), (k4), and (n4), and the following enzymes (i4), (j4), (l4), (m4) and (n4):
  (a4) at least one selected from the group consisting of pyruvate kinase and pyruvate carboxylase; phosphoenolpyruvate carboxylase; and phosphoenolpyruvate carboxykinase;
  (b4) pyruvate carboxylase;
  (c4) malate dehydrogenase;
  (d4) malate thiokinase;
  (e4) malyl-CoA lyase;
  (f4) glycine transaminase;
  (g4) a glycine cleavage system and serine hydroxymethyltransferase;
  (h4) serine dehydratase;
  (i4) serine transaminase;
  (j4) hydroxypyruvate reductase;
  (k4) glycerate 2-kinase;
  (l4) glycerate 3-kinase;
  (m4) phosphoglycerate mutase; and
  (n4) enolase.

[B8] The microorganism according to any one of [B1] to [B7], wherein the microorganism that does not have any of (a2), (b2), (c2), (d2), or (e2) is *Aspergillus niger, Aspergillus terreus,* or *Cupriavidus necator.*

[B9] A method of producing acetyl-CoA including: a culture step of culturing the microorganism according to any one of [B1] to [B8] while contacting the microorganism with a carbon source material, and a collection step of collecting an intended product obtained by the contacting.

[B10] The method of producing acetyl-CoA according to [B9], further including a supply step of supplying at least one selected from the group consisting of a carbonate ion, a bicarbonate ion, carbon dioxide gas, and a reductant, to a culture medium used for the culturing.

[B11] The method of producing acetyl-CoA according to [B9] or [B10], further including a gas supply step of collecting a gas that contains carbon dioxide generated by the culturing and supplying the gas to a culture medium used for the culturing.

[B12] A method of producing citric acid, including producing citric acid from a carbon source material using the microorganism according to any one of [B1] to [B8].

[B13] A method of producing itaconic acid, including producing itaconic acid from a carbon source material using the microorganism according to any one of [B1] to [B8].

[B14] A method of producing (poly)3-hydroxybutyric acid, including producing (poly)3-hydroxybutyric acid from a carbon source material using the microorganism according to any one of [B1] to [B8].

Advantageous Effects of Invention

According to the first invention, a microorganism useful for efficient production of acetyl-CoA using carbon dioxide can be provided. According to the first invention, a method of producing acetyl-CoA or a useful metabolite of acetyl-CoA using the microorganism in high yield can also be provided.

According to the second invention, a microorganism belonging to the genus *Aspergillus* or a microorganism belonging to genus *Cupriavidus* that can efficiently convert carbon dioxide into a useful metabolite via acetyl-CoA can be provided. According to the second invention, a method of producing a useful metabolite using the microorganism can be provided.

DESCRIPTION OF EMBODIMENTS

Figure 1:
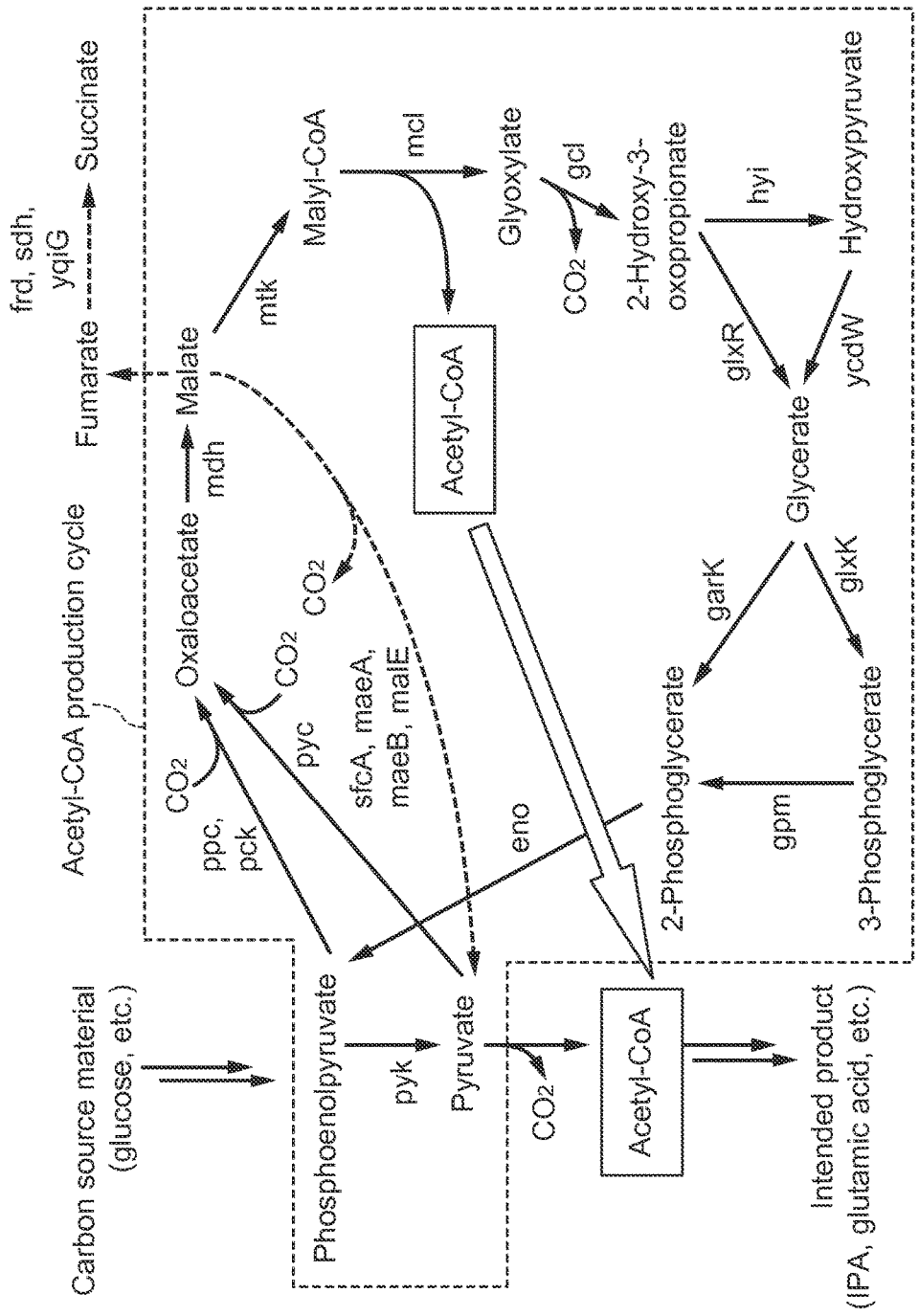
FIG. 1 is a cycle diagram for illustrating the outline of the carbon dioxide fixation cycle according to the first invention (that is, acetyl-CoA production cycle).

Hereinbelow, an embodiment of the invention is described. It should be understood that the following description and examples are provided only to exemplify the present invention, and the scope of the invention is not limited to the following description and examples.

The term "process" as used herein encompasses not only a separate process but also a process that cannot be clearly distinguished from other processes as long as the desired effect of the process is obtained therefrom.

In this specification, each numerical range specified using "(from) . . . to . . . " represents a range including the numerical values noted before and after "to" as the minimum value and the maximum value, respectively.

Furthermore, when two or more substances, each corresponding to a particular component of a composition, are present, the amount of the particular component in the composition mentioned in the present invention means the total amount of the two or more substances present in the composition, unless otherwise specified.

First Invention

An acetyl-CoA producing microorganism according to the first invention is a microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of (a), (b), (c), (d) or (e):

the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto, wherein, in the microorganism: at least one enzymatic activity selected from the group consisting of pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase, is enhanced; at least one enzymatic activity selected from the group consisting of a malic enzyme and fumarate reductase is inactivated or reduced; or any combination thereof.

(a) A carbon dioxide fixation cycle including an enzymatic reaction from malonyl-CoA to malonate semialdehyde or 3-hydroxypropionate.

(b) A carbon dioxide fixation cycle including an enzymatic reaction from acetyl-CoA and $CO_2$ to pyruvate.

(c) A carbon dioxide fixation cycle including an enzymatic reaction from crotonyl-CoA and $CO_2$ to ethylmalonyl-CoA or glutaconyl-CoA.

(d) A carbon dioxide fixation cycle including enzymatic reaction from $CO_2$ to formate.

(e) At least one selected from the group consisting of malate thiokinase and malyl-CoA lyase.

The microorganism according to the first invention, to which a predetermined enzymatic activity is imparted, has a carbon dioxide fixation cycle in which $CO_2$ generated during carbohydrate metabolism or $CO_2$ supplied from outside can be converted into acetyl-CoA. Furthermore, the microorganism according to the first invention, in which a predetermined enzymatic activity is enhanced, and/or a predetermined enzymatic activity is inactivated or reduced, can efficiently convert $CO_2$ into acetyl-CoA.

An example of the acetyl-CoA production method according to the first invention is a method of producing acetyl-CoA in which $CO_2$ can be efficiently converted into acetyl-CoA by use of the microorganism according to the first invention.

Another example of the acetyl-CoA production method according to the first invention is a method of producing acetyl-CoA, including:

a culture step of culturing an acetyl-CoA producing microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of (a), (b), (c), (d) or (e) described above, the acetyl-CoA producing microoranism being obtained without imparting any of (a), (b), (c), or (d) to the microorganism, or such that the microorganism exhibits none of the functions of (a), (b), (c), or (d) even if one or more of (a), (b), (c), or (d) is imparted thereto; and a supply step of supplying at least one selected from the group consisting of a carbonate ion or a bicarbonate ion with a total supply amount of 150 mmol/L or more, carbon dioxide gas with an average bubble diameter of 100 μm or more, and sodium sulfite with a total supply amount of from 0.01 g/l to 50 g/L, to a culture medium used for the culturing.

According to another example, acetyl-CoA can be efficiently produced using the microorganism, in which the carbon dioxide fixation cycle is constructed, by supplying at least one selected from the group consisting of a carbonate ion, a bicarbonate ion, carbon dioxide gas, and sodium sulfite, to a culture medium.

By using the microorganism or the production method according to the first invention, or additionally imparting a predetermined enzymatic activity to the microorganism, acetyl-CoA and useful metabolites derived from acetyl-CoA (such as isopropyl alcohol, ethanol, acetone, citric acid, itaconic acid, acetic acid, butyric acid, (poly)3-hydroxybutyric acid, 3-hydroxyisobutyric acid, 3-aminoisobutyric acid, 2-hydroxyisobutyric acid, methacrylic acid, (poly) glutamic acid, glutamine, arginine, ornithine, citrulline, leucine, isoleucine, or proline) can be efficiently produced.

Second Invention

A microorganism according to the second invention is a microorganism belonging to the genus *Aspergillus* or the genus *Cupriavidus* obtained by imparting at least one enzymatic activity selected from the group consisting of malate thiokinase and malyl-CoA lyase, to a microorganism that does not have any of (a2), (b2), (c2), (d2) or (e2), the microorganism belonging to the genus *Aspergillus* or the genus *Cupriavidus* being obtained without imparting any of (a2), (b2), (c2), or (d2) to the microorganism, or such that the microorganism exhibits none of the functions of (a2), (b2), (c2), or (d2) even if one or more of (a2), (b2), (c2), or (d2) is imparted thereto.

(a2) A carbon dioxide fixation cycle having an enzymatic reaction from malonyl-CoA to malonate semialdehyde or 3-hydroxypropionate.

(b2) A carbon dioxide fixation cycle having an enzymatic reaction from acetyl-CoA and $CO_2$ to pyruvate.

(c2) A carbon dioxide fixation cycle having an enzymatic reaction from crotonyl-CoA and $CO_2$ to ethylmalonyl-CoA or glutaconyl-CoA.

(d2) A carbon dioxide fixation cycle having an enzymatic reaction from $CO_2$ to formate.

(e2) At least one selected from the group consisting of malate thiokinase and malyl-CoA lyase.

The microorganism according to the second invention has a pathway including a predetermined enzymatic action, and therefore $CO_2$ generated during carbohydrate metabolism or $CO_2$ supplied from outside can be efficiently fixed. Furthermore, the microorganism according to the second invention can efficiently convert $CO_2$ into acetyl-CoA.

The acetyl-CoA production method according to the second invention is a method of producing acetyl-CoA in which $CO_2$ can be efficiently converted into acetyl-CoA by use of the microorganism according to the second invention.

By using the microorganism or the production method according to the second invention, or additionally imparting a predetermined enzymatic activity to the microorganism, acetyl-CoA and useful metabolites derived from acetyl-CoA (such as citric acid, itaconic acid, (poly)3-hydroxybutyric acid, proline, leucine, isoleucine, valine, arginine, citrulline, ornithine, acetic acid, (poly)3-hydroxybutyric acid, itaconic acid, citric acid, butyric acid, polyglutamic acid, 4-aminobutyric acid, 4-hydroxybutyric acid, 3-hydroxyisobutyric acid, 2-hydroxyisobutyric acid, or 3-aminoisobutyric acid) can be efficiently produced.

Hereinbelow, the meaning of the term used in the specification and the invention is described.

The term "cycle" as used herein refers to a pathway which starts from any one substance on the pathway, and through which the substance is converted into another substance, and eventually converted into the same substance as the starting substance.

The term "pathway" as used herein refers to a series of reactions composed of enzymatic reactions and/or spontaneous chemical reactions in a fermentor. The pathway may be a cyclic pathway or a non-cyclic pathway. Therefore, the carbon dioxide fixation pathway encompasses the carbon dioxide fixation cycle.

The "carbon dioxide ($CO_2$) fixation" in the invention refers to conversion of $CO_2$ generated in carbohydrate metabolism and/or $CO_2$ supplied from outside into an organic compound. The $CO_2$ may be $HCO_3^-$. Here, "carbon dioxide ($CO_2$) fixation" may also be referred to as "carbon dioxide fixation".

The "enzyme" in the invention includes a "factor" that exhibits no enzymatic activity by itself, unless otherwise specified.

The term "inactivation" of an enzymatic activity in the invention refers to a condition in which the activity of the enzyme as measured by any existing measurement system is $1/10^{th}$ or less of the activity in the microorganism before inactivation, assuming that the activity in the microorganism before inactivation is 100.

The "reduction" of an enzymatic activity in the invention means a condition in which the activity of the enzyme is significantly reduced when a gene encoding the enzyme is processed using genetic recombination technique, as compared to the activity of the enzyme before such processing.

The "enhancement" of an enzymatic activity in the invention broadly means that the an enzymatic activity in a microorganism becomes higher after enhancement compared to the enzymatic activity before enhancement. The method for the enhancement is not particularly limited as long as the activity of an enzyme possessed by a microorganism is enhanced. Examples thereof include enhancement by introduction of an enzyme gene into the cell from outside the cell, enhancement by augmented expression of an enzyme gene in the cell, and any combination thereof.

Specific examples of enhancement by introduction of an enzyme gene into the cell from outside the cell include: introducing a gene encoding an enzyme having a higher activity than that of an intrinsic enzyme of a host into the host cell from outside the cell using a genetic recombination technique, thereby adding the enzymatic activity of the introduced enzyme gene or substituting the introduced enzymatic activity for the enzymatic activity that the host originally possesses; increasing the number of enzyme genes that the host intrinsically has or the number of enzyme genes introduced into the cell from outside the cell; and any combination thereof.

Specific examples of enhancement by augmented expression of an enzyme gene in the cell include: introducing a base sequence that enhances the expression of an enzyme gene into the host cell from outside the cell; enhancing the expression of the enzyme gene by augmenting the promoter activity of an enzyme gene that the host originally possesses on the genome; enhancing the expression of the enzyme gene by the substitution of another promoter for the promoter of an enzyme gene that the host possesses on the genome; and any combination thereof.

The "imparting" of an enzymatic activity in the invention broadly means the provision of the activity of an intended enzyme by introducing an enzyme gene from outside into the cell of the microorganism that does not exhibit the intended enzymatic activity. The method of imparting an activity is not particularly limited as long as the intended enzymatic activity can be imparted to a microorganism, and the imparting can be carried out using a genetic recombination technique. Specific examples thereof include transformation with a plasmid harboring an enzyme gene, introduction of an enzyme gene into the genome, and any combination thereof. The enzyme gene to be introduced may be either homologous or heterologous to that of the host cell.

The "imparting" of an enzymatic activity involved in a substance metabolic cycle or pathway means that the substance metabolic cycle or pathway is functionally constructed as a result of the imparting of the enzymatic activity, and the imparting method can be selected in accordance with the host.

In the present specification, "exhibits none of the functions" of the carbon dioxide fixation cycle "even though imparted" means that the carbon dioxide fixation cycle does not exhibit function even when a relevant enzymatic activity is imparted by introducing an enzyme gene from outside to a microorganism that does not exhibit the relevant enzymatic activity. That "the carbon dioxide fixation cycle does not function" can be confirmed indirectly, for example, by a label originating from $CO_2$ being not detected in a metabolite in the cycle or in a substance derived from the metabolite in a test using labeled $CO_2$, or by an increase in the yield of a substance derived from a metabolite in the cycle per sugar consumption being not detected.

The promoter that may be used for "enhancing" or "imparting" of an enzymatic activity is not particularly limited as long as the promoter allows the gene expression, and a constitutive promoter or an inducible promoter may be used.

Whether or not the microorganism has the intended enzyme gene can be determined with reference to, for example, the gene information of respective strains registered in KEGG (Kyoto Encyclopedia of Genes and Genomes; http://www.genome.jp/kegg/) or NCBI (National Center for Biotechnology Information; http://www.ncbi.nlm.nih.gov/gene/). In the invention, only the gene information of respective strains registered in KEGG or NCBI is used.

Methods for preparation of a genomic DNA necessary to introduce a gene from outside the cell into the cell, cleavage and ligation of DNA, transformation, PCR (Polymerase Chain Reaction), the design and synthesis of oligonucleotides to be used as primers, etc. may be carried out by usual methods well known to those skilled in the art. These methods are described in "Molecular Cloning A Laboratory Manual, Second Edition", Cold Spring Harbor Laboratory Press (1989), etc.

The expression such as "by genetic recombination technique" in the invention encompasses any alteration to the base sequence caused by the insertion of another DNA into a base sequence of a native gene, substitution or deletion of a certain site of a gene, or any combinations thereof. For example, the alteration may be an alteration resulting from a mutation.

In the invention, the microorganism in which the activity of a factor or an enzyme is inactivated refers to a microorganism in which the native activity of the factor or an enzyme is impaired by a certain method. Such microorganism can be generated by, for example, disrupting a gene encoding the factor or the enzyme (gene disruption).

Examples of the gene disruption in the invention include insertion of another DNA into the gene, and introduction of a mutation to the base sequence by substitution or deletion of a certain part of the gene, so as to prevent the function of the gene from being exerted. As a result of the gene disruption, for example, the gene becomes unable to be transcribed into an mRNA and thus the protein is not translated. Alternatively, due to incompleteness of the transcribed mRNA, the amino acid sequence of the translated protein is mutated or deleted, and, therefore, the intrinsic functions thereof become unable to be exerted.

The gene disruption mutant may be produced by any method as long as a disruption mutant in which an enzyme or protein is not expressed can be obtained. Various methods for gene disruption have been reported (natural breeding, addition of a mutagen, UV irradiation, radiation irradiation, random mutagenesis, insertion or transposition of transposons, or site-directed gene disruption). Gene disruption by homologous recombination is preferable due to its ability to disrupt only a specific gene. Methods of gene disruption by homologous recombination are described in Journal of Bacteriology, 1985; 161(3): 1219-1221, Journal of Bacteriology, 1995; 177(6): 1511-1519, and Proceedings of the National Academy of Sciences of the United States of America, 2000; 97(12): 6640-6645, and those skilled in the art can easily perform homologous recombination using these methods or applying these methods.

The expression "not (naturally) have" in the invention means that the lack of intrinsic presence in the host microorganism in nature.

The "host" in the invention means a target microorganism to which one or more genes are to be introduced from outside.

The "host" in the invention becomes in a state in which the effect of the gene can be exerted as a result of the introduction of one or more genes from outside.

The "host" in the invention may have a pathway for producing a useful metabolite. The "useful metabolite" in the invention is used as a generic name for major metabolites in the metabolic pathways of microorganisms, such as alcohols, amino acids, organic acids, and terpenes. The "host" may be any microorganism as long as it can be made to possess the ability to produce a useful metabolite by using a certain means, regardless of whether or not the microorganism intrinsically has the innate ability to produce the useful metabolite.

The classification of the enzyme as used herein is a classification based on the report of the Enzyme Commission of International Union of Biochemistry (IUB.), and the "Enzyme Commission number" is an enzyme number based on the report of the Enzyme Commission of the IUB.

With regard to the first invention, each of the terms "metabolite producible from acetyl-CoA as an intermediate" and "(useful) metabolite derived from acetyl-CoA" is used as a generic name for (useful) metabolites produced via acetyl-CoA in metabolic pathways. Examples thereof include alcohols such as isopropyl alcohol, ethanol, or butanol; amino acids such as L-glutamic acid, L-glutamine, L-arginine, L-ornithine, L-citrulline, L-leucine, L-isoleucine, or L-proline; organic acids such as 3-hydroxybutyric acid, poly-3-hydroxybutyric acid, polyglutamic acid, 3-hydroxyisobutyric acid, 3-aminoisobutyric acid, 2-hydroxyisobutyric acid, methacrylic acid, citric acid, acetic acid, propionic acid, butyric acid, caproic acid, or mevalonic acid; and terpenes such as isoprene, squalene, steroid, or carotenoid. Examples thereof further include acetone.

With regard to the second invention, each of the terms "metabolite producible from acetyl-CoA as an intermediate" and "(useful) metabolite derived from acetyl-CoA" is used as a generic name for (useful) metabolites produced via acetyl-CoA in metabolic pathways. Examples thereof include organic acids such as citric acid, itaconic acid, or (poly-)3-hydroxybutyric acid. Examples thereof further include 3-hydroxybutyric acid, polyglutamic acid, 3-hydroxyisobutyric acid, 3-aminoisobutyric acid, 2-hydroxyisobutyric acid, methacrylic acid, acetic acid, propionic acid, butyric acid, caproic acid, or mevalonic acid.

The "production of acetyl-CoA" in the invention refers to conversion of a certain substance into acetyl-CoA in a metabolic pathway. Since acetyl-CoA is a metabolic intermediate and is quickly converted into various substances in metabolic pathways, the apparent amount of acetyl-CoA does not necessarily increase. However, the effect can be confirmed indirectly by detection of a $CO_2$-derived label in a substance derived from acetyl-CoA, by an increase in the yield of a substance derived from acetyl-CoA relative to sugar consumption, or the like. Since various factors (e.g., the quantity of a coenzyme, the quantity of a substrate, or a change in metabolism caused by feedback inhibition) are involved in conversion of acetyl-CoA into another substance, the production amount of acetyl-CoA is not always proportional to the total amount of substances derived from acetyl-CoA. However, in a case in which the pathway to produce a specific substance from acetyl-CoA is enhanced or in a case in which such pathway is intrinsically intense (for example, in the case of glutamic acid-producing microorganism described below), the conversion efficiency of acetyl-CoA into a downstream substance is less likely to be affected by external factors, and, therefore, the production efficiency of the specific substance can be regarded as an index of the acetyl-CoA production efficiency.

Hereinbelow, the invention is described in more detail.

Acetyl-CoA Producing Microorganism

The acetyl-CoA producing microorganism according to the first invention is a microorganism including an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of (a), (b), (c), (d) or (e) described above, the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto, wherein, in the microorganism: at least one enzymatic activity selected from the group consisting of pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase, is enhanced; at least one enzymatic activity selected from the group consisting of a malic enzyme and fumarate reductase is inactivated or reduced; or any combination thereof.

From the viewpoint of the production efficiency of acetyl-CoA, the microorganism according to the first invention is imparted with preferably an enzymatic activity of malate thiokinase, more preferably enzymatic activities of malate thiokinase and malyl-CoA lyase, still more preferably enzymatic activities of malate thiokinase, malyl-CoA lyase, and glyoxylate carboligase, and even more preferably enzymatic activities of malate thiokinase, malyl-CoA lyase, glyoxylate carboligase, and 2-hydroxy-3-oxopropionate reductase, and/or hydroxypyruvate reductase.

The microorganism according to the first invention has a simple and practical acetyl-CoA production cycle which fixes $CO_2$ and converts it into acetyl-CoA. The cycle is described in more detail with reference to FIG. 1.

The acetyl-CoA production cycle illustrated in FIG. 1 represents one preferable example of the acetyl-CoA production cycle according to the first invention (hereinafter, also referred to as "cycle of FIG. 1").

As illustrated in FIG. 1, the acetyl-CoA production cycle includes the following (f) to (m):

(f) at least one selected from the group consisting of: pyruvate kinase (Pyk) and pyruvate carboxylase (Pyc); phosphoenolpyruvate carboxylase (Ppc); and phosphoenolpyruvate carboxykinase (Pck);

(g) malate dehydrogenase (Mdh);

(h) malate thiokinase (Mtk);

(i) malyl-CoA lyase (Mcl);

(j) glyoxylate carboligase (Gcl);

(k) at least one selected from the group consisting of: 2-hydroxy-3-oxopropionate reductase (GlxR); and hydroxypyruvate isomerase (Hyi) and hydroxypyruvate reductase (YcdW);

(l) at least one selected from the group consisting of: glycerate 2-kinase (GarK); and glycerate 3-kinase (GlxK) and phosphoglycerate mutase (Gpm); and (m) enolase (Eno).

In the invention, the acetyl-CoA production cycle preferably substantively includes only the above-described (f) to (m). The acetyl-CoA production cycle that the microorganism according to the invention has is preferably an acetyl-CoA production cycle composed only of the above-described (f) to (m).

Among the above-described enzymes, Pyc, Ppc, and Pck are involved in $CO_2$ fixation. $CO_2$ is first bound to phosphoenolpyruvate or pyruvate by the action of Ppc, Pck, or Pyc, and converted into oxaloacetate. The oxaloacetate is converted into malate by the action of Mdh. The malate is converted into malyl-CoA (malate CoA) by the action of Mtk. The malyl-CoA (malate CoA) is converted into acetyl-CoA and glyoxylate by the action of Mcl. The glyoxylate is converted into 2-hydroxy-3-oxopropionate by the action of Gcl. The 2-hydroxy-3-oxopropionate is converted into glycerate by the action of GlxR, or alternatively, converted into hydroxypyruvate by the action of Hyi and then into glycerate by the action of YcdW. The glycerate is converted into 2-phosphoglycerate by the action of GarK, or alternatively, converted into 3-phosphoglycerate by the action of GlxK and then converted into 2-phosphoglycerate by the action of Gpm. The 2-phosphoglycerate is converted into phosphoenolpyruvate by the action of Eno. In a case in which Pyk and Pyc is included in the cycle, the phosphoenolpyruvate is converted into pyruvate by the action of Pyk.

The microorganism according to the second invention is a microorganism belonging to the genus *Aspergillus* or the genus *Cupriavidus* obtained by imparting at least one enzymatic activity selected from the group consisting of malate thiokinase and malyl-CoA lyase, to a microorganism that does not have any of (a2), (b2), (c2), (d2) or (e2) described above, the microorganism belonging to the genus *Aspergillus* or the genus *Cupriavidus* being obtained without imparting any of (a2), (b2), (c2), or (d2) to the microorganism, or such that the microorganism exhibits none of the functions of (a2), (b2), (c2), or (d2) even if one or more of (a2), (b2), (c2), or (d2) is imparted thereto. Here, (a2), (b2), (c2), (d2), and (e2) have the same definitions as (a), (b), (c), (d), and (e) in the first invention, respectively.

As a preferable example of the microorganism according to the second invention, a microorganism that includes a pathway via glycine (hereinafter, also referred to as "glycine pathway") is described. The microorganism has at least one type of enzymatic activity selected from the group consisting of glycine transaminase and a glycine cleavage system. The glycine pathway is described with reference to FIG. 2.

Figure 2:
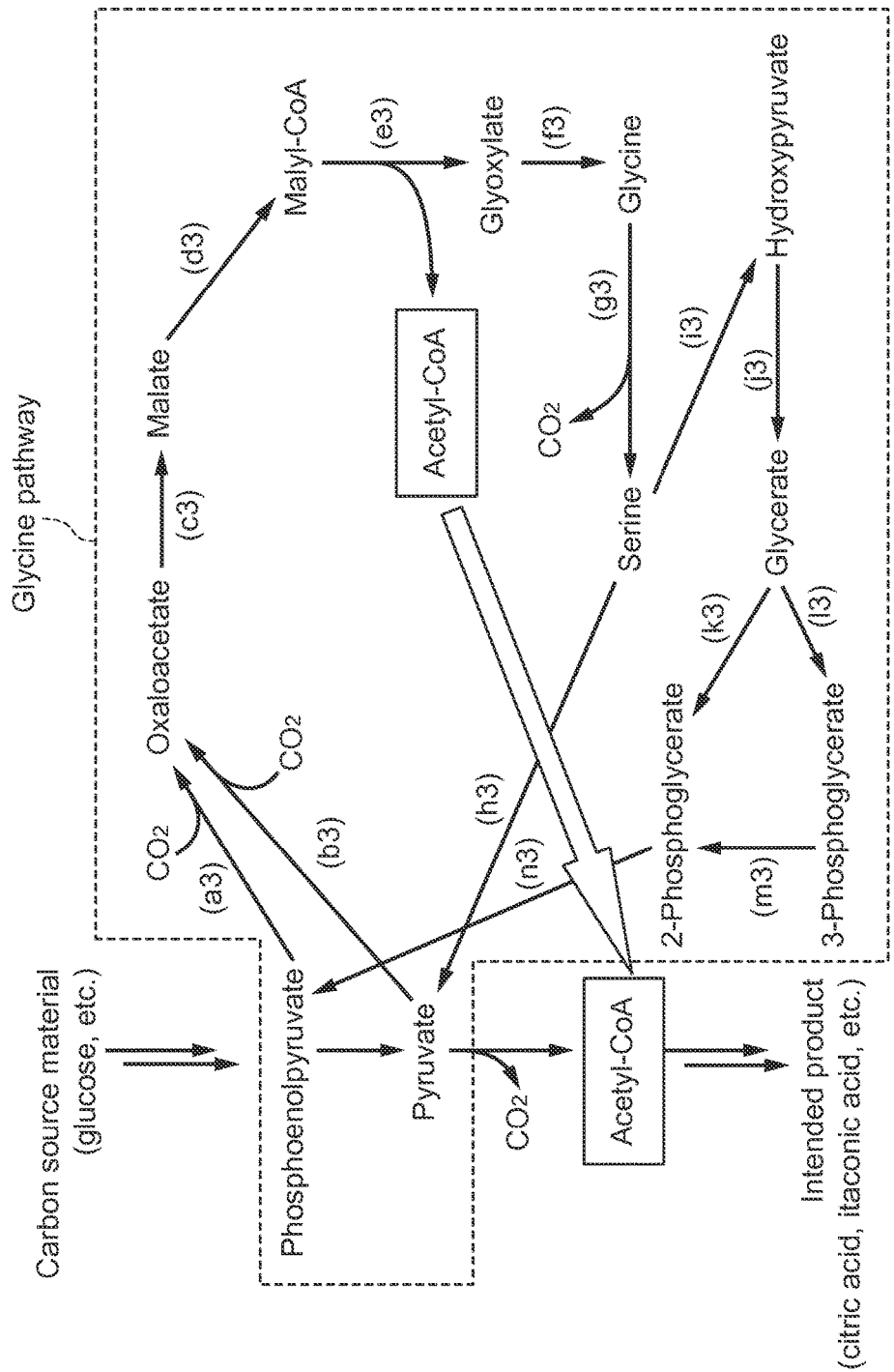
FIG. 2 is a pathway diagram for illustrating the outline of the glycine pathway according to the second invention.

As illustrated in FIG. 2, the glycine pathway includes:

at least one enzymatic reaction selected from the group consisting of (a3) and (b3);

enzymatic reactions of (c3), (d3), (e3), (f3), and (g3); and at least one enzymatic reaction selected from the group consisting of: an enzymatic reaction of (h3); enzymatic reactions of (i3), (j3), (k3), and (n3); and enzymatic reactions of (i3), (j3), (l3), (m3), and (n3).

(a3) An enzymatic reaction from phosphoenolpyruvate to oxaloacetate.

(b3) An enzymatic reaction from pyruvate to oxaloacetate.

(c3) An enzymatic reaction from oxaloacetate to malate.

(d3) An enzymatic reaction from malate to malyl-CoA.

(e3) An enzymatic reaction from malyl-CoA to glyoxylate and acetyl-CoA.

(f3) An enzymatic reaction from glyoxylate to glycine.

(g3) An enzymatic reaction from glycine to serine.

(h3) An enzymatic reaction from serine to pyruvate.

(i3) An enzymatic reaction from serine to 3-hydroxypyruvate.

(j3) An enzymatic reaction from 3-hydroxypyruvate to glycerate.

(k3) An enzymatic reaction from glycerate to 2-phosphoglycerate.

(l3) An enzymatic reaction from glycerate to 3-phosphoglycerate.

(m3) An enzymatic reaction from 3-phosphoglycerate to 2-phosphoglycerate.

(n3) An enzymatic reaction from 2-phosphoglycerate to phosphoenolpyruvate.

Examples of (a3) include an enzymatic reaction involving any one of a reaction mediated by phosphoenolpyruvate carboxylase, a reaction mediated by phosphoenolpyruvate carboxykinase, or a reaction mediated by pyruvate kinase and pyruvate carboxylase.

Examples of (b3) include an enzymatic reaction mediated by pyruvate carboxylase.

Examples of (c3) include an enzymatic reaction mediated by malate dehydrogenase.

Examples of (d3) include an enzymatic reaction mediated by malate thiokinase.

Examples of (e3) include an enzymatic reaction mediated by malyl-CoA lyase.

Examples of (f3) include an enzymatic reaction mediated by glycine transaminase.

Examples of (g3) include an enzymatic reaction mediated by a glycine cleavage system and serine hydroxymethyltransferase.

Examples of (h3) include an enzymatic reaction mediated by serine dehydratase.

Examples of (i3) include an enzymatic reaction mediated by serine transaminase.

Examples of (j3) include an enzymatic reaction mediated by hydroxypyruvate reductase.

Examples of (k3) include an enzymatic reaction mediated by glycerate 2-kinase.

Examples of (l3) include an enzymatic reaction mediated by glycerate 3-kinase.

Examples of (m3) include an enzymatic reaction mediated by phosphoglycerate mutase.

Examples of (n3) include an enzymatic reaction mediated by enolase.

In the glycine pathway, the conversion of serine into pyruvate may be performed by an enzymatic reaction that directly converts serine into pyruvate (the above reaction (h3)), or enzymatic reactions that convert serine into pyruvate via 3-hydroxypyruvate (reactions including above reaction (i3) and downstream reactions thereof).

In a case in which the conversion of serine into pyruvate is achieved by an enzymatic reaction that converts serine into pyruvate via 3-hydroxypyruvate (reactions including the above reaction (i3) and downstream reactions thereof), the conversion of glycerate into 2-phosphoglycerate may be an enzymatic reaction that directly converts glycerate to 2-phosphoglycerate (the above reaction (k3)), or by enzymatic reactions that convert glycerate into 2-phosphoglycerate via 3-phosphoglycerate (reactions including the above reactions (l3) and (m3)).

A preferable example of the microorganism according to the second invention has:

at least one enzyme selected from the group consisting of (a4) and (b4);

enzymes of (c4), (d4), (e4), (f4), and (g4); and at least one selected from the group consisting of:

(h4);

(i4), (j4), (k4), and (n4); and (i4), (j4), (l4), (m4), and (n4).

(a4) At least one selected from the group consisting of pyruvate kinase and pyruvate carboxylase; phosphoenolpyruvate carboxylase; and phosphoenolpyruvate carboxykinase.

(b4) Pyruvate carboxylase.

(c4) Malate dehydrogenase.

(d4) Malate thiokinase.

(e4) Malyl-CoA lyase.

(f4) Glycine transaminase.

(g4) A glycine cleavage system and serine hydroxymethyltransferase.

(h4) Serine dehydratase.

(i4) Serine transaminase.

(j4) Hydroxypyruvate reductase.

(k4) Glycerate 2-kinase.

(l4) Glycerate 3-kinase.

(m4) Phosphoglycerate mutase.

(n4) Enolase.

Hereinbelow, the conversion of substances in the cycle of FIG. 1 and the glycine pathway in FIG. 2 are described in detail.

Pyruvate carboxylase (Pyc) and phosphoenolpyruvate carboxylase (Ppc) are carbon dioxide-fixing enzymes having high activity. For example, RubisCO used in photosynthesis in plants or the like is known to have a specific activity of from about 3 U/mg to about 20 U/mg (Journal of Biological Chemistry, 1999; 274(8): 5078-5082, Salvucci M. E. at al., Analytical Biochemistry, 1986; 153(1): 97-101). On the other hand, pyruvate carboxylase and phosphoenolpyruvate carboxylase are reported to have a specific activity of 30 U/mg in *Escherichia coli*, or as high as 100 U/mg to 150 U/mg (Journal of Biological Chemistry, 1972; 247(18): 5785-5792, Bioscience, Biotechnology, and Biochemistry, 1995; 59(1): 140-142, Biochimica et Biophysica Acta, 2000; 1475(3): 191-206).

Furthermore, neither the cycle of FIG. 1 nor the glycine pathway of FIG. 2 includes an enzyme that consumes acetyl-CoA. Therefore, it can be said that the cycle of FIG. 1 and the glycine pathway of FIG. 2 are ideal cycles for fixing $CO_2$ and converting it into acetyl-CoA.

An enzyme that consumes acetyl-CoA as described above refers to an enzyme that uses acetyl-CoA as a substrate and converts acetyl-CoA into another substance, and examples thereof include acetyl-CoA carboxylase and pyruvate synthase.

That a cycle does not include an enzyme that consumes acetyl-CoA means that the cycle is not a closed cycle in which acetyl-CoA is converted again into acetyl-CoA through the cycle due to an action of an enzyme that consumes acetyl-CoA. A case in which a substance produced by the conversion due to an enzyme that consumes acetyl-CoA is further converted into another product without being returning to acetyl-CoA (for example, a case of conversion into glutamate as the end-product in a glutamate-producing pathway), is not included in the scope of the "cycle including an enzyme that consumes acetyl-CoA", since the pathway is not a closed cycle. A closed cycle refers to a pathway which starts from any one substance on the pathway, and through which the substance is converted into another substance, and eventually converted into the same substance as the starting substance.

Acetyl-CoA carboxylase, which is classified as Enzyme commission number: 6.4.1.2, is a generic name for enzymes that catalyze a reaction of converting acetyl-CoA and $CO_2$ into malonyl-CoA.

Pyruvate synthase, which is classified as Enzyme Commission number: 1.2.7.1, is a generic name for enzymes that catalyze a reaction of converting acetyl-CoA into pyruvate.

Another advantage of the cycle of FIG. 1 and the glycine pathway of FIG. 2 is that, since these pathways are independent from glycolytic pathway, each pathway can be freely combined with various glycolytic pathways. For example, the cycle of FIG. 1 and the glycine pathway of FIG. 2 can be easily combined with the pentose phosphate pathway, which produces NADPH with a high production rate and is often used in production of substances (Japanese National-phase publication (JP-A) No. 2007-510411), since the cycle of FIG. 1 and the glycine pathway of FIG. 2 are independent from the pentose phosphate pathway.

In the cycle of FIG. 1, malate dehydrogenase (Mdh), 2-hydroxy-3-oxopropionate reductase (GlxR), and hydroxypyruvate reductase (YcdW) consume NADH (or NADPH) as the reduction power; malate thiokinase (Mtk), glycerate 2-kinase (GarK), glycerate 3-kinase (GlxK), and pyruvate carboxylase (Pyc) consume ATP; and pyruvate kinase (Pyk) produces pyruvate.

In a case in which phosphoenolpyruvate is used as the starting substance, the balanced equation for the cycle of FIG. 1 is: "phosphoenolpyruvate+2CoA+$CO_2$+3NAD(P)H+3ATP→2acetyl-CoA+3NAD(P)$^+$+3ADP". In a case in which pyruvate is used as the starting substance, the balanced equation is: "pyruvate+2CoA+$CO_2$+3NAD(P)H+4ATP→2acetyl-CoA+3NAD(P)$^+$+4ADP".

That is, the cycle of FIG. 1 requires supply of phosphoenolpyruvate (or pyruvate), NAD(P)H, and ATP for fixing $CO_2$ and converting it into acetyl-CoA.

In the glycine pathway of FIG. 2, malate dehydrogenase (Mdh) and hydroxypyruvate reductase (YcdW) consume NADH (or NADPH) as the reduction power. In a case in which glyoxylate is converted into glycine, the reduction power corresponding to one molecule of NADH (or NADPH) is consumed directly by glycine dehydrogenase or indirectly via another amino acid with mediation by an aminotransferase such as glyoxylate aminotransferase. The glycine cleavage system consumes $NAD^+$ (or $NADP^+$) and converts it into NADH (or NADPH). In a case in which serine is converted into 3-hydroxypyruvate, $NAD^+$ (or $NADP^+$) is consumed and converted into NADH (or NADPH) directly by serine dehydrogenase or indirectly via another amino acid with mediation by an aminotransferase such as serine aminotransferase.

Malate thiokinase (Mtk), glycerate 2-kinase (GarK), glycerate 3-kinase (GlxK), and pyruvate carboxylase (Pyc) consume ATP. In a case in which ammonia is incorporated into the metabolic system, ATP is sometimes consumed. Pyruvate kinase (Pyk) produces pyruvate.

In a case in which phosphoenolpyruvate is used as the starting substance, the balanced equation for the pathway of FIG. 2 is: "phosphoenolpyruvate+2CoA+$CO_2$+3NAD(P)H+3 to 5ATP→2acetyl-CoA+3NAD(P)$^+$+3 to 5ADP". In a case in which pyruvate is used as the starting substance, the balanced equation is: "pyruvate+2CoA+$CO_2$+3NAD(P)H+4 to 6ATP→2acetyl-CoA+3NAD(P)$^+$+4 to 6ADP".

Among fermentation pathways that produce acetyl-CoA as an intermediate, balanced equations of pathways that consume oxygen during fermentation are listed in Table 1. It is assumed that, in these fermentation pathways, a reduced coenzyme such as NADH is produced during the fermentation pathway and the reduced coenzyme is reconverted into a oxidized form by the action of oxygen. Therefore, if the reduced coenzyme produced is consumed by the cycle of FIG. 1 and/or the glycine pathway of FIG. 2 instead of by oxygen, it can be expected that the reduction power generated through fermentation process could be efficiently used in the acetyl-CoA production cycle for fixing $CO_2$ and converting it into products.

Here, the reduced coenzyme refers to a coenzyme in the reduced state that is involved in an oxidation-reduction reaction, and examples thereof include NADH, NADPH, $FADH_2$, $FMNH_2$, and a reduced quinone coenzyme. The reduced coenzyme is preferably NADH or NADPH, and more preferably NADH. The oxidized coenzyme refers to the oxidized form of a reduced coenzyme, and examples thereof include $NAD^+$, $NADP^+$, FAD, FMN, and an oxidized quinone coenzyme. The oxidized coenzyme is preferably $NAD^+$ or $NADP^+$, and more preferably $NAD^+$.

which results in increase in equipment costs and electric power costs. Therefore, by introducing the cycle of FIG. 1 or the glycine pathway of FIG. 2 into a substance production system, surplus reduction power can be consumed by the cycle of FIG. 1 or the glycine pathway of FIG. 2 instead of by oxygen, and excessive aeration/stirring can be moderated, and the cost of fermentative production can be expected to be reduced.

In order to supply the reduction power to the cycle of FIG. 1 or the glycine pathway of FIG. 2, the reduction power may be provided by adding a substance that can generate a reduction power or by imparting energies from outside. Specific means thereof include using a substance that has a higher reduction degree (e.g., hydrogen, sulfite, alcohols, or paraffin) as a substrate; supplying reduction energies directly by electric culture; and supplying a reduction power by a photochemical reaction of an organism. Supply of reducing power from outside enables the carbon dioxide fixation pathway according to the invention to be driven even in cases where fermentation does not involve generation of a reduced coenzyme, dissimilar to the fermentations indicated in Table 1.

Hereinbelow, enzymes included in the cycle of FIG. 1 and enzymes included in the glycine pathway in FIG. 2 are described in detail.

Pyruvate kinase (Pyk), which is classified as Enzyme Commission number: 2.7.1.40, is a generic name for enzymes which convert phosphoenolpyruvate and ADP into pyruvate and ATP. Examples of pyruvate kinase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding pyruvate kinase (pyk), a DNA having a base sequence of a gene encoding pyruvate kinase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Pyruvate carboxylase (Pyc), which is classified as Enzyme Commission number: 6.4.1.1, is a generic name for

TABLE 1

| Compound Name | Fermentation equation |
|---|---|
| Isopropyl alcohol | $C_6H_{12}O_6 + H_2O + 3/2O_2 \rightarrow C_3H_8O + 3CO_2 + 3H_2O$ |
| Acetone | $C_6H_{12}O_6 + 2O_2 \rightarrow C_3H_6O + 3H_2O + 3CO_2$ |
| Glutamic acid | $C_6H_{12}O_6 + 3/2O_2 + NH_3 \rightarrow C_5H_9NO_4 + CO_2 + 3H_2O$ |
| Glutamine | $C_6H_{12}O_6 + 3/2O_2 + 2NH_3 \rightarrow C_5H_{10}N_2O_3 + CO_2 + 4H_2O$ |
| Arginine | $C_6H_{12}O_6 + 1/2O_2 + 4NH_3 \rightarrow C_6H_{14}N_2O_2 + 5H_2O$ |
| Ornithine | $C_6H_{12}O_6 + 1/2O_2 + 2NH_3 \rightarrow C_5H_{12}N_2O_2 + 3H_2O + CO_2$ |
| Citrulline | $C_6H_{12}O_6 + 1/2O_2 + 3NH_3 \rightarrow C_6H_{13}N_3O_3 + 4H_2O$ |
| Proline | $C_6H_{12}O_6 + 1/2O_2 + NH_3 \rightarrow C_5H_9NO_2 + 3H_2O + CO_2$ |
| Acetic acid | $C_6H_{12}O_6 + 2O_2 \rightarrow 2C_2H_4O_2 + 2CO_2 + 2H_2O$ |
| (poly-)3-hydroxybutyric acid | $C_6H_{12}O_6 + 3/2O_2 \rightarrow C_4H_8O_3 + 2CO_2 + 2H_2O$ |
| Itaconic acid | $C_6H_{12}O_6 + 3/2O_2 \rightarrow C_5H_6O_4 + CO_2 + 3H_2O$ |
| Citric acid | $C_6H_{12}O_6 + 3/2O_2 \rightarrow C_6H_8O_7 + 2H_2O$ |
| Butyric acid | $C_6H_{12}O_6 + O_2 \rightarrow C_4H_8O_2 + 2H_2O + 2CO_2$ |
| Leucine (Isoleucine) | $3/2C_6H_{12}O_6 + 3/2O_2 + NH_3 \rightarrow C_6H_{13}NO_2 + 4H_2O + 3CO_2$ |
| 4-Aminobutyric acid | $C_6H_{12}O_6 + 3/2O_2 + NH_3 \rightarrow C_4H_9NO_2 + 3H_2O + 2CO_2$ |
| 4-hydroxybutyric acid | $C_6H_{12}O_6 + 3/2O_2 \rightarrow C_4H_8O_3 + 2H_2O + 2CO_2$ |

As illustrated in Table 1, fermentation in which oxygen is present on the left side of the fermentation equation often requires a large amount oxygen. In such cases, extensive aeration and/or vigorous stirring is sometimes required, enzymes that catalyze a reaction of converting pyruvate and carbon dioxide into oxaloacetate. The reaction consumes ATP, and produces ADP and phosphate. Examples of pyruvate carboxylase include those from *Corynebacterium* bacteria such as *Corynebacterium glutamicum*, or *Mycobacterium* bacteria such as *Mycobacterium smegmatis*.

As a gene encoding pyruvate carboxylase (pyc), a DNA having a base sequence of a gene encoding pyruvate carboxylase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, or a *Mycobacterium* bacterium such as *Mycobacterium smegmatis*.

Phosphoenolpyruvate carboxylase (Ppc), which is classified as Enzyme Commission number: 4.1.1.31, is a generic name for enzymes that catalyze a reaction of converting phosphoenolpyruvate and carbon dioxide into oxaloacetate and phosphate. Examples of phosphoenolpyruvate carboxylase include those from *Corynebacterium* bacteria such as *Corynebacterium glutamicum*, *Escherichia* bacteria such as *Escherichia coli*, *Pantoea* bacteria such as *Pantoea ananatis*, *Hyphomicrobium* bacteria such as *Hyphomicrobium methylovorum*, *Starkeya* bacteria such as *Starkeya novella*, *Rhodopseudomonas* bacteria such as *Rhodopseudomonas* sp., or *Streptomyces* bacteria such as *Streptomyces coelicolor*.

As a gene encoding phosphoenolpyruvate carboxylase (ppc), a DNA having a base sequence of a gene encoding phosphoenolpyruvate carboxylase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, a *Pantoea* bacterium such as *Pantoea ananatis*, a *Hyphomicrobium* bacterium such as *Hyphomicrobium methylovorum*, a *Starkeya* bacterium such as *Starkeya novella*, a *Rhodopseudomonas* bacterium such as *Rhodopseudomonas* sp., or a *Streptomyces* bacterium such as *Streptomyces coelicolor*.

Phosphoenolpyruvate carboxykinase (Pck), which is classified as Enzyme Commission number: 4.1.1.32, Enzyme Commission number: 4.1.1.38, or Enzyme Commission number: 4.1.1.49, is a generic name for enzymes that catalyze a reaction of converting phosphoenolpyruvate and carbon dioxide into oxaloacetate. Among these enzymes, the enzyme classified as Enzyme Commission number: 4.1.1.32 is involved in a reaction of converting GDP into GTP; the enzyme classified as Enzyme Commission number: 4.1.1.38 is involved in a reaction of converting phosphate into pyrophosphate; and the enzyme classified as Enzyme Commission number: 4.1.1.49 is involved in a reaction of converting ADP into ATP. Examples of phosphoenolpyruvate carboxykinase include those from *Actinobacillus* bacteria such as *Actinobacillus succinogenes*, *Mycobacterium* bacteria such as *Mycobacterium smegmatis*, or *Trypanosoma* bacteria such as *Trypanosoma brucei*.

As a gene encoding phosphoenolpyruvate carboxykinase (pck), a DNA having a base sequence of a gene encoding phosphoenolpyruvate carboxykinase obtained from any of the above microorganisms, or a synthesized DNA sequence that is synthesized based on a known base sequence of the gene, may be used. Preferable examples thereof include a DNA having a base sequence of a gene from *Actinobacillus* such as *Actinobacillus succinogenes*, a *Mycobacterium* bacterium such as *Mycobacterium smegmatis*, or a *Trypanosoma* bacterium such as *Trypanosoma brucei*.

Malate dehydrogenase (Mdh), which is classified as Enzyme Commission number: 1.1.1.37, is a generic name for enzymes that catalyze a reaction of producing malate from oxaloacetate using NADH as a coenzyme. Examples of malate dehydrogenase include those from *Corynebacterium* bacteria such as *Corynebacterium glutamicum*, or *Escherichia* bacteria such as *Escherichia coli*.

As a gene encoding malate dehydrogenase (mdh), a DNA having a base sequence of a gene encoding malate dehydrogenase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Malate thiokinase (Mtk), which is classified as Enzyme Commission number: 6.2.1.9, is a generic name for enzymes that catalyze a reaction of binding malate to CoA to produce malyl-CoA. In this reaction, one molecule of ATP is consumed, and one molecule of ADP and one molecule of phosphate are produced. Malate thiokinase is composed of a large subunit having approximately 400 amino acids and a small subunit having 300 amino acids. In the gene, the large subunit and the small subunit are present usually in this order. Here, for convenience, the large subunit is referred to as mtkB, and the small subunit is referred to as mtkA. It is reported that the specific activity of the purified malate thiokinase is, for example, 2.5 U/mg (Analytical Biochemistry, 1995; 227(2): 363-367).

Malate thiokinase is mainly found in an assimilation pathway for C1 carbon sources such as methane (Journal of Bacteriology, 1994; 176(23): 7398-7404) and a 3-hydroxypropionate pathway (Archives of Microbiology, 1989; 151: 252-256). The gene encoding malyl-CoA lyase is present in the vicinity of the gene encoding malate thiokinase in the genome, and such a gene encoding malate thiokinase and being present at such a location is preferably used.

Examples of malate thiokinase include those from *Methylobacterium* such as *Methylobacterium extorquens* (SEQ ID NOs: 1 and 2), those from *Granulibacter* such as *Granulibacter bethesdensis* (SEQ ID NOs: 3 and 4), those from *Hyphomicrobium* such as *Hyphomicrobium methylovorum* (SEQ ID NOs: 5 and 6) or *Hyphomicrobium denitrificans* (SEQ ID NOs: 7 and 8), those from *Rhizobium* such as *Rhizobium* sp. NGR234 (SEQ ID NOs: 9 and 10), those from *Nitrosomonas* such as *Nitrosomonas europaea* (SEQ ID NOs: 11 and 12), those from *Methylococcus* such as *Methylococcus capsulatus* (SEQ ID NOs: 13 and 14), and those from Gammaproteobacteria (SEQ ID NOs: 15 and 16).

From the viewpoint of the production efficiency of useful substances produced via acetyl-CoA, preferable examples of malate thiokinase include those from *Hyphomicrobium* (SEQ ID NOs: 5 and 6, and SEQ ID NOs: 7 and 8), those from *Rhizobium* (SEQ ID NOs: 9 and 10), those from *Nitrosomonas* (SEQ ID NOs: 11 and 12), those from *Methylococcus* (SEQ ID NOs: 13 and 14), and those from Gammaproteobacteria (SEQ ID NOs: 15 and 16).

Malate thiokinase from *Hyphomicrobium* (SEQ ID NOs: 5 and 6, and SEQ ID NOs: 7 and 8), malate thiokinase from *Rhizobium* (SEQ ID NOs: 9 and 10) and malate thiokinase from *Nitrosomonas* (SEQ ID NOs: 11 and 12) share 65% to 80% sequence homology with one another. Malate thiokinase from *Methylococcus* (SEQ ID NOs: 13 and 14) shares 70% to 80% sequence homology with the malate thiokinase from Gammaproteobacteria (e.g., SEQ ID NOs: 15 and 16).

Proteins having at least 70% amino acid sequence homology with any one of the amino sequences of malate thiokinase from *Hyphomicrobium*, malate thiokinase from *Rhizobium*, malate thiokinase from *Nitrosomonas*, malate thiokinase from *Methylococcus*, or malate thiokinase from Gammaproteobacteria disclosed in the invention, and having a malate thiokinase activity may be suitably used for producing acetyl-CoA or useful substances producible from acetyl-CoA.

As a gene encoding malate thiokinase (mtk), a DNA having a base sequence of a gene encoding malate thiokinase obtained from any of the above microorganisms, or a synthetic DNA sequence that is synthesized based on a known base sequence of the gene, may be used. Preferable examples thereof include a DNA having a base sequence of a gene from *Methylobacterium* such as *Methylobacterium extorquens* (SEQ ID NOs: 17 and 18), *Hyphomicrobium* such as *Hyphomicrobium methylovorum* or *Hyphomicrobium denitrificans*, *Rhizobium* such as *Rhizobium* sp. NGR234, *Granulibacter* such as *Granulibacter bethesdensis*, *Nitrosomonas* such as *Nitrosomonas europaea*, *Methylococcus* such as *Methylococcus capsulatus*, or Gammaproteobacterium. From the viewpoint of the production efficiency of acetyl-CoA, preferable examples thereof include a DNA having a base sequence of a gene from *Hyphomicrobium* (SEQ ID NOs: 19 and 20, and SEQ ID NOs: 21 and 22), *Rhizobium* such as *Rhizobium* of which codon usage is optimized (e.g., SEQ ID NO: 23), *Granulibacter* (SEQ ID NOs: 24 and 25), *Nitrosomonas* (SEQ ID NOs: 26 and 27), *Methylococcus* (SEQ ID NOs: 28 and 29), or Gammaproteobacteria (SEQ ID NOs: 30 and 31).

More preferable examples thereof include a base sequence of a gene from *Hyphomicrobium* (SEQ ID NOs: 19 and 20, and SEQ ID NOs: 21 and 22), *Rhizobium* such as *Rhizobium* of which codon usage is optimized (e.g., SEQ ID NO: 23), *Nitrosomonas* (SEQ ID NOs: 26 and 27), *Methylococcus* (SEQ ID NOs: 28 and 29), or Gammaproteobacteria (SEQ ID NOs: 30 and 31).

Methanotrophic microorganisms such as *Methylobacterium extorquens* intrinsically have malate thiokinase and malyl-CoA lyase. However, since vector systems suitable for methanotrophic microorganisms or techniques for modification of genomic genes of methanotrophic microorganisms have not been developed, genetic manipulation of the microorganisms is difficult compared with industrial microorganisms such as *Escherichia coli* and *Corynebacterium*. Further, methanotrophic microorganisms grow slowly in many cases and therefore are not suitable for producing useful metabolites.

Malyl-CoA lyase (Mel), which is classified as Enzyme Commission number: 4.1.3.24, is an enzyme that catalyzes a reaction of producing glyoxylate and acetyl-CoA from malyl-CoA. Examples of malyl-CoA lyase include those from *Methylobacterium* such as *Methylobacterium extorquens*, *Hyphomicrobium* such as *Hyphomicrobium methylovorum* or *Hyphomicrobium denitrificans*, *Chloroflexus* such as *Chloroflexus aurantiacus*, *Nitrosomonas* such as *Nitrosomonas europaea*, or *Methylococcus* such as *Methylococcus capsulatus*. It is reported that the specific activity of purified malyl-CoA lyase in *Methylobacterium extorquens* is, for example, 28.1 U/mg (Biochemical Journal, 1974; 139(2): 399-405).

From the viewpoint of the production efficiency of acetyl-CoA, preferable examples of malyl-CoA lyase include an enzyme having the amino acid sequence from *Methylobacterium* (SEQ ID NO: 32), *Hyphomicrobium* (SEQ ID NO: 33 and 34), *Nitrosomonas* (SEQ ID NO: 35), or *Methylococcus* (SEQ ID NO: 36).

As a gene encoding malyl-CoA lyase (mel), a DNA having a base sequence of a gene encoding malyl-CoA lyase obtained from the above organism, or a synthesized DNA sequence that is synthesized based on a known base sequence of the gene, may be used. Preferable examples thereof include a DNA having a base sequence of a gene from *Methylobacterium* such as *Methylobacterium extorquens*, *Hyphomicrobium* such as *Hyphomicrobium methylovorum* or *Hyphomicrobium denitrificans*, or *Chloroflexus* such as *Chloroflexus aurantiacus*. From the viewpoint of the production efficiency of acetyl-CoA, more preferable examples thereof include a DNA having a base sequence of a gene from *Methylobacterium* and a gene having a base sequence of a gene from *Hyphomicrobium*.

Specific examples of preferable base sequences of the gene from *Methylobacterium* include a base sequence of a gene from *Methylobacterium extorquens* (SEQ ID NO: 37). Specific examples of preferable base sequences of the gene from *Hyphomicrobium* include a base sequence of a gene from *Hyphomicrobium methylovorum* (SEQ ID NO: 38) or *Hyphomicrobium denitrificans* (SEQ ID NO: 39). Specific examples of preferable base sequences of the gene from *Nitrosomonas* include a base sequence of a gene from *Nitrosomonas europaea* (SEQ ID NO: 40). Specific examples of preferable base sequences of the gene from *Methylococcus* include a base sequence of a gene from *Methylococcus capsulatus* (SEQ ID NO: 41).

Glyoxylate carboligase (Gcl), which is classified as Enzyme Commission number: 4.1.1.47, is a generic name for enzymes that catalyze a reaction of converting two molecules of glyoxylate into one molecule of 2-hydroxy-3-oxopropionate. This reaction is accompanied by decarboxylation of one molecule of carbon dioxide. Examples of glyoxylate carboligase include those from *Corynebacterium* bacteria such as *Corynebacterium glutamicum*, *Escherichia* bacteria such as *Escherichia coli*, or *Rhodococcus* bacteria such as *Rhodococcus jostii*.

As a gene encoding glyoxylate carboligase (gcl), a DNA having a base sequence of a gene encoding glyoxylate carboligase obtained from any of the above microorganisms, or a synthesized DNA sequence that is synthesized based on a known base sequence of the gene, may be used. Preferable examples thereof include a DNA having a base sequence of a gene from *Rhodococcus* bacterium such as *Rhodococcus jostii*, or an *Escherichia* bacterium such as *Escherichia coli*.

2-Hydroxy-3-oxopropionate reductase, which is classified as Enzyme Commission number: 1.1.1.60, is a generic name for enzymes that catalyze a reaction of converting 2-hydroxy-3-oxopropionate into glycerate using NADH as a coenzyme. Examples of 2-hydroxy-3-oxopropionate reductase include those from *Rhodococcus* bacteria such as *Rhodococcus jostii*, or *Escherichia* bacteria such as *Escherichia coli*.

As a gene encoding 2-hydroxy-3-oxopropionate reductase (glxR), a DNA having a base sequence of a gene encoding 2-hydroxy-3-oxopropionate reductase obtained from any of the above microorganisms, or a synthesized DNA sequence that is synthesized based on a known base sequence of the gene, may be used. Preferable examples thereof include a DNA having a base sequence of a gene from a *Rhodococcus* bacterium such as *Rhodococcus jostii*, or an *Escherichia* bacterium such as *Escherichia coli*.

Hydroxypyruvate isomerase (Hyi), which is classified as Enzyme Commission number: 5.3.1.22, is a generic name for enzymes that catalyze a reaction of isomerizing 2-hydroxy-3-oxopropionate to hydroxypyruvate. Examples of hydroxypyruvate isomerase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding hydroxypyruvate isomerase (hyi), a DNA having a base sequence of a gene encoding hydroxypyruvate isomerase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Hydroxypyruvate reductase (YcdW), which is classified as Enzyme Commission number: 1.1.1.81, is a generic name for enzymes that catalyze a reaction of converting hydroxypyruvate into glycerate using NADH or NADPH as a coenzyme. Examples of hydroxypyruvate reductase include those from *Escherichia* bacteria such as *Escherichia coli*, or *Pantoea* bacteria such as *Pantoea ananatis*.

As a gene encoding hydroxypyruvate reductase (ycdW), a DNA having a base sequence of a gene encoding hydroxypyruvate reductase obtained from any of the above microorganisms, or a synthetic DNA sequence synthesized based on a known base sequence of the gene, may be used. Preferable examples thereof include a DNA having a base sequence of a gene from an *Escherichia* bacterium such as *Escherichia coli*, or a *Pantoea* bacterium such as *Pantoea ananatis*.

Glycerate 2-kinase (GarK), which is classified as Enzyme Commission number: 2.7.1.165, is a generic name for enzymes that catalyze a reaction of converting glycerate into 2-phosphoglycerate. In this reaction, one molecule of ATP is consumed, and one molecule of ADP and one molecule of phosphate are produced. Examples of glycerate 2-kinase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding glycerate 2-kinase (garK), a DNA having a base sequence of a gene encoding glycerate 2-kinase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Glycerate 3-kinase (GlxK), which is classified as Enzyme Commission number: 2.7.1.31 is a generic name for enzymes that catalyze a reaction of converting glycerate into 3-phosphoglycerate. In this reaction, one molecule of ATP is consumed, and one molecule of ADP and one molecule of phosphate are produced. Examples of glycerate 3-kinase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding glycerate 3-kinase (glxK), a DNA having a base sequence of a gene encoding glycerate 3-kinase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Phosphoglycerate mutase (Gpm), which is classified as Enzyme Commission number: 5.4.2.1, is a generic name for enzymes that catalyze a reaction of converting 3-phosphoglycerate into 2-phosphoglycerate. Examples of phosphoglycerate mutase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding phosphoglycerate mutase (gpm), a DNA having a base sequence of a gene encoding phosphoglycerate mutase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Enolase (Eno), which is classified as Enzyme Commission number: 4.2.1.11, is a generic name for enzymes that catalyze a reaction of converting 2-phosphoglycerate into phosphoenolpyruvate. Examples of enolase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding enolase (eno), a DNA having a base sequence of a gene encoding enolase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Glycine transaminase (Gta) is an enzyme that catalyzes a reaction of transferring an amino group from a compound having an amino group (a secondary amine or a primary amine) to glyoxylate and converting it into glycine. Examples thereof include, among the enzymes classified in the group of Enzyme Commission number: 2.6.1, an enzyme that uses glyoxylate as a substrate. Specific examples thereof include enzymes classified Enzyme Commission number: 2.6.1.*, in which * represents 4, 35, 44, 45, 60, 63, or 73. Furthermore, similar enzymatic activities are reported in some cases regarding enzymes classified Enzyme Commission number: 2.6.1.*, in which * represents 2, 7, 12, 13, 14, 15, 18, 19, 27, 38, 40, 42, 57, 64, 72, or 78. Examples of glycine transaminase include those from *Methylococcus* such as *Methylococcus capsulatus*, *Aspergillus* fungi such as *Aspergillus niger*, or *Cupriavidus* such as *Cupriavidus necator*. Glycine transaminase may have a serine transaminase activity described below. In the invention, glycine dehydrogenase (Gdh) is considered to be included in the scope of glycine transaminase.

As a gene encoding glycine transaminase (gta), a DNA having a base sequence of a gene encoding glycine transaminase obtained from any of the above microorganisms, or a synthesized DNA sequence that is synthesized based on a known base sequence of the gene, may be used. Preferable examples thereof include a DNA having a base sequence of a gene from *Methylococcus* such as *Methylococcus capsulatus*, an *Aspergillus* fungus such as *Aspergillus niger*, or

*Cupriavidus* such as *Cupriavidus necator*. In the invention, a gene encoding glycine dehydrogenase is considered to be included in the scope of a gene encoding glycine transaminase.

As a gene encoding glycine dehydrogenase (gdh), a DNA having a base sequence of a gene encoding glycine dehydrogenase obtained from any of the above microorganisms, or a synthesized DNA sequence that is synthesized based on a known base sequence of the gene, may be used. Preferable examples thereof include a DNA having a base sequence of a gene from a *Mycobacterium* bacterium such as *Mycobacterium tuberculosis* or *Mycobacterium smegmatis*, or a *Hyphomicrobium* bacterium such as *Hyphomicrobium vulgare*.

The glycine cleavage system (Gcs) is a generic name of a series of enzymes that catalyze a reaction of converting glycine, tetrahydrofolate, and $NAD^+$ into 5,10-methylenetetrahydrofolate, $NH_3$, $CO_2$, and NADH. The glycine cleavage system is composed of proteins called H-protein, P-protein, L-protein, and T-protein (Molecular and Cellular Biochemistry, 1973; 1(2): 169-187). P-protein, L-protein, and T-protein are classified as Enzyme Commission number: 1.4.4.2, 1.8.1.4, and 2.1.2.10, respectively. Examples of the glycine cleavage system include those from *Escherichia* bacteria such as *Escherichia coli*, or *Pantoea* bacteria such as *Pantoea ananatis*, *Aspergillus* fungi such as *Aspergillus niger*, or *Cupriavidus* such as *Cupriavidus necator*.

As genes encoding the glycine cleavage system (gcs), a DNA having a base sequence of a gene encoding glycine cleavage system obtained from any of the above microorganisms, or a synthesized DNA sequence that is synthesized based on a known base sequence of the gene, may be used. Preferable examples thereof include a DNA having a base sequence of a gene from an *Escherichia* bacterium such as *Escherichia coli*, or a *Pantoea* bacterium such as *Pantoea ananatis*, an *Aspergillus* fungus such as *Aspergillus niger*, or *Cupriavidus* such as *Cupriavidus necator*.

By the action of serine hydroxymethyltransferase, 5,10-methylenetetrahydrofolate produced by the glycine cleavage system is reacted with another glycine and converted into serine. That is, by the action of serine hydroxymethyltransferase, two molecules of glycine and $NAD^+$ are converted into serine, $NH_3$, $CO_2$, and NADH.

Serine hydroxymethyltransferase (Shmt), which is classified as Enzyme Commission number: 2.1.2.1, is a generic name for enzymes that catalyze a reaction of converting 5,10-methylenetetrahydrofolate and glycine into serine and tetrahydrofolate. Examples of serine hydroxymethyltransferase include those from *Corynebacterium* bacteria such as *Corynebacterium glutamicum*, *Escherichia* bacteria such as *Escherichia coli*, or *Pantoea* bacteria such as *Pantoea ananatis*.

As a gene encoding serine hydroxymethyltransferase (shmt), a DNA having a base sequence of a gene encoding serine hydroxymethyltransferase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, or a *Pantoea* bacterium such as *Pantoea ananatis*.

Serine dehydratase (Sda), which is classified as Enzyme Commission number: 4.3.1.17, is a generic name for enzymes that catalyze a reaction of producing pyruvate and ammonia from serine. Furthermore, similar enzymatic activities are sometimes reported regarding enzymes classified as Enzyme Commission number: 4.3.1.19. Examples of serine dehydratase include those from *Corynebacterium* bacteria such as *Corynebacterium glutamicum*, *Escherichia* bacteria such as *Escherichia coli*, *Pantoea* bacteria such as *Pantoea ananatis*, *Aspergillus* fungi such as *Aspergillus niger*, or *Cupriavidus* such as *Cupriavidus necator*.

As a gene encoding serine dehydratase (sda), a DNA having a base sequence of a gene encoding serine dehydratase obtained from any of the above microorganisms, or a synthesized DNA sequence that is synthesized based on a known base sequence of the gene, may be used. Preferable examples thereof include a DNA having a base sequence of a gene from a *Corynebacterium* bacterium such as *Corynebacterium glutamicum*, an *Escherichia* bacterium such as *Escherichia coli*, a *Pantoea* bacterium such as *Pantoea ananatis*, an *Aspergillus* fungus such as *Aspergillus niger*, or *Cupriavidus* such as *Cupriavidus necator*.

Serine transaminase (Sga) is an enzyme that catalyzes a reaction of transferring an amino group from serine to a compound having a carbonyl group (a ketone group or an aldehyde group) and converting it into 3-hydroxypyruvate. Examples thereof include, among the enzymes classified Enzyme Commission number: 2.6.1, an enzyme that uses serine as a substrate. Specific examples thereof include enzymes classified Enzyme Commission number: 2.6.1.51 or 2.6.1.45. Furthermore, similar enzymatic activities are reported in some cases regarding enzymes classified Enzyme Commission number: 2.6.1.44 or 2.6.1.35. Serine transaminase may have a glycine transaminase described above. Examples of serine transaminase include those from *Methylococcus* such as *Methylococcus capsulatus*, *Aspergillus* fungi such as *Aspergillus niger*, or *Cupriavidus* such as *Cupriavidus necator*. In the invention, serine 2-dehydrogenase is considered to be included in the scope of serine transaminase.

As a gene encoding serine transaminase (sga), a DNA having a base sequence of a gene encoding serine transaminase obtained from any of the above microorganisms, or a synthesized DNA sequence that is synthesized based on a known base sequence of the gene, may be used. Preferable examples thereof include a DNA having a base sequence of a gene from *Methylococcus* such as *Methylococcus capsulatus*, an *Aspergillus* fungus such as *Aspergillus niger*, or *Cupriavidus* such as *Cupriavidus necator*. In the invention, a gene encoding serine 2-dehydrogenase is considered to be included in the scope of a gene encoding serine transaminase.

Serine 2-dehydrogenase (Sdh), which is classified as Enzyme Commission number: 1.4.1.7, is a generic name for enzymes that catalyze a reaction of producing 3-hydroxypyruvate and ammonia from serine. Examples of serine 2-dehydrogenase include those from a plant such as *Petroselinum crispum*.

As a gene encoding serine 2-dehydrogenase (sdh), a DNA having a base sequence of a gene encoding serine 2-dehydrogenase obtained from any of the above microorganisms, or a synthesized DNA sequence that is synthesized based on a known base sequence of the gene, may be used. Preferable examples thereof include a DNA having a base sequence of a gene from a plant such as *Petroselinum crispum*.

In a microorganism in which the cycle of FIG. 1 is not formed because the microorganism does not have some of the enzymes included in the cycle of FIG. 1, the missing enzyme(s) may be supplied.

Among *Escherichia* bacteria, *Escherichia coli*, for example, possesses none of malate thiokinase, malyl-CoA lyase, or glycine transaminase, and therefore, at least malate thiokinase, malyl-CoA lyase, and glycine transaminase may be imparted.

Among *Pantoea* bacteria, *Pantoea ananatis*, for example, possesses none of malate thiokinase, malyl-CoA lyase, or glycine transaminase, and therefore, at least malate thiokinase, malyl-CoA lyase, and glycine transaminase may be imparted.

Among coryneform bacteria, *Corynebacterium glutamicum*, for example, possesses none of malate thiokinase, malyl-CoA lyase, glyoxylate carboligase, 2-hydroxy-3-oxopropionate reductase, or hydroxypyruvate reductase, and therefore, at least malate thiokinase, malyl-CoA lyase, glyoxylate carboligase, and 2-hydroxy-3-oxopropionate reductase, and/or hydroxypyruvate reductase may be imparted.

In a microorganism in which neither the cycle of FIG. 1 or the glycine pathway of FIG. 2 is formed because the microorganism does not have some of the enzymes in the cycle of FIG. 1 and the glycine pathway of FIG. 2, the missing enzyme(s) may be supplied. In the case of *Aspergillus niger*, a species of filamentous fungi, the pathway of FIG. 2 can be formed by imparting malate thiokinase and malyl-CoA lyase.

In the acetyl-CoA producing microorganism according to the first invention, it is preferable that at least one type of enzymatic activity selected from the group consisting of pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase is enhanced. This enables more efficient production of acetyl-CoA.

Pyruvate kinase, pyruvate carboxylase, phosphoenolpyruvate carboxylase, phosphoenolpyruvate carboxykinase, malate dehydrogenase, malate thiokinase, malyl-CoA lyase, glyoxylate carboligase, 2-hydroxy-3-oxopropionate reductase, hydroxypyruvate isomerase, hydroxypyruvate reductase, glycerate 2-kinase, glycerate 3-kinase, phosphoglycerate mutase, and enolase, which may become targets for enhancement, are enzymes constituting the cycle of FIG. 1.

In the acetyl-CoA producing microorganism according to the first invention, it is preferable that at least one type of enzymatic activity selected from the group consisting of a malic enzyme and fumarate reductase is inactivated or reduced. This enables more efficient production of acetyl-CoA.

Malic enzyme is a generic name for enzymes that are classified as Enzyme Commission numbers: 1.1.1.38, 1.1.1.39, and 1.1.1.40 and catalyze a reaction of converting malate into pyruvate and carbon dioxide. In terms of acetyl-CoA production efficiency, it is preferable to inactivate or reduce the enzymatic activity of malic enzyme.

Fumarate reductase is a generic name for enzymes that are classified as Enzyme Commission number: 1.3.99.1 and catalyze a reaction of converting fumarate into succinate. Furthermore, succinate dehydrogenase that is classified as Enzyme Commission number: 1.3.99.1 sometimes has a fumarate reductase activity of converting fumarate into succinate. Therefore, in the invention, succinate dehydrogenase having a fumarate reductase activity is included in the scope of fumarate reductase. In terms of acetyl-CoA production efficiency, it is preferable to inactivate or reduce the enzymatic activity of fumarate reductase. This enables suppression of reduction in the amount of malate due to the conversion of malate into fumarate or succinate, and leads to efficient production of acetyl-CoA.

With regard to the gene encoding the malic enzyme (in many cases, named sfcA, maeA, maeB, or malE, but not limited thereto), some microorganisms may have plural isomers thereof in the genome. *Pantoea ananatis* has sfcA and maeB. *Corynebacterium glutamicum* has malE.

With regard to the gene encoding fumarate reductase (frd, sdh, yqiG, and the like), some microorganisms may have plural isomers thereof in the genome. *Pantoea ananatis* has yqiG. *Corynebacterium glutamicum* has sdh.

The microorganism used as a host in the first invention is not particularly limited as long as it is a microorganism that does not have any of the following (a), (b), (c), (d), or (e).

(a) A carbon dioxide fixation cycle including an enzymatic reaction from malonyl-CoA to malonate semialdehyde or 3-hydroxypropionate.

(b) A carbon dioxide fixation cycle including an enzymatic reaction from acetyl-CoA and $CO_2$ to pyruvate.

(c) A carbon dioxide fixation cycle including an enzymatic reaction from crotonyl-CoA and $CO_2$ to ethylmalonyl-CoA or glutaconyl-CoA.

(d) A carbon dioxide fixation cycle including an enzymatic reaction from $CO_2$ to formate.

(e) At least one selected from the group consisting of malate thiokinase and malyl-CoA lyase.

Here, the "(a) carbon dioxide fixation cycle including an enzymatic reaction from malonyl-CoA to malonate semialdehyde or 3-hydroxypropionate" refers to the following cycles (1) to (7):

(1) the cycle illustrated in FIG. 1 of WO 2011/099006, in which acetyl-CoA is reconverted into acetyl-CoA via malonyl-CoA, 3-hydroxypropionate, propionyl-CoA, malate, and malyl-CoA;

(2) the cycle illustrated in FIG. 4A of WO 2011/099006, in which acetyl-CoA is reconverted into acetyl-CoA via malonyl-CoA, malonate semialdehyde, β-alanine, malate, and malyl-CoA;

(3) the cycle illustrated in FIG. 4B, 16, or 18 of WO 2011/099006, in which acetyl-CoA is reconverted into acetyl-CoA via malonyl-CoA, hydroxypropionate, (R)-lactate or (S)-lactate, malate, and malyl-CoA;

(4) the cycle illustrated in FIG. 8 of WO 2011/099006, in which acetyl-CoA is reconverted into acetyl-CoA via malonyl-CoA, malonate semialdehyde or hydroxypropionate, pyruvate, malate, and malyl-CoA;

(5) the cycle illustrated in FIG. 9A, 9B, or 9C of WO 2011/099006, in which acetyl-CoA is reconverted into acetyl-CoA via malonyl-CoA, hydroxypropionate, 2-ketoglutarate, malate, and malyl-CoA;

(6) the cycle illustrated in FIG. 9D or 9F of WO 2011/099006, in which acetyl-CoA is reconverted into acetyl-CoA via malonyl-CoA, hydroxypropionate, methylmalonyl-CoA, malate, and malyl-CoA; and (7) the cycle illustrated in FIG. 17 of WO 2011/099006, in which acetyl-CoA is reconverted into acetyl-CoA via malonyl-CoA, malonate semialdehyde or hydroxypropionate, methylmalonyl-CoA, pyruvate, oxaloacetate, malate, and malyl-CoA.

All of carbon dioxide fixation cycles (1) to (7) described above have an enzymatic reaction from malonyl-CoA to malonate semialdehyde or from malonyl-CoA to 3-hydroxypropionate. This kind of reaction is catalyzed by malonate semialdehyde dehydrogenase or malonyl-CoA reductase (WO 2011/099006). It is thought that the reduction reaction of carboxylic acid or a (thio)ester thereof, such as reduction of succinyl-CoA or reduction of malonyl-CoA, is generally difficult to carry out as enzymatic reactions and inclusion thereof in a fermentation pathway should be avoided as much as possible (Nature, 2008; 451: 86-89, Nature Chemical Biology, 2011; 7: 445-452).

The "(b) carbon dioxide fixation cycle including an enzymatic reaction from acetyl-CoA and $CO_2$ to pyruvate" in the present specification refers to the following cycles (8) to (10):

(8) the cycle illustrated in FIG. 1 of WO 2011/099006, in which acetyl-CoA is reconverted into acetyl-CoA via pyruvate, phosphoenolpyruvate, oxaloacetate, malate, and malyl-CoA;

(9) the cycle illustrated in FIG. 7C, 7D or 7E of WO 2011/099006, in which acetyl-CoA is reconverted into acetyl-CoA via pyruvate, malate, and malyl-CoA; and

(10) the cycle illustrated in FIG. 9M of WO 2011/099006, in which acetyl-CoA is reconverted into acetyl-CoA via pyruvate, 2-ketoglutarate, malate, and malyl-CoA.

All of carbon dioxide fixation cycles (8) to (10) have an enzyme reaction converting acetyl-CoA and $CO_2$ into pyruvate. This reaction is catalyzed by pyruvate synthase (WO 2011/099006). The pyruvate synthetic reaction by pyruvate synthase requires a strong reduction power from ferredoxin and proceeds slowly, and proceeds only under strictly anaerobic conditions because the reaction is sensitive to oxygen.

The "(c) carbon dioxide fixation cycle including an enzymatic reaction from crotonyl-CoA and $CO_2$ to ethylmalonyl-CoA or glutaconyl-CoA" in the present specification refers to the cycle illustrated in FIG. 9H or 9J of WO 2011/099006, in which acetyl-CoA is reconverted into acetyl-CoA via crotonyl-CoA, ethylmalonyl-CoA or glutaconyl-CoA, oxaloacetate, malate, and malyl-CoA.

The conversion of crotonyl-CoA and $CO_2$ to ethylmalonyl-CoA or glutaconyl-CoA is catalyzed by crotonyl-CoA carboxylase-reductase or methylcrotonyl-CoA carboxylase. Since the Km value of crotonyl-CoA carboxylase-reductase for carbonates is high (14 mM; Proceedings of the National Academy of Sciences of the United States of America, 2007; 104(25): 10631-10636), sufficient activity at low substrate concentration cannot be expected. Crotonyl-CoA, which is a substrate of crotonyl-CoA carboxylase-reductase, is produced from 3-hydroxybutyryl-CoA by a dehydration reaction. In general, an enzyme involved in the dehydration reaction predominantly catalyzes the reverse reaction (i.e., hydration reaction) in an aqueous environment. Therefore, a sufficiently high production rate of crotonyl-CoA cannot be expected. Further, the reported specific activity of methylcrotonyl-CoA carboxylase is not so high (0.2 U/mg to 0.6 U/mg; Archives of Biochemistry and Biophysics, 1994; 310(1): 64-75). In addition, a sufficiently high production rate of crotonyl-CoA as a substrate cannot be expected, similar to the above.

The "(d) carbon dioxide fixation cycle including an enzymatic reaction from $CO_2$ to formate" in the present specification refers to the cycle illustrated in FIG. 5, 6, 13 or 14 of WO 2009/046929, that is, a cycle that is a combination of a pathway in which 5,10-methenyltetrahydrofolate is produced from $CO_2$ via formate and 5-formyltetrahydrofolate; a pathway in which 5,10-methenyltetrahydrofolate is reacted with glycine to produce serine, and the serine is reconverted into glycine via 3-hydroxypyruvate, glycerate, 3-phosphoglycerate, phosphoenol pyruvate, oxaloacetate, malate, malyl-CoA, and glyoxylate; and a pathway in which acetyl-CoA produced via malate and malyl-CoA is reconverted into malate via the TCA cycle and a reaction involving isocitrate lyase.

The enzymatic reaction from $CO_2$ to formate requires a strong reduction power and proceeds slowly, and proceeds only under strictly anaerobic conditions because the reaction is sensitive to oxygen.

Malonate semialdehyde dehydrogenase, which is classified as Enzyme Commission number: 1.2.1.18, is a generic name for enzymes that catalyze a reaction of converting malonyl-CoA into malonate semialdehyde.

Malonyl-CoA reductase is a generic name for enzymes that catalyze a reaction of converting malonyl-CoA into malonate semialdehyde or 3-hydroxypropionate.

Pyruvate synthase, which is classified as Enzyme Commission number: 1.2.7.1, is a generic name for enzymes that catalyzes a reaction of converting acetyl-CoA into pyruvate.

Crotonyl-CoA carboxylase-reductase, which is classified as Enzyme Commission number: 1.3.1.85, is a generic name for enzymes that catalyze the conversion of crotonyl-CoA into ethylmalonyl-CoA.

Methylcrotonyl-CoA carboxylase, which is classified as Enzyme Commission number: 6.4.1.4, is a generic name for enzymes that catalyze a reaction of converting crotonyl-CoA into glutaconyl-CoA.

Examples of the microorganism that does not have any of (a), (b), (c), (d), or (e) include microorganisms belonging to Enterobacteriaceae, microorganisms belonging to *Corynebacterium* bacteria, microorganisms belonging to filamentous fungi, and actinomycetes.

Specific examples of the microorganisms belonging to Enterobacteriaceae include bacteria belonging to *Enterobacter, Erwinia, Escherichia, Klebsiella, Pantoea, Providencia, Salmonella, Serratia, Shigella,* or *Morganella*. Among these, microorganisms belonging to *Escherichia* and microorganisms belonging to *Pantoea* are preferable from the viewpoint of efficient production of useful metabolites. *Escherichia* bacteria and *Pantoea* bacteria are very closely related species (Journal of General and Applied Microbiology, 1997; 43(6): 355-361, International Journal of Systematic Bacteriology, 1997; 47(4): 1061-1067).

The *Escherichia* bacteria are not particularly limited, and examples thereof include *Escherichia coli*. Specific strains of the *Escherichia coli* include prototype wild-type strain *Escherichia coli* B (ATCC 11303); and *Escherichia coli* W3110 (ATCC 27325) and *Escherichia coli* MG1655 (ATCC 47076), derived from the prototype wild-type strain K12.

Examples of representative strains of the *Pantoea* bacteria include *Pantoea ananatis, Pantoea stewartii, Pantoea agglomerans,* and *Pantoea citrea*. Specific examples thereof include the following strains.

*Pantoea ananatis* AJ13355 (FERM BP-6614) (European Patent Application Laid-open No. 0952221)

*Pantoea ananatis* AJ13356 (FERM BP-6615) (European Patent Application Laid-open No. 0952221)

Although these strains are described as *Enterobacter agglomerans* in European Patent Application Laid-open No. 0952221, the strains were reclassified into *Pantoea ananatis* as described above based on base sequence analysis of 16S rRNA and the like.

In recent years, some bacteria belonging to *Enterobacter* have been reclassified into *Pantoea agglomerans, Pantoea dispersa,* or the like (International Journal of Systematic Bacteriology, 1989; 39(3): 337-345). Further, some bacteria belonging to *Erwinia* have been reclassified into *Pantoea ananas* or *Pantoea stewartii* (International Journal of Systematic Bacteriology, 1993; 43(1): 162-173).

Examples of the *Enterobacter* bacteria include *Enterobacter agglomerans* and *Enterobacter aerogenes*. More specifically, strains exemplified in European Patent Application Laid-open No. 952221 may be used. Examples of representative strains of *Enterobacter* include *Enterobacter agglomerans* ATCC 12287.

The "coryneform bacteria" in the invention refers to the microorganisms belonging to *Corynebacterium*, *Brevibacterium*, or *Microbacterium*, as defined in Bergey's Manual of Determinative Bacteriology, 8, 599 (1974).

Examples of the coryneform bacteria further include microorganisms which had been classified into *Brevibacterium* but were reclassified later into *Corynebacterium* (International Journal of Systematic Bacteriology, 1991; 41(2): 255-260), and related bacteria such as microorganisms belonging to *Brevibacterium*. Examples of the coryneform bacteria are listed below.

Examples of the coryneform bacteria include *Corynebacterium acetoacidophilum*, *Corynebacterium acetoglutamicum*, *Corynebacterium alkanolyticum*, *Corynebacterium callunae*, *Corynebacterium glutamicum*, *Corynebacterium lilium*, *Corynebacterium melassecola*, *Corynebacterium thermoaminogenes*, *Corynebacterium herculis*, *Brevibacterium divaricatum*, *Brevibacterium flavum*, *Brevibacterium immariophilum*, *Brevibacterium lactofermentum*, *Brevibacterium roseum*, *Brevibacterium saccharolyticum*, *Brevibacterium thiogenitalis*, *Corynebacterium ammoniagenes*, *Brevibacterium album*, *Brevibacterium cerinum*, and *Microbacterium ammoniaphilum*.

Specific examples of the *Corynebacterium* bacteria include the following strains.

That is, examples thereof include *Corynebacterium acetoacidophilum* ATCC 13870, *Corynebacterium acetoglutamicum* ATCC 15806, *Corynebacterium alkanolyticum* ATCC 21511, *Corynebacterium callunae* ATCC 15991, *Corynebacterium glutamicum* ATCC 13020, ATCC 13032 and ATCC 13060, *Corynebacterium lilium* ATCC 15990, *Corynebacterium melassecola* ATCC 17965, *Corynebacterium thermoaminogenes* AJ 12340 (FERM BP-1539), *Corynebacterium herculis* ATCC13868, *Brevibacterium divaricatum* ATCC 14020, *Brevibacterium flavum* ATCC 13826, ATCC 14067, and AJ 12418 (FERM BP-2205), *Brevibacterium immariophilum* ATCC 14068, *Brevibacterium lactofermentum* (*Corynebacterium glutamicum*) ATCC 13869, *Brevibacterium roseum* ATCC 13825, *Brevibacterium saccharolyticum* ATCC 14066, *Brevibacterium thiogenitalis* ATCC 19240, *Corynebacterium ammoniagenes* ATCC 6871 and ATCC 6872, *Brevibacterium album* ATCC 15111, *Brevibacterium cerinum* ATCC 15112, and *Microbacterium ammoniaphilum* ATCC 15354.

In the second invention, a microorganism belonging to the genus *Aspergillus* or the genus *Cupriavidus* that does not have any of (a), (b), (c), (d), or (e) above is used as a host. Examples of the *Aspergillus* fungi include *Aspergillus niger* (including variants such as *Aspergillus awamori* or *Aspergillus kawachii*), *Aspergillus terreus*, and *Aspergillus itaconicus*. Examples of the *Cupriavidus* bacteria include *Cupriavidus necator* (also known as *Alcaligenes eutropha*, *Ralstonia eutropha*, or *Wautersia eutropha*). In the second invention, in a case in which citric acid is to be produced, it is preferable to use an *Aspergillus* fungus such as *Aspergillus niger*. In a case in which itaconic acid is to be produced, it is preferable to use an *Aspergillus* fungus such as *Aspergillus terreus* or *Aspergillus itaconicus*. In a case in which (poly) 3-hydroxybutyric acid is to be produced, it is preferable to use a *Cupriavidus* bacterium such as *Cupriavidus necator*.

The acetyl-CoA producing microorganism according to the invention may include a pathway of any kind that produce a metabolite producible from acetyl-CoA as an intermediate, or may be a microorganism in which an enzymatic activity associated with such a pathway is enhanced. Examples of the pathway include an isopropyl alcohol producing pathway, an acetone producing pathway, and a glutamic acid producing pathway. Hereinbelow, the microorganism that includes a pathway such as those described above and can produce a useful metabolite derived from acetyl-CoA is explained.

Microorganism Involved in Isopropyl Alcohol Production and Microorganism Involved in Acetone Production The acetyl-CoA producing microorganism according to the invention that includes an isopropyl alcohol production pathway can be obtained by constructing the acetyl-CoA producing microorganism according to the invention using a microorganism having an isopropyl alcohol production pathway as a host, or imparting or enhancing one or more enzymatic activities relating to the isopropyl alcohol production pathway in the acetyl-CoA producing microorganism according to the invention. Hereinafter, the microorganism having an isopropyl alcohol production pathway may be referred to as "isopropyl alcohol-producing microorganism", and *Escherichia coli* having an isopropyl alcohol production pathway may be referred to as "isopropyl alcohol-producing *Escherichia coli*".

The isopropyl alcohol-producing *Escherichia coli* is an *Escherichia coli* having an isopropyl alcohol production pathway, and has an isopropyl alcohol production ability that has been introduced by a genetic recombination technique. The isopropyl alcohol production pathway may be any pathway that allows *Escherichia coli* of interest to produce isopropyl alcohol. In the isopropyl alcohol-producing *Escherichia coli* according to the invention, it is preferable that four enzymatic activities—a thiolase activity, a CoA transferase activity, an acetoacetate decarboxylase activity, and an isopropyl alcohol dehydrogenase activity—are imparted or enhanced.

In a case in which the acetyl-CoA producing microorganism according to the invention is used for producing acetone, a microorganism having thiolase activity, CoA transferase activity, and acetoacetate decarboxylase activity from among those involved in the isopropyl alcohol production pathway may be used. The microorganism does not have an isopropyl alcohol dehydrogenase activity from among those involved in the isopropyl alcohol production pathway.

In a case in which the acetyl-CoA producing microorganism according to the invention is a microorganism that is constructed using an *Escherichia* bacterium as a host, the following embodiments are preferable.

An example of preferable embodiments of the acetyl-CoA producing microorganism is an *Escherichia* bacterium in which a thiolase activity, a CoA transferase activity, an acetoacetate decarboxylase activity, and an isopropyl alcohol dehydrogenase activity have been imparted or enhanced. Such a microorganism allows efficient production of isopropyl alcohol.

Another example of preferable embodiments of the acetyl-CoA producing microorganism is an *Escherichia* bacterium in which a thiolase activity, a CoA transferase activity, and an acetoacetate decarboxylase activity have been imparted or enhanced. Such a microorganism allows efficient production of acetone.

Hereinbelow, the details of the isopropyl alcohol production pathway and enzymes constituting the pathway are described.

Thiolase, which is classified as Enzyme Commission number: 2.3.1.9, is a generic name for enzymes that catalyze a reaction of producing acetoacetyl-CoA from acetyl-CoA.

Examples of thiolase include those from *Clostridium* bacteria such as *Clostridium acetobutylicum* or *Clostridium beijerinckii*, *Escherichia* bacteria such as *Escherichia coli*, *Halobacterium* sp., *Zoogloea* bacteria such as *Zoogloea ramigera*, *Rhizobium* sp., *Bradyrhizobium* bacteria such as *Bradyrhizobium japonicum*, *Candida* such as *Candida tropicalis*, *Caulobacter* bacteria such as *Caulobacter crescentus*, *Streptomyces* bacteria such as *Streptomyces collinus*, or *Enterococcus* bacteria such as *Enterococcus faecalis*.

As a gene encoding thiolase, a DNA having a base sequence of a gene encoding thiolase obtained from any of the above microorganisms, or a synthesized DNA sequence that is synthesized based on a known base sequence of the gene, may be used. Preferable examples thereof include a DNA having a base sequence of a gene from a *Clostridium* bacterium such as *Clostridium acetobutylicum* or *Clostridium beijerinckii*; an *Escherichia* bacterium such as *Escherichia coli*, *Halobacterium* sp., a *Zoogloea* bacterium such as *Zoogloea ramigera*, *Rhizobium* sp., a *Bradyrhizobium* bacterium such as *Bradyrhizobium japonicum*, *Candida* such as *Candida tropicalis*, a *Caulobacter* bacterium such as *Caulobacter crescentus*, a *Streptomyces* bacterium such as *Streptomyces collinus*, or an *Enterococcus* bacterium such as *Enterococcus faecalis*. More preferable examples thereof include a DNA having a base sequence of a gene from a prokaryote such as a *Clostridium* bacterium or an *Escherichia* bacterium, and a DNA having a base sequence of a gene from *Clostridium acetobutylicum* or *Escherichia coli* is still more preferable.

CoA transferase, which is classified as Enzyme Commission number: 2.8.3.8, is a generic name for enzymes that catalyze a reaction of producing acetoacetate from acetoacetyl-CoA. Examples of CoA transferase include those from *Clostridium* bacteria such as *Clostridium acetobutylicum* or *Clostridium beijerinckii*, *Roseburia* bacteria such as *Roseburia intestinalis*, *Faecalibacterium* bacteria such as *Faecalibacterium prausnitzii*, *Coprococcus* bacteria, trypanosomes such as *Trypanosoma brucei*, or *Escherichia* bacteria such as *Escherichia coli*.

As a gene encoding CoA transferase, a DNA having a base sequence of a gene encoding CoA transferase obtained from any of the above microorganisms, or a synthesized DNA sequence synthesized based on a known base sequence of the gene, may be used. Preferable examples thereof include a DNA having a base sequence of a gene from a *Clostridium* bacterium such as *Clostridium acetobutylicum*, a *Roseburia* bacterium such as *Roseburia intestinalis*, a *Faecalibacterium* bacterium such as *Faecalibacterium prausnitzii*, a *Coprococcus* bacterium, trypanosomes such as *Trypanosoma brucei*, or an *Escherichia* bacterium such as *Escherichia coli*. More preferable examples thereof include a DNA having a base sequence of a gene from a *Clostridium* bacterium or an *Escherichia* bacterium, and a DNA having a base sequence of a gene from *Clostridium acetobutylicum* or *Escherichia coli* is still more preferable.

Acetoacetate decarboxylase, which is classified as Enzyme Commission number: 4.1.1.4, is a generic name for enzymes that catalyze a reaction of producing acetone from acetoacetate. Examples of acetoacetate decarboxylase include those from *Clostridium* bacteria such as *Clostridium acetobutylicum* or *Clostridium beijerinckii*, or *Bacillus* bacteria such as *Bacillus polymyxa*.

As a gene encoding acetoacetate decarboxylase, a DNA having a base sequence of a gene encoding acetoacetate decarboxylase obtained from any of the above microorganisms, or a synthesized DNA sequence that is synthesized based on a known base sequence of the gene, may be used. Preferable examples thereof include a DNA having a base sequence of a gene from a *Clostridium* bacterium such as *Clostridium acetobutylicum* or a *Bacillus* bacterium such as *Bacillus polymyxa*. The DNA is more preferably a DNA having a base sequence of a gene from *Clostridium acetobutylicum*.

Isopropyl alcohol dehydrogenase, which is classified as Enzyme Commission number: 1.1.1.80, is a generic name for enzymes that catalyze a reaction of producing isopropyl alcohol from acetone. Examples of isopropyl alcohol dehydrogenase include those from *Clostridium* bacteria such as *Clostridium beijerinckii*.

As a gene encoding isopropyl alcohol dehydrogenase, a DNA having a base sequence of a gene encoding isopropyl alcohol dehydrogenase obtained from any of the above microorganisms, or a synthesized DNA sequence that is synthesized based on a known base sequence of the gene, may be used. Preferable examples thereof include a DNA having a base sequence of a gene from a *Clostridium* bacterium, such as *Clostridium beijerinckii*.

From the viewpoint of the enzymatic activity, it is preferable that each of the above four kinds of enzymes is an enzyme from at least one selected from the group consisting of a *Clostridium* bacterium, a *Bacillus* bacterium, and an *Escherichia* bacterium. In particular, it is preferable that thiolase and CoA transferase are from an *Escherichia* bacterium, and acetoacetate decarboxylase and isopropyl alcohol dehydrogenase are from a *Clostridium* bacterium or *Clostridium* bacteria.

From the viewpoint of the enzymatic activity, it is preferable that each of the above four kinds of enzymes is from at least one selected from the group consisting of *Clostridium acetobutylicum*, *Clostridium beijerinckii*, and *Escherichia coli*. It is more preferable that each of thiolase and CoA transferase is from *Clostridium acetobutylicum* or *Escherichia coli*, that acetoacetate decarboxylase is from *Clostridium acetobutylicum*, and that isopropyl alcohol dehydrogenase is from *Clostridium beijerinckii*. It is still more preferable that thiolase and CoA transferase are from *Escherichia coli*, that acetoacetate decarboxylase is from *Clostridium acetobutylicum*, and that isopropyl alcohol dehydrogenase is from *Clostridium beijerinckii*.

The CoA transferase genes (atoD and atoA) and the thiolase gene (atoB) from *Escherichia coli* form an operon on the genome of *Escherichia coli* in the order of atoD, atoA, and atoB (Journal of Bacteriology, 1987; 169(1): 42-52). Therefore, the expression of the CoA transferase gene and the thiolase gene can be simultaneously controlled by modifying the atoD promoter.

In a case in which the CoA transferase activity and the thiolase activity are those obtained from genomic genes of the host *Escherichia coli*, it is preferable to enhance the expression of both enzyme genes by, for example, replacing the promoter responsible for the expression of both enzyme genes with another promoter, from the viewpoint of obtaining sufficient isopropyl alcohol production ability. Examples of the promoter that may be used for enhancing the expression of the CoA transferase activity and the thiolase activity include a glyceraldehyde-3-phosphate dehydrogenase (GAPDH) promoter from *Escherichia coli*. The GAPDH promoter from *Escherichia coli* is described at Base Nos. 397 to 440 in the base sequence information of GenBank accession number: X02662.

Examples of the isopropyl alcohol-producing *Escherichia coli* include a pIPA/B variant and a plaaa/B variant described in WO 2009/008377, which is capable of producing isopropyl alcohol from a plant-derived raw material. Examples thereof include a variant in which the CoA transferase activity and the thiolase activity are enhanced by enhancing the expression of the respective genes on the *Escherichia coli* genome, and in which the acetoacetate decarboxylase activity and the isopropyl alcohol dehydrogenase activity are enhanced through introduction of a plasmid or plasmids (also referred to as "pIa/B::atoDAB variant" in this specification). Other examples of the isopropyl alcohol-producing *Escherichia coli* include microorganisms described in WO 2009/094485, WO 2009/094485, WO 2009/046929, or WO 2009/046929.

The isopropyl alcohol-producing *Escherichia coli* may be an isopropyl alcohol-producing *Escherichia coli* in which the transcriptional repressor GntR is inactivated, and which has an isopropyl alcohol production pathway and a group of auxiliary enzymes exhibiting an enzymatic activity pattern that maintains or enhances the improved isopropyl alcohol production ability associated with the inactivation of the GntR activity. Such *Escherichia coli* leads to greater production of isopropyl alcohol.

The term "group of auxiliary enzymes" in the invention refers to one enzyme or two or more enzymes, which affect(s) isopropyl alcohol production ability. The group of auxiliary enzymes is not necessarily constituted by plural enzymes, and may be constituted by single kind of enzyme. An activity of each enzyme included in the group of auxiliary enzymes is inactivated, activated, or enhanced. The phrase the "enzymatic activity pattern" of the "group of auxiliary enzymes" as used herein refers to an enzymatic activity pattern of respective enzymes that is capable of maintaining or enhancing the improved isopropyl alcohol production amount achieved solely by inactivation of the GntR activity, and may refer to one enzyme or a combination of two or more enzymes.

Examples of preferable enzymatic activity patterns of the group of auxiliary enzymes include the following:

(i) maintenance of wild-type activities of glucose-6-phosphate isomerase (Pgi), glucose-6-phosphate-1-dehydrogenase (Zwf), and phosphogluconate dehydrogenase (Gnd);

(ii) inactivation of glucose-6-phosphate isomerase (Pgi) activity, and enhancement of glucose-6-phosphate-1-dehydrogenase (Zwf) activity; and (iii) inactivation of glucose-6-phosphate isomerase (Pgi) activity, enhancement of glucose-6-phosphate-1-dehydrogenase (Zwf) activity, and inactivation of phosphogluconate dehydrogenase (Gnd) activity.

Among these, the enzymatic activity pattern of the group of auxiliary enzymes described in item (iii) above is more preferable, from the viewpoint of isopropyl alcohol production ability.

The group of auxiliary enzymes and the enzymatic activity pattern thereof are not limited to those described above. The invention encompasses any group of auxiliary enzymes and enzymatic activity pattern thereof as long the GntR activity is inactivated, and the amount of isopropyl alcohol production in the isopropyl alcohol-producing *Escherichia coli* can be increased due to the group of auxiliary enzymes and the enzymatic activity pattern thereof.

GntR refers to a transcription factor that negatively regulates an operon involved in gluconate metabolism via the Entner-Doudoroff pathway. GntR is a generic name for GntR transcriptional repressors that suppress the functions of two groups of genes (GntI and GntII), which are responsible for the uptake and metabolism of gluconic acid.

Glucose-6-phosphate isomerase (Pgi), which is classified as Enzyme Commission number: 5.3.1.9, is a generic name for enzymes that catalyze a reaction of producing D-fructose-6-phosphate from D-glucose-6-phosphate.

Glucose-6-phosphate-1-dehydrogenase (Zwf), which is classified as Enzyme Commission number: 1.1.1.49, is a generic name for enzymes that catalyze a reaction of producing D-glucono-1,5-lactone-6-phosphate from D-glucose-6-phosphate. Examples of glucose-6-phosphate-1-dehydrogenase include those from *Deinococcus* bacteria such as *Deinococcus radiophilus*, *Aspergillus* fungi such as *Aspergillus niger* or *Aspergillus aculeatus*, *Acetobacter* bacteria such as *Acetobacter hansenii*, *Thermotoga* bacteria such as *Thermotoga maritima*, *Cryptococcus* fungi such as *Cryptococcus neoformans*, *Dictyostelium* fungi such as *Dictyostelium discoideum*, *Pseudomonas* such as *Pseudomonas fluorescens* or *Pseudomonas aeruginosa*, *Saccharomyces* such as *Saccharomyces cerevisiae*; *Bacillus* bacteria such as *Bacillus megaterium*, or *Escherichia* bacteria such as *Escherichia coli*.

As a gene encoding glucose-6-phosphate-1-dehydrogenase (Zwf), a DNA having a base sequence of gene encoding Zwf obtained from any of the above microorganisms, or a synthesized DNA sequence that is synthesized based on a known base sequence of the gene, may be used. Preferable examples thereof include a DNA having a base sequence of a gene from a *Deinococcus* bacterium such as *Deinococcus radiophilus*, an *Aspergillus* fungus such as *Aspergillus niger* or *Aspergillus aculeatus*; an *Acetobacter* bacterium such as *Acetobacter hansenii*, a *Thermotoga* bacterium such as *Thermotoga maritima*, a *Cryptococcus* fungus such as *Cryptococcus neoformans*, a *Dictyostelium* fungus such as *Dictyostelium discoideum*, *Pseudomonas* such as *Pseudomonas fluorescens* or *Pseudomonas aeruginosa*, *Saccharomyces* such as *Saccharomyces cerevisiae*, a *Bacillus* bacterium such as *Bacillus megaterium*, or an *Escherichia* bacterium such as *Escherichia coli*. More preferable examples thereof include a DNA having a base sequence of a gene from a prokaryote such as a *Deinococcus* bacterium, an *Aspergillus* fungus, an *Acetobacter* bacterium, a *Thermotoga* bacterium, *Pseudomonas*, a *Bacillus* bacterium, or an *Escherichia* bacterium. The DNA is more preferably a DNA having a base sequence of a gene from *Escherichia coli*.

Phosphogluconate dehydrogenase (Gnd), which is classified as Enzyme Commission number: 1.1.1.44, is a generic name for enzymes that catalyze a reaction of producing D-ribulose-5-phosphate and $CO_2$ from 6-phospho-D-gluconate.

The above-described impartment or enhancement of the enzymatic activity can be achieved by introducing a gene into a host, or enhancing a promoter activity for the enzyme gene that the host possesses on the genome, or replacing the promoter with another promoter; or any combination thereof.

A promoter in the isopropyl alcohol-producing *Escherichia coli* means a region to which an RNA polymerase having a sigma factor binds to start transcription. The promoter may be any promoter as long as it can control gene expression, and is preferably a potent promoter that constantly functions in the microorganism, and which is not susceptible to repression of expression even in the presence of glucose. Specific examples thereof include GAPDH promoter and a promoter of serine hydroxymethyltransferase.

In the isopropyl alcohol-producing *Escherichia coli*, a gene (ldhA) encoding lactate dehydrogenase (LdhA) may be disrupted. The disruption of lactate dehydrogenase suppresses lactate production even under culture conditions in which oxygen supply is restricted, as a result of which isopropyl alcohol can be efficiently produced. The "conditions in which oxygen supply is restricted" generally means, in a case in which air alone is used as the gas for aeration with agitation of the culture liquid, conditions with 0.02 vvm to 2.0 vvm (vvm: aeration volume [mL]/liquid volume [mL]/time [min]) and an agitation speed of 200 to 600 rpm. The lactate dehydrogenase (LdhA) refers to an enzyme that produces D-lactate and NAD from pyruvate and NADH.

Microorganism Involved in Glutamate Production

The acetyl-CoA producing microorganism according to the invention may have a pathway of any kind that produces glutamate producible from acetyl-CoA as an intermediate. Alternatively, the activity of one or more enzymes involved in a pathway that produces glutamate producible from acetyl-CoA as an intermediate may be enhanced in the acetyl-CoA producing microorganism according to the invention.

The acetyl-CoA producing microorganism according to the invention that has a glutamate production pathway can be obtained by constructing the acetyl-CoA producing microorganism according to the invention using a microorganism having a glutamate production pathway as a host, or imparting or enhancing any of the enzymatic activities relating to the glutamate production pathway in the acetyl-CoA producing microorganism according to the invention. Hereinafter, the microorganism having a glutamate production pathway may be referred to as "glutamate-producing microorganism".

Examples of the glutamate-producing microorganism include microorganisms having an ability to produce L-amino acids.

Specific examples of preferable glutamate-producing microorganisms include Enterobacteriaceae bacteria such as *Escherichia* bacteria and *Pantoea* bacteria, and coryneform bacteria such as *Corynebacterium glutamicum* in which the glutamate production pathway is imparted or enhanced.

A method of imparting the glutamate production ability to a microorganism or enhancing the glutamate production ability in a microorganism includes, for example, modifying the microorganism such that the expression of a gene encoding an enzyme involved in L-glutamate biosynthesis is increased and/or is overexpressed. Examples of the enzymes involved in L-glutamate biosynthesis include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose-phosphate isomerase, fructose-bisphosphate aldolase, phosphofructokinase, and glucose-phosphate isomerase. Among these enzymes, it is preferable to enhance the activity of one or more of citrate synthase, phosphoenolpyruvate carboxylase, or glutamate dehydrogenase, and it is more preferable to enhance the activity of all of the three enzymes. Examples of the glutamate-producing microorganism include a glutamate-producing microorganism described in Japanese Patent Application Laid-Open (JP-A) No. 2005-278643.

For the L-glutamate-producing microorganism, a microorganism having an ability to accumulate L-glutamate in an amount exceeding the saturation concentration of L-glutamate in a liquid medium when the microorganism is cultured under acidic conditions (hereinafter referred to as "L-glutamate-accumulating ability under acidic conditions") may be used. For example, a variant having increased resistance to L-glutamate in a low-pH environment may be obtained by a method described in European Patent Application Laid-open No. 1078989, whereby the ability to accumulate L-glutamate in an amount exceeding the saturation concentration is imparted to the microorganism according to the invention.

Specific examples of microorganisms having an intrinsic L-glutamate-accumulating ability under acidic conditions include *Pantoea ananatis* AJ13356 (FERM BP-6615) and AJ13601 (FERM BP-7207) (see European Patent Application Laid-open No. 0952221). *Pantoea ananatis* AJ13356 was deposited with National Institute of Bioscience and Human-Technology, Agency of Industrial Science and Technology, Ministry of International Trade and Industry (present name: International Patent Organism Depositary, National Institute of Technology and Evaluation (NITE-IPOD)) under accession No. FERM P-16645 on Feb. 19, 1998, and then transferred to an international depositary authority under the Budapest Treaty under accession No. FERM BP-6615 on Jan. 11, 1999. This strain was identified as *Enterobacter agglomerans* and deposited as *Enterobacter agglomerans* AJ13355 when first isolated, but, according to recent base sequence analysis of the 16S rRNA and the like, the strain was reclassified as *Pantoea ananatis* (see Examples below). Similarly, AJ13356 and AJ13601, strains derived from AJ13355, were deposited to the above depositary as *Enterobacter agglomerans*, but these strains are described as *Pantoea ananatis* in the present specification. AJ13601 was deposited with National Institute of Bioscience and Human-Technology, Agency of Industrial Science and Technology, Ministry of International Trade and Industry (present name: International Patent Organism Depositary, National Institute of Technology and Evaluation (NITE-IPOD) under accession No. FERM P-17156 on Aug. 18, 1999, and then transferred to an international depository authority under the Budapest Treaty under accession No. FERM BP-7207 on Jul. 6, 2000.

Other examples of the method of imparting or enhancing the L-glutamate production ability include a method of imparting resistance to an organic acid analogue or a respiratory inhibitor, and a method of imparting sensitivity to a cell wall synthesis inhibitor. Specific examples thereof include: a method of imparting resistance to monofluoroacetic acid (JP-A No. S50-113209); a method of imparting resistance to adenine or resistance to thymine (JP-A No. S57-065198); a method of weakening urease (JP-A No. S52-038088); a method of imparting resistance to malonic acid (JP-A No. S52-038088); a method of imparting resistance to benzopyrone or naphthoquinones (JP-A No. S56-001889); a method of imparting resistance to HOQNO (JP-A No. S56-140895); a method of imparting resistance to α-ketomalonic acid (JP-A No. S57-002689 A); a method of imparting resistance to guanidine (JP-A No. S56-035981), and a method of imparting resistance to penicillin (JP-A No. H04-088994).

Specific examples of such resistant microorganisms include the following strains.

*Brevibacterium flavum* AJ3949 (FERM BP-2632; see JP-A No. S50-113209)

*Corynebacterium glutamicum* AJ11628 (FERM P-5736; see JP-A No. S57-065198)

*Brevibacterium flavum* AJ11355 (FERM P-5007; see JP-A No. S56-001889)

*Corynebacterium glutamicum* AJ11368 (FERM P-5020; see JP-A S56-001889)

*Brevibacterium flavum* AJ11217 (FERM P-4318; see JP-A No. S57-002689)

*Corynebacterium glutamicum* AJ11218 (FERM P-4319; see JP-A No. S57-002689)

*Brevibacterium flavum* AJ11564 (FERM P-5472; see JP-A No. S56-140895)

*Brevibacterium flavum* AJ11439 (FERM P-5136; see JP-A No. S56-035981)

*Corynebacterium glutamicum* H7684 (FERM BP-3004; see JP-A No. H04-088994)

*Brevibacterium lactofermentum* AJ11426 (FERM P-5123; see JP-A No. S56-048890)

*Corynebacterium glutamicum* AJ11440 (FERM P-5137; see JP-A No. S56-048890)

*Brevibacterium lactofermentum* AJ11796 (FERM P-6402; see JP-A No. S58-158192)

Preferable examples of the microorganism having an L-glutamine production ability include a microorganism in which the glutamate dehydrogenase activity is enhanced, a microorganism in which the glutamine synthetase (glnA) activity is enhanced, and a microorganism in which the glutaminase gene is disrupted (see the specification of European Patent Application Laid-open Nos. 1229121 and 1424398). Enhancement of the glutamine synthetase activity can also be achieved by disrupting glutamine adenylyl transferase (glnE) or disrupting the PII regulation protein (glnB). Other preferable examples of the L-glutamine-producing microorganism include a variant belonging to genus *Escherichia* harboring a mutant glutamine synthetase in which the tyrosine residue at position 397 of glutamine synthetase is replaced by another amino acid residue (U.S. Patent Application Laid-open No. 2003-0148474).

Other examples of the method of imparting or enhancing the L-glutamine production ability include: a method of imparting resistance to 6-diazo-5-oxo-norleucine (JP-A No. H03-232497); a method of imparting resistance to a purine analogue and resistance to methionine sulfoxide (JP-A No. S61-202694); and a method of imparting resistance to α-ketomaleic acid (JP-A No. S56-151495). Specific examples of coryneform bacteria having the L-glutamine production ability include the following microorganisms.

*Brevibacterium flavum* AJ11573 (FERM P-5492; JP-A No. S56-161495)

*Brevibacterium flavum* AJ11576 (FERM BP-10381; JP-A No. S56-161495)

*Brevibacterium flavum* AJ12212 (FERM P-8123; JP-A No. S61-202694)

Preferable examples of microorganisms that produce proline, leucine, isoleucine, valine, arginine, citrulline, ornithine, and/or polyglutamic acid include a microorganism described in JP-A No. 2010-41920. Microorganisms that produce acetic acid, (poly)3-hydroxybutyric acid, itaconic acid, citric acid, and/or butyric acid are described in Fermentation Handbook (Kyoritsu Shuppan Co., Ltd.). Examples of microorganisms that produce 4-aminobutyric acid include a microorganism obtained by introducing glutamate decarboxylase into a glutamate-producing microorganism (JP-A No. 2011-167097). Examples of microorganisms that produce 4-hydroxybutyric acid include a microorganism obtained by introducing glutamate decarboxylase, transaminase, and/or aldehyde dehydrogenase into a glutamate-producing microorganism (JP-A No. 2009-171960).

Examples of microorganisms that produce 3-hydroxyisobutyric acid include a microorganism to which a pathway described in WO 2009/135074 or a pathway described in WO 2008/145737 has been introduced. Examples of microorganisms that produce 2-hydroxyisobutyric acid include a microorganism to which a pathway described in WO 2009/135074 or a pathway described in WO 2009/156214 has been introduced. Examples of microorganisms that produce 3-aminoisobutyric acid and/or methacrylic acid include a microorganism to which a pathway described in WO 2009/135074 has been introduced.

Method of Producing Acetyl-CoA and Method of Producing Metabolite Producible from Acetyl-CoA as Intermediate A method of producing acetyl-coA and a method of producing a metabolite producible from acetyl-CoA as an intermediate according to the first invention include: a culture step of culturing the acetyl-CoA producing microorganism according to the first invention while contacting the acetyl-CoA producing microorganism with a carbon source material; and a collection step of collecting an intended product (acetyl-coA, or a metabolite producible from acetyl-coA as an intermediate) obtained by the contacting. Examples of the metabolites producible from acetyl-coA as an intermediate include acetone, isopropyl alcohol, and glutamic acid. In the invention, acetyl-coA and the metabolite producible from acetyl-coA as an intermediate may also be collectively referred to as "intended product".

The method of producing acetyl-coA and the method of producing a metabolite producible from acetyl-coA as an intermediate according to the second invention include: a culture step of culturing the acetyl-CoA producing microorganism according to the second invention while contacting the acetyl-CoA producing microorganism with a carbon source material; and a collection step of collecting an intended product (acetyl-coA, or a metabolite producible from acetyl-coA as an intermediate) obtained by the contacting. Examples of the metabolites producible from acetyl-coA as an intermediate include citric acid, itaconic acid, and (poly)3-hydroxybutyric acid. In the invention, acetyl-coA and the metabolite producible from acetyl-coA as an intermediate may also be collectively referred to as "intended product".

According to the production methods described above, since each microorganism is cultured while contacting the microorganism with a carbon source material, the carbon source material is assimilated by the acetyl-CoA producing microorganism and carbon dioxide is fixed, whereby an intended product can be efficiently produced.

The carbon source material is not specifically limited as long as the material contains a carbon source that can be assimilated by the microorganism, and the material is preferably a plant-derived raw material. The plant-derived raw material refers to an organ such as a root, a stem, a trunk, a branch, a leaf, a flower, and a seed; a plant body containing the organ; and a decomposition product of the plant organ. Furthermore, from among the carbon sources obtained from the plant body, the plant organ, or the decomposition product thereof, those that can be used as carbon sources by the microorganism during cultivation are also included within the scope of the plant-derived raw material.

General examples of carbon sources contained in the plant-derived raw material include sugars such as starch, sucrose, glucose, fructose, xylose, and arabinose; herbaceous or ligneous plant decomposition products containing the above ingredients in large amounts; cellulose hydrolysates; and any combinations thereof. The scope of the carbon source in the invention further includes vegetable oil-derived glycerin or a fatty acid.

Preferable examples of the plant-derived raw material include agricultural crops such as grain, specifically, corn, rice, wheat, soybean, sugarcane, beet, or cotton, and any combinations thereof. The form thereof as the raw material is not specifically limited, and may be a crude product, squeezed juice, a crushed product, or the like. Alternatively, the plant-derived raw material may be in a form that consists only of the carbon source described above.

The contact between the acetyl-CoA producing microorganism and the plant-derived raw material in the culture step is generally achieved by culturing the acetyl-CoA producing microorganism in a culture medium containing the plant-derived raw material.

The density of contact between the plant-derived raw material and the acetyl-CoA producing microorganism may be varied depending on the activity of the acetyl-CoA producing microorganism. In general, the concentration of the plant-derived raw material in the culture medium may be adjusted such that the initial sugar concentration in terms of glucose-equivalent sugar concentration is set to 20% by mass or less with respect to the total mass of the mixture (the mixture containing the acetyl-CoA producing microorganism and carbon source material). From the viewpoint of sugar tolerance of the acetyl-CoA producing microorganism, the initial sugar concentration is preferably set to 15% by mass or less. The addition amounts of other components are not particularly limited as long as they are amounts that are usually added to culture media for microorganisms.

The method of producing acetyl-coA according to the invention may further include a supply step of supplying a carbonate ion, a bicarbonate ion, carbon dioxide gas (carbon dioxide), and/or a reductant, to a culture medium used for cultivation. In a case in which a carbonate ion, a bicarbonate ion, and/or carbon dioxide gas is supplied to a culture medium used for cultivation, the activity of enzymes such as phosphoenolpyruvate carboxylase, pyruvate carboxylase, or phosphoenolpyruvate carboxykinase is enhanced and the fixation amount of carbon dioxide is increased, whereby an intended product can be efficiently produced. The conditions such as the temperature, pH, and the like in the supply step are the same as the conditions in the culture step unless otherwise specified.

Any carbonate ion or bicarbonate ion may be used as long as it is derived from a component capable of generating a carbonate ion and/or a bicarbonate ion when supplied to the culture medium. Examples of the component capable of generating a carbonate ion and/or a bicarbonate ion include sodium carbonate, sodium hydrogen carbonate, potassium carbonate, potassium hydrogen carbonate, ammonium carbonate, ammonium hydrogen carbonate, magnesium carbonate, and calcium carbonate.

The amount of carbonate ions and/or bicarbonate ions supplied to the culture medium is not particularly limited as long as the intended product can be efficiently produced. The total supply amount per 1 L of the culture medium is preferably 150 mmol or more. In a case in which 150 mmol or more of carbonate ions and/or bicarbonate ions is supplied, the yield of the intended product can be sufficiently increased. The total supply amount of carbonate ions and/or bicarbonate ions per 1 L of the culture medium is more preferably 200 mmol or more.

The total supply amount of carbonate ions and/or bicarbonate ions per 1 L of the culture medium is preferably 5 mol or less. In a case in which the total supply amount per 1 L of the culture medium is 5 mol or less, it is less likely that excessive amounts of carbonate ions and bicarbonate ions, which are not utilized by the microorganism cell in the culture step, are produced. The total supply amount of carbonate ions and/or bicarbonate ions per 1 L of the culture medium is more preferably 3 mol or less, and still more preferably 2 mol or less.

The method of supplying carbonate ions and/or bicarbonate ions may be a known method. The timing of supply is not specifically limited, and may be the beginning of the culture or during the culture. The carbonate ions and/or bicarbonate ions may be supplied in a batch, or may be supplied intermittently.

As the carbon dioxide gas, any carbon dioxide gas can be used as long as it is a gas including carbon dioxide. For example, the carbon dioxide gas may be air. The carbon dioxide concentration of the carbon dioxide gas is preferably higher than the carbon dioxide concentration in the air, more preferably 0.1% v/v or more, and still more preferably 1% v/v or more.

The carbon dioxide concentration is preferably 75% v/v or less, more preferably 50% v/v or less, and still more preferably 25% v/v or less.

The carbon dioxide gas can be dissolved in the culture medium by bubbling or the like. The average bubble diameter of the carbon dioxide gas to be supplied to the culture medium is not specifically limited as long as the intended product can be efficiently produced. For example, the carbon dioxide gas with an average bubble diameter of 100 μm or more is preferable. In a case in which the carbon dioxide gas has an average bubble diameter of 100 μm or more, it is less likely that foamability of the culture medium increases drastically, and the increase in foamability makes it difficult to continue the fermentation. The carbon dioxide gas is more preferably one with an average bubble diameter of 200 μm or more, and more preferably carbon dioxide gas with an average bubble diameter of 500 μm or more. The carbon dioxide gas is preferably carbon dioxide gas with an average bubble diameter of 100 cm or less. Carbon dioxide gas with an average bubble diameter of 100 cm or less is preferable, since carbon dioxide can sufficiently dissolve in the culture medium. The carbon dioxide gas is more preferably carbon dioxide gas with an average bubble diameter of 50 cm or less, and more preferably carbon dioxide gas with an average bubble diameter of 20 cm or less.

The carbon dioxide gas can be supplied to the culture medium using a conventionally used bubble generator. Examples of the bubble generator include an air sparger.

Examples of the method of measuring the average bubble diameter include: a measuring method by a laser diffraction/scattering method using a particle size distribution measurement apparatus (for example, LS 13 320 manufactured by Beckman Coulter); a measuring method based on a pore electrical resistance method using a precise particle size distribution measurement apparatus (for example, MULTISIZER 3 manufactured by Beckman Coulter); and a method in which a gray-scale image is processed to make a binary image using a high-speed video camera.

The reductant is not particularly limited as long as it is a component that can reduce components in the culture medium or the microorganism cell during cultivation while the reductant itself is oxidized. Examples thereof include sulfides, carbon compounds, and hydrogen. Specific examples of sulfides include a sulfite (such as sodium sulfite, sodium hydrogen sulfite, potassium sulfite, or ammonium sulfite); a thiosulfate (such as sodium thiosulfate or potassium thiosulfate); a salt of a sulfide ion (such as sodium sulfide, sodium hydrogen sulfide, potassium sulfide, or ammonium sulfide); cysteine, sulfur dioxide, and hydrogen sulfide. Specific examples of the carbon compounds include alcohols, fatty acids, paraffin, and carbon oxide. The reductant is preferably a sulfide, more preferably sodium sulfite, sodium hydrogen sulfite, sodium sulfide, or cysteine, and still more preferably sodium sulfite.

The concentration of the reductant to be supplied to the culture medium is not particularly limited as long as the intended product can be efficiently produced, and may be appropriately set in accordance with the component to be supplied. For example, the concentration of sodium sulfite per 1 L of the culture medium is preferably 0.01 g/L or more, more preferably 0.1 g/L or more, and even more preferably 1 g/L or more. The concentration of the reductant to be supplied is preferably 50 g/L or less, more preferably 20 g/L or less, and even more preferably 10 g/L or less.

The acetyl-CoA production method according to the invention may further include a gas supply step of collecting a gas that contains carbon dioxide generated by the culturing and supplying the gas to a culture medium used for the culturing. That is, the carbon dioxide gas that is not consumed in the culture medium and is released as exhaust air may be circulated and reused by resupplying it to the culture medium.

The method of supplying the gas to the culture medium is not specifically limited as long as it is a conventionally used method. Examples thereof include a method in which a gas is pressurized and discharged to a liquid from a circular or plate-like member having fine pores (in a case in which the gas is air, the method is called an aerate method or an aeration method); a method in which a gas is supplied from a hollow pipe, called draft tube, that has voids on an entire side circumferential surface; and a method using an air sparger (gas dispersion apparatus in which a porous material having numerous pores for generating fine bubbles of air or the like is attached to the tip of a plastic or stainless tube).

The content of the acetyl-CoA producing microorganism in the culture medium may be varied in accordance with the kind and the activity of the microorganism. Generally, a preculture bacterial liquid (OD 660 nm=4 to 8) may be added at the start of cultivation in an amount of from 0.1% by mass to 30% by mass with respect to the culture liquid, and preferably in an amount of from 1% by mass to 10% by mass from the viewpoint of controlling culture conditions.

The culture medium for culture of the acetyl-CoA producing microorganism is not particularly limited as long as it is a culture medium that is usually employed and that includes a carbon source, a nitrogen source, and an inorganic ion, and further an inorganic trace element, a nucleic acid, and a vitamin, etc., required by the microorganism to produce the intended product.

In the first invention, the culture condition in the culture process is not particularly limited, and culturing may be carried out, for example, under aerobic conditions at an appropriately controlled pH and temperature within a range of pH 4 to 9 (preferably pH 6 to 8) and a range of 20° C. to 50° C. (preferably 25° C. to 42° C.).

In the second invention, the culture condition in the culture process is not particularly limited. In the case of *Aspergillus* fungi, culturing may be carried out, for example, under aerobic conditions at an appropriately controlled pH and temperature within a range of pH 1 to 10 (preferably pH 3 to 7) and a range of 20° C. to 50° C. (preferably 25° C. to 42° C.). In the case of *Cupriavidus* bacteria, culturing may be carried out, for example, under aerobic conditions at an appropriately controlled pH and temperature within a range of pH 4 to 9 (preferably pH 6 to 8) and a range of 20° C. to 50° C. (preferably 25° C. to 42° C.).

The aeration volume of a gas into the mixture that contains the acetyl-CoA producing microorganism and the carbon source material is not particularly limited. In a case in which air alone is used as the gas, the aeration volume is generally from 0.02 vvm to 2.0 vvm (vvm: aeration volume [mL]/liquid volume [mL]/time [min]) at 50 to 600 rpm. From the viewpoint of suppressing physical damage to the microorganism, the aeration is carried out preferably at 0.1 vvm to 2.0 vvm, and more preferably at 0.1 vvm to 1.0 vvm.

The culture process may be continued from the beginning of the cultivation until the carbon source material in the mixture is exhausted, or until the activity of the acetyl-CoA producing microorganism disappears. The duration of the culture process may be varied in accordance with the number and the activity of the acetyl-CoA producing microorganism in the mixture and the amount of the carbon source material. In general, the duration may be at least one hour, and preferably at least four hours. In the culture process, the duration of the culture process may be continued indefinitely by addition of the carbon source material or the acetyl-CoA producing microorganism, However, from the viewpoint of process efficiency, the duration may generally be set to 5 days or less, preferably to 72 hours or less. With regard to other conditions, conditions employed for usual cultivation may be applied as they are.

The method of collecting an intended product accumulated in the culture medium is not particularly limited. Since the culture liquid obtained by the culture process is a mixture of the intended product and other component(s), a method in which the microorganism cell is removed from the culture medium by centrifugal separation or the like, and then the intended product is separated using a conventional separation method such as distillation or membrane separation under conditions suitable for the kind of the intended product, for example, may be applied.

The method of producing acetyl-CoA according to the invention may further include, before the culture process, a preculture process for achieving an appropriate number of cells and/or appropriate activated state of the acetyl-CoA producing microorganism to be used. The preculture process may be any cultivation conducted under usually-employed conditions suitable for the type of the acetyl-CoA producing microorganism.

Method of Producing Isopropyl Alcohol and Method of Producing Acetone

The method of producing isopropyl alcohol and the method of producing acetone according to the invention include producing an intended product, which is isopropyl alcohol or acetone, respectively, from a carbon source material using the acetyl-CoA producing microorganism. That is, each of the method of producing isopropyl alcohol and the method of producing acetone according to the invention includes a culture step of culturing the acetyl-CoA producing microorganism while contacting the acetyl-CoA producing microorganism with a carbon source material; and a collection step of collecting an intended product (isopropyl alcohol or acetone) obtained by the contacting.

The acetyl-CoA producing microorganism used in the method of producing isopropyl alcohol is preferably an acetyl-CoA producing microorganism having a thiolase activity, a CoA transferase activity, an acetoacetate decarboxylase activity, and an isopropyl alcohol dehydrogenase activity, described above as a preferable example of the acetyl-CoA producing microorganism, from the viewpoint of the efficiency of isopropyl alcohol production.

The acetyl-CoA producing microorganism used in the method of producing acetone is preferably an acetyl-CoA producing microorganism having a thiolase activity, a CoA transferase activity, and an acetoacetate decarboxylase activity, described above as a preferable example of the acetyl-CoA producing microorganism, from the viewpoint of the efficiency of acetone production.

Each of the method of producing isopropyl alcohol and the method of producing acetone preferably includes a culture step in which the acetyl-CoA producing microorganism is cultured while supplying a gas into the mixture containing the acetyl-CoA producing microorganism and the carbon source material (also referred to as "aeration culture step"); and an intended product collection step in which an intended product (isopropyl alcohol or acetone) produced by the culture step is separated and collected from the mixture. During the aeration culture in the aeration culture step, the intended product is released into the mixture, and evaporates from the mixture. As a result, the intended product can be easily separated from the mixture. Further, since the intended product is continuously separated from the mixture, an increase in the concentration of the intended product in the mixture can be suppressed. Therefore, it is not necessary to pay particular attention to the tolerance of the acetyl-CoA producing microorganism for the intended product. With regard to culture conditions, those described above shall apply as they are.

The method of collecting an intended product in the intended product collection step may be any method as long as the intended product in the gaseous or droplet state that evaporates from the mixture during cultivation can be collected. Examples thereof include a method of collecting the intended product into a collecting member such as a commonly-employed airtight container. In particular, the method preferably includes contacting a trap solution for trapping the intended product with the intended product separated from the mixture, from the viewpoint of collecting only the intended product with high purity.

In the method of producing isopropyl alcohol and the method of producing acetone, an intended product can be collected in a state in which the intended product is dissolved in a trap solution or the mixture. Examples of the collection method include a method described in WO 2009/008377. In a case in which the intended product collected is in the state of aqueous solution, the method according to the invention may further include a dehydration process. The dehydration of the intended product can be carried out by an ordinary method. The intended product collected can be confirmed using a usual detection means such as HPLC. The intended product collected may be further purified, if necessary. Examples of the purification method include distillation.

Examples of apparatuses applicable to the method of producing an intended product in which the intended product can be collected in the state being dissolved in the trap solution or the mixture include the production apparatus illustrated in FIG. 1 of WO 2009/008377. In this production apparatus, an injection pipe for injecting a gas from outside the apparatus is connected to a culture tank that contains a culture medium including the microorganism to be used and a plant-derived raw material, thereby enabling aeration to the culture medium. A trap tank that contains a trap solution (trap liquid) is connected to the culture tank via a connecting pipe. The intended product, which has been produced in the culture tank during aeration culture, evaporates due to aeration, and, therefore, can easily be separated from the culture medium. The gas or liquid that has moved to the trap tank contacts the trap solution, and bubbling occurs. As a result, the gas or liquid is trapped in the trap solution. By using this production apparatus, an intended product can be produced in a more purified state in a simple and continuous manner.

Method of Producing Glutamate

The method of producing glutamate according to the invention includes producing glutamate as an intended product from a carbon source material using the acetyl-CoA producing microorganism. Specifically, the method of producing glutamate according to the invention includes a culture step of culturing the acetyl-CoA producing microorganism while contacting the acetyl-CoA producing microorganism with a carbon source material; and a collection step of collecting an intended product (glutamate) obtained by the contacting.

According to the method of producing glutamate according to the invention, since the acetyl-CoA producing microorganism is cultured while contacting the acetyl-CoA producing microorganism with a carbon source material, the carbon source material is assimilated by the acetyl-CoA producing microorganism, whereby glutamate can be efficiently produced while carbon dioxide is fixed.

The culture medium used for cultivation may be any culture medium usually employed that includes a carbon source, a nitrogen source, and an inorganic salt, and organic trace nutrients such as amino acids and vitamins. A synthetic culture medium and/or a natural culture medium may be used. Each of the carbon source and the nitrogen source used in the culture medium may be of any type that can be utilized by the microorganism to be cultured.

Examples of the carbon source include: a sugar such as glucose, glycerol, fructose, sucrose, maltose, mannose, galactose, starch hydrolysates, or molasses; an organic acid such as acetic acid or citric acid, and an alcohol such as ethanol. These carbon sources may be used singly or in combination with other carbon sources. Examples of the nitrogen source include ammonia, an ammonium salt such as ammonium sulfate, ammonium carbonate, ammonium chloride, ammonium phosphate, or ammonium acetate, and a nitric acid salt. Examples of the inorganic salt include a phosphoric acid salt, a magnesium salt, a calcium salt, an iron salt, and a manganese salt. Examples of the organic trace nutrient include: an amino acid, a vitamin, a fatty acid, and a nucleic acid; and a peptone, a casamino acid, a yeast extract, and soybean protein hydrolysates, which contain the above ingredients. In a case in which an auxotrophic mutant that requires an amino acid or the like for growth is used, it is preferable to supply the required nutrient.

The culture is preferably carried out at a fermentation temperature of 20° C. to 45° C. and a pH of 3 to 9 under aeration. For adjusting pH, an inorganic or organic, acidic or alkaline substance, ammonia gas, etc. may be used. L-amino acid is accumulated in the culture medium or in the bacterial cells when the microorganism is cultured preferably for about 10 hours to about 120 hours under these conditions.

In a case in which the L-amino acid of interest is L-glutamate, the culture may be carried out while L-glutamate is precipitated in the culture medium, by using a liquid medium whose conditions are adjusted to precipitate L-glutamate. For example, the conditions to precipitate L-glutamate may be an acidic condition with pH 4.0 to 5.0, preferably pH 4.0 to 4.5, more preferably pH 4.0 to 4.3, and still more preferably pH 4.0. For achieving both increased growth under acidic conditions and efficient precipitation of L-glutamate, the pH is preferably from 4.0 to 5.0, more preferably from 4.0 to 4.5, and still more preferably from 4.0 to 4.3. Cultivation at the above-described pH may be carried out either throughout the whole culture period or during a part of the culture period.

The L-amino acid may be collected from the culture liquid according to a known collection method after completion of the culture. For example, the collection may be carried out by a method in which concentration crystallization is carried out after removal of bacterial cells from a culture medium, or by ion-exchange chromatography. In a case in which the culture is carried out under conditions that allow precipitation of L-glutamate in a culture medium, the L-glutamate precipitated in the culture medium can be collected by centrifugal separation, filtration, or the like. In such cases, L-glutamate dissolved in the culture medium may be collected together, after being crystallized.

Method of Producing Citric Acid, Method of Producing Itaconic Acid and Method of Producing (Poly)3-Hydroxybutyric Acid Each of a method of producing citric acid, a method of producing itaconic acid, and a method of producing (poly) 3-hydroxybutyric acid according to the invention includes producing a corresponding intended product (citric acid, itaconic acid, or (poly)3-hydroxybutyric acid) from a carbon source material using the acetyl-CoA producing microorganism. Specifically, the method of producing citric acid, the method of producing itaconic acid, and the method of producing (poly)3-hydroxybutyric acid according to the invention include a culture step of culturing the acetyl-CoA producing microorganism while contacting the acetyl-CoA producing microorganism with a carbon source material; and a collection step of collecting an intended product (citric acid, itaconic acid, or (poly)3-hydroxybutyric acid) obtained by the contacting.

According to the above respective methods, since the acetyl-CoA producing microorganism is cultured while the acetyl-CoA producing microorganism is contacted with a carbon source material, the carbon source material is assimilated by the acetyl-CoA producing microorganism, whereby an intended product (citric acid, itaconic acid, or (poly)3-hydroxybutyric acid) can be efficiently produced while carbon dioxide is fixed.

The culture medium used for cultivation may be any culture medium usually employed that includes a carbon source, a nitrogen source, and an inorganic salt, and organic trace nutrients such as amino acids and vitamins. A synthetic culture medium and/or a natural culture medium may be used. Each of the carbon source and nitrogen source used in the culture medium may be of any type that can be utilized by the microorganism to be cultured.

Examples of the carbon source include: a sugar such as glucose, glycerol, fructose, sucrose, maltose, mannose, galactose, starch hydrolysates, or molasses; an organic acid such as acetic acid or citric acid, and an alcohol such as ethanol. These carbon sources may be used singly or in combination with other carbon sources. Examples of the nitrogen source include ammonia, an ammonium salt such as ammonium sulfate, ammonium carbonate, ammonium chloride, ammonium phosphate, or ammonium acetate, and a nitric acid salt. Examples of the inorganic salt include a phosphoric acid salt, a magnesium salt, a calcium salt, an iron salt, and a manganese salt. Examples of the organic trace nutrients include: an amino acid, a vitamin, a fatty acid, and a nucleic acid; and a peptone, a casamino acid, a yeast extract, and soybean protein hydrolysates, which contain the above ingredients. In a case in which an auxotrophic mutant that requires an amino acid or the like for growth is used, it is preferable to supply the required nutrient.

In the method of producing citric acid, the method of producing itaconic acid, and the method of producing (poly) 3-hydroxybutyric acid according to the invention, an intended product (citric acid, itaconic acid, or (poly)3-hydroxybutyric acid) can be collected in a state in which the intended product is dissolved in a culture liquid, in a state in which the intended product is precipitated, as a solid, from a culture liquid, or in a state in which the intended product is accumulated in bacterial cells. In a case in which the intended product collected is in the state of aqueous solution, the method according to the invention may further include a dehydration process. The dehydration of the intended product can be carried out by an ordinary method. The intended product collected can be confirmed using a usual detection means such as HPLC. The intended product collected may be further purified, if necessary. Examples of the purification method include crystallization, and purification by a column such as an ion-exchange resin.

Examples of a method of producing proline, leucine, isoleucine, valine, arginine, citrulline, ornithine, acetic acid, (poly)3-hydroxybutyric acid, itaconic acid, citric acid, butyric acid, or polyglutamic acid to which the microorganism according to the invention can be applied include methods described in p 363-p 364, p 61-p 63, p 61-p 63, p 61-p 63, p 40-p 42, p 40-p 42, p 40-p 42, p 189-p 192, p 377-p 378, p 64-p 65, p 124-p 125, p 19-p 23, and p 373, respectively, of Fermentation Handbook (Kyoritsu Shuppan Co., Ltd.).

Examples of a method of producing 4-aminobutyric acid to which the microorganism according to the invention can be applied include a production method using a microorganism obtained by introducing glutamate decarboxylase to a glutamate-producing microorganism (JP-A No. 2011-167097).

Examples of a method of producing 4-hydroxybutyric acid to which the microorganism according to the invention can be applied include a production method using a microorganism obtained by introducing glutamate decarboxylase, aminotransferase, and aldehyde dehydrogenase to a glutamate-producing microorganism (JP-A No. 2009-171960).

Examples of a method of producing 3-hydroxyisobutyric acid to which the microorganism according to the invention can be applied include a production method using a microorganism to which the pathway described in WO 2009/135074 or the pathway described in WO 2008/145737 is introduced.

Examples of a method of producing 2-hydroxyisobutyric acid to which the microorganism according to the invention can be applied include a production method using a microorganism to which the pathway described in WO 2009/135074 or the pathway described in WO 2009/156214 is introduced.

Examples of a method of producing 3-aminoisobutyric acid or methacrylic acid to which the microorganism according to the invention can be applied include a production method using a microorganism to which the pathway described in WO 2009/135074 is introduced.

EXAMPLES

The present invention will now be described in detail by reference to examples. However, the present invention is by no means restricted to the examples.

The promoter of glyceraldehyde-3-phosphate dehydrogenase (GAPDH) from *Escherichia coli* can be used as a promoter necessary for expression of a gene introduced from outside the cell. The base sequence of the GAPDH promoter from *Escherichia coli* is indicated in Base Nos. 397 to 440 of the base sequence information of GenBank accession number X02662. In the following examples, the term "GAPDH promoter" refers to the GAPDH promoter as specified above.

*Escherichia coli* MG1655 is available from ATCC (American Type Culture Collection).

*Escherichia coli* B (ATCC 11303) is available from ATCC.

Genomic DNA (ATCC 33009D-5) of *Methylococcus capsulatus* ATCC 33009 is available from ATCC.

*Corynebacterium* DSM 1412 is available from DSMZ (German Collection of Microorganisms and Cell Cultures).

*Rhodococcus jostii* NBRC 16295 is available from NBRC (National Institute of Technology and Evaluation, Biological Resource Center).

*Aspergillus niger* ATCC 1015 is available from ATCC.

*Aspergillus terreus* NBRC 6365 is available from NBRC.

*Cupriavidus necator* JMP 134 (DSM 4058) is available from DSMZ.

Example 1

<Preparation of Plasmid pMWGKC>

In order to obtain the GAPDH promoter, amplification was performed by PCR using the genomic DNA of *Escherichia coli* MG1655 as a template and using CGAGCTA-CATATGCAATGATTGACACGATTCCG (SEQ ID NO:42) and CGCGCGCATGCTATTTGTTAGTGAATAAAAGG (SEQ ID NO:43) as primers. The resulting DNA fragment was digested with restriction enzymes NdeI and SphI to obtain an about 110 bp DNA fragment corresponding to the GAPDH promoter. This DNA fragment was mixed with a fragment obtained by digesting plasmid pBR322 (GenBank accession number J01749) with restriction enzymes NdeI and SphI, and the mixed fragments were ligated using a ligase. Then, *Escherichia coli* DH5α strain competent cells (DNA-903, TOYOBO Co., Ltd.) were transformed with the ligation product, and a transformant growing on an LB agar plate containing 50 μg/mL ampicillin was obtained. The obtained colony was cultured overnight at 37° C. in an LB liquid medium containing 50 μg/mL ampicillin, and a plasmid was recovered from the resulting bacterial cells to obtain a plasmid pBRgapP.

Amplification was performed by PCR using this plasmid pBRgapP as a template and using CCGCTCGAGCATAT-GCTGTCGCAATGATTGACACG (SEQ ID NO:44) and GCTATTCCATATGCAGGGTTATTGTCTCATGAGC (SEQ ID NO:45) as primers. The resulting DNA fragment was phosphorylated with T4 Polynucleotide Kinase (Takara) to obtain a DNA fragment containing the GAPDH promoter.

Plasmid pMW119 (GenBank accession number AB005476) was treated with restriction enzymes NdeI, and the ends of the resulting DNA fragment were blunted with KOD plus DNA Polymerase (Takara), thereby obtaining a DNA fragment containing the pMW119 replication origin.

The DNA fragment containing the GAPDH promoter and the DNA fragment containing the pMW119 replication origin were mixed and ligated using a ligase. Then, *Escherichia coli* DH5α strain competent cells were transformed with the ligation product, and a transformant growing on an LB agar plate containing 50 μg/mL ampicillin was obtained. The obtained colony was cultured overnight at 37° C. in an LB liquid medium containing 50 μg/mL ampicillin, and a plasmid was recovered from the resulting bacterial cells to obtain a plasmid pMWG.

In order to obtain the chloramphenicol resistance gene, amplification was performed by PCR using pTH18cs1 (GenBank accession number AB019610) as a template and using TCGGCACGTAAGAGGTTCC (SEQ ID NO:46) and CGGGTCGAATTTGCTTTCG (SEQ ID NO:47) as primers. The resulting DNA fragment was phosphorylated with T4 Polynucleotide Kinase (Takara) to obtain a DNA fragment containing the chloramphenicol resistance gene. Subsequently, amplification was performed by PCR using pMWG as a template and using CTAGATCTGACAG-TAAGACGGGTAAGCC (SEQ ID NO:48) and CTAGATCTCAGGGTTATTGTCTCATGAGC (SEQ ID NO:49) as primers, and the resulting DNA fragment was mixed and ligated with the DNA fragment containing the chloramphenicol resistance gene using a ligase. Then, *Escherichia coli* DH5α strain competent cells were transformed with the ligation product, and a transformant growing on an LB agar plate containing 25 μg/mL chloramphenicol was obtained. The obtained colony was cultured overnight at 37° C. in an LB liquid medium containing 25 μg/mL chloramphenicol, and the resulting plasmid was named "pMWGC".

Amplification was performed by PCR using the plasmid pMWGC as a template and using CCTTTGGT-TAAAGGCTTTAAGATCTTCCAGTGGACAAACTAT-GCC (SEQ ID NO:50) and GGCATAGTTTGTCCACTG-GAAGATCTTAAAGCCTTTAACCAAAGG (SEQ ID NO:51) as primers. Then, *Escherichia coli* DH5α strain competent cells were transformed with the amplification product, and a transformant growing on an LB agar plate containing 25 μg/mL chloramphenicol was obtained. The obtained colony was cultured overnight at 37° C. in an LB liquid medium containing 25 μg/mL chloramphenicol, and a plasmid was recovered from the resulting bacterial cells to obtain a plasmid pMWGKC.

Example 2

<Construction of Expression Plasmid pMWGKC_Mcl (Mc)_ Mtk(Mc) for Mtk and Mcl from *Methylococcus capsulatus* ATCC 33009>

PCR was carried out using the genomic DNA of *Methylococcus capsulatus* as a template and using GGAATTC-CATATGGCTGTTAAAAATCGTCTAC (SEQ ID NO:52) and GCTCTAGATCAGAATCTGATTCCGTGTTC (SEQ ID NO:53) as primers, thereby obtaining a *Methylococcus* mcl-mtk fragment. A fragment obtained by cleaving this mcl-mtk fragment was ligated with a fragment obtained by cleaving the plasmid pMWGKC prepared in Example 1. Then, *Escherichia coli* DH5α strain competent cells were transformed with the ligation product, and a transformant growing on an LB agar plate containing 25 μg/mL chloramphenicol was obtained. The obtained colony was cultured overnight at 30° C. in an LB liquid medium containing 25 μg/mL chloramphenicol, and the resulting plasmid was named "pMWGKC_mcl(Mc)_mtk(Mc)".

The pMWGKC_mcl(Mc)_mtk(Mc) includes the base sequence of the malyl-CoA lyase gene (mcl) (SEQ ID NO:41), the base sequence of the malate thiokinase α subunit gene (mtkA) (SEQ ID NO:28) and the base sequence of the malate thiokinase β subunit gene (mtkB) (SEQ ID NO:29) which are from *Methylococcus capsulatus*. The amino acid sequence of the malyl-CoA lyase (Mcl), the amino acid sequence of the malate thiokinase α subunit (MtkA) and the amino acid sequence of the malate thiokinase β subunit (MtkB) which are from *Methylococcus capsulatus* are indicated in SEQ ID NO:36, SEQ ID NO:13 and SEQ ID NO:14, respectively.

Example 3

<Preparation of Plasmid pCASET>

Amplification was performed by PCR using pHSG298 (Takara) as a template and using CGCCTCGAGTGACT-CATACCAGGCCTG (SEQ ID NO:54) and CGCCTCGAG-GCAACACCTTCTTCACGAG (SEQ ID NO:55) as primers, and the resulting DNA fragment was digested with restriction enzyme XhoI and ligated using a ligase. Then, *Escherichia coli* DH5α strain competent cells (DNA-903, TOYOBO Co., Ltd.) were transformed with the ligation product, and a transformant growing on an LB agar plate containing 25 μg/mL kanamycin was obtained. A plasmid was recovered from the resulting bacterial cells, and the plasmid, in which an XhoI recognition sequence was inserted in pHSG298, was named "pHSG298-XhoI".

In order to obtain the tac promoter, amplification was performed by PCR using pKK223-3 (Pharmacia) as a template and using ATCATCCAGCTGTCAGGCAGCCATCGGAAG (SEQ ID NO:56) and ATCCCCGGGAATTCTGTT (SEQ ID NO:57) as primers. The resulting DNA fragment was digested with restriction enzymes PvuII and SmaI to obtain an about 0.2 kbp DNA fragment encoding the tac promoter.

This DNA fragment encoding the tac promoter was mixed with an about 2.4 kbp DNA fragment prepared by digesting the plasmid pHSG298-XhoI with restriction enzyme PvuII and further treating the resultant with alkaline phosphatase, and these DNA fragments were ligated using a ligase. Then, *Escherichia coli* DH5α strain competent cells (DNA-903, TOYOBO Co., Ltd.) were transformed with the ligation product, and a transformant growing on an LB agar plate containing 25 μg/mL kanamycin was obtained. A plasmid was recovered from the resulting bacterial cells, as a result of which a plasmid pHSGT1 was obtained in which the lac promoter of pHSG298-XhoI was replaced by the tac promoter, the tac promoter having the same orientation as the original lac promoter.

In order to ligate the multicloning site of pHSG298 to a position in the obtained pHSGT1 that is downstream of the tac promoter, pHSG298 was digested with restriction enzymes EcoRI and ClaI to obtain an about 1.0 kbp DNA fragment containing the multicloning site of pHSG298. The obtained DNA fragment was mixed with an about 1.7 kbp DNA fragment prepared by digesting the plasmid pHSGT1 with restriction enzymes EcoRI and ClaI and further treating the resultant with alkaline phosphatase, and these DNA fragments were ligated using a ligase. Then, *Escherichia coli* DH5α strain competent cells (DNA-903, TOYOBO Co., Ltd.) were transformed with the ligation product, and a transformant growing on an LB agar plate containing 25 μg/mL kanamycin was obtained. A plasmid was recovered from the resulting bacterial cells, as a result of which a plasmid pHSGT2 was obtained in which the multicloning site of pHSG298 was ligated to a position that is downstream of the tac promoter.

A DNA fragment (SEQ ID NO:58) containing the replication origin, repA and repB of pCASE1 (Applied Microbiology and Biotechnology, 2009; 81: 1107-1115) isolated from *Corynebacterium casei* JCM12072 was prepared by DNA synthesis. The sequence thereof is indicated below.

```
SEQ ID NO: 58:
CGCCTCGAGCACTGGAAGGGTTCTTCAGGGGAACCCCCGGAAACCGGGGA

AACATCTGACTTGGTTAAATGTCGTATTATGAACACGCCGAGGAATGAAA

ACCGACCGTGCACGCTCGTGTGAGAAAGTCAGCTACATGAGACCAACTAC

CCGCCCTGAGGGACGCTTTGAGCAGCTGTGGCTGCCGCTGTGGCCATTGG

CAAGCGATGACCTCCGTGAGGGCATTTACCGCACCTCACGGAAGAACGCG

CTGGATAAGCGCTACGTCGAAGCCAATCCCGACGCGCTCTCTAACCTCCT
```

```
-continued
GGTCGTTGACATCGACCAGGAGGACGCGCTTTTGCGCTCTTTGTGGGACA

GGGAGGACTGGAGACCTAACGCGGTGGTTGAAAACCCCTTAAACGGGCAC

GCACACGCTGTCTGGGCGCTCGCGGAGCCATTTACCCGCACCGAATACGC

CAAACGCAAGCCTTTGGCCTATGCCGCGGCTGTCACCGAAGGCCTACGGC

GCTCTGTCGATGGCGATAGCGGATACTCCGGGCTGATCACCAAAAACCCC

GAGCACACTGCATGGGATAGTCACTGGATCACCGATAAGCTGTATACGCT

CGATGAGCTGCGCTTTTGGCTCGAAGAAACCGGCTTTATGCCGCCTGCGT

CCTGGAGGAAAACGCGGCGGTTCTCGCCAGTTGGTCTAGGTCGTAATTGC

GCACTCTTTGAAAGCGCACGTACGTGGGCATATCGGGAGGTCAGAAAGCA

TTTTGGAGACGCTGACGGCCTAGGCCGCGCAATCCAAACCACCGCGCAAG

CACTTAACCAAGAGCTGTTTGATGAACCACTACCTGTGGCCGAAGTTGAC

TGTATTGCCAGGTCAATCCATAAATGGATCATCACCAAGTCACGCATGTG

GACAGACGGCGCCGCCGTCTACGACGCCACATTCACCGCAATGCAATCCG

CACGCGGGAAGAAAGGCTGGCAACGAAGCGCTGAGGTGCGTCGTGAGGCT

GGACATACTCTTTGGAGGAACATTGGCTAAGGTTTATGCACGTTATCCAC

GCAACGGAAAAACAGCCCGCGAGCTGGCAGAACGTGCCGGTATGTCGGTG

AGAACAGCTCAACGATGGACTTCCGAACCGCGTGAAGTGTTCATTAAACG

TGCCAACGAGAAGCGTGCTCGCGTCCAGGAGCTGCGCGCCAAAGGTCTGT

CCATGCGCGCTATCGCGGCAGAGATTGGTTGCTCGGTGGGCACGGTTCAC

CGCTACGTCAAAGAAGTTGAAGAGAAGAAAACCGCGTAAATCCAGCGGTT

TAGTCACCCTCGGCGTGTTCAAAGTCCATCGTAACCAAGTCAGCTCGAGG

CG
```

A DNA fragment obtained by digesting the thus prepared DNA fragment with restriction enzyme XhoI was mixed with a DNA fragment prepared by digesting the plasmid pHSGT2 with restriction enzyme XhoI and further treating the resultant with alkaline phosphatase, and these DNA fragments were ligated using a ligase. Then, *Escherichia coli* DH5α strain competent cells (DNA-903, TOYOBO Co., Ltd.) were transformed with the ligation product, and a transformant growing on an LB agar plate containing 25 mg/mL kanamycin was obtained. A plasmid was recovered from the resulting bacterial cells, and the plasmid, in which the DNA fragment containing the replication origin, repA and repB of pCASE1 was inserted at a XhoI recognition site of pHSGT2, was named "pCASET". In the recovered pCASET, the orientation of the repA from pCASE1 was opposite to that of the tac promoter.

Example 4

<Construction of Expression Plasmid pCASET_Mcl(Mc)_Mtk(Mc) for Mtk and Mcl from *Methylococcus capsulatus*>

PCR was carried out using pMWGKC_mcl(Mc)_mtk (Mc) (a gene containing mcl and mtk from *Methylococcus capsulatus*) as a template and using a primer pair of GGAATTCACAAAAAGGATAAAACAATGGCTGTCAAGAACCGTCTAC (SEQ ID NO:59) and CGAATTCTCAGAATCTGATTCCGTGTTCCTG (SEQ ID NO:60), thereby obtaining a DNA fragment containing *Methylococcus* mcl-mtk. Each of the primers of SEQ ID NO: 59 and SEQ ID NO:60 has an EcoRI recognition site in a 5'-end region thereof.

The DNA fragment containing *Methylococcus* mcl-mtk and a fragment obtained by cleaving the plasmid pCASET prepared in Example 3 with EcoRI and dephosphorylating the resultant were ligated using a ligase. Then, *Escherichia coli* JM109 strain competent cells (DNA-900, TOYOBO Co., Ltd.) were transformed with the ligation product, and a transformant growing on an LB agar plate containing 25 μg/mL kanamycin was obtained. A plasmid was recovered from the resulting bacterial cells, and the plasmid, in which the mcl-mtk fragment was inserted in the direction appropriate for expression based on the promoter of the plasmid, was named "pCASET_mcl(Mc)_mtk(Mc)".

The plasmid pCASET_mcl(Mc)_mtk(Mc) includes the base sequence of mcl (SEQ ID NO:41), the base sequence of mtkA (SEQ ID NO:28) and the base sequence of mtkB (SEQ ID NO:29) which are from *Methylococcus capsulatus*.

Example 5

<Construction of Mtk, Mcl, Gcl and GlxR Expression Plasmid for *Corynebacterium*>

*Rhodococcus jostii* NBRC 16295 was cultured in NBRC Medium No. 802, and a genomic DNA was obtained using DNeasy Blood & Tissue Kit (QIAGEN). PCR was carried out using this genomic DNA as a template and using CGAGCTCAAGCTTACAAAAAGGATAAAACAAT-GAGCACCATTGCATTCATCGG (SEQ ID NO:61) and CGGGATCCCTAGTCCAGCAGCATGAGAG (SEQ ID NO:62) as primers, thereby obtaining a *Rhodococcus* glxR-gcl fragment (SEQ ID NO:63).

A fragment obtained by digesting the *Rhodococcus* glxR-gcl fragment with restriction enzymes SacI and BamHI was ligated with a fragment obtained by digesting pCASET_mcl(Mc)_mtk(Mc) constructed in Example 4 with SacI and BamHI. Then, *Escherichia coli* JM109 strain competent cells (DNA-900, TOYOBO Co., Ltd.) were transformed with the ligation product, and a transformant growing on an LB agar plate containing 25 μg/mL kanamycin was obtained. A plasmid was recovered from the resulting bacterial cells, and the plasmid, in which the glxR-gcl fragment was inserted in the pCASET_mcl(Mc)_mtk(Mc), was named "pCASET_mcl(Mc)_mtk(Mc)_glxR(Rj)_gcl(Rj)".

The plasmid pCASET_mcl(Mc)_mtk(Mc)_glxR(Rj)_gcl(Rj) includes the base sequence of 2-hydroxy-3-oxopropionate reductase (glxR) (SEQ ID NO:64) and the base sequence of glyoxylate carboligase (gcl) (SEQ ID NO:65) which are from *Rhodococcus jostii* in addition to the base sequence of mcl (SEQ ID NO:41), the base sequence of mtkA (SEQ ID NO:28) and the base sequence of mtkB (SEQ ID NO:29) which are from *Methylococcus capsulatus*. The amino acid sequence of the 2-hydroxy-3-oxopropionate reductase (GlxR) and the amino acid sequence of glyoxylate carboligase (Gcl) which are from *Rhodococcus jostii* are indicated in SEQ ID NO:66 and SEQ ID NO:67, respectively.

Example 6

<Preparation of Plasmid pMWCBL>

Amplification was performed by PCR using pMWGKC prepared in Example 1 as a template and using ATC-GATCTCGAGTTACCCGTCTTACTGTCAGATCTAG (SEQ ID NO:68) and ATCGATCTCGAGGCCTGTTGAT-GATACCGCTGCCTTA (SEQ ID NO:69) as primers, and the resulting DNA fragment was digested with restriction enzyme XhoI and ligated using a ligase. Then, *Escherichia coli* DH5α strain competent cells (DNA-903, TOYOBO Co., Ltd.) were transformed with the ligation product, and a transformant growing on an LB agar plate containing 10 μg/mL chloramphenicol was obtained. A plasmid was recovered from the resulting bacterial cells, and the plasmid, in which an XhoI recognition sequence was inserted in pMWGKC, was named "pMWGKC-XhoI".

A plasmid pBL1 (Journal of General Microbiology, 1984; 130: 2237-2246) was prepared from *Corynebacterium glutamicum* ATCC 13869, and PCR was carried out using the obtained plasmid as a template and using a primer pair of CCGCTCGAGTCAACAACAAGACCCATCA (SEQ ID NO:70) and CCGCTCGAGCATGCACATGCAGTCATGT (SEQ ID NO:71), thereby amplifying an about 1.8 kb DNA fragment containing the replication origin and repA (SEQ ID NO:72). The sequence thereof is indicated below.

SEQ ID NO: 72:
CCGCTCGAGTCAACAACAAGACCCATCATAGTTTGCCCCCGCGACATTGA

CCATAAATTCATCGCACAAAATATCGAACGGGGTTTATGCCGCTTTTAGT

GGGTGCGAAGAATAGTCTGCTCATTACCCGCGAACACCGCCGCATTCAGA

TCACGCTTAGTAGCGTCCCCATGAGTAGGCAGAACCGCGTCCAAGTCCAC

ATCATCCATAACGATCATGCACGGGGTGGAATCCACACCCAGACTTGCCA

GCACCTCATTAGCGACACGTTGCGCAGCGGCCACGTCCTTAGCCTTATCC

ACGCAATCTAGAACGTACTGCCTAACCGCGAAATCAGACTGAATCAGTTT

CCAATCATCGGGCTTCACCAAAGCAACAGCAACGCGGGTTGATTCGACCC

GTTCCGGTGCTTCCAGACCGGCGAGCTTGTACAGTTCTTCTTCCATTTCA

CGACGTACATCAGCGTCTATGTAATCAATGCCCAAAGCACGCTTAGCCCC

ACGTGACCAGGACGAACGCAGGTTTTTAGAACCAACCTCATACTCACGCC

ACCGAGCCACCAAAACAGCGTCCATATCCTCGCCGGCGTCGCTTTGATCG

GCCAACATATCCAACATCTGAAACGGCGTGTACGACCCCTTAGACGCGGT

TTTAGTAGCGGAGCCAGTCAGTTCCTGAGACATGCCCTTAGCGAGGTAGG

TTGCCATTTTCGCAGCGTCTCCACCCCAGGTAGACACCTGATCAAGTTTG

ACCCCGTGCTCACGCAGTGGCGCGTCCATACCGGCCTTAACCACACCAGC

AGACCAGCGGGAAAACATGGAATCCTCAAACGCCTTGAGTTCATCGTCAG

ACAGTGGACGATCCAAGAACAACAGCATGTTGCGGTGCAAGTGCCAACCG

TTCGCCCAAGAGTCTGTGACCTCATAGTCACTATAGGTGTGCTCCACCCC

GTACCGTGCACGTTCTTTCTTCCACTGAGATGTTTTCACCATCGAAGAGT

ACGCAGTCTTAATACCCGCTTCAACCTGCGCAAATGACTGTGAGCGGTTG

TGTCGAACAGTGCCCACAAACATCATGAGCGCGCCACCCGCCGCCAAGTG

ATTCTTAGTAGCAATAGCCAGCTCAATGCGGCGTTCGCCCATGACTTCCA

ATTCAGCCAGAGGTGACCCCCAGCGAGAGTGAGAGTTTTGCAGACCCTCA

AACTGCGAAGCACCGTTAGACGACCAGGACACCGCAACAGCTTCGTCCCT

GCGCCACCTATGGCACCCCGCCAGAGCCTTACTATTGGTGATCTTGTACA

TGACGTTTTGCCTACGCCACGCCCTAGCGCGAGTGACCTTAGAACCCTCA

TTGACCTGCGGTTCCTTAGAGGTGTTCACTTCTATTTCAGTGTTACCTAG

ACCCGATGTTGTGCGGGGTTGCGCAGTGCGAGTTTGTGCGGGTGTTGTGC

CCGTTGTCTTAGCTAGTGCTATGGTTGTCAATTGAAACCCCTTCGGGTTA

-continued
```
TGTGGCCCCCGTGCATATGAGTTGGTAGCTCGCACGGGGTTTGTCTTGT

CTAGGGACTATTAATTTTTAGTGGTGTTTGGTGGCCGCCTAGCTTGGCTA

TGCGTGCCAGCTTACCCGTACTCAATGTTAAAGATTTGCATCGACATGGG

AGGGTTACGTGTCCGATACCTAGGGGGGGTATCCGCGACTAGGTGCCCCG

GTGCTCACTGTCTGTACCGGCGGGCAAGCCCCACACCCCGCATGGACAG

GGTGGCTCCGCCCCCTGCACCCCCAGCAATCTGCATGTACATGTTTTACA

CATTAGCACGACATGACTGCATGTGCATGCTCGAGCGG
```

A DNA fragment obtained by digesting the amplified DNA fragment with restriction enzyme XhoI was mixed with a DNA fragment obtained by digesting the plasmid pMWGKC-XhoI with restriction enzyme XhoI and further treating the resultant with alkaline phosphatase, and these DNA fragments were ligated using a ligase. Then, *Escherichia coli* JM109 strain competent cells (DNA-900, TOYOBO Co., Ltd.) were transformed with the ligation product, and a transformant growing on an LB agar plate containing 10 μg/mL chloramphenicol was obtained. A plasmid was recovered from the resulting bacterial cells, and the plasmid, in which the DNA fragment containing the replication origin and repA of pBL1 was inserted at the XhoI recognition site of pMWGKC-XhoI, was named "pMWCBL".

Example 7

<Construction of Expression Plasmid pMWCBLpyc for Pyc from *Corynebacterium glutamicum* ATCC 13032>

Referring to the base sequence of pyruvate carboxylase gene from *Corynebacterium glutamicum* ATCC 13032 (GenBank accession number BA000036 GI:21323455), which are already made public, two primers AAGCGAGCT-CACAAAAAGGATAAAACAATGTCGACTCACA-CATCTTCA (SEQ ID NO:73) and ATACATGCATGCT-TAGGAAACGACGACGATCAA (SEQ ID NO:74) were synthesized. The primer of SEQ ID NO:73 has a SacI recognition site in a 5'-end region thereof, and the primer of SEQ ID NO:74 has a SphI recognition site in a 5'-end region thereof.

The genomic DNA of *Corynebacterium glutamicum* ATCC 13032 was prepared, and PCR was carried out using the obtained genomic DNA as a template and using the primer pair of SEQ ID NO:73 and SEQ ID NO:74, thereby amplifying an about 3.5 kb DNA fragment. This DNA fragment was digested with SacI and SphI, and the resulting DNA fragments were separated by agarose gel electrophoresis and recovered. The recovered DNA fragments were mixed with pMWCBL that had been digested with SacI and SphI and further treated with alkaline phosphatase, and the mixed fragments were ligated using a ligase. Then, *Escherichia coli* JM109 strain competent cells (manufactured by TOYOBO Co., Ltd.) were transformed with the ligation product, and a transformant growing at 30° C. on an LB agar plate containing 10 μg/mL chloramphenicol was obtained. From the obtained transformant, a plasmid pMWCBL_pyc in which the pyruvate carboxylase gene was inserted in pMWCBL was recovered.

The plasmid pMWCBL_pyc includes the base sequence of the pyruvate carboxylase gene (pyc) from *Corynebacterium glutamicum* (SEQ ID NO:75). The amino acid sequence of pyruvate carboxylase (Pyc) from *Corynebacterium glutamicum* is indicated in SEQ ID NO:76.

Example 8

<Construction of *Corynebacterium glutamicum* Variants for Evaluation>

The plasmids constructed in Examples 3, 5 and 7 were individually employed to transform *Corynebacterium glutamicum* DSM 1412 (hereinafter also referred to as "CG strain"), serving as a host, by electroporation. The resulting variants were each applied to an LB agar medium containing 15 μg/mL kanamycin and/or 10 μg/mL chloramphenicol, and the variants that grew thereon were used for evaluation. These variants are summarized in Table 2.

TABLE 2

| Variant Name | Strain Name/Plasmid | Feature |
| --- | --- | --- |
| CG/vec1 | *C. glutamicam*/pCASET | Possession of a control vector |
| CG/mtk_mcl/gcl_glxR | *C. glutamicam*/ pCASET_mcl(Mc)_mtk(Mc)_glxR(Rj)_gcl(Rj) | Expression of mtk, mcl, gcl and glxR |
| CG/mtk_mcl/gcl_glxR/vec2 | *C. glutamicam*/ pCASET_mcl(Mc)_mtk(Mc)_glxR(Rj)_gcl(Rj)/ pMWCBL | Expression of mtk, mcl, gcl and glxR Possession of a control vector |
| CG/mtk_mcl/gcl_glxR/pyc | *C. glutamicam*/ pCASET_mcl(Mc)_mtk(Mc)_glxR(Rj)_gcl(Rj)/ pMWCBL_pyc | Expression of mtk, mcl, gcl and glxR Expression of pyc |

Reference Example 1

<Evaluation of *Corynebacterium* Variants Inparted with Mtk, Mcl, Gcl and glxR Genes>

The variants CG/vec1 and CG/mtk_mcl/gcl_glxR constructed in Example 8 were individually cultured in 2-mL of LB liquid medium containing 15 μg/mL kanamycin at 30° C. with stirring at 280 rpm until sufficient growth was attained. Then, in a 100-mL Erlenmeyer flask equipped with a stirring baffles, 10 ml of a minimal medium for *Corynebacterium* containing 20 g/L glucose and 15 μg/mL kanamycin (30 g/L $(NH_4)_2SO_4$, 3 g/L $Na_2HPO_4$, 6 g/L $KH_2PO_4$, 2 g/L NaCl, 84 mg/L $CaCl_2$, 3.9 mg/L $FeCl_3$, 0.9 mg/L $ZnSO_4.7H_2O$, 0.3 mg/L $CuCl_2.H_2O$, 5.56 mg/L $MnSO_4.5H_2O$, 0.1 mg/L $(NH_4)_6 Mo_7O_{24}.4H_2O$, 0.3 mg/L $Na_2B_4O_7.10H_2O$, 0.4 g/L $MgSO_4.7H_2O$, 40 mg/L $FeSO_4.7H_2O$, 500 μg/L Vitamin B1.HCl, 0.1 g/L EDTA and 10 μg/L biotin) was prepared. 1 mL of the culture liquid obtained by the cultivation in the LB liquid medium described above was added thereto, and cultivation was carried out for from 1 to 4 days until sufficient growth was attained, whereby a preculture liquid was obtained. From this preculture liquid, bacterial cells were collected by centrifugation (5,000 rpm for 5 minutes).

Next, 2 mL of the minimal medium for *Corynebacterium* (the biotin final concentration having been changed to 2

μg/L) which contained 100 mM sodium hydrogen carbonate (labeled with $^{13}C$), 20 g/L glucose, 1.5% (w/v) Tween 60 (manufactured by Sigma-Aldrich Co. LLC.) and 15 μg/mL kanamycin was prepared, and the precultured bacterial cells were added thereto such that the OD was adjusted to be within a range of from 1 to 5. After hermetic capping, the bacterial cells were cultured at 30° C. with stirring at 150 rpm for from 1 to 2 days. The culture liquid was sampled periodically, and the bacterial cells were removed from the samples by centrifugation (using a centrifuge manufactured by Millipore Corporation at 12,000 rpm for 3 minutes). The supernatant was filtered through a hydrophilic PTFE membrane filter (MSGVN2B50, Millipore Corporation) to obtain a culture sample.

For quantification of glutamic acid in the culture sample, an HPLC (2695, manufactured by Waters Corporation) equipped with an NN-814 column (Showa Denko K.K.) and a UV/Vis detector (2489, Waters Corporation) were used. For quantification of glucose in the culture sample, an HPLC (2695, Waters Corporation) equipped with an ULTRON PS-80H column (Shinwa Chemical Industries Ltd.) and an RI detector (2414, Waters Corporation) were used.

As a result, the variant imparted with the mtk, mcl, gcl and glxR genes (CG/mtk_mcl/gcl_glxR) exhibited a higher yield per sugar consumed than the control variant (CG/vec1). The improved yield per sugar consumed occurred presumably because a $CO_2$ fixation pathway was newly imparted by the introduction of the mtk, mcl, gcl and glxR genes into *Corynebacterium* and $CO_2$ fixed by this pathway was incorporated into glutamate via acetyl-CoA. The yield per sugar consumed was calculated as follows.

(Yield per sugar consumed)=(Amount of glutamic acid (g) generated)/(Amount of glucose (g) consumed)

Example 9

<Evaluation of *Corynebacterium* Variant which is Imparted with Mtk, Mcl, Gcl and glxR Genes and in which Pyc Gene is Enhanced>

Cultivation and Analysis are carried out in the same manner as in Reference Example 1, except that the variants CG/mtk_mcl/gcl_glxR/vec2 and CG/mtk_mcl/gcl_glxR/pyc constructed in Example 8 are used for evaluation and that 15 μg/mL kanamycin and 10 μg/mL chloramphenicol are used as antibiotics added to the medium. As a result of the analysis, the variant in which pyc is enhanced (CG/mtk_mcl/gcl_glxR/pyc) exhibits a higher yield per sugar consumed than the control variant (CG/mtk_mcl/gcl_glxR/vec2). This suggests that, in *Corynebacterium* variants imparted with a $CO_2$ fixation pathway, enhancement of pyc gene is effective in improving the yield per sugar consumed.

Example 10

<Evaluation of Glutamic Acid Production Under Condition with Sodium Sulfite Addition>

The variant CG/mtk_mcl/gcl_glxR constructed in Example 8, serving as a variant to be evaluated, was inoculated into an LB medium containing 25 μg/mL kanamycin, and cultured at 30° C. for 2 days. Then, 100 μL of the resulting culture liquid was applied to a LB plate that contained 25 μg/mL kanamycin and that had a diameter of 9 cm, and cultivation was carried out at 30° C. for 2 days. Then, bacterial cells in a region that is ⅛ of the total area of the plate were collected by scraping, and inoculated into 5 mL of a minimal medium for *Corynebacterium* strains (60 g/L glucose, 30 g/L $(NH_4)_2SO_4$, 1 g/L $KH_2PO_4$, 0.4 g/L $MgSO_4.7H_2O$, 0.01 g/L $FeSO_4.7H_2O$, 0.01 g/L $MnSO_4.5H_2O$, 200 μg/L thiamine.HCl, 5.1 g/L SOYTONE (Bacto Laboratories Pty Ltd.) and 25 μg/mL kanamycin; pH8.0) that contained 20 μg/L biotin. The bacterial cells were cultured with 0.25 g calcium carbonate in a 125-mL baffle-equipped Erlenmeyer flask for one day at 31.5° C. with stirring at 270 rpm, thereby obtaining a preculture liquid.

0.25 mL of the preculture liquid was inoculated into 5 mL of a minimal medium for *Corynebacterium* strains, and sodium sulfite (reducing agent) was further supplied thereto such that the final concentration of sodium sulfite would be 5 g/L. Cultivation was performed with 0.25 g calcium carbonate in a 125-mL baffle-equipped Erlenmeyer flask for 2 days at 31.5° C. with stirring at 270 rpm, thereby obtaining a main culture liquid.

The test group with the supply of sodium sulfite was named "test group with supply of sodium sulfite". A "test group without supply of sodium sulfite" was also prepared as a control, following the same procedures as those described above except that sodium sulfite was not added.

As a result of analysis, while the yield per sugar consumed in the test group without supply of sodium sulfite was 44%, the yield per sugar consumed observed in the test group with supply of sodium sulfite was 50%. From the results, improvement of the yield due to the addition of sodium sulfite was confirmed.

The OD620 nm values of the culture liquids were measured. Unexpectedly, the OD was 50 in the test group without supply of sodium sulfite while the OD was 29 in the test group with supply of sodium sulfite. Therefore, it was also confirmed that the addition of sodium sulfite has an effect in terms of suppressing an increase in the bacterial cell amount. The suppression of an increase in the bacterial cell amount enables suppression of an increase in the cost incurred for processing waste bacterial cells.

Example 11

<Preparation of *Escherichia coli* B Strain atoD Genome-Enhanced Variant>

The whole base sequence of the genomic DNA of *Escherichia coli* MG1655 is known (GenBank accession number U00096), and the base sequence of a gene encoding the CoA transferase α subunit of *Escherichia coli* MG1655 (hereinafter also referred to as "atoD") has also been reported. Specifically, atoD is indicated in Base Nos. 2321469 to 2322131 of the *Escherichia coli* MG1655 genomic sequence registered with GenBank accession number U00096.

In order to obtain a GAPDH promoter, amplification was performed by PCR using the genomic DNA of *Escherichia coli* MG1655 as a template and using CGCTCAATTG-CAATGATTGACACGATTCCG (SEQ ID NO:77) and ACAGAATTCGCTATTTGTTAGTGAATAAAAGG (SEQ ID NO:78) as primers. The resulting DNA fragment was digested with restriction enzymes MfeI and EcoRI to obtain an about 100 bp DNA fragment encoding the GAPDH promoter.

The obtained DNA fragment was mixed with a fragment obtained by digesting the plasmid pUC19 (GenBank accession number X02514) with restriction enzyme EcoRI and further treating the resultant with alkaline phosphatase, and the mixed fragments were ligated using a ligase. Then, *Escherichia coli* DH5α strain competent cells (DNA-903, TOYOBO Co., Ltd.) were transformed with the ligation product, and transformants growing on an LB agar plate containing 50 μg/mL ampicillin were obtained. Ten of the resulting colonies were individually cultured overnight at 37° C. in an LB liquid medium containing 50 μg/mL ampicillin, and plasmids were recovered. Plasmids from which the GAPDH promoter was not excised when digested with restriction enzymes EcoRI and KpnI were selected, and their DNA sequences were read. A plasmid in which the GAPDH promoter was correctly inserted was named "pUC-gapP". The plasmid pUCgapP obtained was digested with restriction enzymes EcoRI and KpnI.

In order to obtain atoD, amplification was performed by PCR using the genomic DNA of *Escherichia coli* MG1655 as a template and using CGAATTCGCTGGTGAACATATGAAAACAAAATTGATGACATTACAAGAC (SEQ ID NO:79) and GCGGTACCTTATTTGCTCTCCTGTGAAACG (SEQ ID NO:80) as primers. The resulting DNA fragment was digested with restriction enzymes EcoRI and KpnI to obtain an about 690 bp atoD fragment. This DNA fragment was mixed with a fragment obtained by digesting the pUCgapP with restriction enzymes EcoRI and KpnI, and these fragments were ligated using a ligase. Then, *Escherichia coli* DH5α strain competent cells (DNA-903, TOYOBO Co., Ltd.) were transformed with the ligation product, and a transformant growing on an LB agar plate containing 50 μg/mL ampicillin was obtained. A plasmid was recovered from the resulting bacterial cells, and it was confirmed that atoD was correctly inserted. This plasmid was named "pGAPatoD".

PCR was carried out using the genomic DNA of *Escherichia coli* MG1655 as a template and using GCTCTAGATGCTGAAATCCACTAGTCTTGTC (SEQ ID NO:81) and TACTGCAGCGTTCCAGCACCTTATCAACC (SEQ ID NO:82) as primers, which were prepared based on the genetic information of the 5'-flanking region of atoD of *Escherichia coli* MG1655. As a result, an about 1.1 kbp DNA fragment was amplified.

PCR was also carried out using the plasmid pGAPatoD as a template and using primer GGTCTAGAGCAATGATTGACACGATTCCG (SEQ ID NO:83) which was prepared based on the sequence information of the GAPDH promoter of *Escherichia coli* MG1655, and primer GCGGTACCTTATTTGCTCTCCTGTGAAACG (SEQ ID NO:84) which was prepared based on the sequence information of atoD of *Escherichia coli* MG1655. As a result, an about 790 bp DNA fragment composed of the GAPDH promoter and atoD was obtained.

The about 1.1 kbp DNA fragment was digested with restriction enzymes PstI and XbaI, and the about 790 bp DNA fragment was digested with restriction enzymes XbaI and KpnI. The resulting fragments were mixed with a fragment obtained by digesting the temperature-sensitive plasmid pTH18cs1 (GenBank accession number AB019610) (Gene, 2000; 241: 185-191) with restriction enzymes PstI and KpnI, and the mixed fragments were ligated using a ligase. Then, DH5α strain was transformed with the ligation product, and a transformant growing at 30° C. on an LB agar plate containing 10 μg/mL chloramphenicol was obtained. The obtained colony was cultured overnight at 30° C. in an LB liquid medium containing 10 μg/mL chloramphenicol, and a plasmid was recovered from the resulting bacterial cells. *Escherichia coli* B (ATCC 11303) was transformed with this plasmid, and then cultured overnight at 30° C. on an LB agar plate containing 10 μg/mL chloramphenicol, as a result of which a transformant was obtained. The transformant was inoculated into an LB liquid medium containing 10 μg/mL chloramphenicol, and cultured overnight at 30° C. The resulting cultured bacterial cells were applied to an LB agar plate containing 10 mg/mL chloramphenicol, and cultured at 42° C., and a colony was obtained. The obtained colony was cultured in an antibiotic-free LB liquid medium at 30° C. for 2 hours, and then applied to an antibiotic-free LB agar plate, as a result of which a colony growing at 42° C. was obtained.

From the colonies that appeared, 100 colonies were randomly picked. Each of the colonies was allowed to grow on an antibiotic-free LB agar plate and on an LB agar plate containing 10 μg/mL chloramphenicol, and chloramphenicol-sensitive clones were selected. Further, from the chromosomal DNAs of these clones, an about 790 bp fragment containing the GAPDH promoter and atoD was amplified by PCR, and a variant in which the atoD promoter region was replaced by the GAPDH promoter was selected. A clone satisfying the above-described conditions was named "*Escherichia coli* B strain atoD genome-enhanced variant" (hereinafter also referred to as "B::atoDAB variant").

Example 12

<Preparation of *Escherichia coli* B Strain atoD Genome-Enhanced and Pgi Gene-Deleted Variant>

The whole base sequence of the genomic DNA of *Escherichia coli* MG1655 is known (GenBank accession number U00096), and the base sequence of a gene (pgi) encoding phosphoglucose isomerase of *Escherichia coli* has also been reported (GenBank accession number X15196).

In order to clone flanking regions of the pgi-encoding gene (1,650 bp), four primers, specifically, CAGGAATTCGCTATATCTGGCTCTGCACG (SEQ ID NO:85), CAGTCTAGAGCAATACTCTTCTGATTTTGAG (SEQ ID NO:86), CAGTCTAGATCATCGTCGATATGTAGGCC (SEQ ID NO:87) and GACCTGCAGATCATCCGTCAGCTGTACGC (SEQ ID NO:88), were synthesized. The primer of SEQ ID NO:85 has an EcoRI recognition site in a 5'-end region thereof; each of the primers of SEQ ID NO:86 and SEQ ID NO:87 has an XbaI recognition site in a 5'-end region thereof; and the primer of SEQ ID NO:88 has a PstI recognition site in a 5'-end region thereof.

The genomic DNA of *Escherichia coli* MG1655 (ATCC 700926) was prepared, and PCR was carried out using the obtained genomic DNA as a template and a primer pair of SEQ ID NO:85 and SEQ ID NO:86, thereby amplifying an about 1.0 kb DNA fragment (hereinafter also referred to as "pgi-L fragment"). Further, PCR was also carried out using a primer pair of SEQ ID NO:87 and SEQ ID NO:88, thereby amplifying an about 1.0 kb DNA fragment (hereinafter also referred to as "pgi-R fragment"). These DNA fragments were separated by agarose gel electrophoresis and recovered. The pgi-L fragment was digested with EcoRI and XbaI, and the pgi-R fragment was digested with XbaI and PstI. The resulting two types of digested fragments and a fragment produced by digesting the temperature-sensitive plasmid pTH18cs1 (GenBank accession number AB019610) with EcoRI and PstI were mixed and allowed to ligate using T4 DNA ligase. Then, *Escherichia coli* DH5α strain competent cells (TOYOBO Co, Ltd.) were transformed with the ligation product, and a transformant growing at 30° C. on an LB agar plate containing 10 μg/mL chloramphenicol was obtained. A plasmid was recovered from the obtained transformant, and it was confirmed that the two fragments, which are the 5'-upstream flanking region fragment and 3'-downstream flanking region fragment of the pgi-encoding gene, were correctly inserted in pTH18cs1. The obtained plasmid was digested with XbaI and then subjected to a blunting treatment with T4 DNA polymerase. Using T4 DNA ligase, the resulting DNA fragment was ligated with a DNA fragment obtained by digesting the pUC4K plasmid (GenBank accession number X06404) (Pharmacia) with EcoRI and further subjecting the obtained kanamycin resistance gene to a blunting treatment with T4 DNA polymerase. Thereafter, *Escherichia coli* DH5α strain competent cells were transformed with the ligation product, and a transformant growing at 30° C. on an LB agar plate containing 10 µg/mL chloramphenicol and 50 µg/mL kanamycin was obtained. A plasmid was recovered from the obtained transformant, and it was confirmed that the kanamycin resistance gene was correctly inserted between the 5'-upstream flanking region fragment and the 3'-downstream flanking region fragment of the pgi-encoding gene. This plasmid was named "pTH18cs1-pgi".

The B::atoDAB variant prepared in Example 11 was transformed with the obtained plasmid pTH18cs1-pgi and cultured overnight at 30° C. on an LB agar plate containing 10 µg/mL chloramphenicol and 50 µg/mL kanamycin, thereby obtaining a transformant. The obtained transformant was inoculated into an LB liquid medium containing 50 µg/mL kanamycin, and cultured overnight at 30° C. Then, a portion of the culture liquid was applied to an LB agar plate containing 50 µg/mL kanamycin, as a result of which a colony growing at 42° C. was obtained. The obtained colony was further cultured in an LB liquid medium containing 50 µg/mL kanamycin at 30° C. for 24 hours, and applied to an LB agar plate containing 50 µg/mL kanamycin, as a result of which a colony growing at 42° C. was obtained.

From the colonies that appeared, 100 colonies were randomly picked. Each of the colonies was allowed to grow on an LB agar plate containing 50 µg/mL kanamycin and on an LB agar plate containing 10 µg/mL chloramphenicol, and chloramphenicol-sensitive clones that grew only on the kanamycin-containing LB agar plate were selected. Further, PCR was carried out using the chromosomal DNAs of these clones as templates, and a variant from which an about 3.3 kbp fragment could be amplified due to replacement of the pgi gene by the kanamycin resistance gene was selected. The variant obtained was named "*Escherichia coli* B strain atoD genome-enhanced and pgi gene-deleted variant" (hereinafter also referred to as "B::atoDABΔpgi variant").

Example 13

<Preparation of *Escherichia coli* B Strain atoD Genome-Enhanced, Pgi Gene-Deleted and gntR Gene-Deleted Variant>

The whole base sequence of the genomic DNA of the *Escherichia coli* B is known (GenBank accession number CP000819), and the base sequence of the gene encoding transcriptional repressor GntR is indicated in Base Nos. 3509184 to 3510179 of the *Escherichia coli* B genomic sequence registered with GenBank accession number CP000819.

In order to clone a flanking region of the GntR-encoding gene (gntR), four primers, specifically, GGAATTCGGGTCAATTTTCACCCTCTATC (SEQ ID NO:89), GTGGGCCGTCCTGAAGGTACAAAAGAGATAGATTCTC (SEQ ID NO:90), CTCTTTTGTACCTTCAGGACGGCCCACAAATTTGAAG (SEQ ID NO:91) and GGAATTCCCAGCCCCGCAAGGCCGATGGC (SEQ ID NO:92), were synthesized. Each of the primers of SEQ ID NO:89 and SEQ ID NO:92 has an EcoRI recognition site in a 5'-end region thereof.

The genomic DNA of the *Escherichia coli* B strain (GenBank accession number CP000819) was prepared, and PCR was carried out using the obtained genomic DNA as a template and a primer pair of SEQ ID NO:89 and SEQ ID NO:90, thereby amplifying an about 1.0 kb DNA fragment (hereinafter also referred to as "gntR-L fragment"). Further, PCR was also carried out using a primer pair of SEQ ID NO:91 and SEQ ID NO:92 to amplify an about 1.0 kb DNA fragment (hereinafter also referred to as "gntR-R fragment"). These DNA fragments were separated by agarose gel electrophoresis and recovered, and PCR was carried out using the gntR-L fragment and the gntR-R fragment as templates and a primer pair of SEQ ID NO:89 and SEQ ID NO:92, thereby amplifying an about 2.0 kbp DNA fragment (hereinafter also referred to as "gntR-LR fragment"). This gntR-LR fragment was separated by agarose gel electrophoresis, recovered, digested with EcoRI, and then mixed with a fragment obtained by digesting the temperature-sensitive plasmid pTH18cs1 (GenBank accession number AB019610) with EcoRI and dephosphorylating the digestion product. After allowing the mixed fragments to react with each other using T4 DNA ligase, *Escherichia coli* DH5α strain competent cells (TOYOBO Co, Ltd.) were transformed with the ligation product, and a transformant growing at 30° C. on an LB agar plate containing 10 µg/mL chloramphenicol was obtained. A plasmid was recovered from the obtained transformant, and it was confirmed that the gntLR fragment was correctly inserted in pTH18cs1. This plasmid was named "pTH18cs1-gntR".

The B::atoDABΔpgi variant prepared in Example 12 was transformed with the obtained plasmid pTH18cs1-gntR, and cultured overnight at 30° C. on an LB agar plate containing 10 µg/mL chloramphenicol, thereby obtaining a transformant. The obtained transformant was inoculated into an LB liquid medium containing 10 µg/mL chloramphenicol and cultured overnight at 30° C. Then, a portion of the culture liquid was applied to an LB agar plate containing 10 µg/mL chloramphenicol, as a result of which a colony growing at 42° C. was obtained. The obtained colony was further cultured in an LB liquid medium at 30° C. for 24 hours, and applied to an LB agar plate, as a result of which a colony growing at 42° C. was obtained.

From the colonies that appeared, 100 colonies were randomly picked. Each of the colonies was allowed to grow on an LB agar plate and on an LB agar plate containing 10 µg/mL chloramphenicol, and chloramphenicol-sensitive clones were selected. Further, PCR was carried out using the chromosomal DNAs of these clones as templates, and a variant from which an about 2.0 kbp fragment could be amplified due to the deletion of the gntR gene was selected. The variant obtained was named "*Escherichia coli* B strain atoD genome-enhanced, pgi gene-deleted and gntR gene-deleted variant" (hereinafter also referred to as "B::atoDABΔpgiΔgntR variant").

Example 14

<Preparation of *Escherichia coli* B Strain atoD Genome-Enhanced, Pgi Gene-Deleted, gntR Gene-Deleted and Gnd Gene-Deleted Variant>

In order to clone a flanking region of the gene (gnd) encoding the phosphogluconate dehydrogenase, four primers, specifically, CGCCATATGAATGGCGCGGCGGGGCCGGTGG (SEQ ID NO:93), TGGAGCTCTGTTTACTCCTGTCAGGGGG (SEQ ID NO:94), TGGAGCTCTCTGATTTAATCAACAATAAAATTG (SEQ ID NO:95) and CGGGATCCACCACCATAAC- CAAACGACGG (SEQ ID NO:96), were synthesized. The primer of SEQ ID NO:93 has an NdeI recognition site in a 5'-end region thereof; each of the primers of SEQ ID NO:94 and SEQ ID NO:95 has a SacI recognition site in a 5'-end region thereof; and the primer of SEQ ID NO:96 has a BamHI recognition site in a 5'-end region thereof.

The genomic DNA of the *Escherichia coli* B strain (GenBank accession number CP000819) was prepared, and PCR thereof was carried out using a primer pair of SEQ ID NO:93 and SEQ ID NO:94, thereby amplifying an about 1.0 kb DNA fragment (hereinafter also referred to as "gnd-L fragment"). Further, PCR was also carried out using a primer pair of SEQ ID NO:95 and SEQ ID NO:96 to amplify an about 1.0 kb DNA fragment (hereinafter also referred to as "gnd-R fragment"). These DNA fragments were separated by agarose gel electrophoresis and recovered. The gnd-L fragment was digested with NdeI and SacI, and the gnd-R fragment was digested with SacI and BamHI. The resulting two types of digested fragments and a fragment obtained by digesting the temperature-sensitive plasmid pTH18cs1 (GenBank accession number AB019610) with NdeI and BamHI were mixed and allowed to ligate using T4 DNA ligase. Then, *Escherichia coli* DH5α strain competent cells (TOYOBO Co, Ltd.) were transformed with the ligation product, and a transformant growing at 30° C. on an LB agar plate containing 10 μg/mL chloramphenicol was obtained. A plasmid was recovered from the obtained transformant, and it was confirmed that the two fragments, which are the 5'-upstream flanking region fragment and 3'-downstream flanking region fragment of the gnd-encoding gene, were correctly inserted in pTH18cs1. This plasmid was named "pTH18cs1-gnd".

The B::atoDABΔpgiΔgntR variant prepared in Example 13 was transformed with the obtained plasmid pTH18cs1-gnd, and cultured overnight at 30° C. on an LB agar plate containing 10 μg/mL chloramphenicol, thereby obtaining a transformant. The obtained transformant was inoculated into an LB liquid medium containing 10 μg/mL chloramphenicol, and cultured overnight at 30° C. Then, a portion of the culture liquid was applied to an LB agar plate containing 10 μg/mL chloramphenicol, as a result of which a colony growing at 42° C. was obtained. The obtained colony was further cultured in an LB liquid medium at 30° C. for 24 hours, and the resulting culture medium was applied to an LB agar plate, as a result of which a colony growing at 42° C. was obtained.

From the colonies that appeared, 100 colonies were randomly picked. Each of the colonies was allowed to grow on an LB agar plate and on an LB agar plate containing 10 ng/mL chloramphenicol, and chloramphenicol-sensitive clones were selected. Further, PCR was carried out using the chromosomal DNAs of these clones as templates, and a variant from which an about 2.0 kbp fragment could be amplified due to the deletion of the gnd gene was selected. The variant obtained was named "*Escherichia coli* B strain atoD genome-enhanced, pgi gene-deleted, gntR gene-deleted and gnd gene-deleted variant" (hereinafter also referred to as "B::atoDABΔpgiΔgntRΔgnd variant").

Example 15

<Preparation of Plasmid pIaz>

Acetoacetate decarboxylase of *Clostridium* bacteria is described in GenBank accession number M55392, and isopropyl alcohol dehydrogenase of *Clostridium* bacteria is described in GenBank accession number AF157307.

A plasmid pBRgapP was prepared in the same manner as that in Example 1.

In order to obtain the isopropyl alcohol dehydrogenase gene, amplification was performed by PCR using the genomic DNA of *Clostridium beijerinckii* NRRL B-593 as a template and using AATATGCATGCTGGTGGAACATATGAAAGGTTTTGCAATGCTAGG (SEQ ID NO:97) and ACGCGTCGACTTATAATATAACTACTGCTTTAATTAAGTC (SEQ ID NO:98) as primers. The resulting DNA fragment was digested with restriction enzymes SphI and SalI to obtain an about 1.1 kbp isopropyl alcohol dehydrogenase fragment. The obtained DNA fragment was mixed with a fragment obtained by digesting the plasmid pUC119 with restriction enzymes SphI and SalI, and these fragments were ligated using a ligase. Then, *Escherichia coli* DH5α strain competent cells were transformed with the ligation product, and a transformant growing on an LB agar plate containing 50 μg/mL ampicillin was obtained. The obtained colony was cultured overnight at 37° C. in an LB liquid medium containing 50 μg/mL ampicillin, and a plasmid was recovered from the resulting bacterial cells. It was confirmed that IPAdh was correctly inserted, and this plasmid was named "pUC-I".

An IPAdh-containing fragment obtained by digesting the plasmid pUC-I with restriction enzymes SphI and EcoRI was mixed with a fragment obtained by digesting the plasmid pBRgapP with restriction enzymes SphI and EcoRI, and these fragments were ligated using a ligase. Then, *Escherichia coli* DH5α strain competent cells were transformed with the ligation product, and a transformant growing on an LB agar plate containing 50 μg/mL ampicillin was obtained. The obtained colony was cultured overnight at 37° C. in an LB liquid medium containing 50 μg/mL ampicillin, and a plasmid was recovered from the resulting bacterial cells. It was confirmed that IPAdh was correctly inserted, and this plasmid was named "pGAP-I".

In order to obtain the acetoacetate decarboxylase gene, amplification was performed by PCR using the genomic DNA of *Clostridium acetobutylicum* ATCC824 as a template and using ACGCGTCGACGCTGGTGGAACATATGTTAAAGGATGAAGTAATTAAACAAATTAGC (SEQ ID NO:99) and GCTCTAGAGGTACCTTACTTAAGATAATCATATATAACTTCAGC (SEQ ID NO:100) as primers. The resulting DNA fragment was digested with restriction enzymes SalI and XbaI to obtain an about 700 bp acetoacetate decarboxylase fragment. The obtained DNA fragment was mixed with a fragment obtained by digesting the plasmid pGAP-I with restriction enzymes SalI and XbaI, and these fragments were ligated using a ligase. Then, *Escherichia coli* DH5α strain competent cells were transformed with the ligation product, and a transformant growing on an LB agar plate containing 50 μg/mL ampicillin was obtained. The obtained colony was cultured overnight at 37° C. in an LB liquid medium containing 50 μg/mL ampicillin, and a plasmid was recovered from the resulting bacterial cells. It was confirmed that adc was correctly inserted, and this plasmid was named "pIa".

In order to obtain the glucose-6-phosphate-1-dehydrogenase gene (zwf), amplification was performed by PCR using the genomic DNA of the *Escherichia coli* B strain (GenBank accession number CP000819) as a template and using GCTCTAGACGGAGAAAGTCTTATGGCGGTAACGCAAACAGCCCAGG (SEQ ID NO:101) and CGGGATCCGGAGAAAGTCTTATGAAGCAAACAGTTTATATCGCC (SEQ ID NO:102) as primers. The resulting DNA fragment was digested with restriction enzymes XbaI and BamHI to obtain an about 1,500 bp glucose-6-phosphate-1-dehydrogenase fragment. The DNA fragment obtained was mixed with a fragment obtained by digesting the plasmid pIa with restriction enzymes XbaI and BamHI, and these fragments were ligated using a ligase. Then, *Escherichia coli* DH5α strain competent cells were transformed with the ligation product, and a transformant growing on an LB agar plate containing 50 µg/mL ampicillin was obtained. The obtained colony was cultured overnight at 37° C. in an LB liquid medium containing 50 µg/mL ampicillin, and the resulting plasmid was named "pIaz".

Example 16

<Preparation of Plasmids pMWGC2 and pMWGKC2>

In order to obtain the GAPDH promoter, amplification was performed by PCR using the genomic DNA of *Escherichia coli* MG1655 as a template and using CTACTAGTCT-GTCGCAATGATTGACACGATTCCG (SEQ ID NO:103) and GCTCGAATTCCCATATGTTCCACCAGCTATTTGT-TAGTGAATAAAAGG (SEQ ID NO:104) as primers. The resulting DNA fragment was digested with restriction enzyme EcoRI, and the ends of the digestion product were phosphorylated with T4 Polynucleotide Kinase to obtain a DNA fragment containing the GAPDH promoter.

The plasmid pMW119 (GenBank accession number AB005476) was digested with restriction enzyme NdeI, and the ends thereof were blunted. Then, the fragment was further digested with EcoRI, followed by dephosphorylation of ends thereof. The resulting DNA fragment of pMW119 was mixed with the DNA fragment containing the GAPDH promoter described above, and these fragments were ligated using a ligase. Then, *Escherichia coli* DH5α strain competent cells were transformed with the ligation product, and a transformant growing on an LB agar plate containing 50 µg/mL ampicillin was obtained. The obtained colony was cultured overnight at 37° C. in an LB liquid medium containing 50 µg/mL ampicillin, and a plasmid was recovered from the resulting bacterial cells to obtain a plasmid pMWG2.

In order to obtain the chloramphenicol resistance gene, amplification was performed by PCR using pTH18cs1 (GenBank accession number AB019610) as a template and using TCGGCACGTAAGAGGTTCC (SEQ ID NO:46) and CGGGTCGAATTTGCTTTCG (SEQ ID NO:47) as primers. The resulting DNA fragment was phosphorylated with T4 Polynucleotide Kinase (Takara) to obtain a DNA fragment containing the chloramphenicol resistance gene. Subsequently, amplification was performed by PCR using pMWG2 as a template and using CTAGATCTGACAG-TAAGACGGGTAAGCC (SEQ ID NO:48) and CTA-GATCTCAGGGTTATTGTCTCATGAGC (SEQ ID NO:49) as primers, and the resulting DNA fragment was mixed with the DNA fragment containing the chloramphenicol resistance gene. The mixed fragments were ligated using a ligase. Then, *Escherichia coli* DH5α strain competent cells were transformed with the ligation product, and a transformant growing on an LB agar plate containing 25 µg/mL chloramphenicol was obtained. The obtained colony was cultured overnight at 37° C. in an LB liquid medium containing 25 µg/mL chloramphenicol, and the resulting plasmid was named "pMWGC2".

Amplification was performed by PCR using the plasmid pMWGC2 as a template and using CCTTTGGT-TAAAGGCTTTAAGATCTTCCAGTGGACAAACTAT-GCC (SEQ ID NO:50) and GGCATAGTTTGTCCACTG-GAAGATCTTAAAGCCTTTAACCAAAGG (SEQ ID NO:51) as primers. Then, *Escherichia coli* DH5α strain competent cells were transformed with the amplification product, and a transformant growing on an LB agar plate containing 25 µg/mL chloramphenicol was obtained. The obtained colony was cultured overnight at 37° C. in an LB liquid medium containing 25 µg/mL chloramphenicol, and a plasmid was recovered from the resulting bacterial cells to obtain a plasmid pMWGKC2.

Example 17

<Construction of Expression Plasmids pMWGC2_Mtk(Mc)_Mcl and pMWGKC2_Mtk(Mc)_Mcl for Mtk and Mcl from *Methylococcus capsulatus* ATCC 33009>

PCR was carried out using the genomic DNA of *Methylococcus capsulatus* (ATCC33009D-5) as a template and using GGAATTCCATATGGCTGTTAAAAATCGTCTAC (SEQ ID NO:52) and GCTCTAGATCAGAATCTGATTC-CGTGTTC (SEQ ID NO:53) as primers, thereby obtaining a *Methylococcus* mcl-mtk fragment. A fragment obtained by cleaving this mcl-mtk fragment with NdeI and XbaI was ligated with a fragment obtained by cleaving the plasmid pMWGC2 or pMWGKC2 prepared in Example 16 with NdeI and XbaI. Then, *Escherichia coli* DH5α strain competent cells were transformed with the ligation product, and a transformant growing on an LB agar plate containing 25 µg/mL chloramphenicol was obtained. The obtained colony was cultured overnight at 30° C. in an LB liquid medium containing 25 µg/mL chloramphenicol. The plasmids obtained were named "pMWGC2_mtk(Mc)_mcl" and "pMWGKC2_mtk(Mc)_mcl", respectively.

The plasmids pMWGC2_mtk(Mc)_mcl and pMWGKC2_mtk(Mc)_mcl include the base sequence of mcl (SEQ ID NO:41), the base sequence of mtkA (SEQ ID NO:28) and the base sequence of mtkB (SEQ ID NO:29), which are from *Methylococcus capsulatus*. The amino acid sequence of Mcl, the amino acid sequence of MtkA and the amino acid sequence of MtkB that are from *Methylococcus capsulatus* are indicated in SEQ ID NO:36, SEQ ID NO:13 and SEQ ID NO:14, respectively.

Example 18

<Construction of GlxR and GlxK Expression Plasmid>

In order to obtain 2-hydroxy-3-oxopropionate reductase gene (glxR) from *Escherichia coli*, amplification was performed by PCR using the genomic DNA of the *Escherichia coli* B strain (GenBank accession number CP000819) as a template and using GCTCTAGACGGAGAAAGTCTTAT-GAAACTGGGATTTATTGGC (SEQ ID NO:105) and AACTGCAGTCAGGCCAGTTTATGGTTAG (SEQ ID NO:106) as primers. The resulting DNA fragment was digested with restriction enzymes XbaI and PstI to obtain an about 900 bp glxR fragment. In order to obtain glycerate 3-kinase gene (glxK) from *Escherichia coli*, amplification was performed by PCR using the genomic DNA of the *Escherichia coli* B strain (GenBank accession number CP000819) as a template and using AACTGCAGCGGA-GAAAGTCTTATGAAGATTGTCATTGCGCCA (SEQ ID NO:107) and GGAATTCAAGCTTTCAGTTTTTAATTC-CCTGACC (SEQ ID NO:108) as primers. The resulting DNA fragment was digested with restriction enzymes PstI and HindIII to obtain an about 1,100 bp glxK fragment. The glxR fragment and the glxK fragment obtained were mixed with a fragment obtained by cleaving the plasmid pMWGC2_mtk(Mc)_mcl constructed in Example 17 with XbaI and HindIII, and ligated to a position that is downstream of the malate thiokinase (mtk) sequence of the plasmid pMWGC2_mtk(Mc)_mcl. The plasmid obtained was named "pMWGC2_mtk(Mc)_mcl_glxR_glxK".

Example 19

<Preparation of Mtk and Mcl-Introduced, Isopropyl Alcohol-Producing, atoD Genome-Enhanced, Pgi Gene-Deleted, gntR Gene-Deleted and Gnd Gene-Deleted Variant>

Competent cells of the variant prepared in Example 14 (B::atoDABΔpgiΔgntRΔgnd variant) were transformed with the plasmid pIaz prepared in Example 15 and one of the plasmids prepared in Examples 16 to 18, and applied to an LB agar medium containing 25 mg/L chloramphenicol and 100 mg/L ampicillin. The cells were allowed to grow on the LB agar medium containing 25 mg/L chloramphenicol and 100 mg/L ampicillin, as a result of which variants were obtained. These variants are summarized in Table 3.

TABLE 3

| Variant Name | Plasmid/Strain Name | Feature |
|---|---|---|
| vec/atoDAB ΔpgiΔgntRΔgnd | pIaz, pMWGC2/ B::atoDABΔpgiΔgntRΔgnd | IPA production system is included MtkAB is not present Δpgi, ΔgntR, Δgnd |
| MtkAB/atoDAB ΔpgiΔgntRΔgnd | pIaz, pMWGC2_mtk(Mc)_mcl/ B::atoDABΔpgiΔgntRΔgnd | IPA production system is included MtkAB is expressed Δpgi, ΔgntR, Δgnd |
| MtkAB, glxR, glxK/ atoDABΔpgiΔgntRΔgnd | pIaz, pMWGC2_mtk(Mc)_mcl_glxR_glxK/ B::atoDABΔpgiΔgntRΔgnd | IPA production system is included MtkAB is expressed glxR is expressed glxK is expressed Δpgi, ΔgntR, Δgnd |

TABLE 4

| | Products formed (g/L/48 h) | | Glucose Consumed (g/L/48 h) | Yield per Sugar Consumed (48 h) | |
|---|---|---|---|---|---|
| Variant Name | IPA | Acetone | | IPA | IPA + Acetone |
| vec/ atoDABΔpgiΔgntRΔgnd | 4.8 | 0.1 | 33.2 | 14.4 | 14.8 |
| MtkAB/ atoDABΔpgiΔgntRΔgnd | 7.2 | 0.2 | 42.7 | 17.0 | 17.3 |
| MtkAB, glxR, glxK/atoDAB ΔpgiΔgntRΔgnd | 7.9 | 0.3 | 43.9 | 18.1 | 18.8 |

Example 20

<Production of Isopropyl Alcohol>

As preculture, each of the variants for evaluation constructed in Example 19 was individually inoculated into 2 mL of an LB broth Miller's culture liquid (DIFCO 244620) that contained 25 mg/L chloramphenicol and 100 mg/L ampicillin in a test tube, and cultivation was performed overnight at a culture temperature of 30° C. with stirring at 120 rpm. Then, the OD of the preculture was measured, and cells in an amount corresponding to an OD of 3.0 were recovered. The recovered cells were suspended in 300 µl of 0.9% NaCl solution, and 20 µl of the resulting suspension was inoculated into 20 mL of LB broth Miller's culture liquid that contained 5% glucose, 25 mg/L chloramphenicol and 100 mg/L ampicillin in a 100-mL baffle-equipped flask, and cultivation was performed for 48 hours at a temperature of 30° C. with stirring at 120 rpm. The resulting bacterial culture liquid was sampled, and the bacterial cells were removed by centrifugation. Thereafter, the amounts of isopropyl alcohol (IPA), acetone and other major by-products (organic acids such as succinic acid) accumulated in the obtained culture supernatant were measured by HPLC using a conventional method. The results thereof are indicated in Tables 4 and 5.

The amount of isopropyl alcohol produced during the period of 48 hours was 4.8 g in the case of the control variant (vec/atoDABΔpgiΔgntRΔgnd), 7.2 g in the case of the mtk+mcl−introduced variant (MtkAB/atoDABΔpgiΔgntRΔgnd) and 7.9 g in the case of the glxR+glxK+mtk+mcl−introduced variant (MtkAB,glxR,glxK/atoDABΔpgiΔgntRΔgnd).

The amount of acetone produced during the period of 48 hours was 0.1 g in the case of the control variant (vec/atoDABΔpgiΔgntRΔgnd), 0.2 g in the case of the mtk+mcl−introduced variant (MtkAB/atoDABΔpgiΔgntRΔgnd) and 0.3 g in the case of the glxR+glxK+mtk+mcl−introduced variant (MtkAB,glxR,glxK/atoDABΔpgiΔgntRΔgnd).

From these results, it was found that the production amounts of isopropyl alcohol and acetone are higher when glxR and glxK are introduced in addition to introduction of mtk and mcl.

The yield of isopropyl alcohol and acetone per sugar consumed during the period of 48 hours was 14.8% in the case of the control variant (vec/atoDABΔpgiΔgntRΔgnd), 17.3% in the case of the mtk+mcl-introduced variant (MtkAB/atoDABΔpgiΔgntRΔgnd) and 18.8% in the case of the glxR+glxK+mtk+mcl−introduced variant (MtkAB,glxR, glxK/atoDABΔpgiΔgntRΔgnd). From these results, it was demonstrated that the efficiency of conversion of sugar into isopropyl alcohol or acetone is improved by introducing glxR and glxK, in addition to the introduction of mtk and mcl.

TABLE 5

| Variant Name | Succinic acid (mg/L/48 h) | Lactic acid (mg/L/48 h) | Acetic acid (mg/L/48 h) | Formic acid (mg/L/48 h) | Pyruvic acid (mg/L/48 h) |
|---|---|---|---|---|---|
| vec/atoDABΔpgiΔgntRΔgnd | 11.7 | 525.0 | 73.4 | 17.7 | 184.0 |
| MtkAB/atoDABΔpgiΔgntRΔgnd | 0.0 | 311.0 | 89.9 | 24.7 | 1458.0 |
| MtkAB, glxR, glxK/atoDABΔpgiΔgntRΔgnd | 0.0 | 247.0 | 129.0 | 21.1 | 1045.0 |

The amount of lactic acid produced during the period of 48 hours was smaller in the case of the mtk+mcl–introduced variant (MtkAB/atoDABΔpgiΔgntRΔgnd) than that in the case of the control variant (vec/atoDABΔpgiΔgntRΔgnd). Additionally, it was found that the amount of lactic acid was unexpectedly reduced even further in the case of the variant in which glxR and glxK were introduced in addition to the introduction of mtk and mcl (MtkAB,glxR,glxk/atoDABΔpgiΔgntRΔgnd).

Example 21

<Preparation of *Aspergillus niger* Variants for Evaluation>

From the genome of *Aspergillus niger* ATCC 1015, the genes of the promoter region (GlaPr) and transcription termination region (GlaTt) of glucoamylase were obtained by PCR using the method described in a document (Plasmid, 2005; 53: 191-204).

The malyl-CoA lyase gene (SEQ ID NO:41), malate thiokinase α subunit gene (SEQ ID NO:28) and malate thiokinase β subunit gene (SEQ ID NO:29) from *Methylococcus capsulatus* ATCC 33009 were amplified by PCR together with an appropriate Shine-Dalgarno sequence (SD sequence). The amplified fragments were designed such that each protein-coding region was sandwiched between the promoter region (GlaPr) and the transcription termination region (GlaTt), and the fragments were inserted into the HindIII site of the plasmid pPTRII (Takara). The plasmid obtained was named "pPTRII_mcl(Mc)_mtk(Mc)".

From the genome of *Rhodococcus jostii* NBRC 16295, the gene of 2-hydroxy-3-oxopropionate reductase (glxR) (SEQ ID NO:64) and the gene of glyoxylate carboligase (gcl) (SEQ ID NO:65) were amplified by PCR together with an appropriate SD sequence. The amplified fragments were designed such that each protein-coding region was sandwiched between the promoter region (GlaPr) and the transcription termination region (GlaTt), and the fragments were inserted into pPTRII_mcl(Mc)_mtk(Mc). The plasmid obtained was named "pPTRII_mcl(Mc)_mtk(Mc)_glxR (Rj)_ gcl(Rj)".

pPTRII, pPTRII_mcl(Mc)_mtk(Mc) and pPTRII_mcl(Mc)_mtk(Mc)_glxR(Rj)_gcl(Rj) were individually employed to transform *Aspergillus niger* ATCC 1015, thereby preparing a control variant (hereinafter also referred to as "AN/vec"), mtk+mcl-introduced variant (hereinafter also referred to as "AN/mtk_mcl") and mtk+mcl+glxR+gcl–introduced variant (hereinafter also referred to as "AN/mtk_mcl_gcl_glxR") of *Aspergillus niger*, respectively.

Example 22

<Citric Acid Production Test Using *Aspergillus niger*>

When each of the *Aspergillus niger* variants prepared in Example 21 (AN/vec, AN/mtk_mcl and AN/mtk_mcl_gcl_glxR) is cultured at 30° C. using a medium containing a carbon source and pyrithiamine hydrobromide, the AN/mtk_mcl and AN/mtk_mcl_gcl_glxR produce citric acid with higher yields than that exhibited by the control variant AN/vec. By cultivation using $^{13}$C-labeled sodium hydrogen carbonate and measurement of the $^{13}$C content in acetyl-CoA, which is an intermediate, and the $^{13}$C content in citric acid, which is a final product, it can be confirmed that fixed carbonate has been introduced into acetyl-CoA and citric acid.

Example 23

<Preparation of *Aspergillus terreus* Variants for Evaluation>

In the same manner as that in Example 21, pPTRII, pPTRII_mcl(Mc)_mtk(Mc) and pPTRII_mcl(Mc)_mtk (Mc)_ glxR(Rj)_gcl(Rj) were individually employed to transform *Aspergillus terreus* NBRC 6365 in accordance with the instruction manual of pPTRII (Takara), thereby preparing a control variant (hereinafter also referred to as "AT/vec"), mtk+mcl-introduced variant (hereinafter also referred to as "AT/mtk_mcl") and mtk+mcl+glxR+gcl–introduced variant (hereinafter also referred to as "AT/mtk_mcl_gcl_glxR") of *Aspergillus terreus*, respectively.

Example 24

<Itaconic Acid Production Test Using *Aspergillus terreus*>

When each of the *Aspergillus terreus* variants prepared in Example 23 (AT/vec, AT/mtk_mcl and AT/mtk_mcl_gcl_glxR) is cultured at 30° C. using a medium containing a carbon source and pyrithiamine hydrobromide, the AT/mtk_mcl and AT/mtk_mcl_gcl_glxR produce itaconic acid with higher yields than that exhibited by the control variant AT/vec. By cultivation using $^{13}$C-labeled sodium hydrogen carbonate and measurement of the $^{13}$C content in acetyl-CoA, which is an intermediate, and the $^{13}$C content in itaconic acid, which is a final product, it can be confirmed that fixed carbonate has been introduced into acetyl-CoA and itaconic acid.

Cultivation and analysis are performed in the same manner using AT/mtk_mcl_gcl_glxR as a variant to be evaluated and supplying a carbonate, carbon dioxide gas or reducing agent as an additive to the medium. As a result of analysis, the test group supplied with a carbonate, carbon dioxide gas or reducing agent as an additive exhibits a higher yield per sugar consumed than that of the test group not supplied with carbonate, carbon dioxide gas or reducing agent, respectively. That is, it can be thought that, in variants imparted with a $CO_2$ fixation pathway, supplying a carbonate, carbon dioxide gas or reducing agent is effective in the improvement of the yield per sugar consumed.

Example 25

<Preparation of *Cupriavidus necator* Variants for Evaluation>

The malate thiokinase α subunit gene (SEQ ID NO:28) and the malate thiokinase β subunit gene (SEQ ID NO:29), which are from *Methylococcus capsulatus* ATCC 33009, were amplified by PCR together with an appropriate SD sequence. The amplified fragments were ligated to a broad host range vector pBBR1-MCS2 (GenBank accession number U23751) such that the genes came under the control of the lac promoter. The plasmid obtained was named "pBBR-MCS2_mtk(Mc)".

pBBR1-MCS2 and pBBR-MCS2_mtk(Mc) were individually employed to transform *Cupriavidus necator* JMP 134 (DSM 4058), thereby preparing a control variant (hereinafter also referred to as "CP/vec") and a mtk-introduced variant (hereinafter also referred to as "CP/mtk") of *Cupriavidus necator*, respectively.

Example 26

<Poly-3-Hydroxybutyric Acid Production Test Using *Cupriavidus necator*>

When each of the variants for evaluation prepared in Example 25 (CP/vec and CP/mtk) is cultured at 30° C. using a medium containing a carbon source and kanamycin, the mtk-introduced variant CP/mtk produces poly-3-hydroxybutyric acid with a higher yield than that exhibited by the control variant CP/vec. By cultivation using $^{13}$C-labeled sodium hydrogen carbonate and measurement of the $^{13}$C content in acetyl-CoA, which is an intermediate, and the $^{13}$C content in poly-3-hydroxybutyric acid, which is a final product, it can be confirmed that fixed carbonate has been introduced into acetyl-CoA and poly-3-hydroxybutyric acid.

The disclosure of Japanese Patent Application No. 2013-011536, filed Jan. 24, 2013, and the disclosure of Japanese Patent Application No. 2013-011538, filed Jan. 24, 2013, are herein incorporated by reference in their entirety.

All publications, patent applications and technical standards mentioned in this specification are herein incorporated by reference to the same extent as if each individual publication, patent application or technical standard was specifically and individually indicated to be incorporated by reference.

---

The invention claimed is:
1. A method of producing acetyl-CoA, comprising:
culturing an acetyl-CoA producing microorganism comprising an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e):
(a) a carbon dioxide fixation cycle including an enzymatic reaction from malonyl-CoA to malonate semialdehyde catalyzed by malonate semialdehyde dehydrogenase, or an enzymatic reaction from malonyl-CoA to 3-hydroxypropionate catalyzed by malonyl-CoA reductase;
(b) a carbon dioxide fixation cycle including an enzymatic reaction from acetyl-CoA and CO2 to pyruvate catalyzed by pyruvate synthase;
(c) a carbon dioxide fixation cycle including an enzymatic reaction from crotonyl-CoA and $CO_2$ to ethylmalonyl-CoA catalyzed by crotonyl-CoA carboxylase-reductase, or an enzymatic reaction from crotonyl-CoA and $CO_2$ to glutaconyl-CoA catalyzed by methylcrotonyl-CoA carboxylase;
(d) a carbon dioxide fixation cycle including an enzymatic reaction from CO2 to formate catalyzed by formate dehydrogenase; or
(e) at least one selected from the group consisting of malate thiokinase and malyl-CoA lyase,
the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto; and
supplying at least one selected from the group consisting of a carbonate ion or a bicarbonate ion with a total supply amount of 150 mmol/L or more, and carbon dioxide gas with an average bubble diameter of 100 μm or more, to a culture medium used for the culturing wherein the microorganism produces acetyl-CoA.
2. The method of producing acetyl-CoA according to claim 1, further comprising resupplying carbon dioxide generated by the culturing to the culture medium used for the culturing.
3. The method of producing acetyl-CoA according to claim 1,
wherein the acetyl-CoA producing microorganism comprises an acetyl-CoA production cycle including the following (f), (g), (h), (i), (j), (k), (l), and (m):
(f) at least one selected from the group consisting of: pyruvate kinase and pyruvate carboxylase; phosphoenolpyruvate carboxylase; and phosphoenolpyruvate carboxykinase;
(g) malate dehydrogenase;
(h) malate thiokinase;
(i) malyl-CoA lyase;
(j) glyoxylate carboligase;
(k) at least one selected from the group consisting of: 2-hydroxy-3-oxopropionate reductase; and hydroxypyruvate isomerase and hydroxypyruvate reductase;
(l) at least one selected from the group consisting of: glycerate 2-kinase; and glycerate 3-kinase and phosphoglycerate mutase; and
(m) enolase.
4. The method of producing acetyl-CoA according to claim 1, wherein the microorganism that does not have any of (a), (b), (c), (d), or (e), is a microorganism belonging to Enterobacteriaceae or a microorganism belonging to coryneform bacteria.
5. The method of producing acetyl-CoA according to claim 1,
wherein the microorganism that does not have any of (a), (b), (c), (d), or (e), is an *Escherichia* bacterium or a *Pantoea* bacterium belonging to Enterobacteriaceae, or is a *Corynebacterium* bacterium belonging to coryneform bacteria.
6. The method of claim 1 further comprising allowing the acetyl-CoA producing microorganism to produce isopropyl alcohol, using, as an intermediate, the acetyl-CoA produced.
7. The method of claim 1 further comprising allowing the acetyl-CoA producing microorganism to produce acetone, using, as an intermediate, the acetyl-CoA produced.
8. A method of producing glutamic acid, comprising:
culturing an acetyl-CoA producing microorganism comprising an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e) to produce acetyl CoA:
(a) a carbon dioxide fixation cycle including an enzymatic reaction from malonyl-CoA to malonate semialdehyde catalyzed by malonate semialdehyde dehydrogenase, or an enzymatic reaction from malonyl-CoA to 3-hydroxypropionate catalyzed by malonyl-CoA reductase;
(b) a carbon dioxide fixation cycle including an enzymatic reaction from acetyl-CoA and CO2 to pyruvate catalyzed by pyruvate synthase;
(c) a carbon dioxide fixation cycle including an enzymatic reaction from crotonyl-CoA and $CO_2$ to ethylmalonyl-CoA catalyzed by crotonyl-CoA carboxylase-reductase, or an enzymatic reaction from crotonyl-CoA and $CO_2$ to glutaconyl-CoA catalyzed by methylcrotonyl-CoA carboxylase;
(d) a carbon dioxide fixation cycle including an enzymatic reaction from CO2 to formate catalyzed by formate dehydrogenase; or
(e) at least one selected from the group consisting of malate thiokinase and malyl-CoA lyase,
the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto;
supplying at least one selected from the group consisting of a carbonate ion or a bicarbonate ion with a total supply amount of 150 mmol/L or more, and carbon dioxide gas with an average bubble diameter of 100 μm or more, to a culture medium used for the culturing and
allowing the acetyl-CoA producing microorganism to produce glutamic acid, using the acetyl CoA.
9. A method of producing acetyl-CoA comprising:
culturing an acetyl-CoA producing microorganism comprising an acetyl-CoA production cycle obtained by imparting at least one enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d) or (e):
(a) a carbon dioxide fixation cycle including an enzymatic reaction from malonyl-CoA to malonate semialdehyde catalyzed by malonate semialdehyde dehydrogenase, or an enzymatic reaction from malonyl-CoA to 3-hydroxypropionate catalyzed by malonyl-CoA reductase;

(b) a carbon dioxide fixation cycle including an enzymatic reaction from acetyl-CoA and CO2 to pyruvate catalyzed by pyruvate synthase;

(c) a carbon dioxide fixation cycle including an enzymatic reaction from crotonyl-CoA and $CO_2$ to ethylmalonyl-CoA catalyzed by crotonyl-CoA carboxylase-reductase, or an enzymatic reaction from crotonyl-CoA and $CO_2$ to glutaconyl-CoA catalyzed by methylcrotonyl-CoA carboxylase;

(d) a carbon dioxide fixation cycle including an enzymatic reaction from CO2 to formate catalyzed by formate dehydrogenase; or (e) at least one selected from the group consisting of malate thiokinase and malyl-CoA lyase, the acetyl-CoA producing microorganism being obtained without imparting any of (a), (b), (c), or (d) to the microorganism, or such that the microorganism exhibits none of the functions of (a), (b), (c), or (d) even if one or more of (a), (b), (c), or (d) is imparted thereto; and supplying sodium sulfite with a total supply amount of from 0.01 g/l to 50 g/L to a culture medium used for the culturing wherein the microorganism produces acetyl-CoA.

10. The method of producing acetyl-CoA according to claim 1, further comprising supplying sodium sulfite with a total supply amount of from 0.01 g/L to 50 g/L to a culture medium used for the culturing.

\* \* \* \* \*

SEQUENCE LISTING

```
<160> NUMBER OF SEQ ID NOS: 108

<210> SEQ ID NO 1
<211> LENGTH: 296
<212> TYPE: PRT
<213> ORGANISM: Methylobacterium extorquens

<400> SEQUENCE: 1

Met Ser Ile Leu Ile Asp Glu Lys Thr Pro Ile Leu Val Gln Gly Ile
1               5                   10                  15

Thr Gly Asp Lys Gly Thr Phe His Ala Lys Glu Met Ile Ala Tyr Gly
            20                  25                  30

Ser Asn Val Val Gly Gly Val Thr Pro Gly Lys Gly Lys Thr His
        35                  40                  45

Cys Gly Val Pro Val Phe Asn Thr Val Lys Glu Ala Val Glu Ala Thr
    50                  55                  60

Gly Ala Thr Thr Ser Ile Thr Phe Val Ala Pro Pro Phe Ala Ala Asp
65                  70                  75                  80

Ala Ile Met Glu Ala Ala Asp Ala Gly Leu Lys Leu Val Cys Ser Ile
                85                  90                  95

Thr Asp Gly Ile Pro Ala Gln Asp Met Met Arg Val Lys Arg Tyr Leu
            100                 105                 110

Arg Arg Tyr Pro Lys Glu Lys Arg Thr Met Val Val Gly Pro Asn Cys
        115                 120                 125

Ala Gly Ile Ile Ser Pro Gly Lys Ser Met Leu Gly Ile Met Pro Gly
    130                 135                 140

His Ile Tyr Leu Pro Gly Lys Val Gly Val Ile Ser Arg Ser Gly Thr
145                 150                 155                 160

Leu Gly Tyr Glu Ala Ala Ala Gln Met Lys Glu Leu Gly Ile Gly Ile
                165                 170                 175

Ser Thr Ser Val Gly Ile Gly Gly Asp Pro Ile Asn Gly Ser Ser Phe
            180                 185                 190

Leu Asp His Leu Ala Leu Phe Glu Gln Asp Pro Glu Thr Glu Ala Val
        195                 200                 205

Leu Met Ile Gly Glu Ile Gly Gly Pro Gln Glu Ala Glu Ala Ser Ala
```

```
            210                 215                 220
Trp Ile Lys Glu Asn Phe Ser Lys Pro Val Ile Gly Phe Val Ala Gly
225                 230                 235                 240

Leu Thr Ala Pro Lys Gly Arg Arg Met Gly His Ala Gly Ala Ile Ile
                245                 250                 255

Ser Ala Thr Gly Asp Ser Ala Ala Glu Lys Ala Glu Ile Met Arg Ser
                260                 265                 270

Tyr Gly Leu Thr Val Ala Pro Asp Pro Gly Ser Phe Gly Ser Thr Val
            275                 280                 285

Ala Asp Val Leu Ala Arg Ala Ala
            290                 295

<210> SEQ ID NO 2
<211> LENGTH: 390
<212> TYPE: PRT
<213> ORGANISM: Methylobacterium extorquens

<400> SEQUENCE: 2

Met Asp Val His Glu Tyr Gln Ala Lys Glu Leu Leu Ala Ser Phe Gly
1               5                   10                  15

Val Ala Val Pro Lys Gly Ala Val Ala Phe Ser Pro Asp Gln Ala Val
                20                  25                  30

Tyr Ala Ala Thr Glu Leu Gly Gly Ser Phe Trp Ala Val Lys Ala Gln
            35                  40                  45

Ile His Ala Gly Ala Arg Gly Lys Ala Gly Gly Ile Lys Leu Cys Arg
        50                  55                  60

Thr Tyr Asn Glu Val Arg Asp Ala Ala Arg Asp Leu Leu Gly Lys Arg
65                  70                  75                  80

Leu Val Thr Leu Gln Thr Gly Pro Glu Gly Lys Pro Val Gln Arg Val
                85                  90                  95

Tyr Val Glu Thr Ala Asp Pro Phe Glu Arg Glu Leu Tyr Leu Gly Tyr
            100                 105                 110

Val Leu Asp Arg Lys Ala Glu Arg Val Arg Val Ile Ala Ser Gln Arg
        115                 120                 125

Gly Gly Met Asp Ile Glu Glu Ile Ala Ala Lys Glu Pro Glu Ala Leu
    130                 135                 140

Ile Gln Val Val Val Glu Pro Ala Val Gly Leu Gln Gln Phe Gln Ala
145                 150                 155                 160

Arg Glu Ile Ala Phe Gln Leu Gly Leu Asn Ile Lys Gln Val Ser Ala
                165                 170                 175

Ala Val Lys Thr Ile Met Asn Ala Tyr Arg Ala Phe Arg Asp Cys Asp
            180                 185                 190

Gly Thr Met Leu Glu Ile Asn Pro Leu Val Val Thr Lys Asp Asp Arg
        195                 200                 205

Val Leu Ala Leu Asp Ala Lys Met Ser Phe Asp Asp Asn Ala Leu Phe
    210                 215                 220

Arg Arg Arg Asn Ile Ala Asp Met His Asp Pro Ser Gln Gly Asp Pro
225                 230                 235                 240

Arg Glu Ala Gln Ala Ala Glu His Asn Leu Ser Tyr Ile Gly Leu Glu
                245                 250                 255

Gly Glu Ile Gly Cys Ile Val Asn Gly Ala Gly Leu Ala Met Ala Thr
            260                 265                 270

Met Asp Met Ile Lys His Ala Gly Gly Glu Pro Ala Asn Phe Leu Asp
        275                 280                 285
```

```
Val Gly Gly Gly Ala Ser Pro Asp Arg Val Ala Thr Ala Phe Arg Leu
    290             295                 300

Val Leu Ser Asp Arg Asn Val Lys Ala Ile Leu Val Asn Ile Phe Ala
305                 310                 315                 320

Gly Ile Asn Arg Cys Asp Trp Val Ala Glu Gly Val Val Lys Ala Ala
                325                 330                 335

Arg Glu Val Lys Ile Asp Val Pro Leu Ile Val Arg Leu Ala Gly Thr
            340                 345                 350

Asn Val Asp Glu Gly Lys Lys Ile Leu Ala Glu Ser Gly Leu Asp Leu
            355                 360                 365

Ile Thr Ala Asp Thr Leu Thr Glu Ala Ala Arg Lys Ala Val Glu Ala
370                 375                 380

Cys His Gly Ala Lys His
385                 390

<210> SEQ ID NO 3
<211> LENGTH: 298
<212> TYPE: PRT
<213> ORGANISM: Granulibacter bethesdensis

<400> SEQUENCE: 3

Met Ser Ile Leu Ile Asn Lys Gln Thr Lys Ile Ile Ile Gln Gly Phe
1               5                   10                  15

Thr Gly Asp Lys Gly Thr Phe His Gly Arg Glu Met Ile Asp Tyr Gly
            20                  25                  30

Thr Asn Val Val Gly Gly Val Thr Pro Gly Lys Gly Gly Gln Thr His
        35                  40                  45

Leu Gly Arg Pro Val Phe Asn Thr Val Glu Asp Ala Val Arg Glu Thr
    50                  55                  60

Gly Ala Gln Ala Ser Ile Thr Phe Val Ala Pro Ala Phe Cys Ala Asp
65                  70                  75                  80

Ala Ile Met Glu Gly Ala Asp Ala Gly Leu Glu Leu Ile Cys Thr Ile
                85                  90                  95

Thr Asp Gly Ile Pro Ala Gln Asp Met Met Arg Val Lys Arg Tyr Leu
            100                 105                 110

Arg Arg Tyr Gln Lys Asp Arg Arg Thr Arg Leu Val Gly Pro Asn Cys
        115                 120                 125

Ala Gly Ile Ile Ser Pro Gly Gln Ala Met Leu Gly Ile Met Pro Gly
    130                 135                 140

His Ile Tyr Lys Glu Gly His Val Gly Ile Val Ser Arg Ser Gly Thr
145                 150                 155                 160

Leu Gly Tyr Glu Ala Ala Ala Gln Leu Lys Glu Leu Gly Ile Gly Val
                165                 170                 175

Ser Thr Ser Val Gly Ile Gly Gly Asp Pro Ile Asn Gly Ser Ser Phe
            180                 185                 190

Leu Asp His Leu Gln Leu Phe Glu Ala Asp Pro Glu Thr His Ala Val
        195                 200                 205

Leu Met Ile Gly Glu Ile Gly Gly Pro Gln Glu Ala Glu Ala Ala Lys
    210                 215                 220

Trp Ile Ser Glu Asn Met Ser Lys Pro Val Val Gly Tyr Val Ala Gly
225                 230                 235                 240

Leu Thr Ala Pro Lys Gly Arg Arg Met Gly His Ala Gly Ala Ile Ile
                245                 250                 255

Ser Gly Glu Gly Asp Ser Ala Ala Glu Lys Ser Glu Ile Met Arg Ser
            260                 265                 270
```

```
Tyr Gly Leu Thr Val Ala Pro Ser Pro Gly Glu Leu Gly Ser Thr Val
        275                 280                 285

Ala Ala Val Leu Ala Gly Arg Gln Ala Ala
290                 295

<210> SEQ ID NO 4
<211> LENGTH: 389
<212> TYPE: PRT
<213> ORGANISM: Granulibacter bethesdensis

<400> SEQUENCE: 4

Met Asp Val His Glu Tyr Gln Ala Lys Glu Leu Leu Ala Ser Ala Gly
1               5                   10                  15

Val Ala Val Pro Arg Gly Ala Ile Ala Phe Ser Ala Asp Gln Ala Val
            20                  25                  30

Tyr Ala Ala Thr Glu Leu Gly Gly Trp His Trp Ala Val Lys Ala Gln
        35                  40                  45

Ile His Ala Gly Ala Arg Gly Lys Ala Gly Ile Lys Leu Cys Lys
    50                  55                  60

Thr Tyr His Glu Val Arg Glu Ala Ala Ala Gly Met Leu Gly Lys Arg
65                  70                  75                  80

Leu Val Thr His Gln Thr Gly Pro Glu Gly Lys Pro Val Gln Arg Val
                85                  90                  95

Tyr Val Glu Val Ala Asp Pro Phe Glu Lys Glu Phe Tyr Leu Gly Phe
            100                 105                 110

Val Leu Asp Arg Lys Leu Glu Arg Val Arg Val Ile Ala Ser Ala Glu
        115                 120                 125

Gly Gly Met Glu Ile Glu Glu Ile Ala Ser Lys His Pro Glu Lys Leu
    130                 135                 140

Ile Gln Val Ile Val Glu Pro Ala Val Gly Leu Gln Gln Phe Gln Ala
145                 150                 155                 160

Arg Gln Ile Ala Phe Lys Leu Gly Leu Ser Ser Arg Gln Val Gln Arg
                165                 170                 175

Ala Val Thr Ser Ile Met Gly Ala Tyr Arg Ala Phe Arg Asp His Asp
            180                 185                 190

Ala Thr Met Leu Glu Ile Asn Pro Leu Val Leu Thr Lys Asp Asp Arg
        195                 200                 205

Ile Leu Ala Leu Asp Ala Lys Met Ser Phe Asp Asp Asn Ala Leu Phe
    210                 215                 220

Arg Arg Asn Asn Val Ala Asn Met His Asp Pro Ser Gln Asp Pro
225                 230                 235                 240

Arg Glu Ala Gln Ala Ala Glu His Asn Leu Asn Tyr Val Gly Leu Glu
                245                 250                 255

Gly Asp Ile Gly Cys Val Val Asn Gly Ala Gly Leu Ala Met Ala Thr
            260                 265                 270

Met Asp Val Ile Lys Tyr Ala Gly Gly Glu Pro Ala Asn Phe Leu Asp
        275                 280                 285

Val Gly Gly Gly Ala Ser Pro Glu Arg Thr Ala Thr Ala Phe Arg Leu
    290                 295                 300

Val Leu Ser Asp Lys Asn Val Lys Val Val Leu Val Asn Ile Phe Ala
305                 310                 315                 320

Gly Ile Asn Arg Cys Asp Trp Ile Ala Glu Gly Val Val His Ala Val
                325                 330                 335

Lys Glu Val Asp Leu Lys Leu Pro Leu Val Val Arg Leu Ala Gly Thr
```

```
            340                 345                 350
Asn Val Glu Glu Gly Arg Arg Ile Leu Lys Glu Ser Gly Ile Ser Val
            355                 360                 365

Ile Met Ala Glu Ser Leu Thr Glu Ala Ala Glu Lys Ala Val Glu Ala
            370                 375                 380

Ala Lys Ala Ala Ala
385

<210> SEQ ID NO 5
<211> LENGTH: 387
<212> TYPE: PRT
<213> ORGANISM: Hyphomicrobium methylovorum

<400> SEQUENCE: 5

Met Asp Val His Glu Tyr Gln Ala Lys Glu Leu Leu Ala Lys Phe Gly
1               5                   10                  15

Val Pro Ile Ala Arg Gly Gly Leu Ala Tyr Ser Pro Glu Gln Ala Thr
            20                  25                  30

Tyr Arg Ala Ser Glu Leu Gly Gly Thr Val Val Lys Ala Gln Ile
            35                  40                  45

His Ser Gly Ala Arg Gly Lys Ala Gly Gly Val Lys Val Cys Lys Asn
        50                  55                  60

Glu Lys Glu Ile Glu Asp Ala Ala Glu Phe Met Leu Gly Arg Lys Leu
65                  70                  75                  80

Val Thr His Gln Thr Gly Pro Ala Gly Lys Leu Val Ser Arg Leu Tyr
                85                  90                  95

Ile Glu Glu Ala Thr Asn Ile Asp Arg Glu Ile Tyr Leu Gly Phe Val
            100                 105                 110

Met Asp Arg Ala Ser Glu Arg Ile Val Val Ala Ser Ala Ala Gly
            115                 120                 125

Gly Met Asp Ile Glu Glu Ile Ser Ala Ser Gln Pro Asp Thr Ile Ile
        130                 135                 140

Arg Val Ser Val Asp Pro Ala Val Gly Met Gln Gln Phe Gln Ala Arg
145                 150                 155                 160

Glu Leu Ala Phe Gly Leu Gly Val Asp Pro Glu Ile Val Asn Lys Leu
                165                 170                 175

Val Pro Ala Ile Met Gly Cys Tyr Arg Ala Phe Arg Asp Leu Asp Ala
            180                 185                 190

Thr Met Val Glu Val Asn Pro Leu Val Ile Thr Lys Glu Lys Gln Val
            195                 200                 205

Leu Ala Leu Asp Ala Lys Met Ser Phe Asp Asp Asn Ala Leu Phe Arg
        210                 215                 220

Arg Pro His Ile Ala Glu Leu Arg Asp Lys Ser Gln Glu Asp Pro Arg
225                 230                 235                 240

Glu Thr Tyr Ala Ser Asp Arg Gly Leu Ser Tyr Val Gly Leu Asp Gly
                245                 250                 255

Asp Ile Gly Cys Ile Val Asn Gly Ala Gly Leu Ala Met Ala Thr Leu
            260                 265                 270

Asp Met Ile Lys Leu Ala Gly Gly Glu Pro Ala Asn Phe Leu Asp Ile
            275                 280                 285

Gly Gly Gly Ala Ser Pro Glu Arg Val Thr Lys Ser Phe Lys Ala Val
        290                 295                 300

Leu Arg Asp Lys Asn Val Lys Ala Ile Leu Val Asn Val Phe Ala Gly
305                 310                 315                 320
```

```
Ile Asn Arg Cys Asp Trp Val Ala Lys Gly Val Val Asp Ala Val Lys
            325                 330                 335

Glu Leu Glu Ile Lys Met Pro Ile Val Val Arg Leu Ala Gly Thr Asn
        340                 345                 350

Val Glu Glu Gly Arg Lys Ile Ile Asp Asn Ser Gly Leu Thr Val Ile
            355                 360                 365

Ser Ala Asp Thr Leu Ala Asp Ala Ala Lys Gln Ala Val Asp Ala Ala
        370                 375                 380

Lys Lys Ala
385

<210> SEQ ID NO 6
<211> LENGTH: 299
<212> TYPE: PRT
<213> ORGANISM: Hyphomicrobium methylovorum

<400> SEQUENCE: 6

Met Ala Ile Phe Ile Asn Glu Lys Thr Pro Ile Leu Ile Gln Gly Phe
1               5                   10                  15

Thr Gly Arg Ile Gly Thr Phe His Ala Gln Glu Met Ile Asp Tyr Gly
            20                  25                  30

Ser Asn Val Val Gly Val Thr Pro Gly Lys Gly Thr Ser His
        35                  40                  45

Leu Gly Arg Pro Val Phe Asn Thr Val Lys Gly Ala Ala Asp Glu Thr
    50                  55                  60

Gly Ala Glu Ala Ser Ile Val Phe Val Pro Pro Phe Ala Ala Asp
65                  70                  75                  80

Ala Ile Met Glu Ala Ala Asp Ala Gly Ile Lys Tyr Cys Val Cys Ile
                85                  90                  95

Thr Asp Gly Ile Pro Ala Gln Asp Met Ile Arg Val Lys Arg Tyr Met
            100                 105                 110

Arg Arg Tyr Lys Lys Glu Ser Arg Met Val Leu Thr Gly Pro Asn Cys
        115                 120                 125

Ala Gly Thr Ile Ser Pro Gly Lys Ala Met Leu Gly Ile Met Pro Gly
    130                 135                 140

His Ile Phe Leu Pro Gly Arg Val Gly Ile Val Gly Arg Ser Gly Thr
145                 150                 155                 160

Leu Gly Tyr Glu Ala Ala Gln Leu Lys Ala Leu Gly Ile Gly Val
                165                 170                 175

Ser Thr Ser Val Gly Ile Gly Gly Asp Pro Ile Asn Gly Ser Ser His
            180                 185                 190

Arg Asp Ile Leu Glu Ala Phe Glu Ser Asp Pro Glu Thr Asp Ala Val
        195                 200                 205

Leu Met Ile Gly Glu Ile Gly Gly Pro Gln Glu Ala Gly Leu
    210                 215                 220

Phe Ala Lys Glu His Met Lys Lys Pro Val Ile Ala Tyr Ile Ala Gly
225                 230                 235                 240

Leu Ser Ala Pro Lys Gly Arg Arg Met Gly His Ala Gly Ala Ile Val
                245                 250                 255

Ser Ala Phe Gly Glu Ser Ala Ala Glu Lys Val Glu Ile Leu Lys Gly
            260                 265                 270

Cys Asn Val Thr Ile Ala Ala Thr Pro Ser Glu Met Gly Ser Thr Val
        275                 280                 285

Ala Gln Val Leu Asn Gln Arg Lys Lys Val Ala
    290                 295
```

<210> SEQ ID NO 7
<211> LENGTH: 299
<212> TYPE: PRT
<213> ORGANISM: Hyphomicrobium denitrificans

<400> SEQUENCE: 7

```
Met Ala Ile Phe Ile Asn Glu Lys Thr Pro Ile Leu Ile Gln Gly Phe
1               5                   10                  15

Thr Gly Arg Ile Gly Thr Phe His Ala Gln Glu Met Ile Asp Tyr Gly
            20                  25                  30

Ser Asn Val Val Gly Gly Val Thr Pro Gly Lys Gly Thr Ser His
        35                  40                  45

Leu Gly Arg Pro Val Phe Asn Thr Val Lys Gly Ala Val Asp Glu Thr
    50                  55                  60

Gly Ala Glu Ala Ser Ile Val Phe Val Pro Pro Phe Ala Ala Asp
65                  70                  75                  80

Ala Ile Met Glu Ala Ala Asp Ala Gly Ile Lys Tyr Cys Val Cys Ile
                85                  90                  95

Thr Asp Gly Ile Pro Ala Gln Asp Met Ile Arg Val Lys Arg Tyr Met
            100                 105                 110

Arg Arg Tyr Lys Lys Glu Ala Arg Met Ile Leu Thr Gly Pro Asn Cys
        115                 120                 125

Ala Gly Thr Ile Ser Pro Gly Lys Ala Met Leu Gly Ile Met Pro Gly
    130                 135                 140

His Ile Tyr Leu Pro Gly Arg Val Gly Ile Val Gly Arg Ser Gly Thr
145                 150                 155                 160

Leu Gly Tyr Glu Ala Ala Ala Gln Leu Lys Ala Leu Gly Ile Gly Val
                165                 170                 175

Ser Thr Ser Val Gly Ile Gly Gly Asp Pro Ile Asn Gly Ser Ser His
            180                 185                 190

Arg Asp Val Leu Glu His Phe Glu Asn Asp Pro Glu Thr Asp Ala Ile
        195                 200                 205

Leu Met Ile Gly Glu Ile Gly Gly Pro Gln Glu Ala Glu Ala Gly Leu
    210                 215                 220

Phe Ala Lys Glu His Met Lys Lys Pro Val Ile Ala Tyr Ile Ala Gly
225                 230                 235                 240

Leu Ser Ala Pro Lys Gly Arg Arg Met Gly His Ala Gly Ala Ile Val
                245                 250                 255

Ser Ala Phe Gly Glu Ser Ala Ala Glu Lys Val Glu Ile Leu Lys Gly
            260                 265                 270

Cys Gly Val Ala Ile Ala Pro Thr Pro Ser Glu Met Gly Ser Thr Val
        275                 280                 285

Ala Gln Val Leu Gly Lys Gln Lys Lys Val Ala
    290                 295
```

<210> SEQ ID NO 8
<211> LENGTH: 387
<212> TYPE: PRT
<213> ORGANISM: Hyphomicrobium denitrificans

<400> SEQUENCE: 8

```
Met Asp Ile His Glu Tyr Gln Ala Lys Glu Leu Leu Ala Lys Phe Gly
1               5                   10                  15

Val Pro Ile Ala Arg Gly Gly Leu Ala Tyr Ser Pro Glu Gln Ala Thr
            20                  25                  30
```

Tyr Arg Ala Ser Glu Leu Gly Gly Thr Val Val Lys Ala Gln Ile
         35                  40                  45

His Ser Gly Ala Arg Gly Lys Ala Gly Gly Val Lys Val Cys Lys Thr
 50                  55                  60

Glu Lys Glu Ile Glu Asp Ala Ala Glu Phe Met Leu Gly Arg Lys Leu
 65                  70                  75                  80

Val Thr His Gln Thr Gly Ser Ala Gly Lys Leu Val Ser Arg Leu Tyr
                 85                  90                  95

Ile Glu Glu Ala Thr Asn Ile Asp Arg Glu Ile Tyr Leu Gly Phe Val
             100                 105                 110

Met Asp Arg Ala Ser Glu Arg Ile Val Val Ala Ser Ala Ala Gly
             115                 120                 125

Gly Met Asp Ile Glu Glu Ile Ser Ala Ser Gln Pro Asp Thr Ile Ile
130                 135                 140

Arg Val Ala Val Asp Pro Ala Val Gly Met Gln Gln Phe Gln Ala Arg
145                 150                 155                 160

Glu Leu Ala Phe Gly Leu Gly Val Asp Pro Glu Ile Val Asn Lys Leu
                165                 170                 175

Val Pro Ala Ile Met Gly Cys Tyr Arg Ala Phe Arg Asp Leu Asp Ala
            180                 185                 190

Met Met Val Glu Ile Asn Pro Leu Val Ile Thr Lys Glu Lys Gln Val
        195                 200                 205

Val Ala Leu Asp Ala Lys Met Ser Phe Asp Asp Asn Ala Leu Phe Arg
    210                 215                 220

Arg Pro His Ile Ala Glu Leu Arg Asp Lys Ser Gln Glu Asp Pro Arg
225                 230                 235                 240

Glu Thr Tyr Ala Ser Asp Arg Gly Leu Ser Tyr Val Gly Leu Asp Gly
                245                 250                 255

Asp Ile Gly Cys Ile Val Asn Gly Ala Gly Leu Ala Met Ala Thr Leu
            260                 265                 270

Asp Met Ile Lys Leu Ala Gly Gly Glu Pro Ala Asn Phe Leu Asp Ile
        275                 280                 285

Gly Gly Gly Ala Ser Pro Glu Arg Val Thr Lys Ser Phe Lys Ala Val
    290                 295                 300

Leu Arg Asp Lys Asn Val Lys Ala Ile Leu Val Asn Val Phe Ala Gly
305                 310                 315                 320

Ile Asn Arg Cys Asp Trp Val Ala Lys Gly Val Val Asp Ala Val Lys
                325                 330                 335

Glu Leu Asp Ile Lys Leu Pro Ile Val Val Arg Leu Ala Gly Thr Asn
            340                 345                 350

Val Glu Glu Gly Arg Lys Ile Ile Asp Asn Ser Gly Leu Thr Val Ile
        355                 360                 365

Ser Ala Glu Thr Leu Ala Asp Ala Ala Lys Gln Ala Val Glu Ala Ala
    370                 375                 380

Lys Lys Ala
385

<210> SEQ ID NO 9
<211> LENGTH: 299
<212> TYPE: PRT
<213> ORGANISM: Rhizobium sp.

<400> SEQUENCE: 9

Met Ser Ile Leu Leu Asp Lys Asn Thr Arg Val Ile Val Gln Gly Phe

-continued

```
              1               5                  10                 15
            Thr Gly Lys Ile Gly Ser Phe His Ala Glu Asp Met Lys Arg Tyr Gly
                            20                 25                 30
            Thr Asn Val Val Gly Gly Val Thr Pro Gly Lys Gly Gln Ala His
                         35                 40                 45
            Leu Gly Met Pro Val Phe Asn Thr Val Lys Gly Ala Val Gln Glu Thr
                         50                 55                 60
            Gly Ala Asp Ala Ser Ile Ile Phe Val Pro Pro Phe Ala Ala Asp
             65                 70                 75                 80
            Ser Ile Met Glu Ala Ala Asp Ala Gly Ile Arg Leu Cys Val Cys Ile
                             85                 90                 95
            Thr Asp Gly Ile Pro Ser Gln Asp Met Ile Arg Val Lys Arg Tyr Met
                            100                105                110
            Arg Arg Tyr Arg Phe Glu Asp Arg Met Thr Leu Ile Gly Pro Asn Cys
                            115                120                125
            Ala Gly Met Ile Thr Pro Gly Glu Ala Met Met Gly Ile Met Pro Gly
                         130                135                140
            Ser Ile Tyr Leu Pro Gly Arg Ile Gly Ile Val Gly Arg Ser Gly Thr
            145                150                155                160
            Leu Gly Tyr Glu Ala Ala Ser Gln Met Lys Ala Leu Gly Val Gly Val
                             165                170                175
            Ser Thr Ser Ile Gly Ile Gly Gly Asp Pro Val Asn Gly Ser Ser Phe
                         180                185                190
            Lys Asp Met Leu Glu Leu Phe Glu Lys Asp Pro Gly Thr Asp Ala Val
                         195                200                205
            Leu Met Ile Gly Glu Ile Gly Gly Pro Gln Glu Ala Glu Ala Ala Leu
                         210                215                220
            Trp Ala Arg Asp His Met Lys Lys Pro Leu Ile Ala Tyr Ile Ala Gly
            225                230                235                240
            Leu Ser Ala Pro Lys Gly Arg Arg Met Gly His Ala Gly Ala Ile Ile
                             245                250                255
            Ser Ala Phe Gly Glu Ser Ala Gln Glu Lys Val Glu Ile Leu Lys Ser
                         260                265                270
            Ala Gly Val Thr Ile Val Pro Thr Pro Ser Ser Phe Gly Glu Thr Val
                         275                280                285
            Ala Asp Val Leu Ser Ala Met Ser Lys Ala Ala
                         290                295

<210> SEQ ID NO 10
<211> LENGTH: 394
<212> TYPE: PRT
<213> ORGANISM: Rhizobium sp.

<400> SEQUENCE: 10

Met Asp Ile His Glu Tyr Gln Ala Lys Glu Leu Leu Ser Arg Tyr Gln
            1               5                  10                 15
            Ile His Ile Pro Arg Gly Gly Leu Ala Tyr Ser Pro Glu Gln Ala Ala
                            20                 25                 30
            Tyr Arg Ala Arg Glu Ile Gly Gly Asp Arg Trp Val Val Lys Ala Gln
                         35                 40                 45
            Ile His Ser Gly Ala Arg Gly Lys Ala Gly Gly Ile Lys Leu Cys Ser
                         50                 55                 60
            Thr Asp His Glu Ile Val Glu Ala Ala Asp Ser Met Leu Gly Arg Thr
            65                 70                 75                 80
```

-continued

Ile Val Thr His Gln Thr Gly Pro Gln Gly Lys Leu Val Ser Arg Leu
            85                  90                  95

Tyr Val Glu Glu Ala Met Asp Ile Ala Arg Glu Ile Tyr Ile Gly Phe
            100                 105                 110

Val Leu Asp Arg Lys Ser Glu Arg Ile Met Ile Val Ala Ser Ser Ser
            115                 120                 125

Gly Gly Met Glu Ile Glu Ile Ala Glu Ala Glu Pro Asp Ser Ile
    130                 135                 140

Ile Arg Ala Thr Val Asp Pro Gly Val Gly Met Gln Asp Phe Gln Ala
145                 150                 155                 160

Arg Glu Ile Ala Phe Gly Leu Gly Ile Asp Asn Ala Leu Ile Gly Arg
                165                 170                 175

Ala Thr Gln Thr Leu Leu Gly Cys Tyr Arg Ala Phe Val Asp Tyr Asp
            180                 185                 190

Ala Ser Met Leu Glu Ile Asn Pro Leu Val Val Thr Arg Arg Gly Asp
            195                 200                 205

Leu Val Ala Leu Asp Ala Lys Met Ser Phe Asp Glu Asn Ala Leu Phe
    210                 215                 220

Arg Arg Pro His Ile Ala Glu Met Arg Asp Lys Ser Gln Glu Asp Gln
225                 230                 235                 240

Arg Glu Thr Tyr Ala Ser Asp Arg Gly Leu Ser Tyr Val Gly Leu Asp
                245                 250                 255

Gly Asn Ile Gly Cys Ile Ile Asn Gly Ala Gly Leu Ala Met Ala Thr
            260                 265                 270

Met Asp Met Ile Lys Ile Ala Gly Gly Glu Pro Ala Asn Phe Leu Asp
    275                 280                 285

Ile Gly Gly Gly Ala Ser Pro Asp Arg Val Ala Lys Ser Phe Arg Ala
    290                 295                 300

Val Leu Thr Asp Arg Gln Val Glu Thr Ile Leu Val Asn Ile Phe Ala
305                 310                 315                 320

Gly Ile Asn Arg Cys Asp Trp Val Ala Glu Gly Val Ile Lys Ala Leu
                325                 330                 335

Arg Glu Val Gly Val Pro Val Pro Leu Val Val Arg Leu Ser Gly Thr
            340                 345                 350

Asn Met Glu Glu Gly Arg Arg Ile Leu Ala Glu Ser Gly Glu Asn Ile
        355                 360                 365

Ile Val Ala Glu Thr Leu Ala Glu Ala Ala Asp Lys Ala Val Ala Ala
    370                 375                 380

Trp Arg Ser Phe Thr Ala Asn Lys Ala Ala
385                 390

<210> SEQ ID NO 11
<211> LENGTH: 295
<212> TYPE: PRT
<213> ORGANISM: Nitrosomonas europaea

<400> SEQUENCE: 11

Met Ala Ile Leu Ile Asn Glu Gln Thr Arg Ile Ile Val Gln Gly Phe
1               5                   10                  15

Thr Gly Arg Ile Gly Thr Phe His Ala Gln Glu Met Ile Asp Tyr Gly
            20                  25                  30

Ser Asn Val Val Gly Gly Val Thr Pro Gly Lys Gly Gly Gln Lys His
        35                  40                  45

Leu Gly Leu Pro Val Phe Asn Thr Val Arg Glu Ala Val Glu Gln Ala
    50                  55                  60

```
Gly Ala Glu Ala Ser Ile Val Phe Val Pro Pro Ala Phe Ala Ala Asp
 65                  70                  75                  80

Ser Ile Met Glu Ala Ala Asp Ala Gly Ile Lys Tyr Cys Val Ser Ile
                 85                  90                  95

Thr Asp Gly Ile Pro Thr Gln Asp Met Met Thr Val Lys Asn Phe Leu
            100                 105                 110

Arg Leu Phe Pro Glu Glu Asp Arg Met Met Leu Thr Gly Pro Asn Cys
        115                 120                 125

Ser Gly Thr Ile Ser Pro Gly Arg Ala Met Leu Gly Ile Met Pro Gly
    130                 135                 140

His Ile Tyr Ser Arg Gly Val Val Gly Val Val Gly Arg Ser Gly Thr
145                 150                 155                 160

Leu Gly Tyr Glu Ala Ala Asp Gln Met Arg Arg Leu Asn Ile Gly Ile
                165                 170                 175

Ser Thr Ser Val Gly Ile Gly Gly Asp Pro Ile Ile Gly Ser Ser His
            180                 185                 190

Arg Asn Val Leu Gln Lys Leu Glu Glu Asp Pro Glu Thr Lys Val Thr
        195                 200                 205

Leu Met Ile Gly Glu Ile Gly Gly Pro Met Glu Val Glu Ala Gly Leu
    210                 215                 220

Phe Ala Lys Glu Asn Met Ser Lys Pro Leu Val Ala Tyr Ile Ala Gly
225                 230                 235                 240

Leu Thr Ala Pro Pro Gly Arg Arg Met Gly His Ala Gly Ala Ile Ile
                245                 250                 255

Ser Ser Ala Gly Glu Ser Ala Ala Glu Lys Val Glu Arg Leu Lys Glu
            260                 265                 270

Leu Gly Val Thr Ile Cys Pro Thr Pro Ser Leu Met Gly Glu Thr Val
        275                 280                 285

Ala Lys Val Leu Ala Gly Leu
    290                 295

<210> SEQ ID NO 12
<211> LENGTH: 390
<212> TYPE: PRT
<213> ORGANISM: Nitrosomonas europaea

<400> SEQUENCE: 12

Met Asp Ile His Glu Tyr Gln Ala Lys Glu Ile Leu Ala Glu Tyr Gly
 1               5                  10                  15

Ile Lys Leu Ala Glu Gly Gly Leu Ala His Thr Val Glu Glu Ala Val
                 20                  25                  30

Gln Arg Ser Arg Glu Ile Asp Gly Asn Val Trp Val Val Lys Ala Gln
             35                  40                  45

Ile His Ser Gly Ala Arg Gly Lys Ala Gly Gly Val Lys Val Cys Arg
 50                  55                  60

Thr His Glu Glu Ile Glu Val Ala Ala Glu Ser Leu Leu Gly Lys Lys
 65                  70                  75                  80

Leu Val Thr His Gln Thr Gly Pro Ala Gly Lys Leu Cys Ser Arg Leu
                 85                  90                  95

Tyr Ile Glu Ala Gly Thr Glu Ile Ala Arg Glu Val Tyr Leu Ala Phe
            100                 105                 110

Met Ile Asp Arg Ser His Glu Arg Ile Val Met Val Gly Ser Ala Gln
        115                 120                 125

Gly Gly Met Asp Ile Glu Thr Leu Ala Ala Thr Asn Pro Asp Ala Ile
```

130                 135                 140
Lys Lys Ile His Ile Glu Pro Ala Val Gly Leu Gln Asp Phe Gln Ala
145                 150                 155                 160

Arg Thr Met Ala Phe Ala Leu Gly Leu Glu Asp Val Leu Leu Asn His
                    165                 170                 175

Ala Val Lys Thr Ile Arg Gly Cys Tyr Arg Ala Met Arg Asp Leu Asp
                180                 185                 190

Ala Asn Ile Leu Glu Ile Asn Pro Leu Val Val Thr Arg Asn Asn Glu
                    195                 200                 205

Leu Ile Ala Leu Asp Ala Lys Met Ser Phe Asp Glu Asn Ala Leu Phe
210                 215                 220

Arg Arg His Arg Ile Ser Glu Leu Arg Asp Asn Ser Gln Ile Asp Ser
225                 230                 235                 240

Arg Glu Ile Ala Ala Ala Glu Ala Gly Leu Ser Tyr Val Gly Leu Asp
                    245                 250                 255

Gly Asp Ile Gly Cys Met Ile Asn Gly Ala Gly Leu Ala Met Ala Thr
                260                 265                 270

Met Asp Met Ile Lys Leu Ala Gly Gly Glu Pro Ala Asn Phe Leu Asp
                275                 280                 285

Val Gly Gly Gly Ala Ser Ala Glu Arg Thr Glu Lys Ala Phe Arg Leu
290                 295                 300

Val Leu Ala Asp Asn Asn Val Lys Ala Met Leu Val Asn Ile Phe Ala
305                 310                 315                 320

Gly Ile Asn Arg Cys Asp Trp Ile Ala Glu Gly Val Val Gln Ala Val
                    325                 330                 335

Arg Asn Ile Gly Met Thr Val Pro Leu Val Val Arg Leu Ser Gly Thr
                340                 345                 350

Asn Val Glu Glu Gly Arg Arg Ile Ile Ala Asp Ser Gly Leu Pro Ile
                    355                 360                 365

Ile Thr Ala Glu Thr Leu Ala Asp Ala Ala Glu Lys Val Val His Ala
                370                 375                 380

Arg Asn Gln Ala Ala Val
385                 390

<210> SEQ ID NO 13
<211> LENGTH: 300
<212> TYPE: PRT
<213> ORGANISM: Methylococcus capsulatus

<400> SEQUENCE: 13

Met Ser Val Phe Val Asn Lys His Ser Lys Val Ile Phe Gln Gly Phe
1               5                   10                  15

Thr Gly Glu His Ala Thr Phe His Ala Lys Asp Ala Met Arg Met Gly
                    20                  25                  30

Thr Arg Val Val Gly Gly Val Thr Pro Gly Lys Gly Gly Thr Arg His
                35                  40                  45

Pro Asp Pro Glu Leu Ala His Leu Pro Val Phe Asp Thr Val Ala Glu
                    50                  55                  60

Ala Val Ala Ala Thr Gly Ala Asp Val Ser Ala Val Phe Val Pro Pro
65                  70                  75                  80

Pro Phe Asn Ala Asp Ala Leu Met Glu Ala Ile Asp Ala Gly Ile Arg
                    85                  90                  95

Val Ala Val Thr Ile Ala Asp Gly Ile Pro Val His Asp Met Ile Arg
                100                 105                 110

```
Leu Gln Arg Tyr Arg Val Gly Lys Asp Ser Ile Val Ile Gly Pro Asn
            115                 120                 125

Thr Pro Gly Ile Ile Thr Pro Gly Glu Cys Lys Val Gly Ile Met Pro
        130                 135                 140

Ser His Ile Tyr Lys Lys Gly Asn Val Gly Ile Val Ser Arg Ser Gly
145                 150                 155                 160

Thr Leu Asn Tyr Glu Ala Thr Glu Gln Met Ala Ala Leu Gly Leu Gly
                165                 170                 175

Ile Thr Thr Ser Val Gly Ile Gly Gly Asp Pro Ile Asn Gly Thr Asp
            180                 185                 190

Phe Val Thr Val Leu Arg Ala Phe Glu Ala Asp Pro Glu Thr Glu Ile
            195                 200                 205

Val Val Met Ile Gly Glu Ile Gly Gly Pro Gln Glu Val Ala Ala Ala
        210                 215                 220

Arg Trp Ala Lys Glu Asn Met Thr Lys Pro Val Ile Gly Phe Val Ala
225                 230                 235                 240

Gly Leu Ala Ala Pro Thr Gly Arg Arg Met Gly His Ala Gly Ala Ile
                245                 250                 255

Ile Ser Ser Glu Ala Asp Thr Ala Gly Ala Lys Met Asp Ala Met Glu
            260                 265                 270

Ala Leu Gly Leu Tyr Val Ala Arg Asn Pro Ala Gln Ile Gly Gln Thr
        275                 280                 285

Val Leu Arg Ala Ala Gln Glu His Gly Ile Arg Phe
        290                 295                 300

<210> SEQ ID NO 14
<211> LENGTH: 389
<212> TYPE: PRT
<213> ORGANISM: Methylococcus capsulatus

<400> SEQUENCE: 14

Met Asn Ile His Glu Tyr Gln Ala Lys Glu Leu Leu Lys Thr Tyr Gly
1               5                   10                  15

Val Pro Val Pro Asp Gly Ala Val Ala Tyr Ser Asp Ala Gln Ala Ala
            20                  25                  30

Ser Val Ala Glu Glu Ile Gly Gly Ser Arg Trp Val Lys Ala Gln
        35                  40                  45

Ile His Ala Gly Arg Gly Lys Ala Gly Gly Val Lys Val Ala His
    50                  55                  60

Ser Ile Glu Glu Val Arg Gln Tyr Ala Asp Ala Met Leu Gly Ser His
65                  70                  75                  80

Leu Val Thr His Gln Thr Gly Pro Gly Gly Ser Leu Val Gln Arg Leu
                85                  90                  95

Trp Val Glu Gln Ala Ser His Ile Lys Lys Glu Tyr Tyr Leu Gly Phe
            100                 105                 110

Val Ile Asp Arg Gly Asn Gln Arg Ile Thr Leu Ile Ala Ser Ser Glu
        115                 120                 125

Gly Gly Met Glu Ile Glu Val Ala Lys Glu Thr Pro Glu Lys Ile
        130                 135                 140

Val Lys Glu Val Val Asp Pro Ala Ile Gly Leu Leu Asp Phe Gln Cys
145                 150                 155                 160

Arg Lys Val Ala Thr Ala Ile Gly Leu Lys Gly Lys Leu Met Pro Gln
                165                 170                 175

Ala Val Arg Leu Met Lys Ala Ile Tyr Arg Cys Met Arg Asp Lys Asp
            180                 185                 190
```

```
Ala Leu Gln Ala Glu Ile Asn Pro Leu Ala Ile Val Gly Glu Ser Asp
            195                 200                 205

Glu Ser Leu Met Val Leu Asp Ala Lys Phe Asn Phe Asp Asp Asn Ala
210                 215                 220

Leu Tyr Arg Gln Arg Thr Ile Thr Glu Met Arg Asp Leu Ala Glu Glu
225                 230                 235                 240

Asp Pro Lys Glu Val Glu Ala Ser Gly His Gly Leu Asn Tyr Ile Ala
            245                 250                 255

Leu Asp Gly Asn Ile Gly Cys Ile Val Asn Gly Ala Gly Leu Ala Met
            260                 265                 270

Ala Ser Leu Asp Ala Ile Thr Leu His Gly Gly Arg Pro Ala Asn Phe
            275                 280                 285

Leu Asp Val Gly Gly Ala Ser Pro Glu Lys Val Thr Asn Ala Cys
290                 295                 300

Arg Ile Val Leu Glu Asp Pro Asn Val Arg Cys Ile Leu Val Asn Ile
305                 310                 315                 320

Phe Ala Gly Ile Asn Arg Cys Asp Trp Ile Ala Lys Gly Leu Ile Gln
                325                 330                 335

Ala Cys Asp Ser Leu Gln Ile Lys Val Pro Leu Ile Val Arg Leu Ala
            340                 345                 350

Gly Thr Asn Val Asp Glu Gly Arg Lys Ile Leu Ala Glu Ser Gly Leu
            355                 360                 365

Ser Phe Ile Thr Ala Glu Asn Leu Asp Asp Ala Ala Ala Lys Ala Val
370                 375                 380

Ala Ile Val Lys Gly
385

<210> SEQ ID NO 15
<211> LENGTH: 298
<212> TYPE: PRT
<213> ORGANISM: Uncultured gamma proteobacterium

<400> SEQUENCE: 15

Met Ser Ile Phe Val Asn Arg His Ser Arg Val Ile Ile Gln Gly Phe
1               5                   10                  15

Thr Gly Gln His Ala Thr Phe His Ala Ser Glu Ala Ile Arg Tyr Gly
            20                  25                  30

Thr Gln Val Val Gly Val Thr Pro Gly Lys Gly Gly Ser Lys His
        35                  40                  45

Leu Gly Leu Pro Val Phe Asp Thr Val Ser Glu Ala Val Ser Glu Thr
    50                  55                  60

Gly Ala Asp Val Ser Gly Ile Phe Val Pro Pro Ala Phe Ala Ala Asp
65                  70                  75                  80

Ala Ile Met Glu Ala Ile Glu Ala Gly Ile Arg Val Ile Val Val Ile
                85                  90                  95

Ala Asp Gly Ile Pro Val Gln Asp Met Ile Arg Val Gln Arg Tyr Arg
            100                 105                 110

Leu Gly Arg Asp Cys Leu Val Leu Gly Pro Asn Thr Pro Gly Ile Ile
            115                 120                 125

Thr Pro Gly Glu Cys Lys Val Gly Ile Met Pro Ala Gly Ile Tyr Arg
            130                 135                 140

Pro Gly Arg Ile Gly Val Val Ser Arg Ser Gly Thr Leu Asn Tyr Glu
145                 150                 155                 160

Ala Val Glu Gln Leu Gly Lys Leu Gly Leu Gly Gln Ser Thr Ala Val
```

```
              165                 170                 175
Gly Ile Gly Gly Asp Pro Val Asn Gly Thr Asp Phe Val Thr Val Leu
            180                 185                 190

Lys Ala Phe Glu Gln Asp Pro Asp Thr Asp Ala Ile Val Met Ile Gly
            195                 200                 205

Glu Ile Gly Gly Pro Gln Glu Val Ala Ala Ala Arg Trp Ala Lys Glu
            210                 215                 220

Asn Met Gln Lys Pro Leu Ile Gly Phe Val Ala Gly Ala Ser Ala Pro
225                 230                 235                 240

Pro Gly Arg Arg Met Gly His Ala Gly Ala Ile Ile Glu Gly Glu Glu
                245                 250                 255

Asp Thr Ala Lys Ala Lys Met Asp Ala Met Glu Glu Leu Gly Val Tyr
            260                 265                 270

Val Val Arg Asn Pro Ala Arg Ile Gly Glu Thr Val Leu Arg Ala Leu
            275                 280                 285

Lys Glu Arg Leu Gly Ser Ala Val Ser Gly
            290                 295

<210> SEQ ID NO 16
<211> LENGTH: 392
<212> TYPE: PRT
<213> ORGANISM: Uncultured gamma proteobacterium

<400> SEQUENCE: 16

Met Asn Ile His Glu Tyr Gln Ala Lys Glu Leu Leu Arg Ser Tyr Gly
1               5                   10                  15

Val Pro Val Pro Ala Gly Asn Val Ala Tyr Ser Asp Arg Gln Ala Gln
            20                  25                  30

Ala Val Ala Glu Gln Ile Gly Gly Asp Gly Trp Val Val Lys Ala Gln
        35                  40                  45

Ile His Thr Gly Gly Arg Gly Lys Ala Gly Gly Val Lys Leu Ala Gln
    50                  55                  60

Ser Leu Glu Glu Val Arg Lys Ile Ala Asp Glu Met Ile Gly Lys Thr
65                  70                  75                  80

Leu Val Thr Pro Gln Thr Gly Pro Lys Gly Lys Val Val Arg Arg Val
            85                  90                  95

Leu Val Glu Glu Ala Val Ser Pro Gln Arg Glu Leu Tyr Leu Gly Leu
            100                 105                 110

Val Ile Asp Arg Arg Ser Gln Arg Ile Thr Ile Val Ala Ser Ala Glu
            115                 120                 125

Gly Gly Val Glu Ile Glu Val Ala Ala Arg Ser Pro Glu Lys Ile
            130                 135                 140

Val Arg Glu Ala Ile Asp Pro Ala Ile Gly Leu Arg Asp Phe Gln Cys
145                 150                 155                 160

Arg Lys Val Ala Ala Ala Ile Gly Leu Arg Asp Lys His Leu Met Ala
                165                 170                 175

Gln Ala Val Arg Leu Met Gln Arg Ile Tyr Arg Leu Phe Arg Asp Lys
            180                 185                 190

Asp Ala Leu Gln Val Glu Ile Asn Pro Leu Gly Ile Val Gly Ser Glu
            195                 200                 205

Pro Lys Leu Val Cys Leu Asp Ala Lys Phe Asn Phe Asp Pro Asn Ala
        210                 215                 220

Leu Phe Arg His Pro Glu Ile Asn Glu Leu Arg Asp Leu Glu Glu Glu
225                 230                 235                 240
```

Asp Pro Arg Glu Val Glu Ala Leu Gly His Gly Leu Asn Tyr Ile Ala
            245                 250                 255

Leu Asp Gly Asp Ile Gly Cys Ile Val Asn Gly Ala Gly Leu Ala Met
        260                 265                 270

Ala Thr Met Asp Ala Ile Val Phe His Gly Gly Trp Pro Ala Asn Phe
    275                 280                 285

Leu Asp Ile Gly Gly Gly Ala Ser Pro Glu Lys Val Gln Asn Ala Cys
290                 295                 300

Arg Ile Val Ile Gln Asp Gln Asn Val Lys Thr Leu Leu Val Asn Ile
305                 310                 315                 320

Phe Ala Gly Ile Asn Arg Cys Asp Trp Ile Ala Thr Gly Leu Val Gln
                325                 330                 335

Ala Tyr Thr Ser Leu Arg Ile Asp Lys Pro Cys Val Val Arg Leu Ala
            340                 345                 350

Gly Thr Asn Val Glu Glu Gly Leu Arg Ile Leu Thr Asp Ser Gly Leu
        355                 360                 365

Ala Phe Val Lys Ala Ser Asn Leu Asp Asp Ala Ala Lys Ala Val
    370                 375                 380

Ala Ile Ala His Gly Arg Asn Val
385                 390

<210> SEQ ID NO 17
<211> LENGTH: 891
<212> TYPE: DNA
<213> ORGANISM: Methylobacterium extorquens

<400> SEQUENCE: 17
atgagcattc tcatcgacga aagaccccg atcctggtcc agggcatcac gggcgacaag      60
ggcaccttcc acgccaagga gatgatcgcc tacggctcga acgtcgtcgg cggcgtcacc     120
ccgggcaagg gcggcaagac ccattgcggc gtgccggtgt caacaccgt caaggaggcc     180 gtggaggcga ccggcgccac cacctcgatc accttcgtgg cgcccccctt cgcggcggac     240
gcgatcatgg aggcggccga cgccggcctc aagctcgtct gctcgatcac cgacggcatc     300
cccgctcagg acatgatgcg ggtgaaacgc taccteccgg gctatccgaa ggagaagcgc     360
acgatggtgg tgggcccgaa ctgcgcgggc atcatctcgc cggcaagtc gatgctcggc     420 atcatgcccg ccacatctacc tccccgggc aaggtcggcg tcatctcccg ttccggcacg     480
ctgggctacg aggccgccgc gcagatgaag gagctcggca tcggcatctc gacctccgtc     540
ggcatcggcg cgatccgat caacggctcc tccttcctcg accacctcgc tctgttcgag     600
caggatcccg agacggaagc cgtgctgatg atcggcgaga tcgccgggcc gcaggaggcc     660
gaggcctcgg cctggatcaa ggagaacttt tccaagcccg tgatcggctt cgtggcgggc     720
ctcaccgccc ccaagggccg ccgcatgggg catgccggcg cgatcatctc ggcgaccggc     780
gacagcgccg cggagaaggc cgagatcatg cgctcctatg cctgaccgt ggcgccgat     840 ccgggctcct tcggcagcac cgtggccgac gtgctcgccc cgcggcgtg a              891

<210> SEQ ID NO 18
<211> LENGTH: 1173
<212> TYPE: DNA
<213> ORGANISM: Methylobacterium extorquens

<400> SEQUENCE: 18
atggacgttc acgagtacca agccaaggag ctgctcgcga gcttcgggt cgccgtcccg      60 aagggcgccg tggctttcag cccggatcaa gcggtctatg cggcgaccga gctcggcggc     120

```
tcgttctggg cggtgaaggc tcagatccat gccggcgcgc gcggcaaggc gggcgggatc      180
aagctttgcc gcacctacaa tgaagtgcgc gacgccgccc gcgacctgct gggaaaacgc      240
ctcgtgacgc tccagaccgg ccccgagggc aagccggtgc agcgcgtcta cgtcgagacc      300
gccgacccgt tcgagcgtga actctatctc ggctacgtgc tcgatcggaa ggccgagcgc      360
gtccgtgtca tcgcctccca gcgcggcggc atggatatcg aggagatcgc cgccaaggag      420
cccgaggcgc tgatccaggt cgtggtcgag ccggcggtgg gcctgcagca gttccaggcc      480
cgcgagatcg cgttccagct cggcctcaac atcaagcagg tctcggccgc ggtgaagacc      540
atcatgaacg cctaccgggc gttccgcgac tgcgacggca ccatgctgga gatcaacccg      600
ctcgtcgtca ccaaggacga ccgggttctg gcactcgacg ccaagatgtc cttcgacgac      660
aacgccctgt tccgccgccg caacatcgcg gacatgcacg atccatcgca gggcgatccc      720
cgcgaggccc aggctgccga gcacaatctc agctatatcg gcctcgaggg cgaaattggc      780
tgcatcgtca acgcgcgggt ctggccatg gcgaccatgg acatgatcaa gcacgcgggc      840
ggcgagccgg caaacttcct ggatgtgggc ggcggtgcca gcccggaccg cgtcgccacg      900
gccttccgcc tcgttctgtc ggaccgcaac gtgaaggcga tcctcgtcaa catcttcgcc      960
ggcatcaacc gctgcgactg ggtcgcggag ggcgtggtca aggccgcgcg cgaggtgaag     1020
atcgacgtgc cgctcatcgt gcggctcgcc ggcacgaacg tcgatgaagg caagaagatc     1080
ctcgccgaga gcgggctcga cctcatcacc gccgacaccc ttacggaagc cgcgcgcaag     1140
gctgtcgaag cctgccacgg cgccaagcac tga                                 1173
```

<210> SEQ ID NO 19
<211> LENGTH: 1161
<212> TYPE: DNA
<213> ORGANISM: Hyphomicrobium methylovorum

<400> SEQUENCE: 19

```
atggacgttc acgagtatca ggccaaagag cttctcgcga agttcggcgt gccgatcgcg       60
cgcggcgggc ttgcttacag cccggagcag gcaacatatc gtgcaagcga gcttggcggc      120
accgtcgtcg tcaaggcgca gattcactct ggcgcgcgcg gcaaagctgg cggcgtcaaa      180
gtctgcaaga acgagaaaga gatcgaagac gcggctgagt tcatgctcgg ccgcaagctg      240
gtcacgcatc agaccggccc ggcgggcaag ctcgtctcgc gtctttacat cgaagaagcg      300
accaacatcg atcgcgagat ctatctcggc ttcgtgatgg atcgcgcctc cgagcgtatc      360
gtcgtcgttg catccgccgc tggcggcatg gacatcgagg aaatctctgc gagccagccc      420
gacacgatca tccgcgtgag cgttgatccg gccgtcggca tgcagcagtt ccaggcgcgt      480
gaactcgcgt tcggtctcgg cgtcgatccg agatcgtca caagctcgt tccggcgatc      540 atgggatgct accgcgcatt ccgcgatctc gacgcgacca tggttgaggt caacccgctc      600
gtcatcacca aggaaaagca ggttctcgcg ctcgacgcta agatgtcgtt cgatgacaac      660
gcgctgttcc gccgtccgca catcgcagag ctgcgggaca agagccagga agaccgcgc      720 gaaacctacg cgtcggatcg tggcctctcc tacgttggtc tcgatggcga catcggctgc      780
atcgtcaacg gcgcaggtct cgccatggcg acgctcgaca tgatcaagct cgcaggcggt      840
gagccggcga acttcctcga cattggcggc ggagcgtctc cggaacgcgt caccaagtcg      900
ttcaaggctg ttcttcgcga caagaacgtc aaggcgatcc tcgtgaacgt cttcgccggt      960
atcaaccgtt gcgactgggt tgccaagggc gtggtcgatg ccgtgaagga actcgagatc     1020
```

```
aagatgccga tcgtcgttcg cctcgcaggc acgaacgtcg aagaaggccg caagatcatc   1080
gacaacagcg gcttgaccgt catcagtgca gatactctcg ctgacgcggc caagcaggcc   1140
gtcgacgctg cgaaaaaagc g                                             1161

<210> SEQ ID NO 20
<211> LENGTH: 897
<212> TYPE: DNA
<213> ORGANISM: Hyphomicrobium methylovorum

<400> SEQUENCE: 20
atggctatct tcatcaatga aaagacgccg atcctgatcc agggcttcac cggacgtatc     60
ggcacctttc acgctcaaga atgatcgac tacggctcca atgttgtcgg cggtgttacg    120
cccggcaaag gcgtacctc gcacctcggc cgtccggtgt tcaacaccgt gaagggcgcg    180
gccgatgaaa ccggcgccga agcctcgatc gtattcgtgc cgccgccgtt cgcggcggac    240
gcgatcatgg aagcagcaga cgctggcatc aaatactgcg tctgcatcac ggacggcatt    300
cctgctcagg atatgatccg cgtgaagcgc tacatgcgcc gctacaagaa agagagccgc    360
atggttctca ccggcccgaa ctgcgccggc acgatctcgc ccggtaaggc gatgctcggc    420
attatgccgg acacatctt ccttccgggt gcgtcggca tcgtcggacg ctcgggcacg    480
ctgggctatg aagccgcagc gcagctcaag gcgctgggca tcggcgtttc gacctcggtc    540
ggtatcggcg gcgatccgat caacggttcg tcgcatcgtg acattctcga agcgttcgag    600
agcgatcccg agaccgatgc ggtgctcatg atcggtgaaa tcggcggacc gcaggaagcg    660
gaagccggtc tcttcgcgaa agagcacatg aagaagccgg tcatcgccta catcgcaggc    720
ctttcggcac cgaagggtcg ccgcatgggc cacgcaggcg ctatcgtttc ggcattcggt    780
gaatcggccc tgagaaggt cgagatcctg aaaggctgca acgtgacgat cgccgcgacg    840
ccgtcggaga tgggttcgac ggtcgcgcag gttctcaacc agcgtaagaa agtcgcg      897

<210> SEQ ID NO 21
<211> LENGTH: 900
<212> TYPE: DNA
<213> ORGANISM: Hyphomicrobium denitrificans

<400> SEQUENCE: 21
atggcaatct ttatcaatga aaagacgccg atcctgatcc agggctttac cggtcgcatc     60
ggcacgttcc acgcccagga atgatcgac tacggctcca acgtcgttgg cggcgtgacg    120
cccggtaaag gcggcacctc gcatctcggc cgtccggtgt tcaacaccgt caagggcgcc    180
gtcgacgaga cgggcgctga agcctccatc gtgttcgtgc cgccgccgtt cgcggctgac    240
gcgatcatgg aagcggccga cgctgggatc aaatactgcg tctgcatcac ggacggcatt    300
cctgctcagg atatgatccg cgtgaagcgc tacatgcgcc gctacaagaa agaagcgcgc    360
atgatcctga ccggcccgaa ctgcgccggc acgatctcgc caggcaaggc gatgctcggc    420
atcatgccgg acacatcta ccttccgggc gcgtcggca tcgtcggccg ctccggtacg    480
ctcggctacg aagccgccgc gcagctcaag gcccttggca tcggcgtctc gacgtcggtt    540
ggtatcggcg gcgacccgat caacggctcg tcgcatcgtg acgtcctcga gcacttcgag    600
aacgatcccg agaccgacgc gatcctgatg atcggcgaaa tcggtggtcc gcaggaagcc    660
gaagccggcc tcttcgccaa agagcacatg aagaagcctg tcatcgccta catcgccggt    720
ctgtcggccc cgaagggccg ccgcatgggc cacgctggcg ccatcgtttc ggcattcggc    780
gagtcggctg ctgagaaggt cgagatcctg aagggctgcg gcgtcgctat cgcgccgacg    840
```

```
ccgtcggaaa tgggctcgac cgtcgcgcag gttctcggca agcagaaaaa agttgcctga      900
```

<210> SEQ ID NO 22
<211> LENGTH: 1164
<212> TYPE: DNA
<213> ORGANISM: Hyphomicrobium denitrificans

<400> SEQUENCE: 22

```
atggacattc atgaatacca ggccaaagag cttcttgcga agttcggcgt gccgatcgcc       60
cgcggcggac ttgcctacag ccctgaacag gccacctatc gcgccagcga gcttggcggc      120
acggtcgtcg tcaaggcgca gattcactcc ggcgcgcgcg gtaaagccgg cggcgtcaag      180
gtctgcaaga cggaaaagga atcgaggat gcagccgagt tcatgctcgg ccgcaagctc       240
gtcacgcacc aaacgggatc ggccggcaag ctggtctcgc gcctctacat cgaagaagcg      300
acgaacatcg atcgcgaaat ctatctcggt ttcgtgatgg accgcgcttc ggagcgcatc      360
gtcgtcgtgg cctcggccgc gggcggcatg gacatcgagg aaatctcggc gtcgcagccc      420
gacacgatca tccgcgtcgc cgtcgacccg gcggtcggca tgcagcagtt ccaggcacgt      480
gagctggcat tcggacttgg cgtcgatcct gagatcgtca acaagctcgt gcccgcgatc      540
atgggctgct atcgcgcctt ccgcgatctc gatgcgatga tggttgaaat caacccgctc      600
gtcatcacca aggaaaagca ggtcgttgcg ctcgacgcca agatgtcgtt cgacgacaac      660
gcgctgttcc gccgtccgca catcgccgag ctgcgcgaca agagccagga agatccccgc      720
gaaacctacg cgtcggatcg tggtctctcg tacgtcggtc tcgatggcga catcggctgc      780
atcgtcaacg gtgccggtct cgcgatggcg acgctcgaca tgatcaagct gcgggcggc      840 gagcctgcga acttcctcga catcggcggc ggcgcctctc ccgagcgcgt caccaagtcg      900
ttcaaggcgg ttctgcgcga caagaacgtc aaggccatcc tggtcaacgt cttcgccggc      960
atcaaccgtt gcgactgggt tgccaagggt gtcgtcgacg ccgtcaagga actcgatatc     1020
aagctgccga tcgtcgttcg cctcgcaggc accaacgtcg aagaaggccg caagatcatc     1080
gacaacagcg gcctgacggt catcagcgcg gaaactctcg ccgatgctgc caagcaggcg     1140
gtcgaagcgg ccaaaaaagc ctaa                                            1164
```

<210> SEQ ID NO 23
<211> LENGTH: 2105
<212> TYPE: DNA
<213> ORGANISM: Rhizobium sp. NGR234

<400> SEQUENCE: 23

```
catatggaca ttcacgaata tcaagcgaaa gaactgctga gccgttatca aattcacatc       60
ccgcgtggtg gtctggccta ctccccggaa caagctgcct atcgtgcacg cgaaatcggc      120
ggtgatcgct gggtggttaa agctcagatt catagcggtg cacgtggcaa agctggcggt      180
atcaaactgt gctctaccga tcacgaaatt gttgaagcgg ccgacagtat gctgggccgc      240
accatcgtga cgcatcagac cggtccgcaa ggcaaactgg tttctcgcct gtatgtcgaa      300
gaagcgatgg atattgcccg tgaaatttac atcggttttg ttctggaccg taaaagtgaa      360
cgcattatga tcgtcgcgag ctctagtggc ggtatggaaa ttgaagaaat cgcagaagct      420
gaaccggata gcattatccg cgccacggtg gatccgggtg ttggcatgca ggactttcaa      480
gcacgtgaaa ttgctttcgg tctgggcatc gataacgcgc tgattggccg cgccaccccaa      540 acgctgctgg gttgttatcg tgcattcgtt gattacgacg cttctatgct ggaaattaac      600
```

```
ccgctggtcg tgaccegtcg cggtgatctg gtggcgctgg acgccaaaat gtcgtttgat    660
gaaaatgcac tgttccgtcg cccgcacatc gctgaaatgc gcgataaaag ccaggaagac    720
caacgcgaaa cgtatgcatc cgatcgtggt ctgtcatacg ttggtctgga cggcaacatt    780
ggttgcatta tcaatggtgc cggcctggcg atggccacca tggatatgat taaaatcgca    840
ggcggtgaac cggctaattt tctggatatc ggcggtggcg catcgccgga ccgtgtcgca    900
aaaagcttcc gcgccgtgct gacgatcgt caggtggaaa ccattctggt taacatcttt    960
gcgggcatta atcgttgtga ctgggtcgcg gaaggcgtga tcaaagcact gcgtgaagtg   1020
ggtgttccgg tcccgctggt tgtccgtctg tccggtacga acatggaaga aggtcgtcgc   1080
attctggcgg aatcaggtga aaatattatc gtggccgaaa ccctggcaga agctgctgat   1140
aaagcagtgg ctgcgtggcg ttcgttcacc gctaataaag ctgcgtaagg tcgcctccca   1200
tgtccattct gctggataaa aatacccgtg tgatcgtgca aggctttacc ggcaaaatcg   1260
gctcattcca tgctgaagat atgaaacgct acggcaccaa cgtggttggc ggtgttacgc   1320
cgggcaaagg cggtcaggca catctgggta tgccggtgtt taataccgtt aaaggcgcgg   1380
tccaagaaac gggtgcggat gccagtatta tctttgtccc gccgccgttc gcggccgatt   1440
ccattatgga agcagctgac gcgggcatcc gtctgtgcgt gtgtattacc gatggtatcc   1500
cgagtcagga catgattcgt gttaaacgct atatgcgtcg ctaccgtttc gaagaccgca   1560
tgaccctgat tggtccgaac tgcgcaggca tgatcacgcc gggtgaagct atgatgggta   1620
ttatgccggg ctctatctat ctgccgggcc gtattggtat cgttggtcgt agcggtaccc   1680
tgggttacga agcagcctct caaatgaaag cgctgggcgt cggtgtgagt acgtccattg   1740
gcatcggcgg tgatccggtc aatggtagct cttttaaaga catgctggaa ctgttcgaaa   1800
aagatccggg caccgacgcc gtgctgatga ttggtgaaat cggcggtccg caggaagcgg   1860
aagcagctct gtgggcccgc gatcacatga aaaaaccgct gatcgcgtat atcgcaggtc   1920
tgtcagcacc gaaaggtcgt cgcatgggtc acgcaggcgc tattatctca gcatttggcg   1980
aatcggctca agaaaaagtg gaaattctga atcggcagg tgttacgatc gtcccgaccc   2040
cgtcctcttt tggtgaaacc gttgcggatg tgctgtcggc tatgagtaaa gcggcttaat   2100
ctaga                                                               2105

<210> SEQ ID NO 24
<211> LENGTH: 897
<212> TYPE: DNA
<213> ORGANISM: Granulibacter bethesdensis

<400> SEQUENCE: 24
atgagcattc tgatcaataa gcagaccaag atcatcattc agggcttcac cggcgacaag     60
ggcacgttcc acggtcgcga gatgatcgat tacggcacca atgtcgtcgg tggcgtgacg    120
cccggtaaag cggccagac ccatctgggt cgtcccgtgt caacacggt cgaggacgcg     180
gtgcgtgaaa ccggtgccca ggcgtcgatc acctttgtgg cacctgcctt ttgcgccgat    240
gcgatcatgg aaggcgccga tgcggggctg gagctgatct gcaccatcac ggacggtatt    300
ccggcgcagg atatgatgcg cgtgaagcgt tatctgcgcc gctaccagaa ggatcgtcgc    360
acgcgtctgg tggggccgaa ctgcgcgggc atcatcagcc cgggccaggc catgctgggc    420
atcatgccgg ccatatccta caaggaaggc catgtcggca ttgtttcccg ctcaggcacg    480
ctcggctatg aagccgccgc gcagctgaag gagctgggca tcggtgtgtc caccagtgtg    540
ggtatcggtg gtgacccgat caatggttct tccttccttg atcaccttca gctgttcgaa    600
```

```
gccgacccccg agactcatgc cgtgctgatg atcggcgaga tcggtggccc gcaggaagcc    660
gaagcggcga agtggatcag cgagaacatg tcgaagccgg tggttggcta cgttgccggc    720
ctgaccgctc cgaaggggcg tcgtatgggc catgccggtg cgatcatctc tggcgaaggc    780
gacagcgccg ccgaaaagag cgagatcatg cgctcctacg gtctgacggt tgctcccagc    840
ccgggtgaac tcggctcgac cgttgccgcg gtgctggctg ggcgtcaggc agcctga       897
```

<210> SEQ ID NO 25
<211> LENGTH: 1170
<212> TYPE: DNA
<213> ORGANISM: Granulibacter bethesdensis

<400> SEQUENCE: 25

```
atggacgtcc atgagtacca ggcaaaagaa ttgcttgcga cgccggtgt ggccgtgccc     60 cgcggtgcaa tcgctttcag cgctgatcag gccgtgtatg ccgcgaccga actgggtggc    120
tggcactggg cggtgaaagc ccagattcat gccggtgcgc gcggcaaggc cggcggcatc    180
aagctgtgca agacgtatca tgaagtgcgc gaggctgctg ccggtatgct cggcaagcgt    240
ctggtcacgc atcagaccgg tccggaaggc aagcctgtcc agcgcgtgta tgtcgaggtc    300
gccgatccct tcgagaaaga attctatctg ggctttgtgc tggatcgtaa gctggagcgc    360
gtgcgtgtga tcgcctccgc cgagggcggc atggagatcg aggaaatcgc ttccaagcat    420
ccggaaaagc tgatccaggt gatcgtggag ccggcggttg gtcttcagca gttccaggcc    480
cgccagatcg ccttcaagct gggcctgtcc agccgtcagg tacagcgtgc ggtgaccagc    540
atcatgggcg cttatcgcgc attccgcgat cacgacgcga ccatgctgga aatcaatcct    600
ctggttctga ccaaggatga ccgtattctg cgcctcgatg cgaagatgag cttcgacgac    660
aacgccttgt tccgtcgcaa caacgtcgcc aacatgcatg accctctca ggacgatccg    720 cgtgaggcgc aggctgccga gcacaacctc aactatgtgg gtctggaagg cgatatcggc    780
tgcgtggtga atggcgccgg cctggcgatg gcgaccatgg acgtcatcaa atatgcgggt    840
ggtgagcctg ccaacttcct cgatgtcggc ggcggggcaa gccccgagcg taccgcgacg    900
gcgttccgtc tggtgctgtc cgacaagaac gtgaaggttg ttctggtcaa catcttcgcc    960
ggcatcaacc gctgcgactg gatcgcggaa ggcgtggtgc acgcggtgaa agaagtcgat   1020
ctgaagcttc gctggtggt gcgtctggca ggcaccaatg tggaggaagg ccgccgtatt   1080
ctgaaagaaa gcggcatttc cgtcatcatg gccgaaagcc tgaccgaagc ggccgaaaag   1140
gccgtcgagg ccgcgaaggc cgcggcgtaa                                    1170
```

<210> SEQ ID NO 26
<211> LENGTH: 888
<212> TYPE: DNA
<213> ORGANISM: Nitrosomonas europaea

<400> SEQUENCE: 26

```
gtggcaattc tcatcaatga gcagacgcgg atcatcgtac agggctttac cggccggatc     60
ggcaccttcc atgctcagga aatgatcgat tacggatcta atgtagtggg aggcgtaacg    120
cccggcaaag gcgggcagaa acacctgggg ctgccagtat tcaataccgt ccggaaagca    180
gtcgagcagg caggtgcgga agccagcatt gtattcgtcc cgccggcatt tgcggctgat    240
tcgattatgg aagcagccga tgccggtatc aaatattgcg tatccatcac cgatggcatt    300
ccaacccagg acatgatgac cgtcaaaaac ttcttacgcc tcttccctga ggaggacaga    360
```

| | |
|---|---|
| atgatgctga ccggccccaa ctgttcaggc actatcagcc ccggacgggc gatgttgggc | 420 |
| atcatgccgg ggcatattta cagccgtggg gtcgttggtg tcgtcggccg ttccggtaca | 480 |
| ctgggttatg aagctgccga ccagatgcga cggctgaata tcgggatttc gacttcggta | 540 |
| ggtattggcg gagacccgat catcggcagt tcgcaccgga atgtgctgca aaagctggaa | 600 |
| gaagatccgg aaaccaaagt cacgctgatg attggtgaaa ttggtggccc aatggaagta | 660 |
| gaagccggac tgttcgcaaa ggaaaacatg agcaaaccgc tggttgccta cattgccggc | 720 |
| ctgactgcac ctcccggaag acggatgggg cacgccggag caatcatctc ttcagccggt | 780 |
| gaaagcgcag cagaaaaagt ggaaagactg aaagaactgg gcgtcaccat ctgcccgact | 840 |
| ccgtctctga tgggtgaaac cgtcgcaaaa gttctggccg gactctaa | 888 |

<210> SEQ ID NO 27
<211> LENGTH: 1173
<212> TYPE: DNA
<213> ORGANISM: Nitrosomonas europaea

<400> SEQUENCE: 27

| | |
|---|---|
| ttggatatcc atgaatatca ggccaaggaa atcctggctg aatacggtat caagctggct | 60 |
| gaaggcggat tggcgcacac tgtggaagaa gcggtacaac gcagccggga aatcgatggc | 120 |
| aatgtgtggg tcgtcaaggc acaaatccat tccggcgccc gtggtaaagc aggcggtgtc | 180 |
| aaagtatgcc ggacacatga agaaatcgaa gtcgcagctg aatcactgct ggggaaaaaa | 240 |
| ctggtcacac accaaaccgg cccggcgggt aaactctgct ccagactgta tatcgaagcc | 300 |
| ggtaccgaaa ttgcccggga agtgtatctc gctttcatga tcgatcgcag tcatgaacgt | 360 |
| atcgtcatgg tgggttccgc acaggggga atggatatcg agaccctggc agccacgaat | 420 |
| cctgatgcca tcaaaaaaat tcacatcgag cctgctgtcg gcctgcagga tttccaggca | 480 |
| agaaccatgg cttttgcact gggtctggaa gatgttctgc tcaatcacgc cgtcaagacg | 540 |
| atcagaggtt gctaccgcgc catgcgcgat ctggatgcga acatactcga aatcaacccg | 600 |
| ctggttgtca cgcgcaacaa cgagctgatc gcactggatg cgaagatgag cttgatgaa | 660 |
| aatgcactgt tccggcgcca ccggatttcc gaattgcgtg acaactcaca aatcgattcg | 720 |
| cgcgaaattg ctgcagcgga agcaggcttg agctacgtcg ggctggatgg agacatcggc | 780 |
| tgcatgatca atggcgccgg gctggcaatg gccaccatgg acatgatcaa actgccggc | 840 |
| ggcgaaccgg ccaattttct ggatgtcggc ggcggcgcat ctgccgagcg aactgaaaaa | 900 |
| gcattccggc tggtactggc ggataacaac gtaaaagcca tgctggtcaa tatctttgcc | 960 |
| ggtattaacc gctgtgactg gattgccgaa ggtgtggttc aggctgtacg gaatatcgga | 1020 |
| atgacggtcc ctctggtcgt gcgcctgtct ggcaccaacg tggaagaagg ccgccgtatc | 1080 |
| atcgctgaca gcggggttgcc gatcattact gcagaaaccc tggccgatgc agcagagaaa | 1140 |
| gtagtgcacg ctcgcaacca ggctgcagtt tga | 1173 |

<210> SEQ ID NO 28
<211> LENGTH: 903
<212> TYPE: DNA
<213> ORGANISM: Methylococcus capsulatus

<400> SEQUENCE: 28

| | |
|---|---|
| atgagcgtat tcgttaacaa gcactccaag gtcatcttcc agggcttcac cggcgagcac | 60 |
| gccaccttcc acgccaagga cgccatgcgg atgggcaccc gggtggtcgg cggtgtcacc | 120 |
| cctggcaaag gcggcacccg ccatcccgat cccgaactcg ctcatctgcc ggtgttcgac | 180 |

```
accgtggctg aagccgtggc cgccaccggc gccgacgtct ccgccgtgtt cgtgccgccg    240
cccttcaatg cggacgcgtt gatggaagcc atagacgccg gcatccgggt cgccgtgacc    300
atcgccgacg gcatcccggt acacgacatg atccgactgc agcgctaccg ggtgggtaag    360
gattccatcg tgatcggacc gaacaccccc ggcatcatca cgccgggcga gtgcaaggtg    420
ggcatcatgc cttcgcacat ttacaagaag gcaacgtcg gcatcgtgtc gcgctccggc    480
accctcaatt acgaggcgac ggaacagatg gccgcgcttg gctgggcat caccacctcg    540 gtcggtatcg gcggtgaccc catcaacgga accgatttcg tcactgtcct gcgcgccttc    600
gaagccgacc cggaaaccga gatcgtggtg atgatcggcg aaatcggcgg cccccaggaa    660
gtcgccgccg cccgctgggc caaggaaaac atgacaaagc cggtcatcgg cttcgtcgca    720
ggccttgccg caccgaccgg ccgacgcatg ggccatgccg cgccatcat ctccagcgag    780 gccgacaccg ccggagccaa gatggacgcc atggaagcct gggctgta tgtcgcccgc    840 aacccggcac agatcggcca gaccgtgcta cgcgccgcgc aggaacacgg aatcagattc    900
tga                                                                  903

<210> SEQ ID NO 29
<211> LENGTH: 1170
<212> TYPE: DNA
<213> ORGANISM: Methylococcus capsulatus

<400> SEQUENCE: 29
gtgaatatcc atgagtacca ggccaaggag ctgctcaaga cctatggcgt gcccgtgccc     60
gacggcgccg ttgcctattc cgacgcgcag gccgccagcg tcgccgagga gatcggcggc    120
agccgctggg tggtcaaggc gcagatccat gccggcggtc gcggcaaggc cggggggcgta   180 aaggtcgccc actccatcga ggaagtccgc caatacgccg acgccatgct cggcagccac    240
ctcgtcaccc atcagaccgg cccgggaggc tcgctggttc agcgtctgtg ggtggaacag    300
gccagccata tcaaaaagga atactacctg ggcttcgtga tcgatcgcgg caatcaacgc    360
atcaccctga tcgcctccag cgagggcggc atggaaatcg aggaagtcgc aaaggaaacc    420
ccggagaaaa tcgtcaagga agtcgtcgat ccggcctag gcctgctgga cttccagtgc    480
cgcaaggtcg ccacggcgat cggcctgaaa ggcaaactga tgccccaggc cgtcaggctg    540
atgaaggcca tctaccgctg catgcgcgac aaagatgccc tgcaggccga aatcaatcct    600
ctggccatcg tgggcgaaag cgacgaatcg ctcatggtcc tggatgccaa gttcaacttc    660
gacgacaacg ccctgtaccg gcagcgcacc atcaccgaga tgcgcgacct ggccgaggaa    720 gaccccgaaag aggtcgaagc ctccggccac ggtctcaatt acatcgccct cgacggcaac    780
atcggctgca tcgtcaatgg cgccggcctc gccatggctt cgctcgacgc catcaccctg    840
catggcggcc gtccggccaa cttcctcgac gtgggcggcg cgcctccc gagaaggtc     900 accaatgcct gccgcatcgt actgaagat cccaacgtcc gctgcatcct ggtcaacatc    960
tttgccggca tcaaccgctg tgactggatc gccaagggcc tgatccaggc ctgcgacagc   1020
ctgcagatca aggtgccgct gatcgtgcgc ctggccggga cgaacgtcga cgagggccgc   1080
aagatcctgg ccgaatccgg cctctccttc atcaccgcgg aaaatctgga cgacgcggcc   1140
gccaaggccg tcgccatcgt caagggataa                                    1170

<210> SEQ ID NO 30
<211> LENGTH: 897
<212> TYPE: DNA
```

<213> ORGANISM: Uncultured gamma proteobacterium

<400> SEQUENCE: 30

| | | | | | | |
|---|---|---|---|---|---|---|
| atgagtattt | ttgtcaaccg | ccattcgcgg | gtgatcatcc | agggattcac | cggccaacac | 60 |
| gctacgtttc | acgccagcga | ggcgattcgg | tacggcactc | aagtggtcgg | cggcgtcacc | 120 |
| ccgggcaagg | gaggaagtaa | gcaccttgga | ttgccggtgt | tcgatacagt | ttctgaagcg | 180 |
| gtttcagaga | cgggcgccga | tgtctctggg | attttttgtgc | ccccagcgtt | tgctgccgac | 240 |
| gccatcatgg | aagcgatcga | agccgggatc | cgggtaatcg | tggtgattgc | cgatggcatc | 300 |
| ccggtgcaag | acatgattcg | agtgcagcgc | taccggctcg | acgcgactg | tctggtgctt | 360 |
| gggccaaaca | cgcctggaat | catcactcct | ggagagtgca | aggtggggat | catgcctgct | 420 |
| ggaatttacc | gtccaggaag | aattgggtta | gtgtcgcggt | ccggaacgct | gaattacgag | 480 |
| gccgtcgaac | aattgggcaa | actgggtttg | ggtcaatcca | ccgcggttgg | catcggtggg | 540 |
| gatccggtca | acggcaccga | ctttgtgact | gtgctcaaag | ccttcgaaca | agatccggac | 600 |
| accgatgcga | tcgtcatgat | cggcgaaatc | ggcgggccgc | aagaagtcgc | cgctgcccgc | 660 |
| tgggccaaag | aaaatatgca | aaagccgctc | atcggttttg | tggcgggggc | ctcggctcca | 720 |
| ccggggcggc | gcatggggca | tgctggggcg | atcatcgaag | gtgaggaaga | caccgccaaa | 780 |
| gccaagatgg | acgcgatgga | ggagcttggg | gtatacgtgg | tcagaaatcc | cgcccggatc | 840 |
| ggcgaaacgg | ttttaagggc | gctcaaggag | cgcctgggat | ctgcagtttc | tggctaa | 897 |

<210> SEQ ID NO 31
<211> LENGTH: 1179
<212> TYPE: DNA
<213> ORGANISM: Uncultured gamma proteobacterium

<400> SEQUENCE: 31

| | | | | | | |
|---|---|---|---|---|---|---|
| atgaacattc | acgaatatca | ggccaaggag | ctgcttcgtt | cttacggtgt | ccccgttcca | 60 |
| gccgggaacg | tcgcctattc | cgatcgccaa | gcgcaggcag | tggccgaaca | gatcggcggg | 120 |
| gacggatggg | tagtaaaagc | gcaaatccat | accggcgggc | gaggcaaggc | cggcggcgtt | 180 |
| aaactcgccc | aatccttgga | ggaagtccgc | aagatagccg | acgaaatgat | cggcaaaact | 240 |
| ttggtgactc | ctcaaaccgg | gcccaaaggc | aaagtggtcc | ggcgcgtatt | ggtggaagaa | 300 |
| gcggttagtc | cgcaacggga | attgtaccct | gggttggtca | tcgaccggcg | cagccaacgc | 360 |
| atcaccatcg | tggcttccgc | ggaaggaggg | gtagagatcg | aggaagtggc | ggccaggagt | 420 |
| ccggagaaaa | tcgtgcggga | ggcgatcgac | ccggccatcg | gtctgcgcga | ttttcaatgc | 480 |
| cgtaaggtcg | ccgccgccat | tggcctgcgc | gacaaacatc | taatggcgca | ggcggtgcgc | 540 |
| ctcatgcagc | gcatctatcg | cctgtttcgt | gacaaggatg | ccctccaggt | ggagatcaat | 600 |
| cctctaggca | tcgtcggcag | cgagccaaag | ctggtttgtt | tggacgccaa | attcaatttc | 660 |
| gaccccaacg | cccttttccg | acatccggaa | atcaacgagc | tgcgcgattt | ggaagaggaa | 720 |
| gacccgcggg | aggtggaagc | cttaggtcac | gggctcaact | acatcgcttt | agacggcgat | 780 |
| atcggctgca | tcgtcaacgg | cgccggcctg | gccatggcga | ccatggacgc | catcgtgttt | 840 |
| catggtggtt | ggccggcgaa | tttcctggat | atcgggggtg | gggcctcgcc | ggagaaagtg | 900 |
| caaaacgctt | gtcggatcgt | gattcaggac | cagaacgtca | agactttgtt | ggtcaatatc | 960 |
| tttgccggca | tcaaccgctg | cgattggatc | gctaccggtc | tagtccaggc | ttacaccagc | 1020 |
| ttgcgcatcg | acaagccctg | cgtcgtgcgc | cttgcaggaa | cgaatgtaga | ggaggggcta | 1080 |
| aggattttga | ccgactcggg | tcttgctttc | gtaaaagcga | gcaatctgga | cgatgcggca | 1140 | gctaaagccg tcgccatcgc tcatgggagg aacgtatga                                    1179

<210> SEQ ID NO 32
<211> LENGTH: 324
<212> TYPE: PRT
<213> ORGANISM: Methylobacterium extorquens

<400> SEQUENCE: 32

Met Ser Phe Thr Leu Ile Gln Gln Ala Thr Pro Arg Leu His Arg Ser
1               5                   10                  15

Glu Leu Ala Val Pro Gly Ser Asn Pro Thr Phe Met Glu Lys Ser Ala
            20                  25                  30

Ala Ser Lys Ala Asp Val Ile Phe Leu Asp Leu Glu Asp Ala Val Ala
        35                  40                  45

Pro Asp Asp Lys Glu Gln Ala Arg Lys Asn Ile Ile Gln Ala Leu Asn
50                  55                  60

Asp Leu Asp Trp Gly Asn Lys Thr Met Met Ile Arg Ile Asn Gly Leu
65                  70                  75                  80

Asp Thr His Tyr Met Tyr Arg Asp Val Val Asp Ile Val Glu Ala Cys
                85                  90                  95

Pro Arg Leu Asp Met Ile Leu Ile Pro Lys Val Gly Val Pro Ala Asp
            100                 105                 110

Val Tyr Ala Ile Asp Val Leu Thr Thr Gln Ile Glu Gln Ala Lys Lys
        115                 120                 125

Arg Glu Lys Lys Ile Gly Phe Glu Val Leu Ile Glu Thr Ala Leu Gly
    130                 135                 140

Met Ala Asn Val Glu Ala Ile Ala Thr Ser Ser Lys Arg Leu Glu Ala
145                 150                 155                 160

Met Ser Phe Gly Val Ala Asp Tyr Ala Ala Ser Thr Arg Ala Arg Ser
                165                 170                 175

Thr Val Ile Gly Gly Val Asn Ala Asp Tyr Ser Val Leu Thr Asp Lys
            180                 185                 190

Asp Glu Ala Gly Asn Arg Gln Thr His Trp Gln Asp Pro Trp Leu Phe
        195                 200                 205

Ala Gln Asn Arg Met Leu Val Ala Cys Arg Ala Tyr Gly Leu Arg Pro
    210                 215                 220

Ile Asp Gly Pro Phe Gly Asp Phe Ser Asp Pro Asp Gly Tyr Thr Ser
225                 230                 235                 240

Ala Ala Arg Arg Cys Ala Ala Leu Gly Phe Glu Gly Lys Trp Ala Ile
                245                 250                 255

His Pro Ser Gln Ile Asp Leu Ala Asn Glu Val Phe Thr Pro Ser Glu
            260                 265                 270

Ala Glu Val Thr Lys Ala Arg Arg Ile Leu Glu Ala Met Glu Glu Ala
        275                 280                 285

Ala Lys Ala Gly Arg Gly Ala Val Ser Leu Asp Gly Arg Leu Ile Asp
    290                 295                 300

Ile Ala Ser Ile Arg Met Ala Glu Ala Leu Ile Gln Lys Ala Asp Ala
305                 310                 315                 320

Met Gly Gly Lys

<210> SEQ ID NO 33
<211> LENGTH: 321
<212> TYPE: PRT
<213> ORGANISM: Hyphomicrobium methylovorum

<400> SEQUENCE: 33

Met Ser Tyr Thr Leu Tyr Pro Thr Arg Lys Gln Arg Leu Gln Arg Ser
1               5                   10                  15

Tyr Leu Ala Val Pro Gly Ser Asn Pro Ser Met Ile Asp Arg Ala Leu
            20                  25                  30

Lys Ser Ala Ala Asp Tyr Val Phe Leu Asp Cys Glu Asp Ala Val Ala
        35                  40                  45

Pro Pro Glu Lys Glu Gln Ala Arg Lys Asn Ile Ile Gln Ala Leu Asn
    50                  55                  60

Asp Leu Asp Trp Lys Gly Ala Gly Lys Ser Val Ser Val Arg Ile Asn
65                  70                  75                  80

Gly Leu Asp Thr His Tyr Met Tyr Arg Asp Val Val Asp Ile Val Glu
                85                  90                  95

Gln Ala Gly Ser Lys Leu Asp Thr Ile Leu Ile Pro Lys Val Gly Val
            100                 105                 110

Pro Ala Asp Val Tyr Thr Val Glu Cys Ile Val Ser Gln Ile Glu Val
        115                 120                 125

Ala Lys Gly Leu Pro His Gln Ile Gly Thr Glu Ala Leu Ile Glu Thr
    130                 135                 140

Pro Leu Gly Met Ala Asn Val Glu Ala Ile Ala Ser Ala Ser Ser Arg
145                 150                 155                 160

Leu Glu Ser Met His Phe Gly Val Ala Asp Tyr Ser Ala Phe Asn Lys
                165                 170                 175

Ala Arg Thr Val Val Ile Gly Gly Leu Asn Pro Asp Tyr Pro Gly Asp
            180                 185                 190

Gln Trp His Phe Pro Leu Ser Arg Met Thr Val Ala Cys Arg Ala Phe
        195                 200                 205

Gly Leu Arg Pro Ile Asp Gly Pro Phe Gly Ile Asp Asp Pro Glu
    210                 215                 220

Gly Tyr Lys Ala Ala Arg Arg Gly Ala Ala Leu Gly Met Glu Gly
225                 230                 235                 240

Lys Trp Ala Ile His Pro Ser Gln Ile Glu Leu Ala Asn Glu Ile Tyr
                245                 250                 255

Ser Pro Thr Ala Lys Glu Val Glu Arg Ala Glu Arg Ile Leu Val Ala
            260                 265                 270

Leu Lys Glu Ala Glu Ala Gln Gly Lys Gly Ala Ala Ser Leu Asp Gly
        275                 280                 285

Lys Met Ile Asp Ala Ala Ser Glu Lys Met Ala Arg Asn Leu Leu Ser
    290                 295                 300

Thr Ala Glu Gln Ile Lys Lys Ala Glu Ala His Ala Ala Gln Lys
305                 310                 315                 320

Lys

<210> SEQ ID NO 34
<211> LENGTH: 320
<212> TYPE: PRT
<213> ORGANISM: Hyphomicrobium denitrificans

<400> SEQUENCE: 34

Met Ser Tyr Thr Leu Tyr Pro Asn Arg Lys Gln Arg Leu Gln Arg Ser
1               5                   10                  15

Tyr Leu Ala Val Pro Gly Ser Asn Pro Thr Met Ile Asp Arg Ala Leu
            20                  25                  30

Lys Ser Ala Ala Asp Tyr Val Phe Leu Asp Cys Glu Asp Ala Val Ala

-continued

```
                35                  40                  45
Pro Pro Glu Lys Glu Gln Ala Arg Lys Asn Ile Ile Gln Ala Leu Asn
 50                  55                  60

Asp Leu Asp Trp Lys Gly Ala Gly Lys Ser Val Ser Val Arg Ile Asn
 65                  70                  75                  80

Gly Leu Asp Thr His Tyr Cys Tyr Arg Asp Val Val Asp Ile Val Glu
                 85                  90                  95

Gln Ala Gly Ala Lys Leu Asp Thr Ile Leu Ile Pro Lys Val Gly Val
                100                 105                 110

Pro Ala Asp Val Tyr Ala Ile Glu Ser Phe Val Ser Gln Ile Glu Val
                115                 120                 125

Ala Lys Gly Leu Pro His Gln Ile Gly Met Glu Ala Leu Ile Glu Thr
                130                 135                 140

Pro Leu Gly Met Ala Asn Val Glu Ala Ile Ala Ser Ala Asn Ser Arg
145                 150                 155                 160

Leu Glu Ser Met His Phe Gly Val Ala Asp Tyr Ser Ala Phe Asn Lys
                165                 170                 175

Ala Arg Thr Val Val Ile Gly Leu Asn Pro Asp Tyr Pro Gly Asp
                180                 185                 190

Gln Trp His Phe Pro Leu Ser Arg Met Thr Val Ala Cys Arg Ala Phe
                195                 200                 205

Gly Leu Arg Pro Ile Asp Gly Pro Phe Gly Ile Asp Asp Pro Glu
210                 215                 220

Gly Tyr Lys Ala Ala Arg Arg Gly Ala Ala Leu Gly Met Glu Gly
225                 230                 235                 240

Lys Trp Ala Ile His Pro Ser Gln Ile Glu Leu Ala Asn Glu Ile Tyr
                245                 250                 255

Ser Pro Thr Ala Lys Glu Ile Glu Arg Ala Glu Arg Ile Leu Val Ala
                260                 265                 270

Leu Lys Glu Ala Glu Ala Gln Gly Lys Gly Ala Ala Ser Leu Asp Gly
                275                 280                 285

Lys Met Ile Asp Ala Ala Ser Glu Lys Met Ala Lys Asn Leu Leu Val
                290                 295                 300

Thr Ala Ala Ala Ile Lys Ala Gly Glu Glu Ala Arg Ala Lys Ser Lys
305                 310                 315                 320
```

<210> SEQ ID NO 35
<211> LENGTH: 316
<212> TYPE: PRT
<213> ORGANISM: Nitrosomonas europaea

<400> SEQUENCE: 35

```
Met Ser His Thr Leu Tyr Glu Thr Lys Thr Pro Arg Val Gln Arg Cys
 1               5                  10                  15

Glu Leu Ala Val Pro Gly Ser Arg Pro Glu Met Phe Glu Lys Ala Leu
                20                  25                  30

Lys Ser Gly Val Asp Phe Ile Phe Leu Asp Leu Glu Asp Ala Val Ala
                35                  40                  45

Pro Asp Asp Lys Ile Gln Ala Arg Lys Asn Ile Ile Gln Ala Ile Asn
                50                  55                  60

Asp Leu Asp Trp Lys Ser His Gly Val Thr Leu Ser Val Arg Ile Asn
 65                  70                  75                  80

Gly Leu Asp Thr Gln Tyr Met Val Arg Asp Val Val Asp Leu Val Glu
                 85                  90                  95
```

```
Gln Ala Gly His Lys Ile Asp Thr Leu Leu Ile Pro Lys Val Gly Val
                100                 105                 110

Tyr Ala Asp Val Tyr Met Val Glu Ala Met Leu Ser Gln Leu Glu Met
            115                 120                 125

Gln Gln Gly Leu Lys Asn Arg Ile Gly Val Glu Ala Leu Ile Glu Thr
        130                 135                 140

Ala Leu Gly Met Ala Asn Val Glu Asp Ile Ala Arg Arg Gly Thr Ala
145                 150                 155                 160

Gly Arg Leu Glu Ala Leu His Phe Gly Val Ala Asp Tyr Ala Ala Ser
                165                 170                 175

Asn Arg Ala Arg Thr Thr Asn Ile Gly Gly Leu Asn Pro Asp Tyr Pro
            180                 185                 190

Gly Asp Gln Trp His Ala Ala Ile Ser Arg Met Thr Val Ala Cys Arg
        195                 200                 205

Ala Phe Gly Leu Arg Pro Ile Asp Gly Pro Phe Gly Asp Ile Gln Asp
210                 215                 220

Pro Glu Gly Tyr Lys Gln Ala Ala Arg Arg Ala Ala Leu Gly Cys
225                 230                 235                 240

Glu Gly Lys Trp Ala Ile His Pro Thr Gln Ile Ala Leu Ala Asn Glu
                245                 250                 255

Val Phe Thr Pro Pro Thr Ala Glu Val Asp Lys Ala Lys Arg Ile Leu
            260                 265                 270

Thr Ala Leu Lys Glu Ala Ala Gln Gly Lys Gly Ala Ala Ser Leu
        275                 280                 285

Asp Gly Arg Leu Ile Asp Ala Ala Ser Glu Arg Met Ala Asn Asn Ile
290                 295                 300

Val Lys Met Ala Glu Ala Ile Ala Ala Lys Ser Lys
305                 310                 315

<210> SEQ ID NO 36
<211> LENGTH: 320
<212> TYPE: PRT
<213> ORGANISM: Methylococcus capsulatus

<400> SEQUENCE: 36

Met Ala Val Lys Asn Arg Leu His Arg Ser Glu Leu Ala Val Pro Gly
1               5                   10                  15

Ser Asn Pro Arg Met Leu Glu Lys Ala Pro Glu Ala Gly Ala Asp Ile
            20                  25                  30

Val Phe Leu Asp Leu Glu Asp Ala Val Ala Pro Asp Asp Lys Glu Gln
        35                  40                  45

Ala Arg Arg Asn Ile Val Phe Ala Leu Asn Thr Tyr Asp Trp Ser Arg
50                  55                  60

Cys Ala Val Ser Val Arg Ile Asn Gly Leu Asp Thr His Tyr Ala Tyr
65                  70                  75                  80

Arg Asp Leu Val Glu Ile Val Glu Ser Cys Gly Asp Lys Leu Asp Thr
                85                  90                  95

Ile Leu Val Pro Lys Val Gly Ser Ala Ser Asp Val Leu Phe Val Ala
            100                 105                 110

Thr Leu Leu Ser Gln Ile Glu Ala Tyr Lys Gly Phe Lys Pro Ile Asn
        115                 120                 125

Ile His Val Leu Ile Glu Thr Ala Met Gly Met Ala Asn Val Glu Glu
    130                 135                 140

Ile Ala Arg Thr Cys Pro Glu Arg Met Glu Ala Met Val Phe Gly Val
145                 150                 155                 160
```

Ala Asp Tyr Ala Ala Ser Val Arg Ala Arg Thr Thr Asn Ile Gly Gly
                165                 170                 175

Ala Asn Pro Asp Tyr Gly Met Leu Thr Asp Pro Asp Glu Ser Gly Thr
            180                 185                 190

Arg Ala Tyr His Trp Ala Asp Gln Trp His Phe Gly Ile Ser Arg Met
        195                 200                 205

Val Ala Ala Cys Arg Ala Tyr Gly Leu Arg Pro Ile Asp Gly Pro Phe
    210                 215                 220

Gly Asp Phe Ser Asp Pro Glu Gly Phe Arg Ala Ala Arg Arg Ala
225                 230                 235                 240

Ala Ala Leu Gly Cys Glu Gly Lys Trp Ala Ile His Pro Ser Gln Ile
                245                 250                 255

Pro Leu Cys Asn Glu Ile Phe Thr Pro Thr Glu Lys Glu Val Thr Arg
            260                 265                 270

Ala Tyr Arg Ile Leu Glu Ala Met Glu Gln Ala Ala Lys Glu Gly Lys
        275                 280                 285

Gly Ala Val Ser Leu Asp Gly Arg Leu Ile Asp Ala Ala Ser Ile Arg
    290                 295                 300

Met Ala Glu Asn Val Val Arg Gln Met Lys Gln Ile Glu Ser Arg Arg
305                 310                 315                 320

<210> SEQ ID NO 37
<211> LENGTH: 975
<212> TYPE: DNA
<213> ORGANISM: Methylobacterium extorquens

<400> SEQUENCE: 37

```
atgagcttca ccctgatcca gcaggccacc ccgcgcctgc accgctcgga actcgcggtt      60
cccggctcca acccgacctt catggagaag tcggctgcct cgaaggccga cgtgatcttc     120
ctcgacctcg aggacgcggt cgcgcccgac gacaaggagc aggcccgcaa gaacatcatc     180
caggctctta cgacctgga ttggggcaac aagaccatga tgatccgcat caacggtctc     240
gacacccact acatgtaccg cgacgtggtg gacatcgtgg aggcctgccc gcgcctcgac     300
atgatcctga tccccaaggt cggcgtgccg gccgacgtct acgccatcga cgtgctgacg     360
acgcagatcg agcaggccaa gaagcgcgag aagaagatcg gcttcgaggt gctgatcgag     420
accgcgctcg gcatggccaa tgtcgaggcg atcgcgacct cgtccaagcg cctcgaggcg     480
atgtccttcg gtgtcgccga ctacgccgcc tccactcgcg cccgctccac cgtgatcggc     540
ggcgtcaacg ccgattacag cgtgctcacc gacaaggacg aggcgggcaa ccgccagacc     600
cactggcagg atccgtggct gttcgcccag aaccgcatgc tggtcgcctg ccgcgcctac     660
ggcctgcgcc cgatcgacgg tcccttcggc gacttctccg atccggacgg ctacacctcg     720
gccgctcgcc gctgcgccgc gctcggcttc gagggcaagt gggcgatcca ccctcgcag      780 atcgatctgg ccaacgaggt gttcacccc tccgaggccg aggtcaccaa ggcccgccgc      840
atcctggaag ccatggaaga ggccgccaag gccggccgcg gcgccgtctc gctcgacggc     900
cgcctcatcg acatcgcctc gatccgcatg gccgaggcgc tgatccagaa ggccgacgcg     960
atgggcggga agtaa                                                      975
```

<210> SEQ ID NO 38
<211> LENGTH: 963
<212> TYPE: DNA
<213> ORGANISM: Hyphomicrobium methylovorum

<400> SEQUENCE: 38

```
atgagctaca cgctttaccc gacccgcaag cagcgcctgc agcgctcgta cctcgcagtg      60
ccgggctcca acccgagcat gatcgatcgc gcactcaaga gcgcagccga ctatgtgttt     120
ctcgattgcg aagacgccgt cgcgccgccc gagaaagaac aggctcgcaa gaacatcatt     180
caggcgctga cgatctcga ctggaagggc gcaggcaaga gcgtctcggt tcgcatcaac      240
ggcctcgaca cgcactacat gtaccgcgac gttgtcgaca tcgtggagca ggctggctcc     300
aagctcgaca cgatcctcat tcccaaggtc ggcgttccgg ctgacgtcta cacggtcgaa     360
tgcatcgtga gccagatcga agtcgcgaag ggtcttccgc accagatcgg caccgaagcg     420
ctcatcgaaa cgccgctcgg catggcaaac gtcgaagcca tcgcgtcggc aagcagccgc     480
ctcgagtcca tgcacttcgg cgttgctgac tactccgcct tcaacaaggc acgcaccgtc     540
gtcatcggcg gcttgaaccc tgattaccg ggtgaccagt ggcacttccc gctgtcgcgt      600
atgaccgttg cctgccgcgc attcggcctt cgtccgatcg acggcccgtt cggtggcatc     660
gacgatccgg aaggctacaa ggccgccgct cgccgtggcg ctgctctcgg catggaaggc     720
aagtgggcca tccatccgtc gcagatcgaa ctcgccaacg aaatctattc gccgacggcg     780
aaggaagtcg aacgcgctga cgcatcctc gttgcactga aggaagctga agctcaaggt     840
aagggcgcag cgtcgcttga cggcaagatg atcgacgccg catctgaaaa gatggcgcgc     900
aacctgctct cgactgccga gcagatcaag aaggccgagg ccgctcacgc agctcagaag     960
aaa                                                                    963
```

<210> SEQ ID NO 39
<211> LENGTH: 963
<212> TYPE: DNA
<213> ORGANISM: Hyphomicrobium denitrificans

<400> SEQUENCE: 39

```
atgagctata ccctctaccc gaaccgtaag cagcgtctgc agcgttctta tctcgccgtg      60
ccgggctcca acccgacgat gatcgaccgc gccctcaaga gcgccgccga ctacgttttc     120
cttgattgcg aagacgccgt cgcgccgccc gagaaagagc aggctcgcaa gaacatcatc     180
caggctctga cgatctcga ctggaagggc gcgggcaaga gcgtctcggt ccgcatcaac      240
ggcctcgaca cgcattattg ctaccgcgac gtcgtcgaca tcgtcgagca ggctggtgcc     300
aagctcgata cgatcctcat tccgaaggtc ggcgttccgg ccgacgtcta cgccatcgaa     360
agcttcgtca gccagatcga agtcgcgaag ggtctcccgc accagatcgg catggaagcc     420
ctcatcgaaa cgccgctcgg catggccaac gtcgaagcca tcgcgtctgc caacagccgc     480
cttgagtcga tgcacttcgg cgttgccgac tactccgcat tcaacaaggc ccgcaccgtc     540
gtcatcggcg gcttgaaccc cgactatccg ggtgaccagt ggcacttccc gctgtcgcgc     600
atgacggtcg cctgccgcgc attcggtctc cgtccgatcg acggcccgtt cggcggcatc     660
gacgatccgg aaggctacaa ggccgctgcg cgccgtggtg ccgctctcgg catggaaggc     720
aagtgggcga tccacccctc gcagatcgaa ctcgccaacg aaatctactc tccgacggcg     780
aaggaaatcg aacgcgccga cgcatcctg gtcgcactca aggaagccga agcgcagggc     840
aagggcgcag catcgctcga cggcaagatg atcgacgcgg catctgaaaa gatggcgaag     900
aacctgctgg tcacggcagc ggcgatcaag gcaggcgaag aagctcgcgc aaagagcaaa     960
taa                                                                    963
```

```
<210> SEQ ID NO 40
<211> LENGTH: 951
<212> TYPE: DNA
<213> ORGANISM: Nitrosomonas europaea

<400> SEQUENCE: 40
atgagtcata ccctgtatga aaccaaaaca ccgcgtgtac agcgctgcga actggctgtt      60
ccgggttccc gtcccgaaat gtttgaaaaa gcgctgaaaa gcggagtgga cttcatattt     120
ctggatctgg aggatgcagt cgcaccagat gacaagatcc aggcaagaaa aaatatcatt     180
caggcaatca atgatctgga ctggaaaagt cacggtgtca cgctttctgt acgcatcaat     240
ggtctcgata cccaatatat ggtgcgtgat gtggtcgatc tggtagagca ggccgggcac     300
aagatcgata cgttgctgat tcccaaagta ggtgtttatg ctgatgttta catggtcgaa     360
gccatgctca gccagcttga aatgcagcag gggctgaaaa accgaattgg tgtggaagca     420
ctgatcgaaa cggcactggg gatggccaat gttgaagata tcgcccgcag aggaacggcc     480
gggcgtctgg aagcattgca tttcggtgta gctgactacg ctgccagcaa tcgtgcacgt     540
accaccaata tcggcgggct caatccggat tatccagggg atcagtggca cgcagccatc     600
agcagaatga ccgttgcctg ccgcgcattc ggcctgcgac caatcgatgg cccatttggt     660
gacattcagg atcccgaagg ttacaaacag gcagccagac gtgctgcagc actgggttgt     720
gaaggtaaat gggcaattca tccgacacag atcgcgctgg ccaatgaagt ctttacgccg     780
cccacagcag aagtcgacaa agccaaacgc attctgacag cattgaagga agctgcagct     840
caaggtaaag gtgcagcctc acttgatggc cgcctgatcg atgccgcttc ggaaagaatg     900
gcaaataaca tcgtcaaaat ggcggaagca attgctgcca aaagcaaata a              951

<210> SEQ ID NO 41
<211> LENGTH: 963
<212> TYPE: DNA
<213> ORGANISM: Methylococcus capsulatus

<400> SEQUENCE: 41
atggctgtca agaaccgtct acaccgcagc gaactcgcgg tgccgggcag caatccacgc      60
atgctcgaga aagcgccgga agccggcgcc gacatcgtct ttctggacct ggaagatgcg     120
gttgcgccgg atgacaagga gcaagcgcgc cggaacatcg tcttcgcgct caacacctac     180
gactggtcca gatgcgcggt ctccgtccgc atcaacggcc tcgacaccca ttacgcctac     240
cgggacctcg ttgagatcgt cgagtcctgc ggcgacaagc tcgacaccat tctggtgccg     300
aaagtcggca cgcctcgga cgttctgttc gtcgcgactt actttcccca gatcgaggcc     360
tacaaaggtt tcaaaccgat caatatccac gtgctgatcg aaacggccat gggcatggcc     420
aacgtggagg agatcgcccg cacctgtcct gaacgcatgg aggccatggt gttcggcgtg     480
gccgactacg ctgcgtcggt gcgcgcccgc acgaccaaca tcggcggcgc caacccggat     540
tacggcatgc tgaccgaccc tgacgaaagc ggtaccgcg cctatcactg gccgaccag      600 tggcatttcg gcatttcccg catggtcgcg gcctgccgcg cctatgggct tcgccccatc     660
gacggcccct tcggcgattt cagcgatccg gaaggattcc gcgccgcagc ccgccgtgcc     720
gcggcactgg gctgcgaagg gaagtggcg atccatccct cccagattcc actgtgcaac     780
gaaatcttca cacccacgga aaaagaggtc acgcgggcct accgcatcct ggaagccatg     840
gagcaggcgg caaaggaggg caaaggcgcg gtgtctctgg atgggcggct gatcgatgcc     900 gccctcgatcc ggatggcgga gaacgtggtc cgccagatga agcagatcga gtcgcgtcgg     960
``` tag                                                                963

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
cgagctacat atgcaatgat tgacacgatt ccg                                33

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
cgcgcgcatg ctatttgtta gtgaataaaa gg                                 32

<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
ccgctcgagc atatgctgtc gcaatgattg acacg                              35

<210> SEQ ID NO 45
<211> LENGTH: 34
<212> TYPE: DNA
<213> ORGANISM: Artificial Sequence
<220> FEATURE:
<223> OTHER INFORMATION: primer

<400> SEQUENCE: 45
gctattccat atgcagggtt attgtctcat gagc                               34

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
tcggcacgta agaggttcc                                                19

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
cgggtcgaat ttgctttcg                                                19

<210> SEQ ID NO 48
<211> LENGTH: 28
<212> TYPE: DNA
<213> ORGANISM: Artificial Sequence
<220> FEATURE:
<223> OTHER INFORMATION: primer

<400> SEQUENCE: 48
ctagatctga cagtaagacg ggtaagcc                                28

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
ctagatctca gggttattgt ctcatgagc                               29

<210> SEQ ID NO 50
<211> LENGTH: 45
<212> TYPE: DNA
<213> ORGANISM: Artificial Sequence
<220> FEATURE:
<223> OTHER INFORMATION: primer

<400> SEQUENCE: 50
cctttggtta aaggctttaa gatcttccag tggacaaact atgcc             45

<210> SEQ ID NO 51
<211> LENGTH: 45
<212> TYPE: DNA
<213> ORGANISM: Artificial Sequence
<220> FEATURE:
<223> OTHER INFORMATION: primer

<400> SEQUENCE: 51
ggcatagttt gtccactgga agatcttaaa gcctttaacc aaagg             45

<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
ggaattccat atggctgtta aaaatcgtct ac                           32

<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
gctctagatc agaatctgat tccgtgttc                               29

<210> SEQ ID NO 54
<211> LENGTH: 27
<212> TYPE: DNA
<213> ORGANISM: Artificial Sequence
<220> FEATURE:
<223> OTHER INFORMATION: primer

<400> SEQUENCE: 54
cgcctcgagt gactcatacc aggcctg                                 27

<210> SEQ ID NO 55
<211> LENGTH: 28
<212> TYPE: DNA
<213> ORGANISM: Artificial Sequence
<220> FEATURE:
<223> OTHER INFORMATION: primer

<400> SEQUENCE: 55
cgcctcgagg caacaccttc ttcacgag                                       28

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
atcatccagc tgtcaggcag ccatcggaag                                     30

<210> SEQ ID NO 57
<211> LENGTH: 18
<212> TYPE: DNA
<213> ORGANISM: Artificial Sequence
<220> FEATURE:
<223> OTHER INFORMATION: primer

<400> SEQUENCE: 57
atccccggga attctgtt                                                  18

<210> SEQ ID NO 58
<211> LENGTH: 1352
<212> TYPE: DNA
<213> ORGANISM: Artificial Sequence
<220> FEATURE:
<223> OTHER INFORMATION: pCASE1 fragment

<400> SEQUENCE: 58
cgcctcgagc actggaaggg ttcttcaggg gaaccccgg aaaccgggga aacatctgac      60
ttggttaaat gtcgtattat gaacacgccg aggaatgaaa accgaccgtg cacgctcgtg    120
tgagaaagtc agctacatga gaccaactac ccgccctgag ggacgctttg agcagctgtg    180
gctgccgctg tggccattgg caagcgatga cctccgtgag ggcatttacc gcacctcacg    240
gaagaacgcg ctggataagc gctacgtcga agccaatccc gacgcgctct ctaacctcct    300
ggtcgttgac atcgaccagg aggacgcgct tttgcgctct ttgtgggaca gggaggactg    360
gagacctaac gcggtggttg aaaacccctt aaacgggcac gcacacgctg tctgggcgct    420
cgcggagcca tttacccgca ccgaatacgc caaacgcaag cctttggcct atgccgcggc    480
tgtcaccgaa ggcctacggc gctctgtcga tggcgatagc ggatactccg ggctgatcac    540
caaaaacccc gagcacactg catgggatag tcactggatc accgataagc tgtatacgct    600
cgatgagctg cgcttttggc tcgaagaaac cggcttatg ccgcctgcgt cctggaggaa     660
aacgcggcgg ttctcgccag ttggtctagg tcgtaattgc gcactctttg aaagcgcacg    720
tacgtgggca tatcgggagg tcagaaagca ttttggagac gctgacggcc taggccgcgc    780
aatccaaacc accgcgcaag cacttaacca agagctgttt gatgaaccac tacctgtggc    840
cgaagttgac tgtattgcca ggtcaatcca taaatggatc atcaccaagt cacgcatgtg    900
gacagacggc gccgccgtct acgacgccac attcaccgca atgcaatccg cacgcgggaa    960
gaaaggctgg caacgaagcg ctgaggtgcg tcgtgaggct ggacatactc tttggaggaa   1020

```
cattggctaa ggtttatgca cgttatccac gcaacggaaa acagcccgc gagctggcag      1080 aacgtgccgg tatgtcggtg agaacagctc aacgatggac ttccgaaccg cgtgaagtgt     1140
tcattaaacg tgccaacgag aagcgtgctc gcgtccagga gctgcgcgcc aaaggtctgt     1200
ccatgcgcgc tatcgcggca gagattggtt gctcggtggg cacggttcac cgctacgtca     1260
aagaagttga agagaagaaa accgcgtaaa tccagcggtt tagtcaccct cggcgtgttc     1320
aaagtccatc gtaaccaagt cagctcgagg cg                                   1352
```

<210> SEQ ID NO 59
<211> LENGTH: 46
<212> TYPE: DNA
<213> ORGANISM: Artificial Sequence
<220> FEATURE:
<223> OTHER INFORMATION: primer

<400> SEQUENCE: 59

```
ggaattcaca aaaggataa acaatggct gtcaagaacc gtctac                      46
```

<210> SEQ ID NO 60
<211> LENGTH: 31
<212> TYPE: DNA
<213> ORGANISM: Artificial Sequence
<220> FEATURE:
<223> OTHER INFORMATION: primer

<400> SEQUENCE: 60

```
cgaattctca gaatctgatt ccgtgttcct g                                    31
```

<210> SEQ ID NO 61
<211> LENGTH: 53
<212> TYPE: DNA
<213> ORGANISM: Artificial Sequence
<220> FEATURE:
<223> OTHER INFORMATION: primer

<400> SEQUENCE: 61

```
cgagctcaag cttacaaaaa ggataaaaca atgagcacca ttgcattcat cgg            53
```

<210> SEQ ID NO 62
<211> LENGTH: 28
<212> TYPE: DNA
<213> ORGANISM: Artificial Sequence
<220> FEATURE:
<223> OTHER INFORMATION: primer

<400> SEQUENCE: 62

```
cgggatccct agtccagcag catgagag                                        28
```

<210> SEQ ID NO 63
<211> LENGTH: 2727
<212> TYPE: DNA
<213> ORGANISM: Rhodococcus jostii

<400> SEQUENCE: 63

```
atgagcacca ttgcattcat cggactcgga atcatgggca gcccatggc cgttcatctc      60 gccaaggccg gccaccaggt ggtcggatac aaccgctcgc cgagcgcac gcggcgctc      120 gtcgacgccg ggggcaccgc ggccgactcc atcgccaagg ccgttgccgg cgccgacgtc    180
gtggccgtga tggtccccga ctcccccgac gtccaggccg tactcgccgg cgaggacgga    240
gtcttcgagc acgccccggc cggcgccctg atcatcgact tctccagcat ccggcccgac    300
```

```
gtcaccaccg ccctcgccgc gcaggcaacc gagcggggct tccggctgat cgacgccccg    360
gtatcgggtg gcgaggccgg tgcggtcaac gccgcactgt cgatcatggt cggcggcgcg    420
ccggaggatt tcgaggcggc caagccgatc ctcgacaccg tcggcaagac cgtggtgcac    480
gtgggcccga acggttccgg gcagacggtg aaggccgcga accagctgat cgtcgcgggc    540
aacatccaac tcctcgccga ggcgatcatc ttcctcgagg cctacggtgt cgacaccgcg    600
gctgcggtcg aggtgctcgg cggcgggctg gccggatcgg ccgtcctgaa ccagaaggca    660
cagaagatgc tggaccggtc cttcgaaccg ggattccgca tcgaactgca ccacaaggac    720
ctcggcatcg tgaccagcgc cgctcgcgag gccggtgtcg tgacacccct cggcgcggtc    780
gtcgcccagc tgatggcctc cgcccgtgcg aacggtgatg gtggcctgga ccattcgggc    840
ctgctgcgtg gagtggagcg gctgtccggc cgcccctccc agtgacccgt tccaactcgt    900
aatcctcgat ggagaagtga tatgcctcgt atgcgcgccg ctgacgcagc ggtcaagatt    960
ctggaactcg aaggtgccac tcaggccttc ggccttcccg gtgcggcgat caacccgttc   1020
tacgcagcaa tgcgtaacca cggaggaatc aagcacatcc tcgcccgcca cgtcgagggc   1080
gcctcccaca tggccgaggg attcacccgc gccaaggccg gaaacatcgg agtctgcatc   1140
ggcacctccg ggcccgccgg aaccgacatg atcaccggtc tgtattcggc catggcggac   1200
tcgatcccga tcctcgcgat caccggccaa gctcccgtgg cgcgcctgca caaggaagac   1260
ttccaggccg tcgacatcgc ctcgatcgca ggcccggtca cgaagatggc gatgacggtg   1320
ctcgagccgg cccaggttcc gggagcgttc gcgcaggcat ttcacttgat gcggtctggt   1380
cggccaggac cggtgctcat cgacctgccg atcgacgtgc agttggcgga gatcgacttc   1440
gacccggata cctaccagcc gctgcccgtg tacaagccgg ccgcgacccg cgcgcaggcg   1500
gagaaggcac tcgacatgct gggtgccgcc gaacgcccgc tgatcgttgc gggcggtggc   1560
atcatcaacg ccgacgccgc ggacctgctg gtggaactgg ccgaactgct ggacattccg   1620
gtcgtgccga cgctgatggg ctggggcacc atcccggacg accaccgtct cgccgccggg   1680
atggtcggac tgcagaccgc ccaccgatac ggcaacgcca cgatgctggc gtcggacttc   1740
gtcctcggca tcggcaaccg gtgggccaac cggcacacgg gcggtctcga cacctaccgg   1800
aagggccgca agttcgttca cgtcgacatc gaacccaccc agatcggtcg cgtgttcgcg   1860
cccgactacg ggatcgtgtc cgacgccaag gctgcgctcg aactgttcgt cgccgtcgcg   1920
aaggagcgca aggccgccgg aaccctggcg gaccgcagca cctgggtcga ggactgtgcc   1980
acccggaagc ggaccatgca gcgcaagacc cacttcgacg acgtcccggt caaaccgcag   2040
cgcgtgtacg aggagatgaa ccgcgtcttc gggcgcgaca cccggtacgt gagcacgatc   2100
gggctctcgc agatcgccgg cggccagttc ctgcacgtct acaaggcccg caactggatc   2160
aactgcgggc aggccgggcc gctcggctgg acgatccccg ccgctctcgg agtggttgcc   2220
gcggagccgg agacgcccgt cgtggcgctg tccggtgact acgacttcca gttcatgatc   2280
gaggaactgg ccgtgggcgc ccagttcaac ctgccgtaca tccacgtcgt ggtgaacaac   2340
tcctacctgg gactgatccg tcaggcacag cgcgcgttcg acatggactt ctgcgtgcaa   2400
ctgggcttcg acaacatcaa cacccaggag cggagcgagc acgagacgat gcccgcggtc   2460 ccgaagggt acggcgtcga tcacgtcaag gtcgccgagg gcctgggctg caaggccctg   2520
cgggtcaccg agccgggcga gatcgccggc gccctggaga aggcccgcga actcgccgga   2580
gaacacaagg tgccggtggt cgtcgaggtc ttcctcgagc gggtcaccaa catcgcgatg   2640
ggcaccgaac tcgacaacgt cgccgagttc gaggatctgg cggagagctg ggagcacgct   2700
```

-continued

```
cccacagccc tcatgctgct ggactag                                        2727
```

<210> SEQ ID NO 64
<211> LENGTH: 885
<212> TYPE: DNA
<213> ORGANISM: Rhodococcus jostii

<400> SEQUENCE: 64

```
atgagcacca ttgcattcat cggactcgga atcatgggca gccccatggc cgttcatctc     60
gccaaggccg ccaccaggt ggtcggatac aaccgctcgc ccgagcgcac cgcggcgctc    120
gtcgacgccg ggggcaccgc ggccgactcc atcgccaagg ccgttgccgg cgccgacgtc    180
gtggccgtga tggtccccga ctccccggac gtccaggccg tactcgccgg cgaggacgga    240
gtcttcgagc acgccccggc cggcgccctg atcatcgact tctccagcat ccggcccgac    300
gtcaccaccg ccctcgccgc gcaggcaacc gagcggggct tccggctgat cgacgccccg    360
gtatcgggtg gcgaggccgg tgcggtcaac gccgcactgt cgatcatggt cggcggcgcg    420
ccggaggatt tcgaggcggc caagccgatc ctcgacaccg tcggcaagac cgtggtgcac    480
gtgggcccga acggttccgg gcagacggtg aaggccgcga accagctgat cgtcgcgggc    540
aacatccaac tcctcgccga ggcgatcatc ttcctcgagg cctacggtgt cgacaccgcg    600
gctgcggtcg aggtgctcgg cggcgggctg gccggatcgg ccgtcctgaa ccagaaggca    660
cagaagatgc tggaccggtc cttcgaaccg ggattccgca tcgaactgca ccacaaggac    720
ctcggcatcg tgaccagcgc cgctcgcgag gccggtgtcg tgacacccct cggcgcggtc    780
gtcgcccagc tgatggcctc cgcccgtgcg aacggtgatg gtggcctgga ccattcgggc    840
ctgctgcgtg gagtggagcg gctgtccggc cgcccctccc agtga                    885
```

<210> SEQ ID NO 65
<211> LENGTH: 1806
<212> TYPE: DNA
<213> ORGANISM: Rhodococcus jostii

<400> SEQUENCE: 65

```
atgcctcgta tgcgcgccgc tgacgcagcg gtcaagattc tggaactcga aggtgccact     60
caggcctttcg gccttcccgg tgcggcgatc aaccgttct acgcagcaat gcgtaaccac    120
ggaggaatca agcacatcct cgcccgccac gtcgagggcg cctcccacat ggccgaggga    180
ttcacccgcg ccaaggccgg aaacatcgga gtctgcatcg gcacctccgg gcccgccgga    240
accgacatga tcaccggtct gtattcggcc atggcggact cgatcccgat cctcgcgatc    300
accggccaag ctcccgtggc gcgcctgcac aaggaagact tccaggccgt cgacatcgcc    360
tcgatcgcag gccggtcac gaagatggcg atgacggtgc tcgagccggc ccaggttccg    420
ggagcgttcg cgcaggcatt tcacttgatg cggtctggtc ggccaggacc ggtgctcatc    480
gacctgccga tcgacgtgca gttggcgag tcgacttcg accgggatac ctaccagccg    540
ctgcccgtgt acaagccggc cgcgacccgc gcgcaggcgg agaaggcact cgacatgctg    600
ggtgccgccg aacgcccgct gatcgttgcg ggcggtggca tcatcaacgc cgacgccgcg    660
gacctgctgg tggaactggc cgaactgctg acattccgg tcgtgccgac gctgatgggc    720
tggggcacca tcccggacga ccaccgtctc gccgcgggga tggtcggact gcagaccgcc    780
caccgatacg gcaacgccac gatgctggcg tcggacttcg tcctcggcat cggcaaccgg    840
tgggccaacc ggcacacggg cggtctcgac acctaccgga agggccgcaa gttcgttcac    900
```

```
gtcgacatcg aacccaccca gatcggtcgc gtgttcgcgc ccgactacgg gatcgtgtcc    960
gacgccaagg ctgcgctcga actgttcgtc gccgtcgcga aggagcgcaa ggccgccgga   1020
accctggcgg accgcagcac ctgggtcgag gactgtgcca cccggaagcg gaccatgcag   1080
cgcaagaccc acttcgacga cgtcccggtc aaaccgcagc gcgtgtacga ggagatgaac   1140
cgcgtcttcg ggcgcgacac ccggtacgtg agcacgatcg ggctctcgca gatcgccggc   1200
ggccagttcc tgcacgtcta caaggcccgc aactggatca actgcgggca ggccgggccg   1260
ctcggctgga cgatccccgc cgctctcgga gtggttgccg cggagccgga cgcccgtc     1320 gtggcgctgt ccggtgacta cgacttccag ttcatgatcg aggaactggc cgtgggcgcc   1380
cagttcaacc tgccgtacat ccacgtcgtg gtgaacaact cctacctggg actgatccgt   1440
caggcacagc gcgcgttcga catggacttc tgcgtgcaac tgggcttcga acatcaac     1500 acccaggagc ggagcgagca cgagacgatg cccgcggtcc cgaaggggta cggcgtcgat   1560
cacgtcaagg tcgccgaggg cctgggctgc aaggccctgc gggtcaccga gccgggcgag   1620
atcgccggcg ccctggagaa ggcccgcgaa ctcgccggag aacacaaggt gccggtggtc   1680
gtcgaggtct cctcgagcg ggtcaccaac atcgcgatgg caccgaact cgacaacgtc    1740 gccgagttcg aggatctggc ggagagctgg gagcacgctc ccacagccct catgctgctg   1800
gactag                                                              1806
```

<210> SEQ ID NO 66
<211> LENGTH: 294
<212> TYPE: PRT
<213> ORGANISM: Rhodococcus jostii

<400> SEQUENCE: 66

```
Met Ser Thr Ile Ala Phe Ile Gly Leu Gly Ile Met Gly Ser Pro Met
1               5                   10                  15

Ala Val His Leu Ala Lys Ala Gly His Gln Val Val Gly Tyr Asn Arg
            20                  25                  30

Ser Pro Glu Arg Thr Ala Ala Leu Val Asp Ala Gly Gly Thr Ala Ala
        35                  40                  45

Asp Ser Ile Ala Lys Ala Val Ala Gly Ala Asp Val Val Ala Val Met
    50                  55                  60

Val Pro Asp Ser Pro Asp Val Gln Ala Val Leu Ala Gly Glu Asp Gly
65                  70                  75                  80

Val Phe Glu His Ala Pro Ala Gly Ala Leu Ile Ile Asp Phe Ser Ser
                85                  90                  95

Ile Arg Pro Asp Val Thr Thr Ala Leu Ala Ala Gln Ala Thr Glu Arg
            100                 105                 110

Gly Phe Arg Leu Ile Asp Ala Pro Val Ser Gly Gly Glu Ala Gly Ala
        115                 120                 125

Val Asn Ala Ala Leu Ser Ile Met Val Gly Gly Ala Pro Glu Asp Phe
    130                 135                 140

Glu Ala Ala Lys Pro Ile Leu Asp Thr Val Gly Lys Thr Val Val His
145                 150                 155                 160

Val Gly Pro Asn Gly Ser Gly Gln Thr Val Lys Ala Ala Asn Gln Leu
                165                 170                 175

Ile Val Ala Gly Asn Ile Gln Leu Leu Ala Glu Ala Ile Ile Phe Leu
            180                 185                 190

Glu Ala Tyr Gly Val Asp Thr Ala Ala Ala Val Glu Val Leu Gly Gly
        195                 200                 205
```

Gly Leu Ala Gly Ser Ala Val Leu Asn Gln Lys Ala Gln Lys Met Leu
    210                 215                 220

Asp Arg Ser Phe Glu Pro Gly Phe Arg Ile Glu Leu His His Lys Asp
225                 230                 235                 240

Leu Gly Ile Val Thr Ser Ala Ala Arg Glu Ala Gly Val Val Thr Pro
                245                 250                 255

Leu Gly Ala Val Val Ala Gln Leu Met Ala Ser Ala Arg Ala Asn Gly
            260                 265                 270

Asp Gly Gly Leu Asp His Ser Gly Leu Leu Arg Gly Val Glu Arg Leu
        275                 280                 285

Ser Gly Arg Pro Ser Gln
    290

<210> SEQ ID NO 67
<211> LENGTH: 601
<212> TYPE: PRT
<213> ORGANISM: Rhodococcus jostii

<400> SEQUENCE: 67

Met Pro Arg Met Arg Ala Ala Asp Ala Ala Val Lys Ile Leu Glu Leu
1               5                   10                  15

Glu Gly Ala Thr Gln Ala Phe Gly Leu Pro Gly Ala Ala Ile Asn Pro
            20                  25                  30

Phe Tyr Ala Ala Met Arg Asn His Gly Gly Ile Lys His Ile Leu Ala
        35                  40                  45

Arg His Val Glu Gly Ala Ser His Met Ala Glu Gly Phe Thr Arg Ala
    50                  55                  60

Lys Ala Gly Asn Ile Gly Val Cys Ile Gly Thr Ser Gly Pro Ala Gly
65                  70                  75                  80

Thr Asp Met Ile Thr Gly Leu Tyr Ser Ala Met Ala Asp Ser Ile Pro
                85                  90                  95

Ile Leu Ala Ile Thr Gly Gln Ala Pro Val Ala Arg Leu His Lys Glu
            100                 105                 110

Asp Phe Gln Ala Val Asp Ile Ala Ser Ile Ala Gly Pro Val Thr Lys
        115                 120                 125

Met Ala Met Thr Val Leu Glu Pro Ala Gln Val Pro Gly Ala Phe Ala
    130                 135                 140

Gln Ala Phe His Leu Met Arg Ser Gly Arg Pro Gly Pro Val Leu Ile
145                 150                 155                 160

Asp Leu Pro Ile Asp Val Gln Leu Ala Glu Ile Asp Phe Asp Pro Asp
                165                 170                 175

Thr Tyr Gln Pro Leu Pro Val Tyr Lys Pro Ala Ala Thr Arg Ala Gln
            180                 185                 190

Ala Glu Lys Ala Leu Asp Met Leu Gly Ala Ala Glu Arg Pro Leu Ile
        195                 200                 205

Val Ala Gly Gly Gly Ile Ile Asn Ala Asp Ala Ala Asp Leu Leu Val
    210                 215                 220

Glu Leu Ala Glu Leu Leu Asp Ile Pro Val Val Pro Thr Leu Met Gly
225                 230                 235                 240

Trp Gly Thr Ile Pro Asp Asp His Arg Leu Ala Ala Gly Met Val Gly
                245                 250                 255

Leu Gln Thr Ala His Arg Tyr Gly Asn Ala Thr Met Leu Ala Ser Asp
            260                 265                 270

Phe Val Leu Gly Ile Gly Asn Arg Trp Ala Asn Arg His Thr Gly Gly
        275                 280                 285

-continued

Leu Asp Thr Tyr Arg Lys Gly Arg Lys Phe Val His Val Asp Ile Glu
    290                 295                 300

Pro Thr Gln Ile Gly Arg Val Phe Ala Pro Asp Tyr Gly Ile Val Ser
305                 310                 315                 320

Asp Ala Lys Ala Ala Leu Glu Leu Phe Val Ala Val Ala Lys Glu Arg
                325                 330                 335

Lys Ala Ala Gly Thr Leu Ala Asp Arg Ser Thr Trp Val Glu Asp Cys
            340                 345                 350

Ala Thr Arg Lys Arg Thr Met Gln Arg Lys Thr His Phe Asp Asp Val
        355                 360                 365

Pro Val Lys Pro Gln Arg Val Tyr Glu Glu Met Asn Arg Val Phe Gly
    370                 375                 380

Arg Asp Thr Arg Tyr Val Ser Thr Ile Gly Leu Ser Gln Ile Ala Gly
385                 390                 395                 400

Gly Gln Phe Leu His Val Tyr Lys Ala Arg Asn Trp Ile Asn Cys Gly
                405                 410                 415

Gln Ala Gly Pro Leu Gly Trp Thr Ile Pro Ala Ala Leu Gly Val Val
            420                 425                 430

Ala Ala Glu Pro Glu Thr Pro Val Val Ala Leu Ser Gly Asp Tyr Asp
        435                 440                 445

Phe Gln Phe Met Ile Glu Glu Leu Ala Val Gly Ala Gln Phe Asn Leu
    450                 455                 460

Pro Tyr Ile His Val Val Asn Asn Ser Tyr Leu Gly Leu Ile Arg
465                 470                 475                 480

Gln Ala Gln Arg Ala Phe Asp Met Asp Phe Cys Val Gln Leu Gly Phe
                485                 490                 495

Asp Asn Ile Asn Thr Gln Glu Arg Ser Glu His Glu Thr Met Pro Ala
            500                 505                 510

Val Pro Lys Gly Tyr Gly Val Asp His Val Lys Val Ala Glu Gly Leu
        515                 520                 525

Gly Cys Lys Ala Leu Arg Val Thr Glu Pro Gly Glu Ile Ala Gly Ala
    530                 535                 540

Leu Glu Lys Ala Arg Glu Leu Ala Gly Glu His Lys Val Pro Val Val
545                 550                 555                 560

Val Glu Val Phe Leu Glu Arg Val Thr Asn Ile Ala Met Gly Thr Glu
                565                 570                 575

Leu Asp Asn Val Ala Glu Phe Glu Asp Leu Ala Glu Ser Trp Glu His
            580                 585                 590

Ala Pro Thr Ala Leu Met Leu Asp
        595                 600

<210> SEQ ID NO 68
<211> LENGTH: 37
<212> TYPE: DNA
<213> ORGANISM: Artificial Sequence
<220> FEATURE:
<223> OTHER INFORMATION: primer

<400> SEQUENCE: 68
atcgatctcg agttacccgt cttactgtca gatctag                              37

<210> SEQ ID NO 69
<211> LENGTH: 37
<212> TYPE: DNA
<213> ORGANISM: Artificial Sequence
<220> FEATURE:

```
<223> OTHER INFORMATION: primer

<400> SEQUENCE: 69
atcgatctcg aggcctgttg atgataccgc tgcctta                                 37

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
ccgctcgagt caacaacaag acccatca                                          28

<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
ccgctcgagc atgcacatgc agtcatgt                                          28

<210> SEQ ID NO 72
<211> LENGTH: 1838
<212> TYPE: DNA
<213> ORGANISM: Artificial Sequence
<220> FEATURE:
<223> OTHER INFORMATION: pBL1 fragment

<400> SEQUENCE: 72
ccgctcgagt caacaacaag acccatcata gtttgccccc gcgacattga ccataaattc        60
atcgcacaaa atatcgaacg gggtttatgc cgcttttagt gggtgcgaag aatagtctgc       120
tcattacccg cgaacaccgc cgcattcaga tcacgcttag tagcgtcccc atgagtaggc       180
agaaccgcgt ccaagtccac atcatccata cgatcatgc acggggtgga atccacaccc        240
agacttgcca gcacctcatt agcgacacgt tgcgcagcgg ccacgtcctt agccttatcc       300
acgcaatcta gaacgtactg cctaaccgcg aaatcagact gaatcagttt ccaatcatcg       360
ggcttcacca aagcaacagc aacgcgggtt gattcgaccc gttccggtgc ttccagaccg       420
gcgagcttgt acagttcttc ttccatttca cgacgtacat cagcgtctat gtaatcaatg       480
cccaaagcac gcttagcccc acgtgaccag gacgaacgca ggtttttaga accaacctca       540
tactcacgcc accgagccac caaaacagcg tccatatcct cgccggcgtc gctttgatcg       600
gccaacatat ccaacatctg aaacggcgtg tacgacccct tagacgcggt tttagtagcg       660
gagccagtca gttcctgaga catgccctta gcgaggtagg ttgccatttt cgcagcgtct       720
ccaccccagg tagacacctg atcaagtttg acccgtgct cacgcagtgg cgcgtccata       780
ccggccttaa ccacaccagc agaccagcgg gaaaacatgg aatcctcaaa cgccttgagt       840
tcatcgtcag acagtggacg atccaagaac aacagcatgt tgcggtgcaa gtgccaaccg       900
ttcgcccaag agtctgtgac ctcatagtca ctataggtgt gctccacccc gtaccgtgca       960
cgttctttct tccactgaga tgttttcacc atcgaagagt acgcagtctt aatacccgct      1020
tcaacctgcg caaatgactg tgagcggttg tgtcgaacag tgcccacaaa catcatgagc      1080
gcgccacccg ccgccaagtg attcttagta gcaatagcca gctcaatgcg gcgttcgccc      1140
atgacttcca attcagccag aggtgacccc cagcgagagt gagagttttg cagaccctca      1200
```

-continued

| | |
|---|---|
| aactgcgaag caccgttaga cgaccaggac accgcaacag cttcgtccct gcgccaccta | 1260 |
| tggcaccccg ccagagcctt actattggtg atcttgtaca tgacgttttg cctacgccac | 1320 |
| gccctagcgc gagtgacctt agaaccctca ttgacctgcg gttccttaga ggtgttcact | 1380 |
| tctatttcag tgttacctag acccgatgtt gtgcggggtt gcgcagtgcg agtttgtgcg | 1440 |
| ggtgttgtgc ccgttgtctt agctagtgct atggttgtca attgaaaccc cttcgggtta | 1500 |
| tgtgcccccc gtgcatatga gttggtagct cgcacggggg tttgtcttgt ctagggacta | 1560 |
| ttaattttta gtggtgtttg gtggccgcct agcttggcta tgcgtgccag cttacccgta | 1620 |
| ctcaatgtta aagatttgca tcgacatggg agggttacgt gtccgatacc tagggggggt | 1680 |
| atccgcgact aggtgccccg gtgctcactg tctgtaccgg cggggcaagc cccacacccc | 1740 |
| gcatggacag ggtggctccg cccctgcac cccagcaat ctgcatgtac atgttttaca | 1800 |
| cattagcacg acatgactgc atgtgcatgc tcgagcgg | 1838 |

<210> SEQ ID NO 73
<211> LENGTH: 48
<212> TYPE: DNA
<213> ORGANISM: Artificial Sequence
<220> FEATURE:
<223> OTHER INFORMATION: primer

<400> SEQUENCE: 73

| | |
|---|---|
| aagcgagctc acaaaaagga taaaacaatg tcgactcaca catcttca | 48 |

<210> SEQ ID NO 74
<211> LENGTH: 33
<212> TYPE: DNA
<213> ORGANISM: Artificial Sequence
<220> FEATURE:
<223> OTHER INFORMATION: primer

<400> SEQUENCE: 74

| | |
|---|---|
| atacatgcat gcttaggaaa cgacgacgat caa | 33 |

<210> SEQ ID NO 75
<211> LENGTH: 3423
<212> TYPE: DNA
<213> ORGANISM: Corynebacterium glutamicum

<400> SEQUENCE: 75

| | |
|---|---|
| gtgtcgactc acacatcttc aacgcttcca gcattcaaaa agatcttggt agcaaaccgc | 60 |
| ggcgaaatcg cggtccgtgc tttccgtgca gcactcgaaa ccggtgcagc cacggtagct | 120 |
| atttaccccc gtgaagatcg gggatcattc caccgctctt ttgcttctga agctgtccgc | 180 |
| attggtaccg aaggctcacc agtcaaggcg tacctggaca tcgatgaaat tatcggtgca | 240 |
| gctaaaaaag ttaaagcaga tgccattac ccgggatacg gcttcctgtc tgaaaatgcc | 300 |
| cagcttgccc gcgagtgtgc ggaaaacggc attactttta ttggcccaac cccagaggtt | 360 |
| cttgatctca ccggtgataa gtctcgcgcg gtaaccgccg cgaagaaggc tggtctgcca | 420 |
| gttttggcgg aatccacccc gagcaaaaac atcgatgaga tcgttaaaag cgctgaaggc | 480 |
| cagacttacc ccatctttgt gaaggcagtt gccggtggtg gcggacgcgg tatgcgtttt | 540 |
| gttgcttcac ctgatgagct tcgcaaatta gcaacagaag catctcgtga agctgaagcg | 600 |
| gctttcggcg atggcgcggt atatgtcgaa cgtgctgtga ttaaccctca gcatattgaa | 660 |
| gtgcagatcc ttgcgatca cactggagaa gttgtacacc tttatgaacg tgactgctca | 720 |

```
ctgcagcgtc gtcaccaaaa agttgtcgaa attgcgccag cacagcattt ggatccagaa      780
ctgcgtgatc gcatttgtgc ggatgcagta aagttctgcc gctccattgg ttaccagggc      840
gcgggaaccg tggaattctt ggtcgatgaa aagggcaacc acgtcttcat cgaaatgaac      900
ccacgtatcc aggttgagca caccgtgact gaagaagtca ccgaggtgga cctggtgaag      960
gcgcagatgc gcttggctgc tggtgcaacc ttgaaggaat gggtctgac  ccaagataag     1020 atcaagaccc acggtgcagc actgcagtgc cgcatcacca cggaagatcc aaacaacggc     1080
ttccgcccag ataccggaac tatcaccgcg taccgctcac caggcggagc tggcgttcgt     1140
cttgacggtg cagctcagct cggtggcgaa atcaccgcac actttgactc catgctggtg     1200
aaaatgacct gccgtggttc cgactttgaa actgctgttg ctcgtgcaca gcgcgcgttg     1260
gctgagttca ccgtgtctgg tgttgcaacc aacattggtt tcttgcgtgc gttgctgcgg     1320
gaagaggact tcacttccaa gcgcatcgcc accggattca ttgccgatca cccgcacctc     1380
cttcaggctc cacctgctga tgatgagcag ggacgcatcc tggattactt ggcagatgtc     1440
accgtgaaca agcctcatgg tgtgcgtcca aaggatgttg cagctcctat cgataagctg     1500
cctaacatca aggatctgcc actgccacgc ggttcccgtg accgcctgaa gcagcttggc     1560
ccagccgcgt ttgctcgtga tctccgtgag caggacgcac tggcagttac tgataccacc     1620
ttccgcgatg cacaccagtc tttgcttgcg acccgagtcc gctcattcgc actgaagcct     1680
gcggcagagg ccgtcgcaaa gctgactcct gagcttttgt ccgtggaggc ctggggcggc     1740
gcgacctacg atgtggcgat gcgtttcctc tttgaggatc cgtgggacag gctcgacgag     1800
ctgcgcgagg cgatgccgaa tgtaaacatt cagatgctgc ttcgcggccg caacaccgtg     1860
ggatacaccc cgtacccaga ctccgtctgc cgcgcgtttg ttaaggaagc tgccagctcc     1920
ggcgtggaca tcttccgcat cttcgacgcg cttaacgacg tctcccagat gcgtccagca     1980
atcgacgcag tcctggagac caacaccgcg gtagccgagg tggctatggc ttattctggt     2040
gatctctctg atccaaatga aaagctctac accctggatt actacctaaa gatggcagag     2100
gagatcgtca gtctggcgc  tcacatcttg gccattaagg atatggctgg tctgcttcgc     2160
ccagctgcgt taaccaagct ggtcaccgca ctgcgccgtg aattcgatct gccagtgcac     2220
gtgcacaccc acgacactgc gggtggccag ctggcaacct actttgctgc agctcaagct     2280
ggtgcagatg ctgttgacgg tgcttccgca ccactgtctg gcaccacctc ccagccatcc     2340
ctgtctgcca ttgttgctgc attcgcgcac acccgtcgcg ataccggttt gagcctcgag     2400
gctgtttctg acctcgagcc gtactgggaa gcagtgcgcg gactgtacct gccatttgag     2460
tctggaaccc caggcccaac cggtcgcgtc taccgccacg aaatcccagg cggacagttg     2520
tccaacctgc gtgcacaggc caccgcactg ggccttgcgg atcgtttcga actcatcgaa     2580
gacaactacg cagccgttaa tgagatgctg ggacgcccaa ccaaggtcac cccatcctcc     2640
aaggttgttg gcgacctcgc actccacctc gttggtgcgg gtgtggatcc agcagacttt     2700
gctgccgatc acaaaagta cgacatccca gactctgtca tcgcgttcct gcgcggcgag     2760
cttggtaacc ctccaggtgg ctggccagag ccactgcgca cccgcgcact ggaaggccgc     2820
tccgaaggca aggcacctct gacggaagtt cctgaggaag agcaggcgca cctcgacgct     2880
gatgattcca aggaacgtcg caatagcctc aaccgcctgc tgttcccgaa gccaaccgaa     2940
gagttcctcg agcaccgtcg ccgcttcggc aacacctctg cgctggatga tcgtgaattc     3000
ttctacggcc tggtcgaagg ccgcgagact ttgatccgcc tgccagatgt gcgcaccccca    3060 ctgcttgttc gcctggatgc gatctctgag ccagacgata agggtatgcg caatgttgtg     3120
```

```
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                  3423
```

<210> SEQ ID NO 76
<211> LENGTH: 1140
<212> TYPE: PRT
<213> ORGANISM: Corynebacterium glutamicum

<400> SEQUENCE: 76

```
Val Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
```

-continued

```
            305                 310                 315                 320
        Ala Gln Met Arg Leu Ala Ala Gly Ala Thr Leu Lys Glu Leu Gly Leu
                            325                 330                 335

Thr Gln Asp Lys Ile Lys Thr His Gly Ala Ala Leu Gln Cys Arg Ile
                            340                 345                 350

Thr Thr Glu Asp Pro Asn Asn Gly Phe Arg Pro Asp Thr Gly Thr Ile
                            355                 360                 365

Thr Ala Tyr Arg Ser Pro Gly Gly Ala Gly Val Arg Leu Asp Gly Ala
                            370                 375                 380

Ala Gln Leu Gly Gly Glu Ile Thr Ala His Phe Asp Ser Met Leu Val
        385                 390                 395                 400

Lys Met Thr Cys Arg Gly Ser Asp Phe Glu Thr Ala Val Ala Arg Ala
                            405                 410                 415

Gln Arg Ala Leu Ala Glu Phe Thr Val Ser Gly Val Ala Thr Asn Ile
                            420                 425                 430

Gly Phe Leu Arg Ala Leu Leu Arg Glu Glu Asp Phe Thr Ser Lys Arg
                            435                 440                 445

Ile Ala Thr Gly Phe Ile Ala Asp His Pro His Leu Leu Gln Ala Pro
                            450                 455                 460

Pro Ala Asp Asp Glu Gln Gly Arg Ile Leu Asp Tyr Leu Ala Asp Val
        465                 470                 475                 480

Thr Val Asn Lys Pro His Gly Val Arg Pro Lys Asp Val Ala Ala Pro
                            485                 490                 495

Ile Asp Lys Leu Pro Asn Ile Lys Asp Leu Pro Leu Pro Arg Gly Ser
                            500                 505                 510

Arg Asp Arg Leu Lys Gln Leu Gly Pro Ala Ala Phe Ala Arg Asp Leu
                            515                 520                 525

Arg Glu Gln Asp Ala Leu Ala Val Thr Asp Thr Thr Phe Arg Asp Ala
                            530                 535                 540

His Gln Ser Leu Leu Ala Thr Arg Val Arg Ser Phe Ala Leu Lys Pro
        545                 550                 555                 560

Ala Ala Glu Ala Val Ala Lys Leu Thr Pro Glu Leu Leu Ser Val Glu
                            565                 570                 575

Ala Trp Gly Gly Ala Thr Tyr Asp Val Ala Met Arg Phe Leu Phe Glu
                            580                 585                 590

Asp Pro Trp Asp Arg Leu Asp Glu Leu Arg Glu Ala Met Pro Asn Val
                            595                 600                 605

Asn Ile Gln Met Leu Leu Arg Gly Arg Asn Thr Val Gly Tyr Thr Pro
                            610                 615                 620

Tyr Pro Asp Ser Val Cys Arg Ala Phe Val Lys Glu Ala Ala Ser Ser
        625                 630                 635                 640

Gly Val Asp Ile Phe Arg Ile Phe Asp Ala Leu Asn Asp Val Ser Gln
                            645                 650                 655

Met Arg Pro Ala Ile Asp Ala Val Leu Glu Thr Asn Thr Ala Val Ala
                            660                 665                 670

Glu Val Ala Met Ala Tyr Ser Gly Asp Leu Ser Asp Pro Asn Glu Lys
                            675                 680                 685

Leu Tyr Thr Leu Asp Tyr Tyr Leu Lys Met Ala Glu Glu Ile Val Lys
                            690                 695                 700

Ser Gly Ala His Ile Leu Ala Ile Lys Asp Met Ala Gly Leu Leu Arg
        705                 710                 715                 720

Pro Ala Ala Val Thr Lys Leu Val Thr Ala Leu Arg Arg Glu Phe Asp
                            725                 730                 735
```

-continued

```
Leu Pro Val His Val His Thr His Asp Thr Ala Gly Gln Leu Ala
            740                 745                 750

Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
            930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
            1010                1015                1020

Arg Leu Asp Ala Ile Ser Glu Pro Asp Asp Lys Gly Met Arg Asn
            1025                1030                1035

Val Val Ala Asn Val Asn Gly Gln Ile Arg Pro Met Arg Val Arg
            1040                1045                1050

Asp Arg Ser Val Glu Ser Val Thr Ala Thr Ala Glu Lys Ala Asp
            1055                1060                1065

Ser Ser Asn Lys Gly His Val Ala Ala Pro Phe Ala Gly Val Val
            1070                1075                1080

Thr Val Thr Val Ala Glu Gly Asp Glu Val Lys Ala Gly Asp Ala
            1085                1090                1095

Val Ala Ile Ile Glu Ala Met Lys Met Glu Ala Thr Ile Thr Ala
            1100                1105                1110

Ser Val Asp Gly Lys Ile Asp Arg Val Val Pro Ala Ala Thr
            1115                1120                1125

Lys Val Glu Gly Gly Asp Leu Ile Val Val Ser
            1130                1135                1140
```

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
cgctcaattg caatgattga cacgattccg                               30

<210> SEQ ID NO 78
<211> LENGTH: 32
<212> TYPE: DNA
<213> ORGANISM: Artificial Sequence
<220> FEATURE:
<223> OTHER INFORMATION: primer

<400> SEQUENCE: 78
acagaattcg ctatttgtta gtgaataaaa gg                            32

<210> SEQ ID NO 79
<211> LENGTH: 50
<212> TYPE: DNA
<213> ORGANISM: Artificial Sequence
<220> FEATURE:
<223> OTHER INFORMATION: primer

<400> SEQUENCE: 79
cgaattcgct ggtggaacat atgaaaacaa aattgatgac attacaagac         50

<210> SEQ ID NO 80
<211> LENGTH: 30
<212> TYPE: DNA
<213> ORGANISM: Artificial Sequence
<220> FEATURE:
<223> OTHER INFORMATION: primer

<400> SEQUENCE: 80
gcggtacctt atttgctctc ctgtgaaacg                               30

<210> SEQ ID NO 81
<211> LENGTH: 31
<212> TYPE: DNA
<213> ORGANISM: Artificial Sequence
<220> FEATURE:
<223> OTHER INFORMATION: primer

<400> SEQUENCE: 81
gctctagatg ctgaaatcca ctagtcttgt c                             31

<210> SEQ ID NO 82
<211> LENGTH: 29
<212> TYPE: DNA
<213> ORGANISM: Artificial Sequence
<220> FEATURE:
<223> OTHER INFORMATION: primer

<400> SEQUENCE: 82
tactgcagcg ttccagcacc ttatcaacc                                29

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
ggtctagagc aatgattgac acgattccg									29

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
gcggtacctt atttgctctc ctgtgaaacg								30

<210> SEQ ID NO 85
<211> LENGTH: 29
<212> TYPE: DNA
<213> ORGANISM: Artificial Sequence
<220> FEATURE:
<223> OTHER INFORMATION: primer

<400> SEQUENCE: 85
caggaattcg ctatatctgg ctctgcacg									29

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
cagtctagag caatactctt ctgattttga g								31

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
cagtctagat catcgtcgat atgtaggcc									29

<210> SEQ ID NO 88
<211> LENGTH: 29
<212> TYPE: DNA
<213> ORGANISM: Artificial Sequence
<220> FEATURE:
<223> OTHER INFORMATION: primer

<400> SEQUENCE: 88
gacctgcaga tcatccgtca gctgtacgc									29

<210> SEQ ID NO 89
<211> LENGTH: 29
<212> TYPE: DNA
<213> ORGANISM: Artificial Sequence
<220> FEATURE:
<223> OTHER INFORMATION: primer

<400> SEQUENCE: 89
ggaattcggg tcaattttca ccctctatc									29

<210> SEQ ID NO 90

<211> LENGTH: 37
<212> TYPE: DNA
<213> ORGANISM: Artificial Sequence
<220> FEATURE:
<223> OTHER INFORMATION: primer

<400> SEQUENCE: 90
gtgggccgtc ctgaaggtac aaaagagata gattctc                              37

<210> SEQ ID NO 91
<211> LENGTH: 37
<212> TYPE: DNA
<213> ORGANISM: Artificial Sequence
<220> FEATURE:
<223> OTHER INFORMATION: primer

<400> SEQUENCE: 91
ctcttttgta ccttcaggac ggcccacaaa tttgaag                              37

<210> SEQ ID NO 92
<211> LENGTH: 29
<212> TYPE: DNA
<213> ORGANISM: Artificial Sequence
<220> FEATURE:
<223> OTHER INFORMATION: primer

<400> SEQUENCE: 92
ggaattccca gccccgcaag gccgatggc                                       29

<210> SEQ ID NO 93
<211> LENGTH: 31
<212> TYPE: DNA
<213> ORGANISM: Artificial Sequence
<220> FEATURE:
<223> OTHER INFORMATION: primer

<400> SEQUENCE: 93
cgccatatga atggcgcggc ggggccggtg g                                    31

<210> SEQ ID NO 94
<211> LENGTH: 28
<212> TYPE: DNA
<213> ORGANISM: Artificial Sequence
<220> FEATURE:
<223> OTHER INFORMATION: primer

<400> SEQUENCE: 94
tggagctctg tttactcctg tcaggggg                                        28

<210> SEQ ID NO 95
<211> LENGTH: 33
<212> TYPE: DNA
<213> ORGANISM: Artificial Sequence
<220> FEATURE:
<223> OTHER INFORMATION: primer

<400> SEQUENCE: 95
tggagctctc tgatttaatc aacaataaaa ttg                                  33

<210> SEQ ID NO 96
<211> LENGTH: 29
<212> TYPE: DNA
<213> ORGANISM: Artificial Sequence
<220> FEATURE:
<223> OTHER INFORMATION: primer

<400> SEQUENCE: 96
cgggatccac caccataacc aaacgacgg                                             29

<210> SEQ ID NO 97
<211> LENGTH: 45
<212> TYPE: DNA
<213> ORGANISM: Artificial Sequence
<220> FEATURE:
<223> OTHER INFORMATION: primer

<400> SEQUENCE: 97
aatatgcatg ctggtggaac atatgaaagg ttttgcaatg ctagg             45

<210> SEQ ID NO 98
<211> LENGTH: 40
<212> TYPE: DNA
<213> ORGANISM: Artificial Sequence
<220> FEATURE:
<223> OTHER INFORMATION: primer

<400> SEQUENCE: 98
acgcgtcgac ttataatata actactgctt taattaagtc                   40

<210> SEQ ID NO 99
<211> LENGTH: 56
<212> TYPE: DNA
<213> ORGANISM: Artificial Sequence
<220> FEATURE:
<223> OTHER INFORMATION: primer

<400> SEQUENCE: 99
acgcgtcgac gctggtggaa catatgttaa aggatgaagt aattaaacaa attagc       56

<210> SEQ ID NO 100
<211> LENGTH: 44
<212> TYPE: DNA
<213> ORGANISM: Artificial Sequence
<220> FEATURE:
<223> OTHER INFORMATION: primer

<400> SEQUENCE: 100
gctctagagg taccttactt aagataatca tatataactt cagc              44

<210> SEQ ID NO 101
<211> LENGTH: 46
<212> TYPE: DNA
<213> ORGANISM: Artificial Sequence
<220> FEATURE:
<223> OTHER INFORMATION: primer

<400> SEQUENCE: 101
gctctagacg gagaaagtct tatggcggta acgcaaacag cccagg            46

<210> SEQ ID NO 102
<211> LENGTH: 45
<212> TYPE: DNA
<213> ORGANISM: Artificial Sequence
<220> FEATURE:
<223> OTHER INFORMATION: primer

<400> SEQUENCE: 102
cgggatcccg gagaaagtct tatgaagcaa acagtttata tcgcc             45

<210> SEQ ID NO 103
<211> LENGTH: 34
<212> TYPE: DNA

```
<213> ORGANISM: Artificial Sequence
<220> FEATURE:
<223> OTHER INFORMATION: primer

<400> SEQUENCE: 103
ctactagtct gtcgcaatga ttgacacgat tccg                           34

<210> SEQ ID NO 104
<211> LENGTH: 48
<212> TYPE: DNA
<213> ORGANISM: Artificial Sequence
<220> FEATURE:
<223> OTHER INFORMATION: primer

<400> SEQUENCE: 104
gctcgaattc ccatatgttc caccagctat ttgttagtga ataaaagg            48

<210> SEQ ID NO 105
<211> LENGTH: 42
<212> TYPE: DNA
<213> ORGANISM: Artificial Sequence
<220> FEATURE:
<223> OTHER INFORMATION: primer

<400> SEQUENCE: 105
gctctagacg gagaaagtct tatgaaactg ggatttattg gc                  42

<210> SEQ ID NO 106
<211> LENGTH: 28
<212> TYPE: DNA
<213> ORGANISM: Artificial Sequence
<220> FEATURE:
<223> OTHER INFORMATION: primer

<400> SEQUENCE: 106
aactgcagtc aggccagttt atggttag                                  28

<210> SEQ ID NO 107
<211> LENGTH: 42
<212> TYPE: DNA
<213> ORGANISM: Artificial Sequence
<220> FEATURE:
<223> OTHER INFORMATION: primer

<400> SEQUENCE: 107
aactgcagcg gagaaagtct tatgaagatt gtcattgcgc ca                  42

<210> SEQ ID NO 108
<211> LENGTH: 34
<212> TYPE: DNA
<213> ORGANISM: Artificial Sequence
<220> FEATURE:
<223> OTHER INFORMATION: primer

<400> SEQUENCE: 108
ggaattcaag ctttcagttt ttaattccct gacc                           34
```